US011145820B2

(12) United States Patent
Jung et al.

(10) Patent No.: US 11,145,820 B2
(45) Date of Patent: Oct. 12, 2021

(54) ORGANIC OPTOELECTRONIC DEVICE AND DISPLAY DEVICE

(71) Applicant: SAMSUNG SDI CO., LTD., Yongin-si (KR)

(72) Inventors: Ho-Kuk Jung, Suwon-si (KR); Jae-Jin Oh, Suwon-si (KR); Dong-Wan Ryu, Suwon-si (KR); Su-Jin Han, Suwon-si (KR); Gi-Wook Kang, Suwon-si (KR); Eui-Su Kang, Suwon-si (KR); Youn-Hwan Kim, Suwon-si (KR); Hun Kim, Suwon-si (KR); Jae-Han Park, Suwon-si (KR); Yong-Tak Yang, Suwon-si (KR); Eun-Sun Yu, Suwon-si (KR); Han-Ill Lee, Suwon-si (KR); Woo-Seok Jeong, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 573 days.

(21) Appl. No.: 15/490,110

(22) Filed: Apr. 18, 2017

(65) Prior Publication Data

US 2017/0222158 A1 Aug. 3, 2017

Related U.S. Application Data

(63) Continuation of application No. PCT/KR2015/006585, filed on Jun. 26, 2015.

(30) Foreign Application Priority Data

Oct. 31, 2014 (KR) ........................ 10-2014-0150590

(51) Int. Cl.
*H01L 51/54* (2006.01)
*H01L 51/00* (2006.01)
(Continued)

(52) U.S. Cl.
CPC ........ *H01L 51/0067* (2013.01); *C07D 213/06* (2013.01); *C07D 213/16* (2013.01); *C07D 251/24* (2013.01); *C07D 307/77* (2013.01); *C07D 333/50* (2013.01); *C07D 409/12* (2013.01); *C09K 11/06* (2013.01); *H01L 27/32* (2013.01); *H01L 51/006* (2013.01); *H01L 51/0061* (2013.01); *H01L 51/0073* (2013.01); *H01L 51/50* (2013.01); *H05B 33/20* (2013.01); *H01L 51/0052* (2013.01); *H01L 51/0058* (2013.01); *H01L 51/0074* (2013.01); *H01L 51/508* (2013.01); *H01L 51/5012* (2013.01); *H01L 51/5064* (2013.01); *H01L 2251/308* (2013.01); *Y02E 10/549* (2013.01)

(58) Field of Classification Search
CPC ..... H05B 33/20; Y02E 10/549; C07D 213/06; C07D 213/16; C07D 251/24; C07D 307/77; C07D 333/50; C07D 409/12; C09K 11/06; C09K 2211/00; C09K 2211/10; C09K 2211/1007; C09K 2211/1011; C09K 2211/1029; H01L 27/32; H01L 51/0032; H01L 51/005; H01L 21/0052; H01L 51/0058; H01L 51/006; H01L 51/0061; H01L 51/0067; H01L 51/0072; H01L 51/0073; H01L 51/0074; H01L 51/50; H01L 51/5012; H01L 51/5016; H01L 51/5056; H01L 51/5064; H01L 51/508; H01L 2251/308
USPC ..... 428/690, 691, 917, 411.4, 336; 427/586, 427/66; 313/500–512; 257/40, 88–104, 257/E51.001–E51.052; 252/301.16–301.35
See application file for complete search history.

(56) References Cited

U.S. PATENT DOCUMENTS

2007/0015007 A1 1/2007 Shin et al.
2011/0288295 A1* 11/2011 Aihara ................ C07D 401/14 544/180

(Continued)

FOREIGN PATENT DOCUMENTS

CN 102558121 A 7/2012
JP 2008-127326 A 6/2008

(Continued)

OTHER PUBLICATIONS

Machine translation of JP2009-021336. (Year: 2009).*

(Continued)

*Primary Examiner* — Andrew K Bohaty
(74) *Attorney, Agent, or Firm* — Lee IP Law, PC

(57) ABSTRACT

An organic optoelectronic device and a display device including the same, the organic optoelectronic device including: an anode and a cathode facing each other; a light-emitting layer positioned between the anode and the cathode; a hole transport layer positioned between the anode and the light-emitting layer; an auxiliary hole transport layer positioned between the hole transport layer and the light-emitting layer; an electron transport layer positioned between the cathode and the light-emitting layer; and an auxiliary electron transport layer positioned between the electron transport layer and the light-emitting layer, wherein the auxiliary electron transport layer includes at least one kind of first compound represented by chemical formula 1, and the auxiliary hole transport layer includes at least one kind of second compound represented by a combination of a moiety represented by chemical formula 2, a moiety represented by chemical formula 3 and a moiety represented by chemical formula 4.

10 Claims, 2 Drawing Sheets

(51) Int. Cl.

| | |
|---|---|
| ***C09K 11/06*** | (2006.01) |
| ***H01L 51/50*** | (2006.01) |
| ***H01L 27/32*** | (2006.01) |
| ***H05B 33/20*** | (2006.01) |
| ***C07D 213/06*** | (2006.01) |
| ***C07D 213/16*** | (2006.01) |
| ***C07D 251/24*** | (2006.01) |
| ***C07D 307/77*** | (2006.01) |
| ***C07D 333/50*** | (2006.01) |
| ***C07D 409/12*** | (2006.01) |

(56) References Cited

U.S. PATENT DOCUMENTS

| | | | | |
|---|---|---|---|---|
| 2012/0112174 | A1* | 5/2012 | Lee ...................... | C07D 307/93 257/40 |
| 2014/0034938 | A1* | 2/2014 | Ishibashi .............. | C07D 239/26 257/40 |

FOREIGN PATENT DOCUMENTS

| | | | | | |
|---|---|---|---|---|---|
| JP | 2009021336 | A | * | 1/2009 | |
| KR | 10-2000-0064244 | A | | 11/2000 | |
| KR | 10-2004-0057862 | A | | 7/2004 | |
| KR | 10-2007-0009074 | A | | 1/2007 | |
| KR | 10-2009-0105072 | A | | 10/2009 | |
| KR | 10-2012-0047706 | A | | 5/2012 | |
| KR | 10-2014-0087883 | A | | 7/2014 | |
| WO | WO 2006/073059 | A1 | | 7/2006 | |
| WO | WO 2010/083872 | A2 | | 7/2010 | |
| WO | WO 2010/136109 | A1 | | 12/2010 | |
| WO | WO-2012137958 | A1 | * | 10/2012 | ........... C07D 405/14 |

OTHER PUBLICATIONS

Chinese Office Action dated Oct. 31, 2018, and the accompanying Search Report dated Oct. 19, 2018, of the corresponding Chinese Patent Application No. 201580056578.1.
International Search Report for PCT/KR2015/006585 dated Jul. 21, 2015.

* cited by examiner

ORGANIC OPTOELECTRONIC DEVICE AND DISPLAY DEVICE

CROSS-REFERENCE TO RELATED APPLICATION

This application is a continuation of pending International Application No. PCT/KR2015/006585, entitled "Organic Optoelectronic Device and Display Device," which was filed on Jun. 26, 2015, the entire contents of which are hereby incorporated by reference.

Korean Patent Application No. 10-2014-0150590, filed on Oct. 31, 2014, in the Korean Intellectual Property Office, and entitled: "Organic Optoelectronic Device and Display Device," is incorporated by reference herein in its entirety.

BACKGROUND (a) Field of the Invention

An organic optoelectronic device and a display device are disclosed.

(b) Description of the Related Art

An organic optoelectronic device (organic optoelectric diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and has a structure in which an organic layer is interposed between an anode and a cathode.

A blue organic light emitting diode having a long life-span is considered to be one of the critical factors for realizing a long life-span full color display. Accordingly, development of a blue organic light emitting diode having a long life-span is being actively researched. In order to solve this problem, a blue organic light emitting diode having a long life-span is provided in this invention.

SUMMARY

An embodiment provides an organic optoelectronic device capable of realizing high efficiency characteristics.

Another embodiment provides a display device including the organic optoelectronic device.

According to an embodiment, an organic optoelectronic device includes an anode and a cathode facing each other, a light-emitting layer positioned between the anode and the cathode, a hole transport layer positioned between the anode and the light-emitting layer, a auxiliary hole transport layer positioned between the hole transport layer and the light-emitting layer, an electron transport layer positioned between the cathode and the light-emitting layer and an auxiliary electron transport layer positioned between the electron transport layer and the light-emitting layer, wherein the auxiliary electron transport layer includes at least one kind of a first compound represented by Chemical Formula 1 and the auxiliary hole transport layer includes at least one kind of a second compound represented by a combination of a moiety represented by Chemical Formula 2, a moiety represented by Chemical Formula 3, and a moiety represented by Chemical Formula 4.

[Chemical Formula 1]

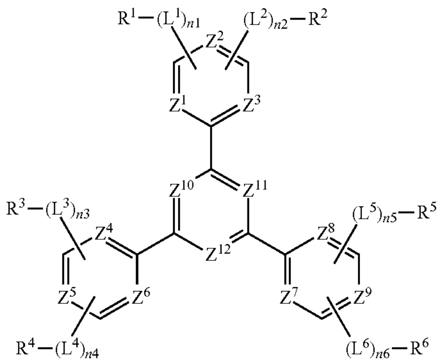

In Chemical Formula 1, $Z^1$ to $Z^{12}$ are independently N, C, or $CR^a$, at least one of $Z^1$ to $Z^{12}$ is N, $R^1$ to $R^6$ and $R^a$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, $L^1$ to $L^6$ are independently a single bond, a substituted or unsubstituted C6 to C30 arylene group, a substituted or unsubstituted heteroarylene group, or a combination thereof, and n1 to n6 are independently an integer ranging from 0 to 5,

[Chemical Formula 2]

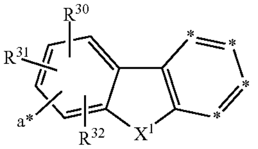

[Chemical Formula 3]

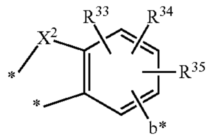

[Chemical Formula 4]

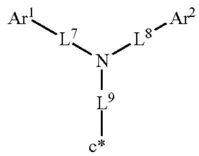

wherein, in Chemical Formulas 2 to 4, $X^1$ and $X^2$ are independently O, S, or $CR^cR^d$, $R^{30}$ to $R^{35}$, $R^c$, and $R^d$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof or a linking point with c* of Chemical Formula 5, Ar1 and Ar2 are independently a substituted or unsubstituted C6 to C30 aryl group or a substituted or unsubstituted C2 to C30 heteroaryl group, $L^7$ to $L^9$ are independently a single bond, a substituted or unsubstituted C6 to C30 arylene group, a substituted or unsubstituted heteroarylene group, or a combination thereof, adjacent two *'s of Chemical Formula 3 are bound to two *'s of Chemical Formula 4 to form a fused ring, one of a*, b*, and $R^{30}$ to $R^{35}$ of above Chemical Formula 3 or 4 is linked with c* of Chemical Formula 5 by a sigma bond, and a*, b*, and $R^{30}$ to $R^{35}$ that are not linked with c* of Chemical Formula 5 are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof.

wherein, "substituted" refers to replacement of at least one hydrogen by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group)

According to another embodiment, a display device including the organic optoelectronic device is provided.

An organic optoelectronic device having high efficiency may be realized.

DETAILED DESCRIPTION

Figure 1:
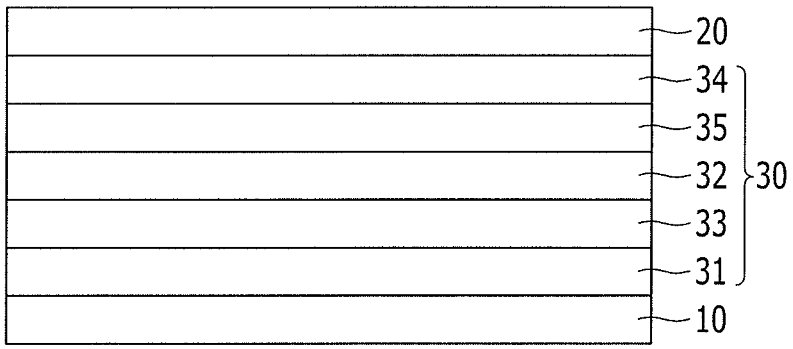
FIGS. 1 and 2 are schematic cross-sectional views of organic optoelectronic devices according to an embodiment.

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group such as a trifluoromethyl group, or a cyano group.

In addition, two adjacent substituents of the substituted halogen, a hydroxy group, an amino group, a substituted or unsubstituted C1 to C20 amine group, a nitro group, a substituted or unsubstituted C3 to C40 silyl group, C1 to C30 alkyl group, C1 to C10 alkylsilyl group, C3 to C30 cycloalkyl group, C2 to C30 heterocycloalkyl group, C6 to C30 aryl group, C2 to C30 heteroaryl group, C1 to C20 alkoxy group, a fluoro group, C1 to C10 trifluoroalkyl group such as trifluoromethyl group, or cyano group may be fused with each other to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including one to three heteroatoms selected from the group consisting of N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a substituent including all element of the cycle having p-orbitals which form conjugation, and may be monocyclic, polycyclic or fused ring polycyclic (i.e., rings sharing adjacent pairs of carbon atoms) functional group.

In the present specification, "heteroaryl group" may refer to an aryl group including one to three heteroatoms selected from N, O, S, P, and Si and remaining carbon. When the heteroaryl group is a fused ring, each ring may include one to three heteroatoms.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazolyl group, or a combination thereof, but are not limited thereto.

In the present specification, hole characteristics refer to an ability to donate an electron to form a hole when an electric field is applied, and that a hole formed in the anode may be easily injected into the light-emitting layer, and a hole formed in a light-emitting layer may be easily transported into an anode and transported in the light-emitting layer due to conductive characteristics according to a highest occupied molecular orbital (HOMO) level.

In addition, electron characteristics refers to an ability to accept an electron when an electric field is applied, and that an electron formed in a cathode may be easily injected into the light-emitting layer (LUMO) level, and an electron formed in a light-emitting layer may be easily transported into a cathode and transported in the light-emitting layer due to conductive characteristics according to a lowest unoccupied molecular orbital (LUMO) level.

Hereinafter, an organic optoelectronic device according to an embodiment is described.

The organic optoelectronic device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectronic device is described, but the present invention can be applied to other organic optoelectronic devices in the same way.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Figure 2:
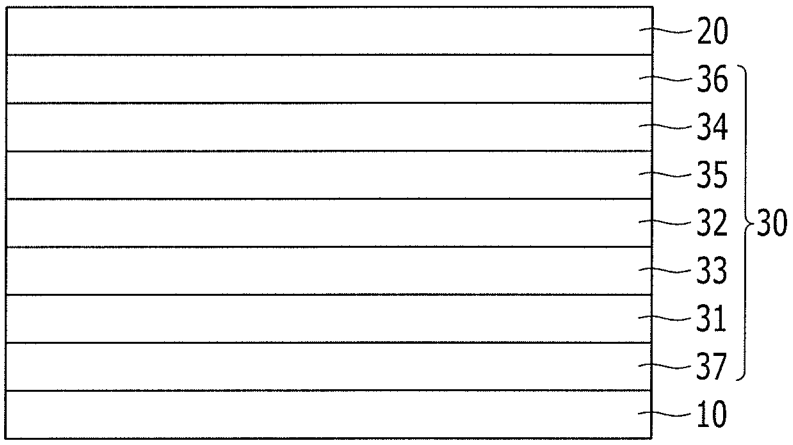

FIGS. 1 and 2 are schematic cross-sectional views of an organic optoelectronic device according to an embodiment.

Referring to FIG. 1, an organic optoelectronic device according to an embodiment includes an anode 10 and a cathode 20 facing each other and an organic layer 30 between the anode 10 and the cathode 20.

The anode 10 may be made of a conductor having a large work function to help hole injection, and may be for example a metal, a metal oxide, and/or a conductive polymer. The anode 10 may be, for example a metal such as nickel, platinum, vanadium, chromium, copper, zinc, and gold or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy) thiophene) (PEDT), polypyrrole, and polyaniline, but is not limited thereto.

The cathode 20 may be made of a conductor having a small work function to help electron injection, and may be for example a metal, a metal oxide, and/or a conductive polymer. The cathode 20 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al, and $BaF_2$/Ca, but is not limited thereto.

The organic layer 30 includes a hole transport layer 31, a light-emitting layer 32, and an auxiliary hole transport layer 33 between the hole transport layer 31 and the light-emitting layer 32.

In addition, the organic layer 30 includes an electron transport layer 34 and an auxiliary electron transport layer 35 between the electron transport layer 34 and the light-emitting layer 32.

Referring to FIG. 2, the organic layer 30 may further include a hole injection layer 37 between the hole transport layer 31 and the anode 10, and an electron injection layer 36 between the electron transport layer 34 and the cathode 20.

The hole injection layer 37 between the hole transport layer 31 and the anode 10 the improves interface characteristics an organic material used as the hole transport layer 31 and ITO used as the anode 10 and is coated on the ITO to smooth uneven upper surface of ITO. For example, the hole injection layer 37 may be selected from materials having a median value between work functions of the ITO and HOMO of the hole transport layer 31 to adjust a difference between the work functions of the ITO and the HOMO of the hole transport layer 31 and particularly, materials having appropriate conductivity. The materials forming the hole injection layer 37 of the present invention may be N4,N4'-diphenyl-N4,N4'-bis(9-phenyl-9H-carbazol-3-yl)biphenyl-4,4'-diamine, but is not limited thereto. A conventional material of the hole injection layer 37 may be also used together, for example, copper phthlalocyanine (CuPc), aromatic amines such as N,N'-dinaphthyl-N,N'-phenyl-(1,1'-biphenyl)-4,4'-diamine (NPD), 4,4',4"-tris[methylphenyl (phenyl)amino]triphenyl amine (m-MTDATA), 4,4',4"-tris [1-naphthyl(phenyl)amino]triphenyl amine (1-TNATA), 4,4',4"-tris[2-naphthyl(phenyl)amino]triphenyl amine (2-TNATA), 1,3,5-tris[N-(4-diphenylaminophenyl)phenylamino]benzene (p-DPA-TDAB), a compound such 4,4'-bis[N-[4-{N,N-bis(3-methylphenyl)amino}phenyl]-N-phenylamino]biphenyl (DNTPD), hexaazatriphenylene-hexacarbonitirile (HAT-CN), and the like, a conductive polymer such as a polythiophene derivative of poly(3,4-ethylenedioxythiophene)-poly(styrnesulfonate) (PEDOT). The hole injection layer 37 may be coated with a thickness, for example of 10 to 300 Å on ITO used as an anode.

The electron injection layer 36 is disposed on the electron transport layer and thus, facilitates injection of electrons from a cathode and ultimately improves power efficiency and may, for example, include LiF, Liq, NaCl, CsF, $Li_2O$, BaO, and the like, which are conventionally used in a related art.

The hole transport layer 31 is a layer that makes hole transport from the anode 10 into the light-emitting layer 32, and may include, for example an amine compound but is not limited thereto.

The amine compound may include, for example at least one aryl group and/or heteroaryl group. The amine compound may be represented by, for example Chemical Formula a or b, but is not limited thereto.

[Chemical Formula a]

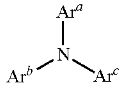

-continued

[Chemical Formula b]

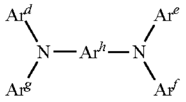

In Chemical Formula a or b, $Ar^a$ to $Ar^g$ are independently hydrogen, deuterium, a substituted or unsubstituted C1 to C20 alkyl group, a substituted or unsubstituted C6 to C30 aryl group, a substituted or unsubstituted C2 to C30 heteroaryl group, or a combination thereof, at least one of $Ar^a$ to $Ar^c$ and at least one of $Ar^d$ to $Ar^g$ are a substituted or unsubstituted C6 to C30 aryl group, a substituted or unsubstituted C2 to C30 heteroaryl group, or a combination thereof, and $Ar^h$ is a single bond, a substituted or unsubstituted C1 to C20 alkylene group, a substituted or unsubstituted C6 to C30 arylene group, a substituted or unsubstituted C2 to C30 heteroarylene group, or a combination thereof.

The electron transport layer 34 is a layer that makes electron transport from the cathode 20 into the light-emitting layer 32, and for example a material of the electron transport layer may be aluminum trihydroxyquinoline ($Alq_3$), 2-(4-biphenylyl)-5-phenyl-1,3,4-oxadiazole (PBD) that is a 1,3,4-oxadiazole derivative, 1,3,4-tris[(3-phenyl-6-trifluoromethyl)quinoxaline-2-yl]benzene (TPQ) that is a quinoxaline derivative, a triazole derivative, and a triazine derivative, but is not limited thereto.

The light-emitting layer 32 is an organic layer emitting light and includes a host and a dopant when a doping system is adopted. Herein, the host mainly promotes a recombination of electrons and holes and holds excitons in a light-emitting layer, while the dopant efficiently emits light from the excitons obtained from the recombination.

The light-emitting layer may include a known host and dopant.

The known host may be, for example, Alq3, CBP (4,4'-N,N'-dicarbazole-biphenyl), PVK (poly(n-vinylcarbazole)), 9,10-di(naphthalen-2-yl)anthracene (ADN), TCTA, TPBI (1,3,5-tris(N-phenylbenzimidazol-2-yl)benzene), TBADN (3-tert-butyl-9,10-di(naphth-2-yl)anthracene), mCP, OXD-7, and the like, but is not limited thereto.

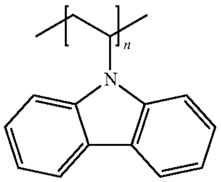

PVK

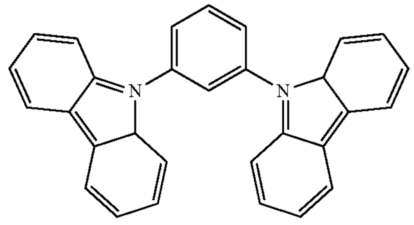

mCP

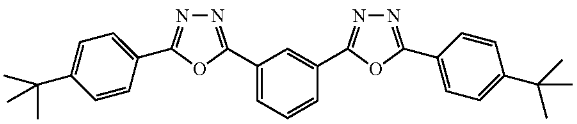

OXD-7

The dopant may be at least one of a fluorescent dopant and a phosphorescent dopant. The phosphorescent dopant may be an organometal complex including Ir, Pt, Os, Re, Ti, Zr, Hf, or a combination of two or more, but is not limited thereto.

Examples of known blue dopants may be $F_2$Irpic, $(F_2ppy)_2Ir(tmd)$, $Ir(dfppz)_3$, ter-fluorene(fluorene), 4,4'-bis(4-diphenylaminostyryl)biphenyl (DPAVBi), 2,5,8,11-tetra-tert-butyl perylene (TBPe), DPVBi, a pyrene derivative (KR0525408, LG Electronics Inc.), and the like, but are not limited thereto.

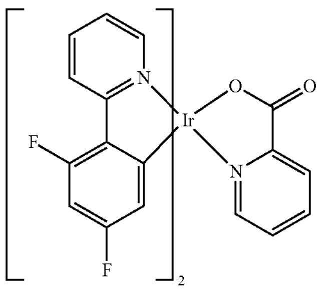

$F_2$Irpic

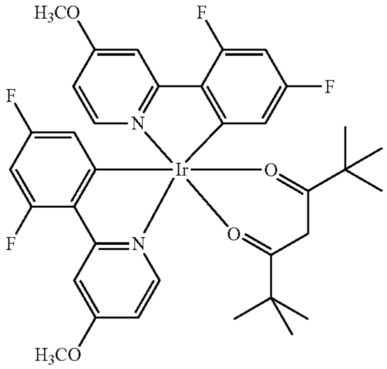

$(F_2ppy)_2Ir(tmd)$

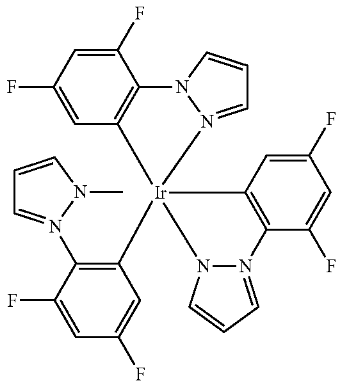

$Ir(dfppz)_3$

-continued
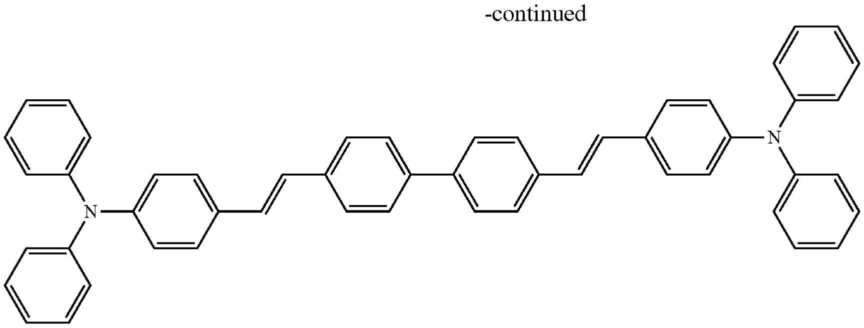
DPAVBi
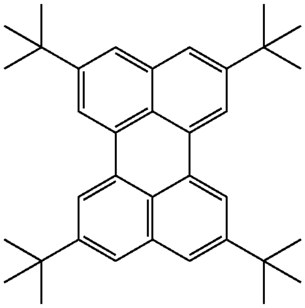
TBPe
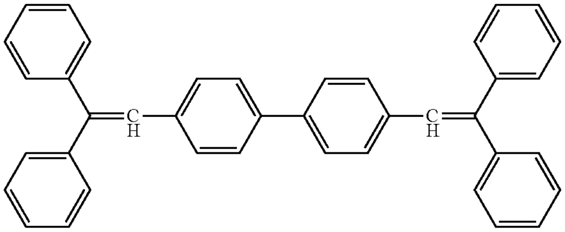
DPVBi
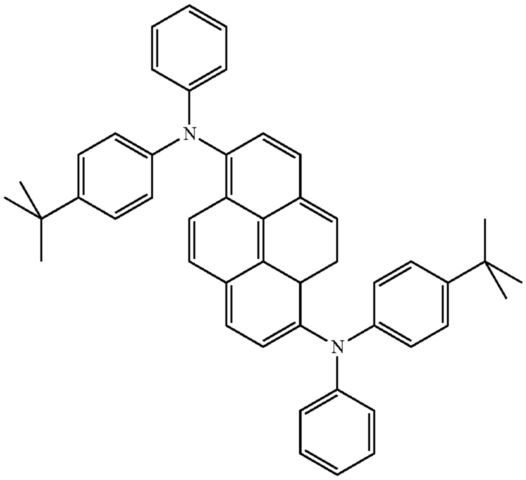
Examples of known red dopants may include, PtOEP, $Ir(piq)_3$, BtpIr, and the like, but are not limited thereto.
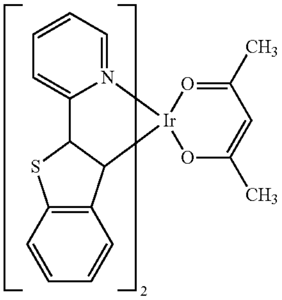
BtpIr
-continued
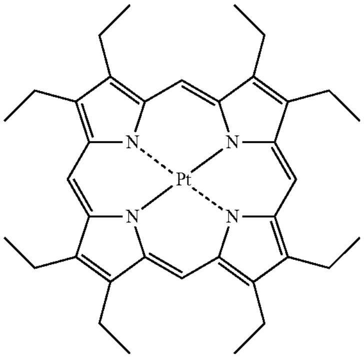
PtOEP -continued

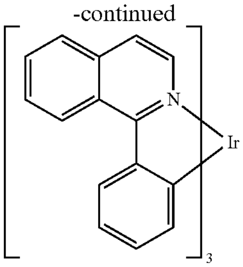

$Ir(piq)_3$

Examples of known green dopant may be $Ir(ppy)_3$ (ppy=phenylpyridine), $Ir(ppy)_2(acac)$, $Ir(mpyp)_3$, and the like, but are not limited thereto.

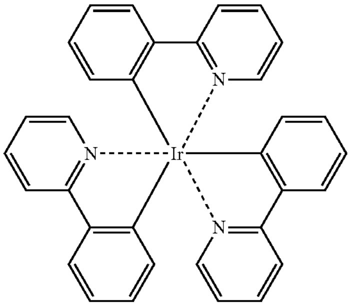

$Ir(ppy)_3$

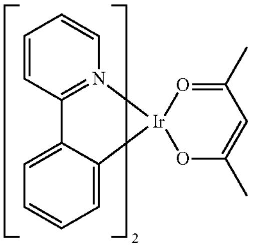

$Ir(ppy)_2(acac)$

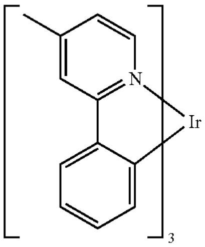

$Ir(mpyp)_3$

When the light-emitting layer includes hosts and dopants, an amount of the dopants may be generally about 0.01 to about 15 wt % based on 100 wt % of the light-emitting layer, without limitation.

The light-emitting layer may have a thickness of about 200 Å to about 700 Å.

The auxiliary electron transport layer 35 includes at least one kind of a first compound represented by Chemical Formula 1.

[Chemical Formula 1]

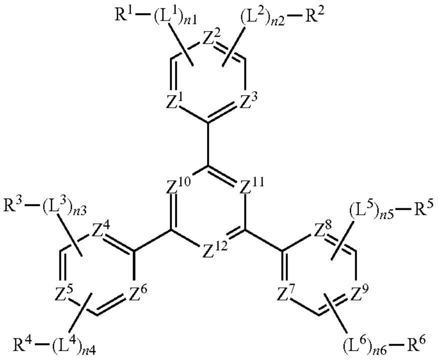

In Chemical Formula 1, $Z^1$ to $Z^{12}$ are independently N, C, or $CR^a$, at least one of $Z^1$ to $Z^{12}$ is N, $R^1$ to $R^6$ and $R^a$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, $L^1$ to $L^6$ are independently a single bond, a substituted or unsubstituted C6 to C30 arylene group, a substituted or unsubstituted heteroarylene group, or a combination thereof, and n1 to n6 are independently an integer ranging from 0 to 5.

The first compound may include a ring containing at least one nitrogen and thus has a structure easily accepting electrons when an electric field is applied thereto and accordingly, may increase the injection amount of electrons and may decrease a driving voltage when used to manufacture an organic optoelectronic device.

In one example of the present invention, n1 to n6 may independently may an integer ranging from 0 to 5, and $n1+n2+n3+n4+n5+n6\geq 1$, $n1+n2+n3+n4+n5+n6\geq 2$, $n1+n2+n3+n4+n5+n6\geq 3$, or $n1+n2+n3+n4+n5+n6\geq 4$. In addition, $n1+n2+n3+n4+n5+n6\leq 15$, $n1+n2+n3+n4+n5+n6\leq 12$, $n1+n2+n3+n4+n5+n6\leq 10$, $n1+n2+n3+n4+n5+n6\leq 8$, $n1+n2+n3+n4+n5+n6\leq 7$, or $n1+n2+n3+n4+n5+n6\leq 6$.

The first compound represented by Chemical Formula 1 has at least one of a kink structure in the center of an arylene group and/or a heteroarylene group.

For example, the first compound may be represented by Chemical Formula 1-I or Chemical Formula 1-II. The Chemical Formulas are examples but it is not limited to the following disclosure.

[Chemical Formula 1-I]

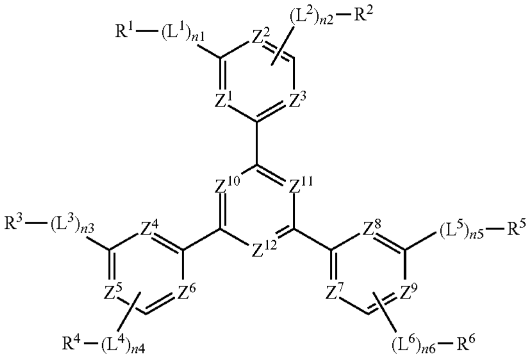

-continued

[Chemical Formula 1-I]

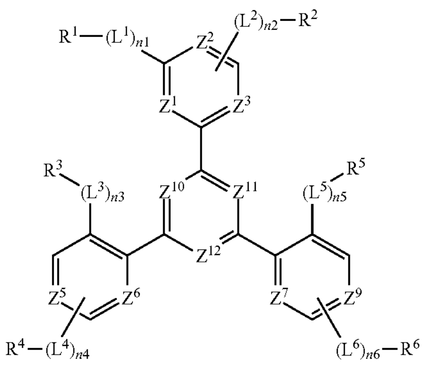

In Chemical Formulas 1-I and Chemical Formula 1-II, definitions of $Z^1$ to $Z^{12}$, $R^1$ to $R^6$, $L^1$ to $L^6$, and n1 to n6 are the same as described above.

The kink structure indicates a structure that arylene group and/or a heteroarylene group are not linked linearly at the linking point. For example, as for phenylene, ortho-phenylene (o-phenylene) and meta phenylene (m-phenylene) have the kink structure in which their linking point are not straight, while para phenylene (p-phenylene) has no kink structure.

$L^1$ to $L^6$ of the first compound may be specifically a single bond, a substituted or unsubstituted phenylene group, a substituted or unsubstituted biphenylene group, a substituted or unsubstituted terphenylene group, a substituted or unsubstituted quaterphenylene group, or a substituted or unsubstituted naphthalenylene group, and the like, and may be for example one of the following linking groups.

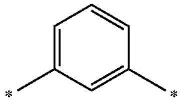

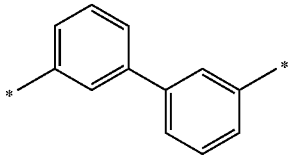

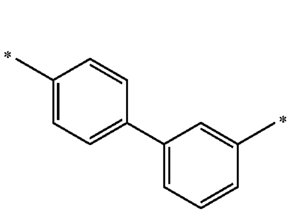

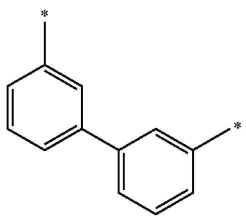

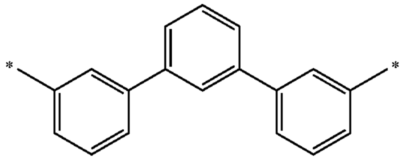

-continued

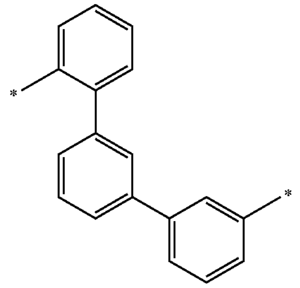

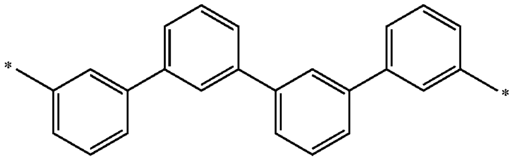

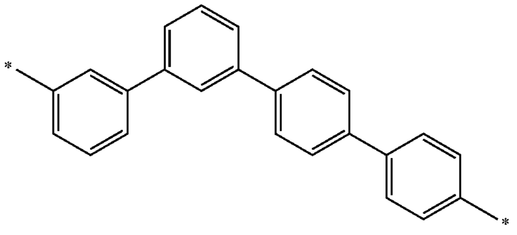

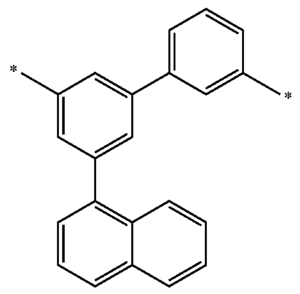

The first compound may be for example represented by at least one of Chemical Formula 1-III to Chemical Formula 1-IX, but is not limited thereto.

[Chemical Formula 1-III]

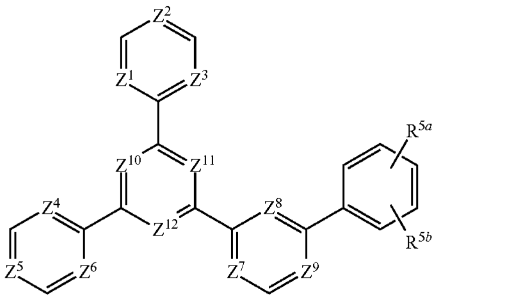

-continued

[Chemical Formula 1-IV]

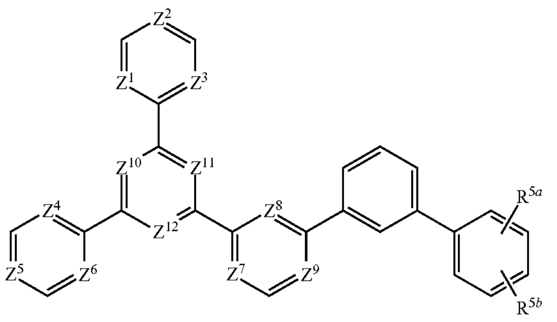

[Chemical Formula 1-V]

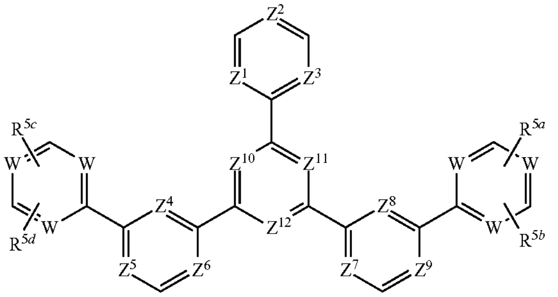

[Chemical Formula 1-VI]

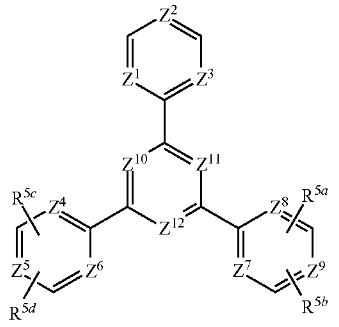

[Chemical Formula 1-VII]

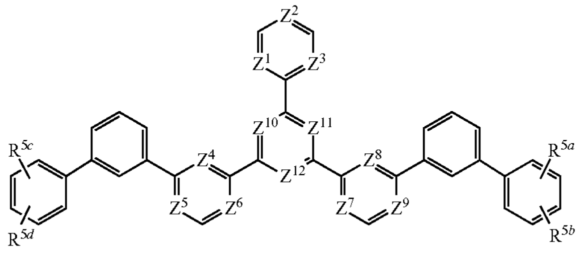

[Chemical Formula 1-VIII]

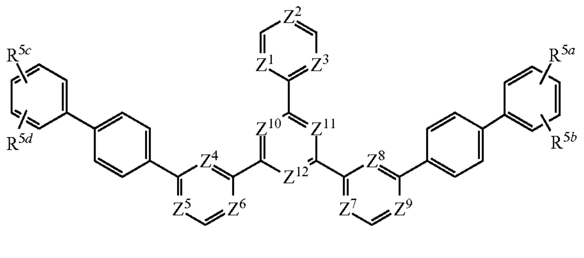

-continued

[Chemical Formula 1-IX]

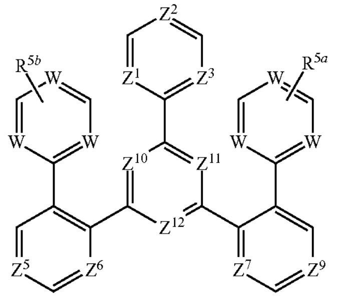

In Chemical Formulas 1-III to Chemical Formula 1-IX, $Z^1$ to $Z^{12}$ are the same as described above, W is independently N, C, or $CR^b$, $R^{5a}$ to $R^{5d}$ and $R^b$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof.

$R^{5a}$ to $R^{5d}$ are specifically hydrogen, deuterium, a substituted or unsubstituted phenyl group, a substituted or unsubstituted biphenyl group, a substituted or unsubstituted terphenyl group, a substituted or unsubstituted quaterphenyl group, a substituted or unsubstituted naphthalene group, a substituted or unsubstituted pyridine group, a substituted or unsubstituted pyrimidine group, a substituted or unsubstituted triazine group, a substituted or unsubstituted quinolinyl group, a substituted or unsubstituted isoquinolinyl group, a substituted or unsubstituted phenanthroline, or a substituted or unsubstituted quinazoline, and may be for example, one selected from substituted or unsubstituted groups of Group 1.

[Group 1]

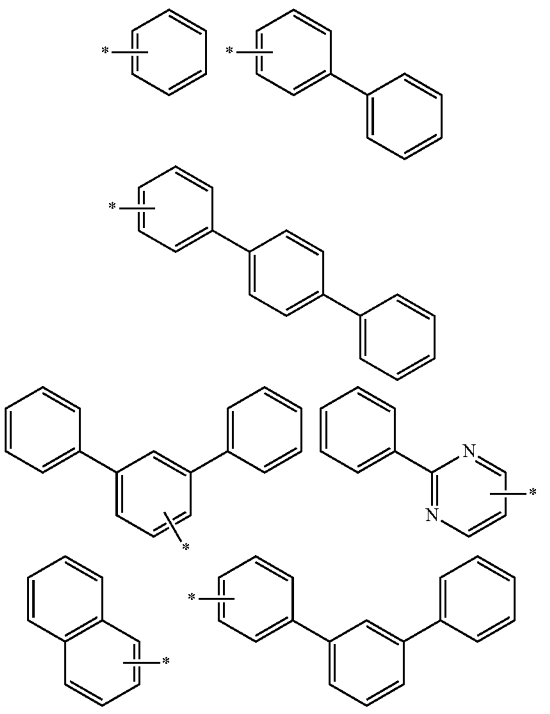

-continued
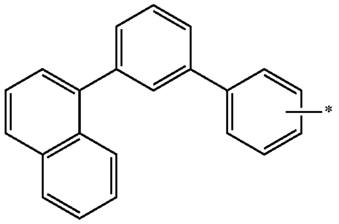
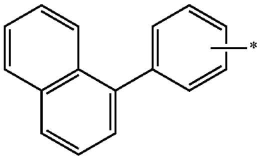
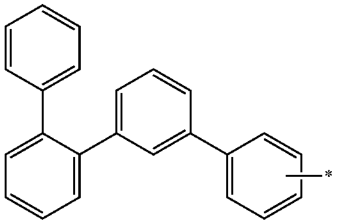
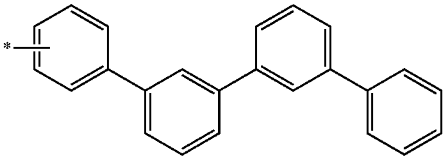
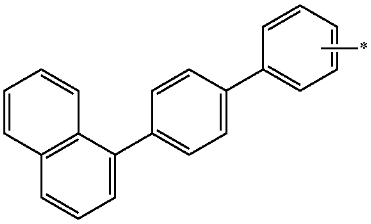
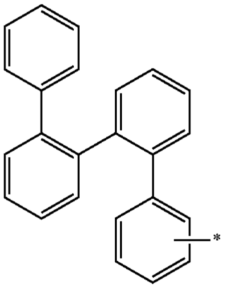
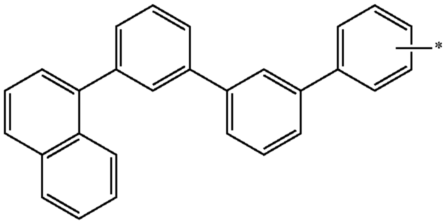
-continued
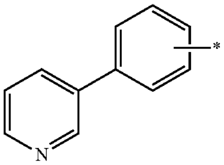
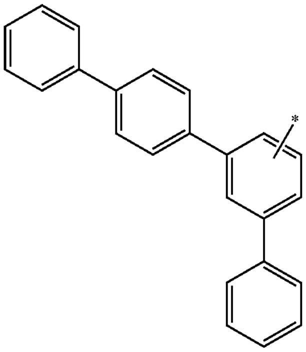
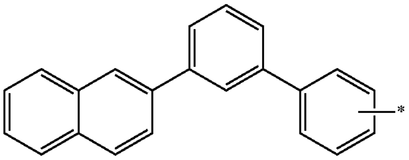
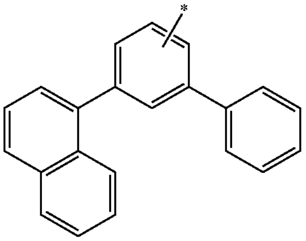
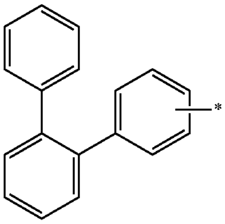
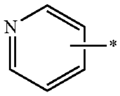
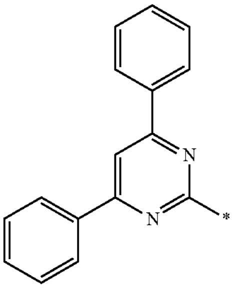
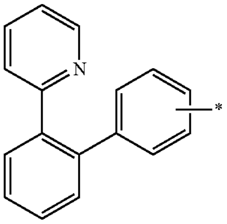
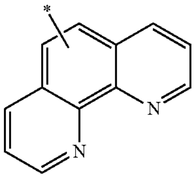
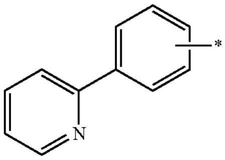
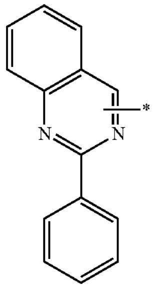
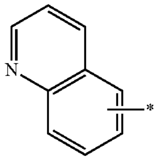

-continued

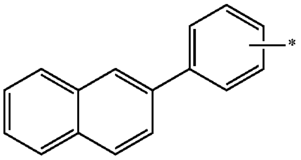

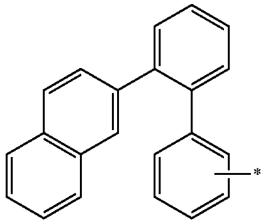

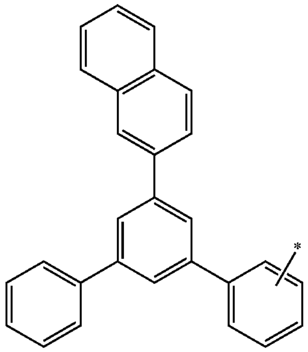

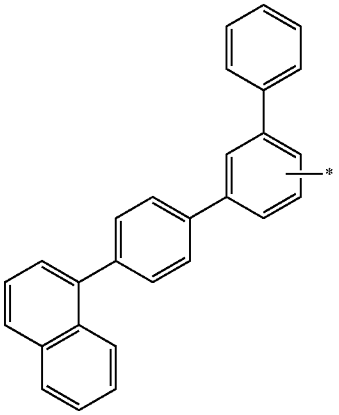

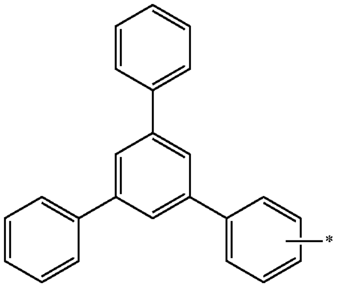

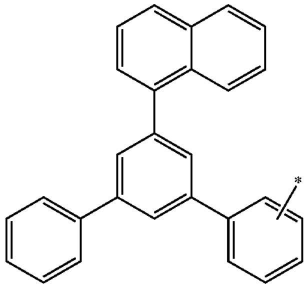

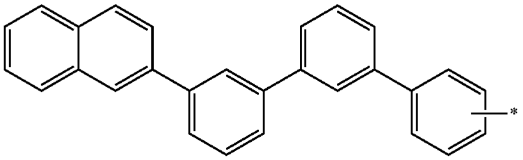

-continued

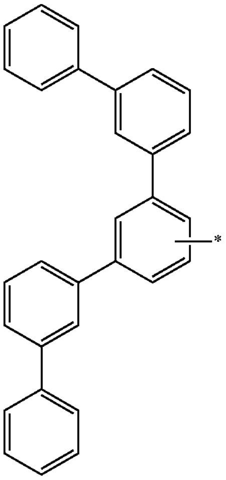

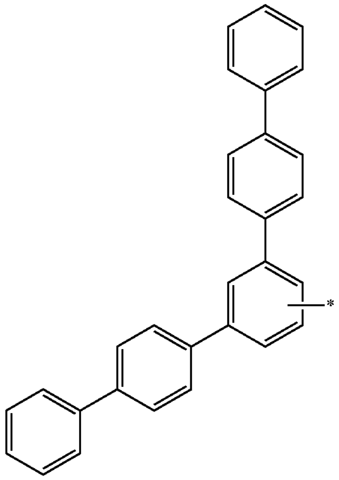

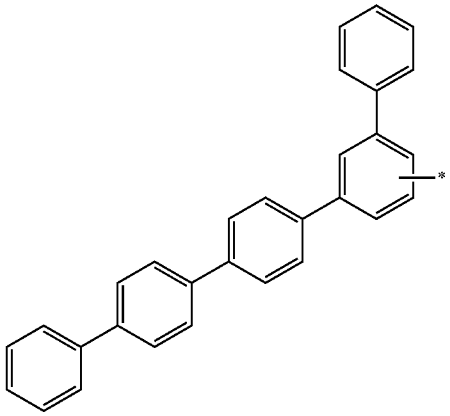

In Group 1, * is a linking point, wherein, "substituted" refers to replacement of at least one hydrogen by deuterium, a halogen, a C1 to C20 alkyl group, a C3 to C20 cycloalkyl group, a C1 to C20 alkoxy group, a C3 to C20 cycloalkoxy group, a C1 to C20 alkylthio group, a C6 to C30 aralkyl group, a C6 to C30 aryl group, a C6 to C30 aryloxy group, a C6 to C30 arylthio group, a C2 to C30 heteroaryl group, a C2 to C30 amino group, a C3 to C30 silyl group, a cyano group, a nitro group, a hydroxyl group, or a carboxyl group.

For example, the first compound may be represented by Chemical Formula 1-IV or Chemical Formula 1-VII.

The first compound may be for example compounds of Group 2, but is not limited thereto.

[Group 2]

[A-1]

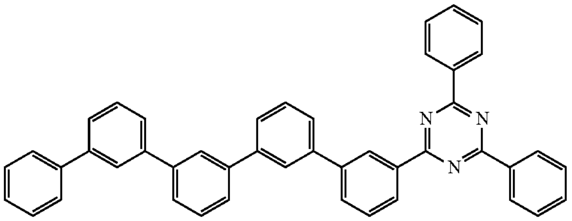

-continued
[A-2]
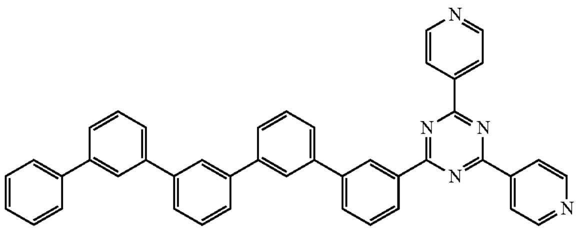
[A-3]
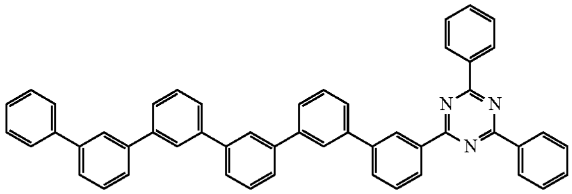
[A-4]
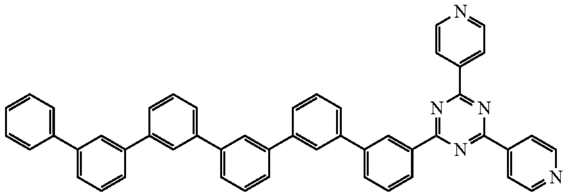
[A-5]
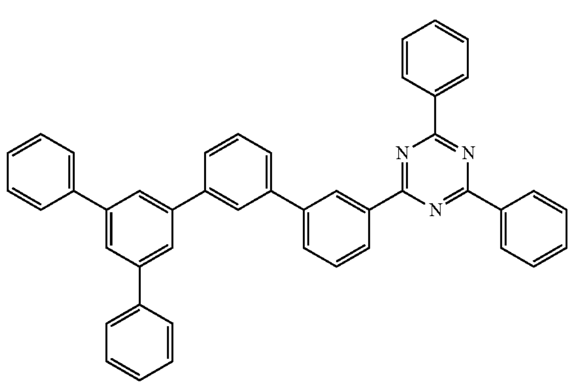
[A-6]
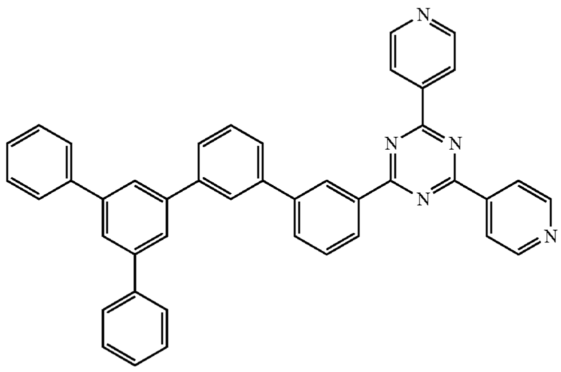
-continued
[A-7]
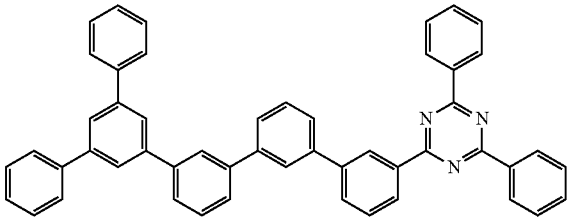
[A-8]
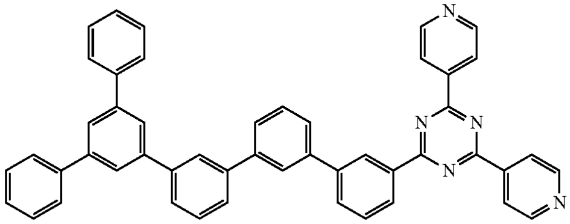
[A-9]
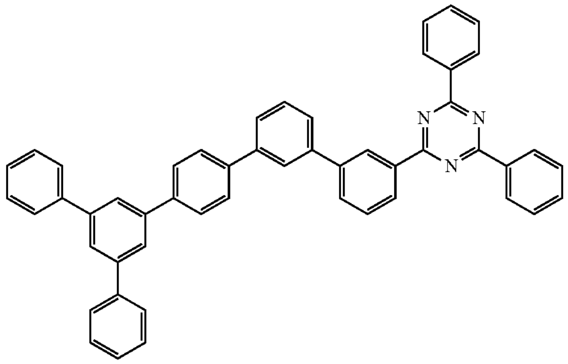
[A-10]
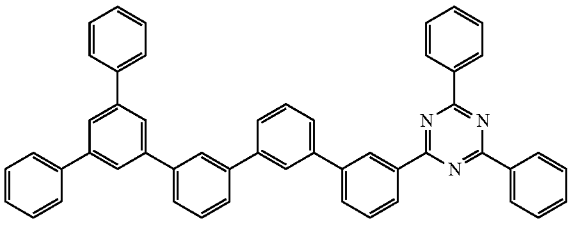
[A-11]
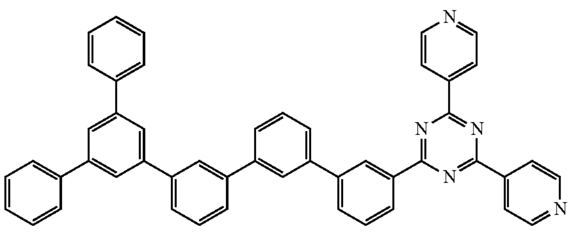

-continued
[A-12]
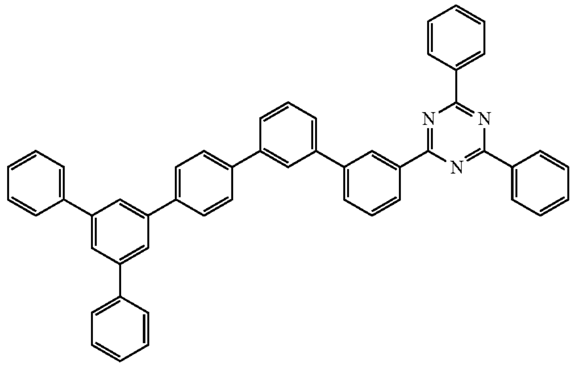
[A-13]
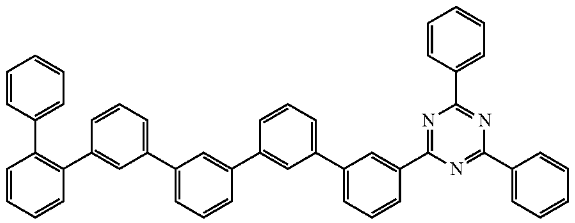
[A-14]
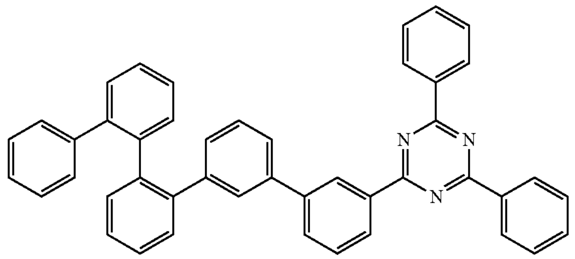
[A-15]
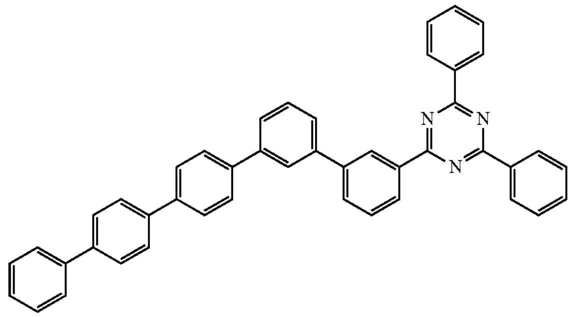
[A-16]
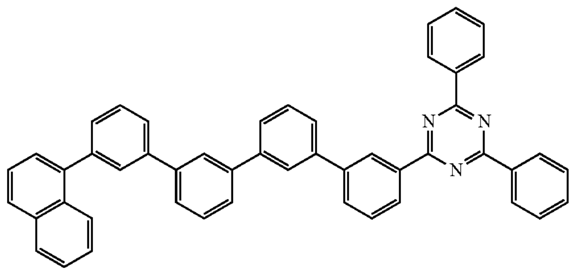
-continued
[A-17]
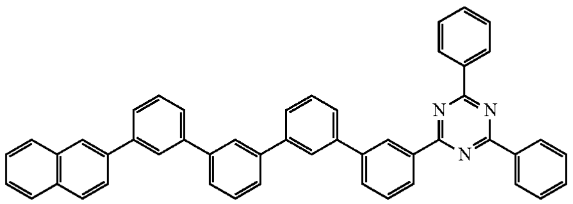
[A-18]
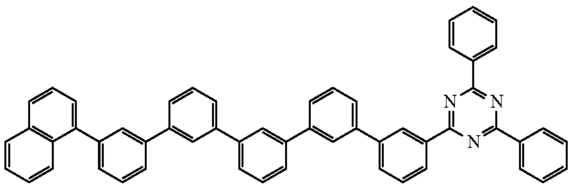
[A-19]
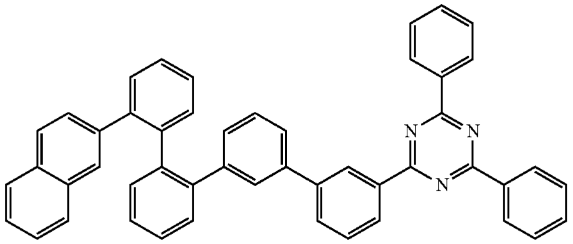
[A-20]
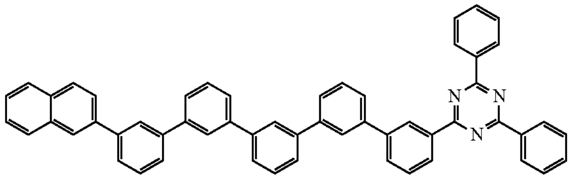
[A-21]
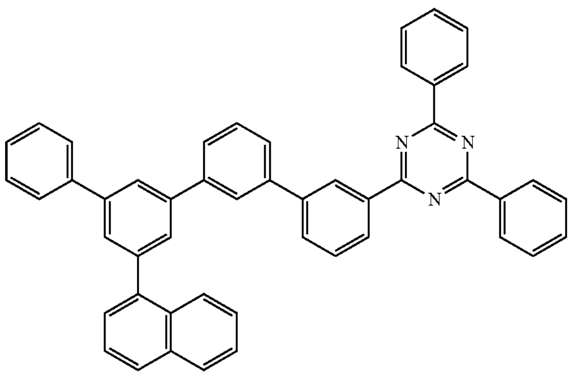
[A-22]
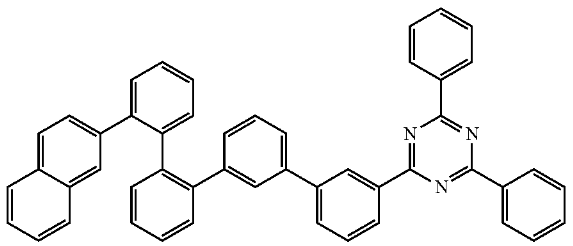

[A-23]
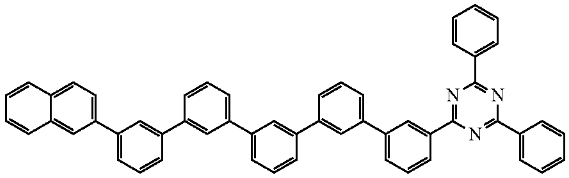
[A-24]
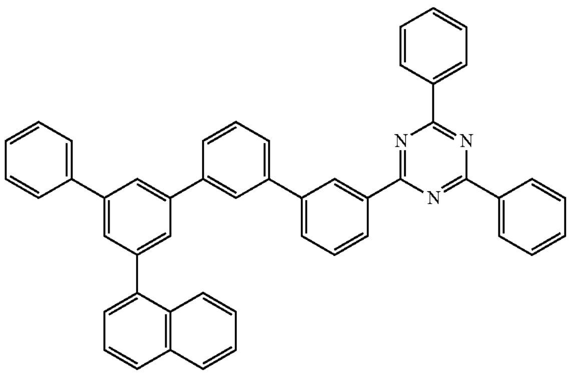
[A-25]
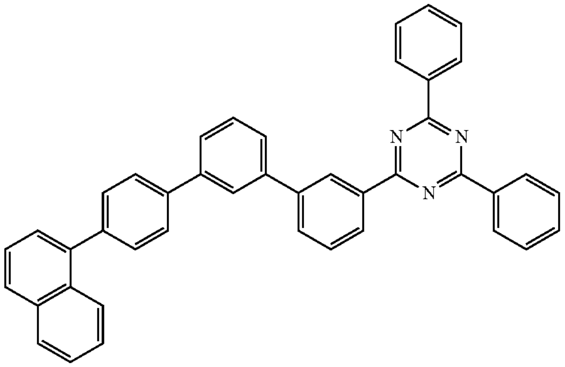
[A-26]
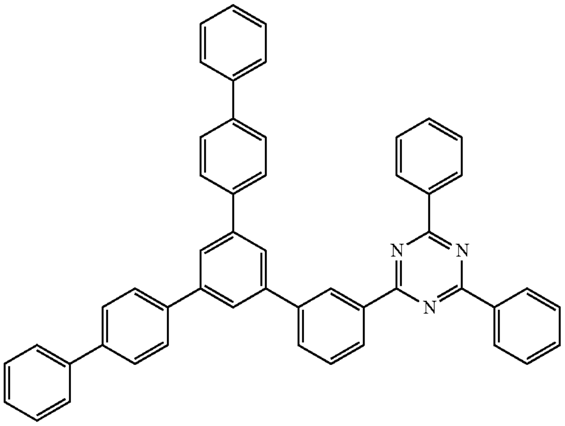
[A-27]
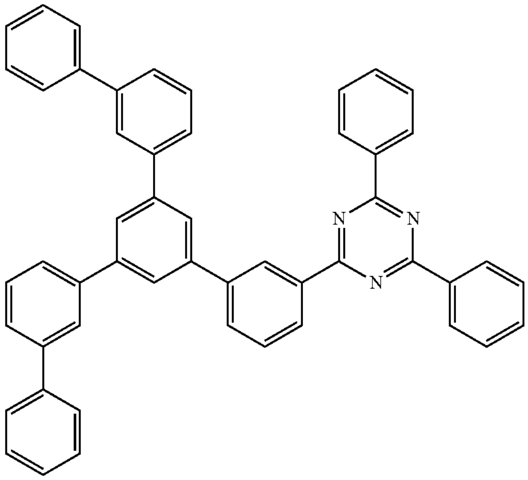
[A-28]
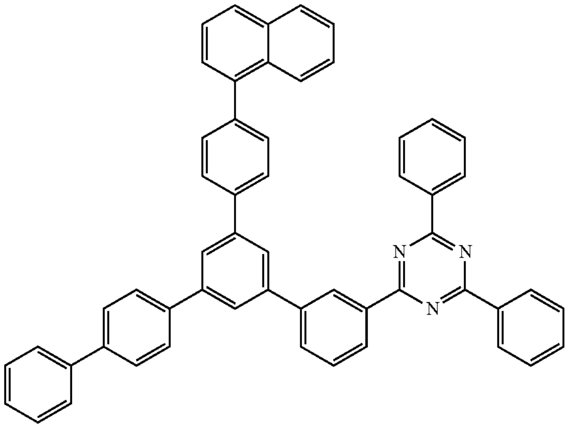
[A-29]
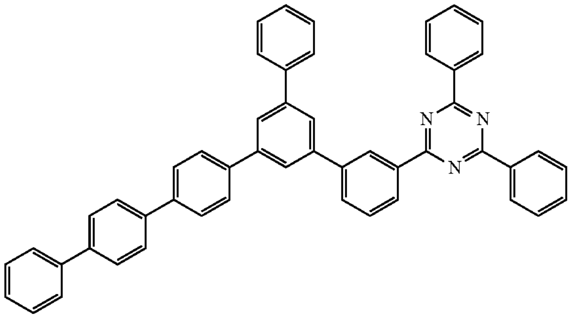

-continued
[A-30]
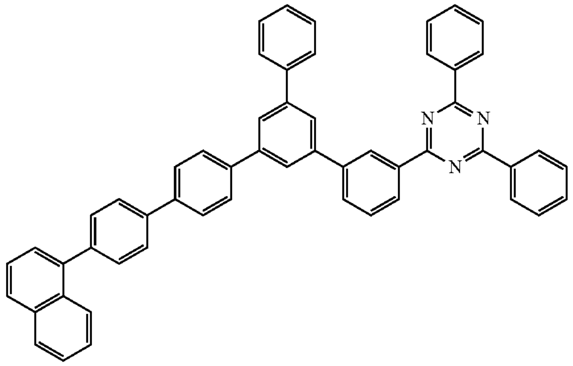
[A-31]
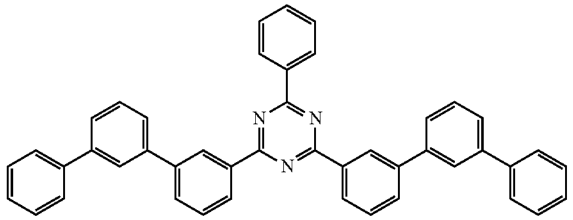
[A-32]
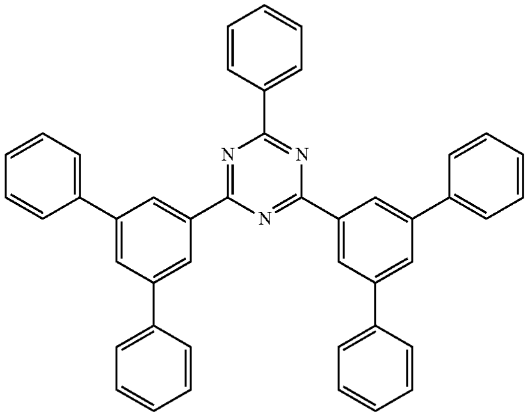
[A-33]
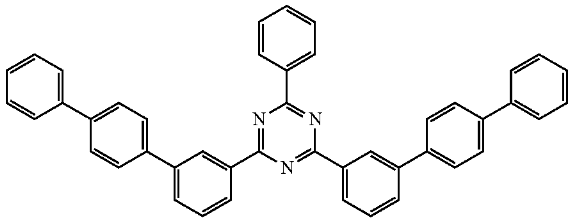
-continued
[A-34]
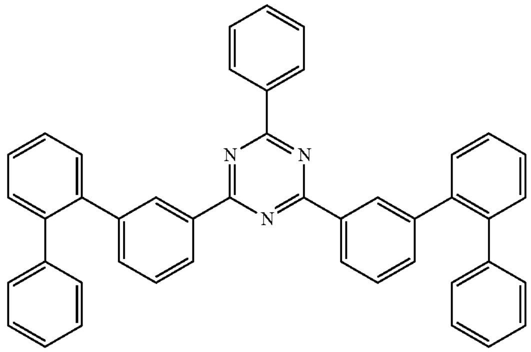
[A-35]
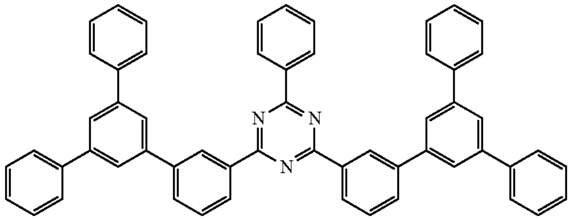
[A-36]
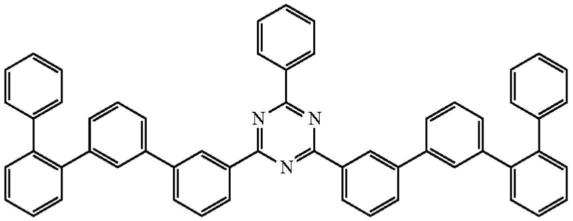
[A-37]
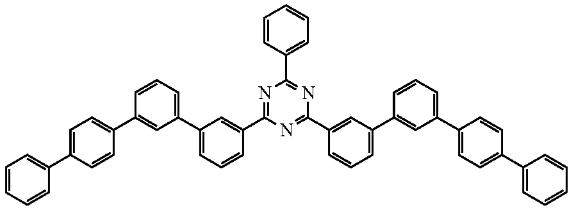
[A-38]
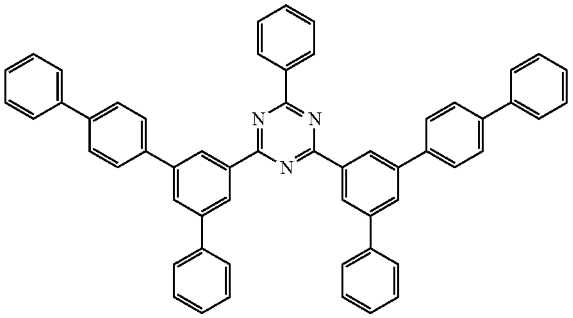

-continued
[A-39]
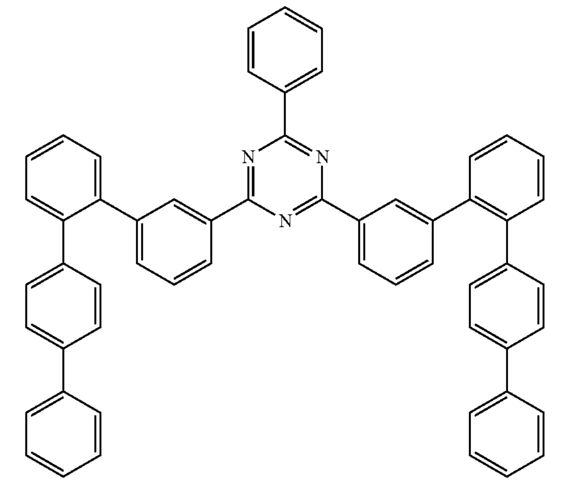
[A-40]
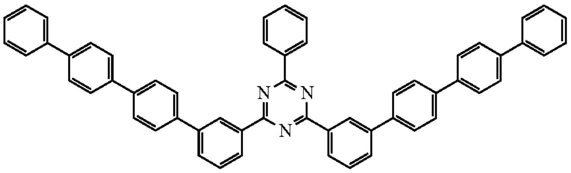
[A-41]
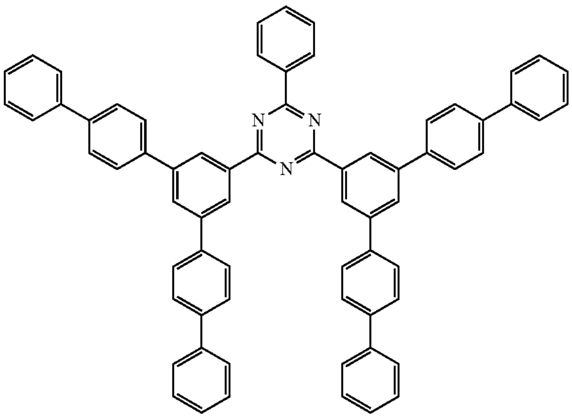
[A-42]
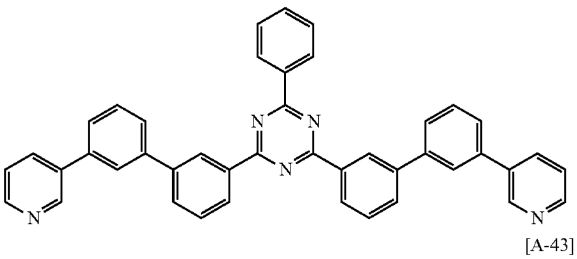
[A-43]
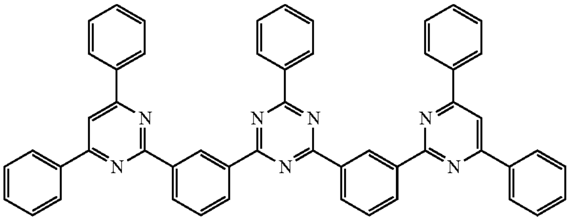
-continued
[A-44]
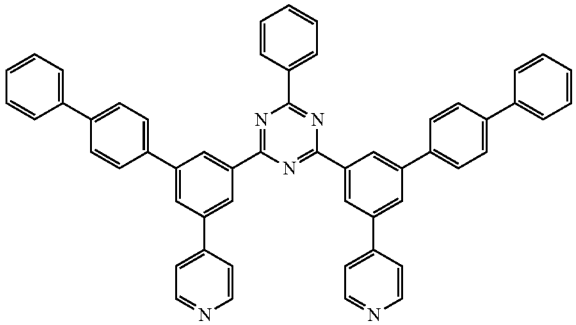
[A-45]
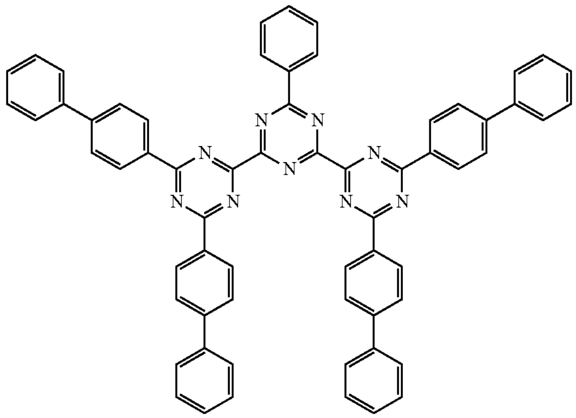
[A-46]
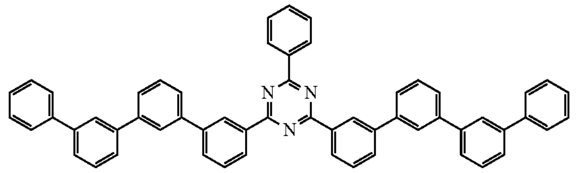
[A-47]
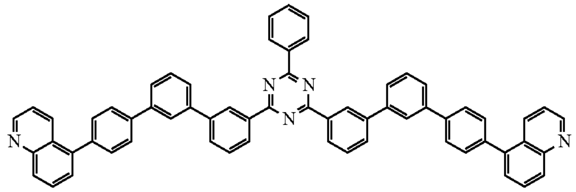
[A-48]
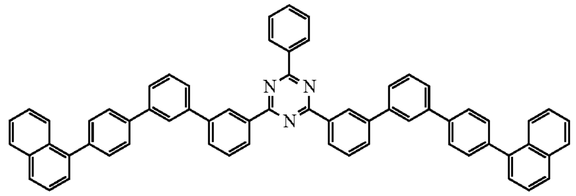

-continued
[A-49]
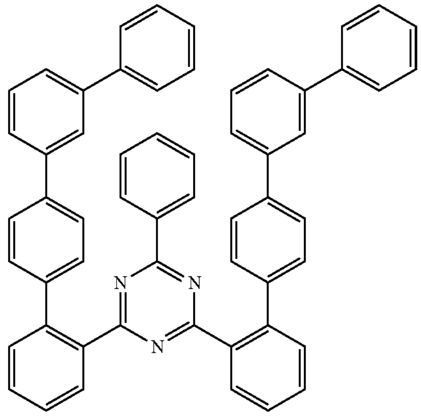
[A-50]
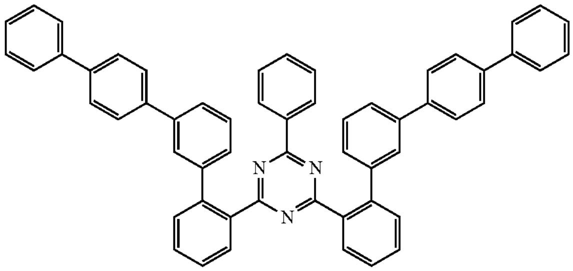
[A-51]
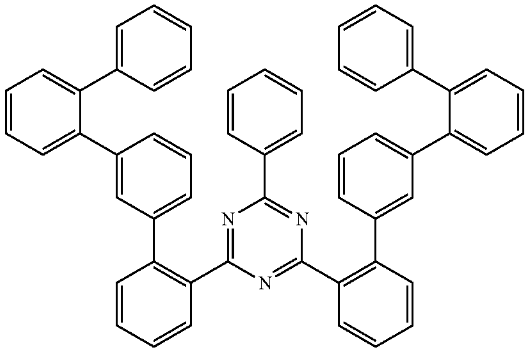
[A-52]
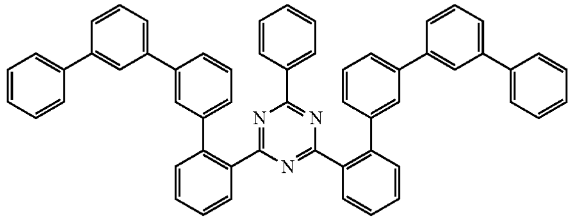
-continued
[A-53]
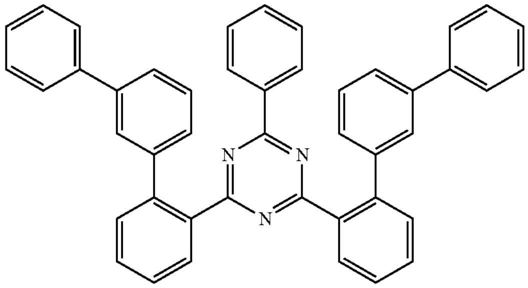
[A-54]
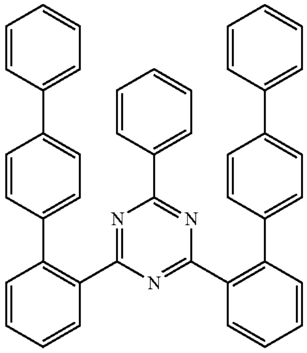
[A-55]
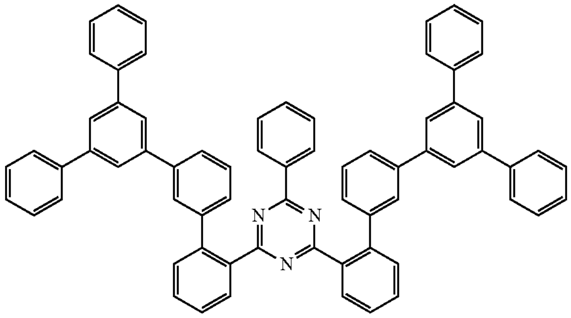
[A-56]
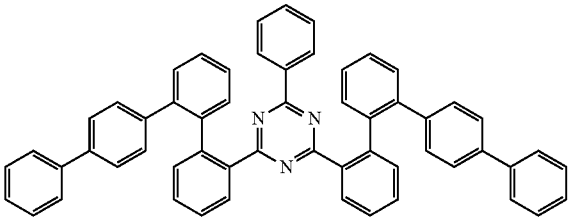
[A-57]
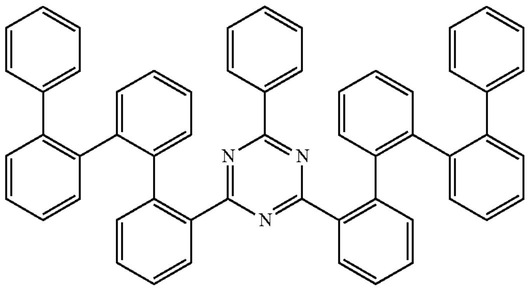

-continued
[A-58]
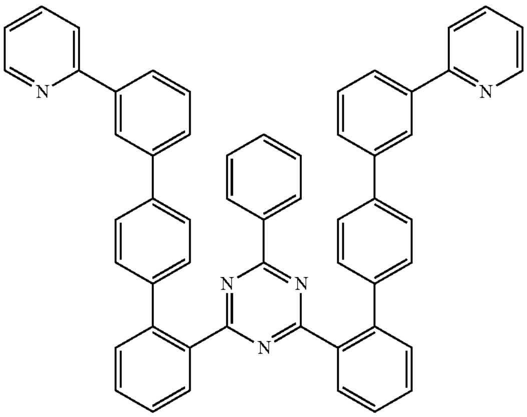
[A-59]
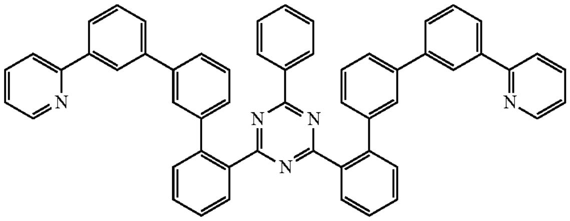
[A-60]
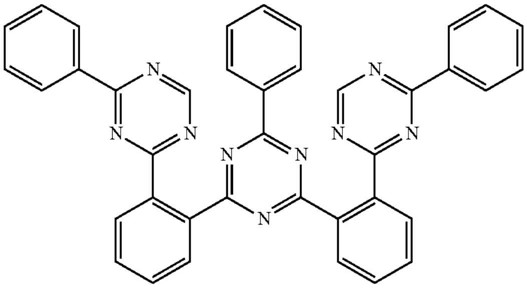
[A-61]
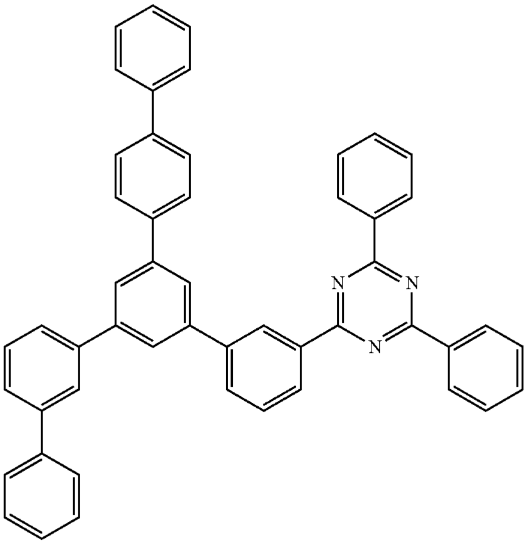
-continued
[A-62]
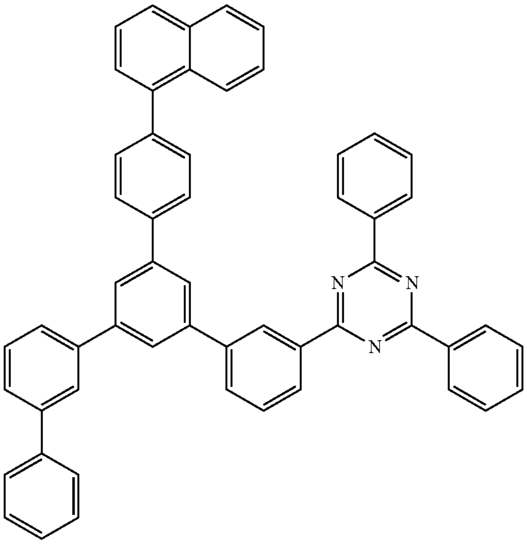
[A-63]
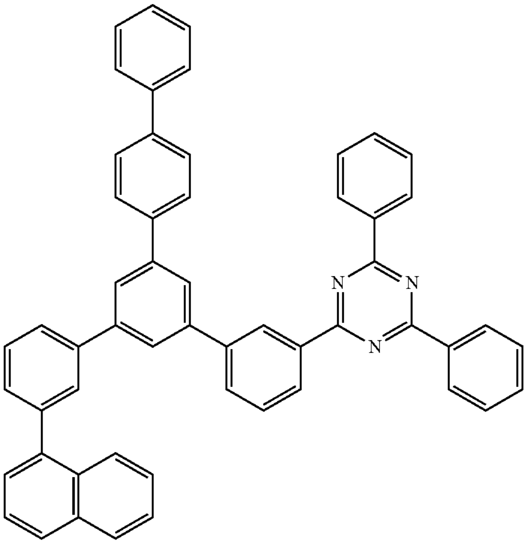

-continued
[A-64]
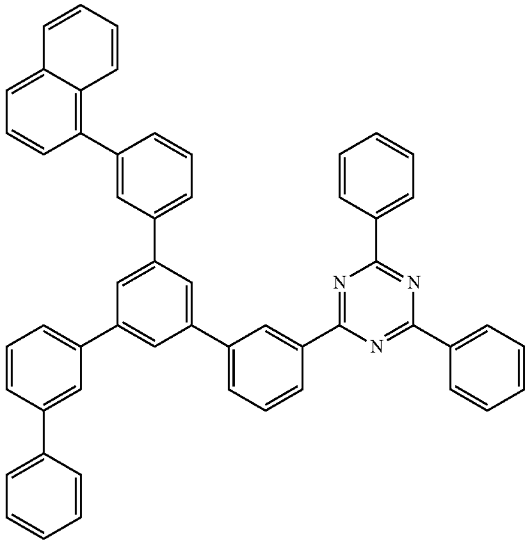
[A-65]
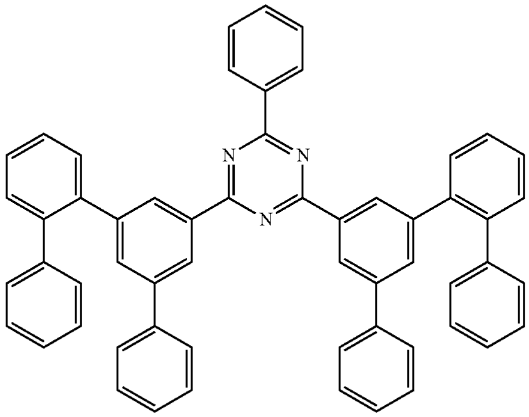
[A-66]
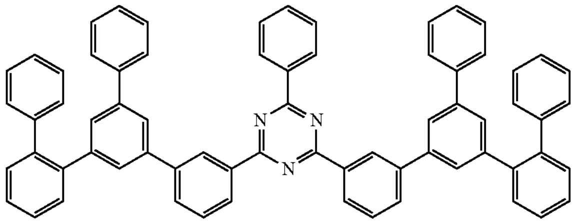
[A-67]
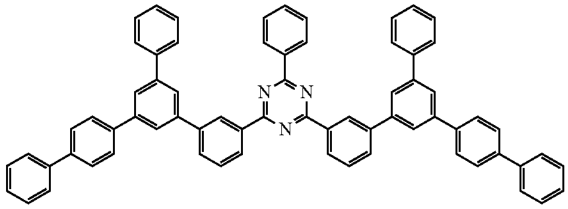
-continued
[A-68]
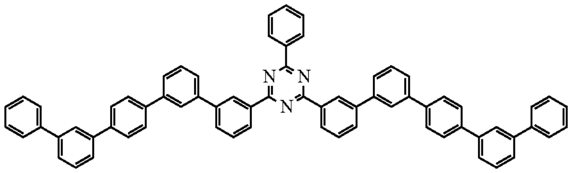
[A-69]
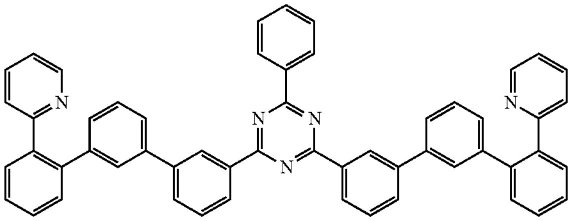
[A-70]
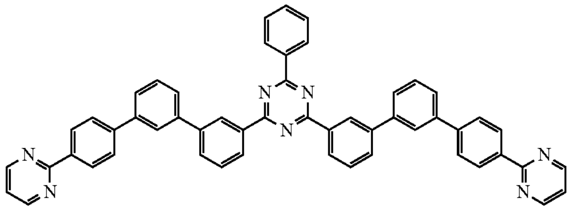
[A-71]
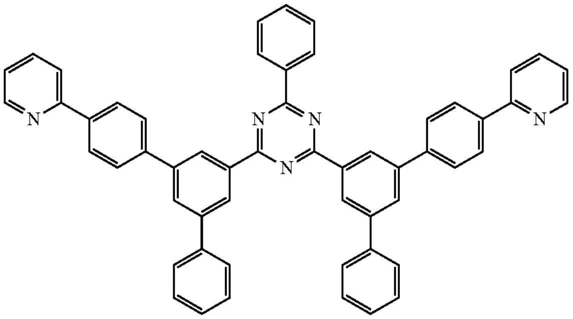
[A-72]
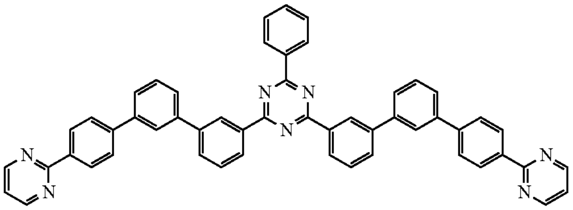
[A-73]
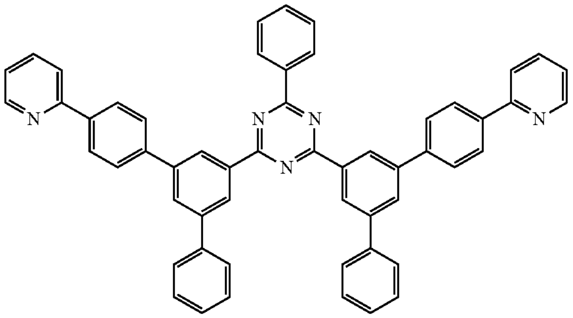

-continued
[A-74]
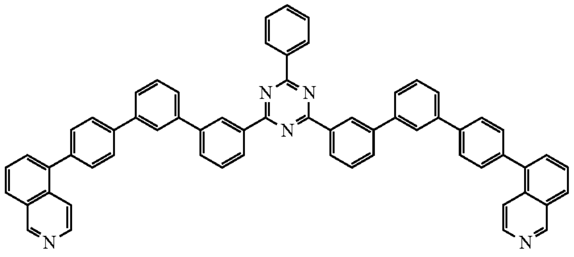
[A-75]
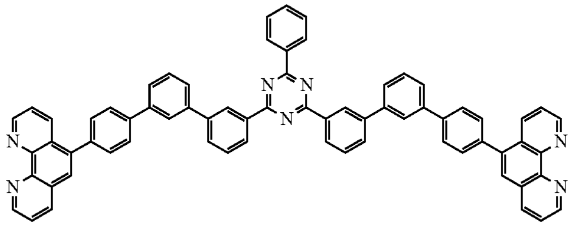
[A-76]
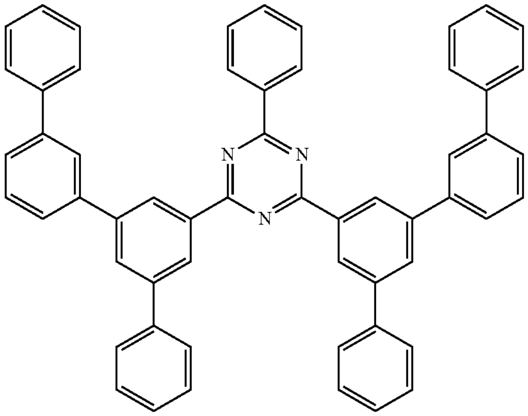
[A-77]
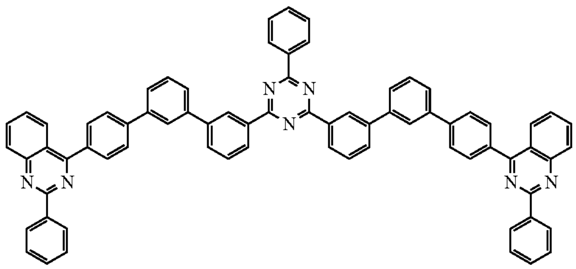
[A-78]
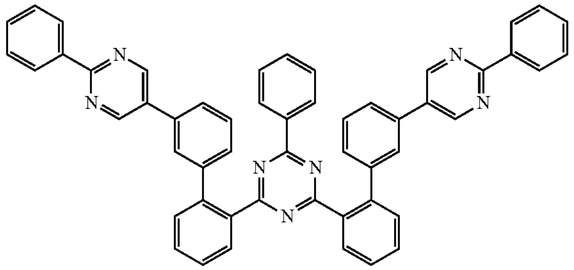
-continued
[A-79]
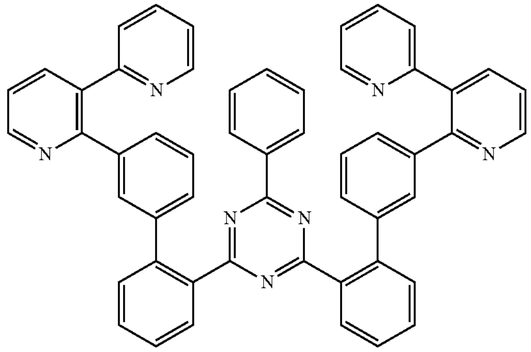
[A-80]
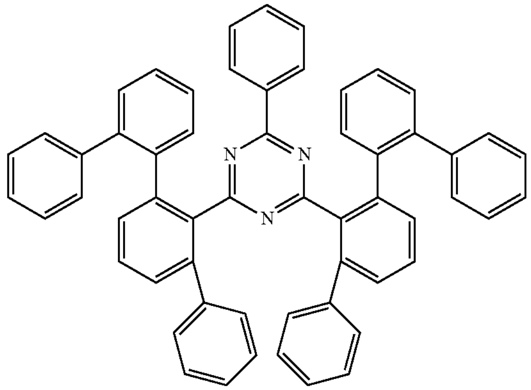
[A-81]
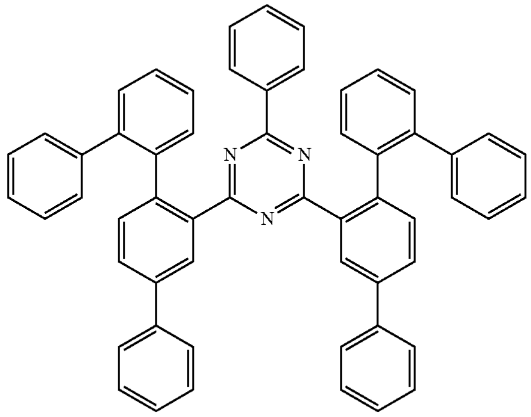

-continued
[A-82]
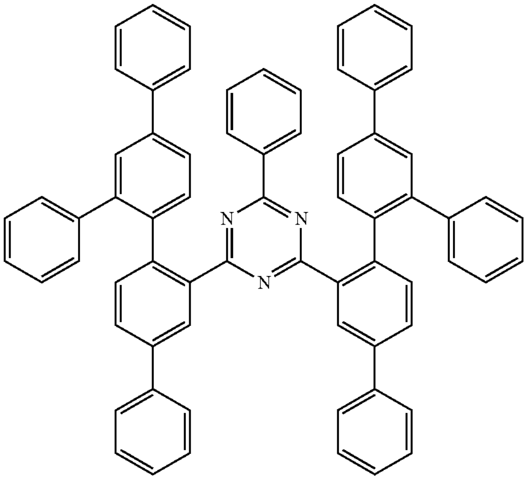
[A-83]
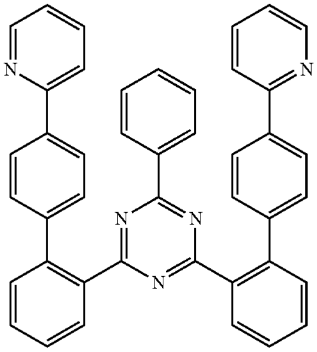
[A-84]
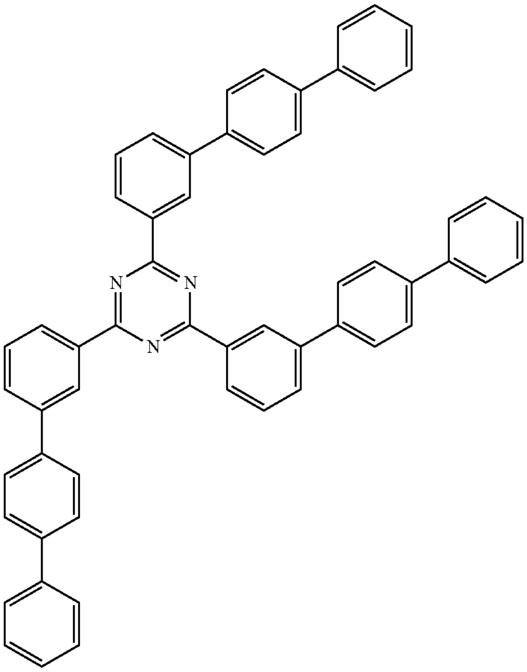
-continued
[A-85]
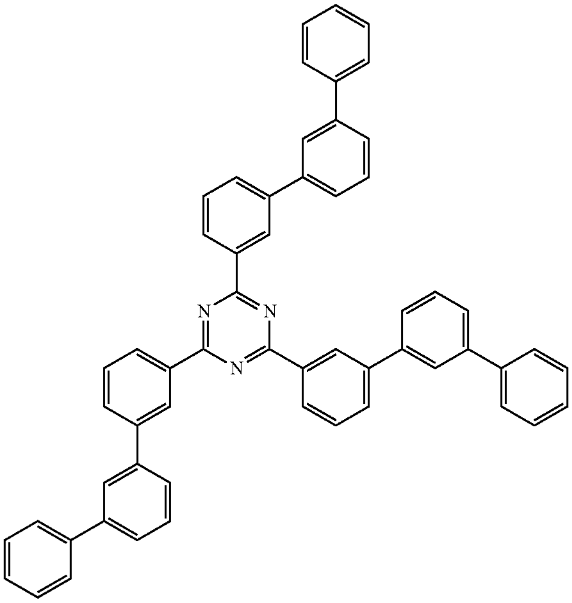
[A-86]
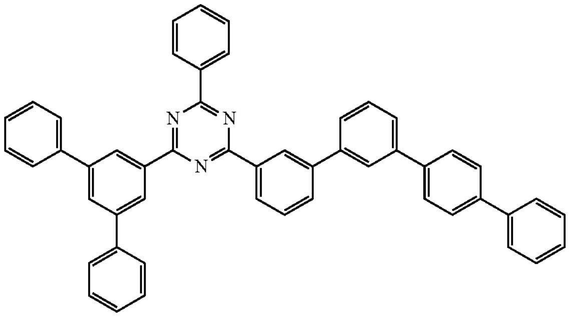
[A-87]
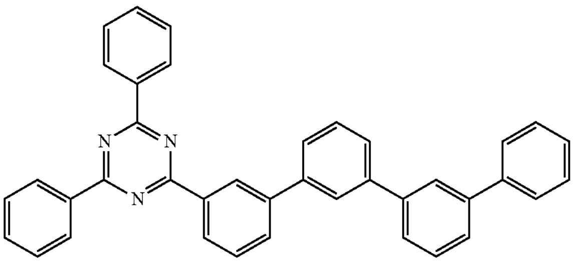
[A-88]
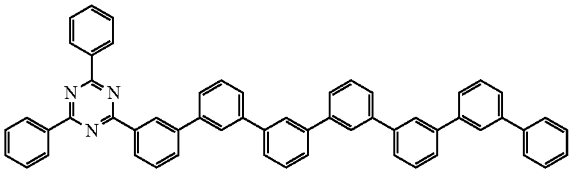

-continued
[B-1]
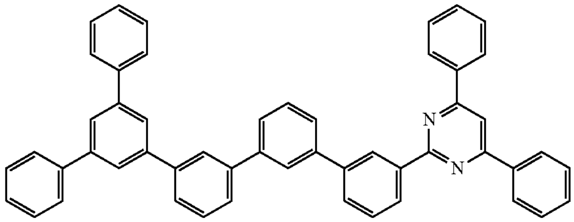
[B-2]
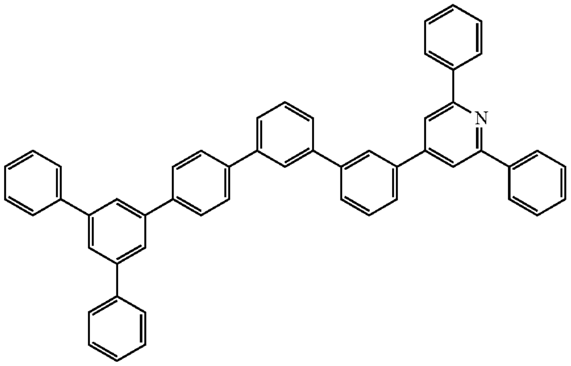
[B-3]
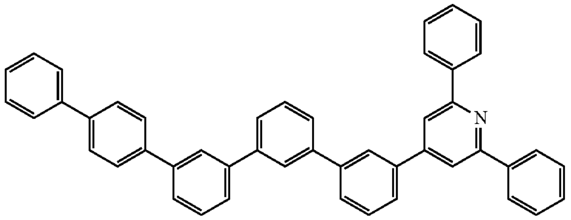
[B-4]
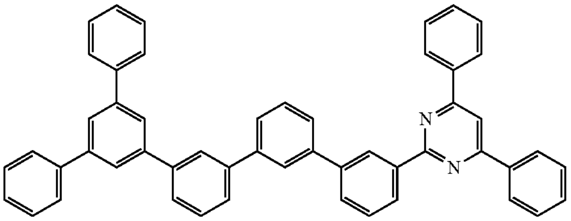
[B-5]
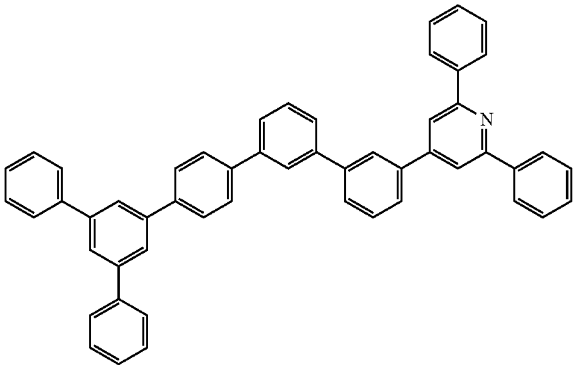
-continued
[B-6]
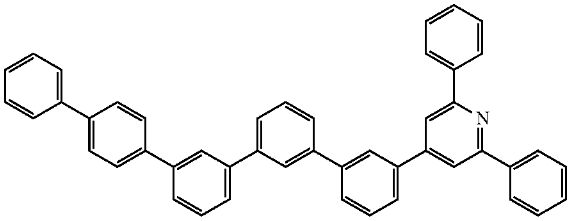
[B-7]
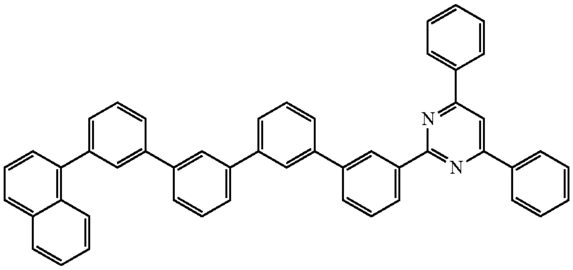
[B-8]
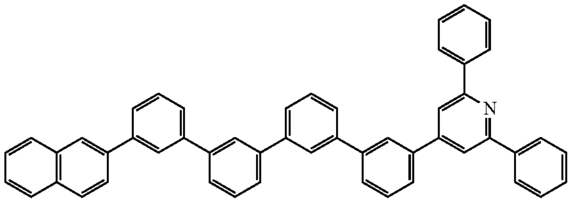
[B-9]
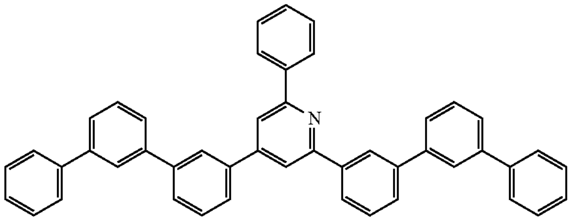
[B-10]
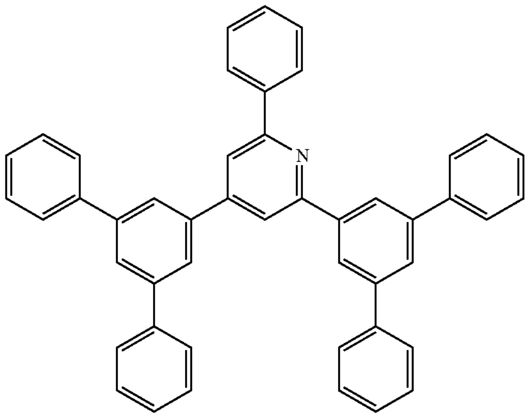

-continued
[B-11]
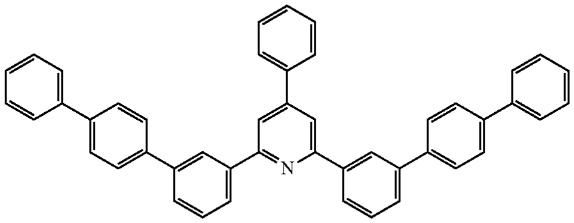
[B-12]
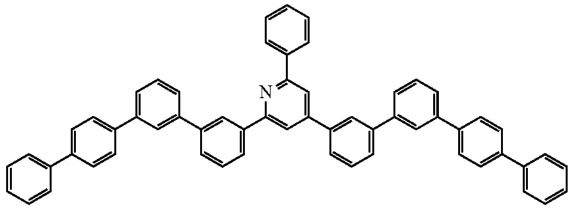
[B-13]
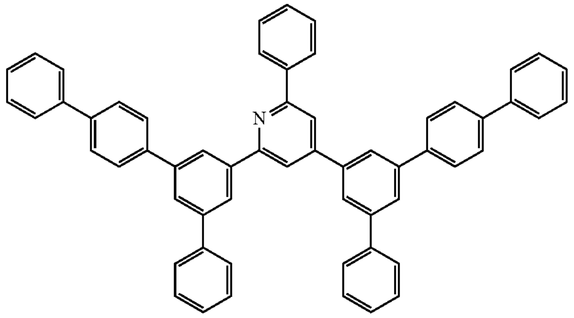
[B-14]
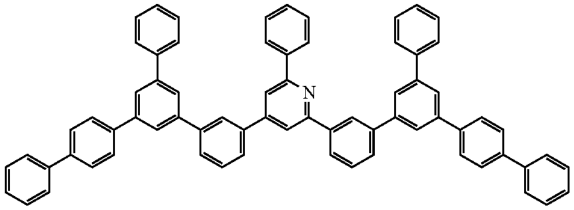
[B-15]
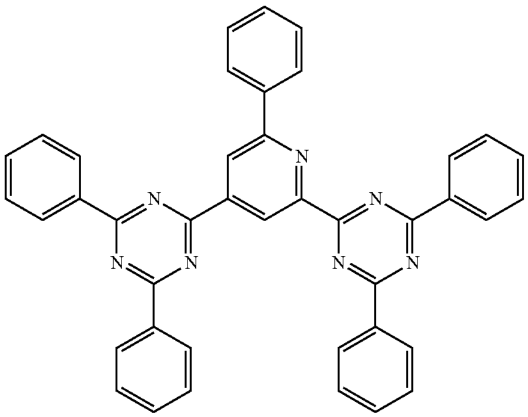
-continued
[B-16]
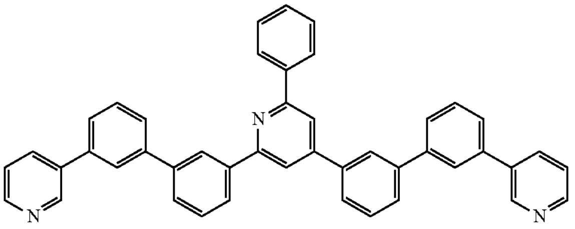
[B-17]
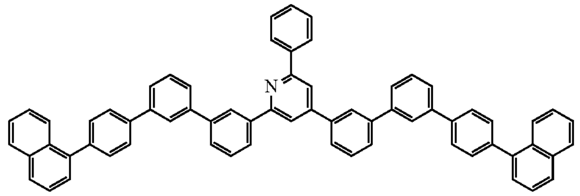
[B-18]
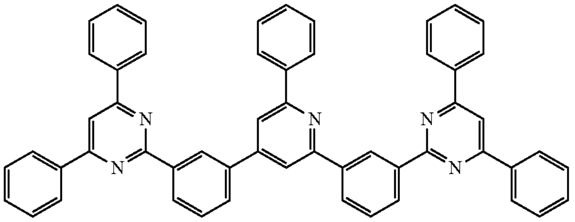
[B-19]
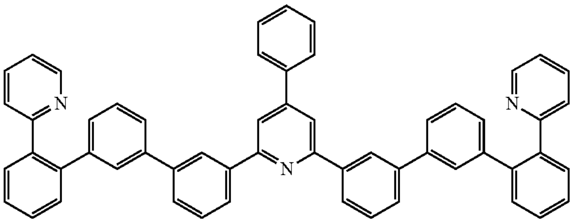
[B-20]
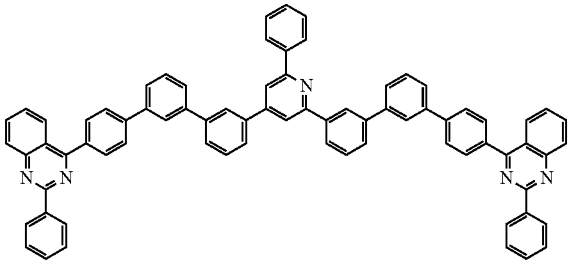
[B-21]
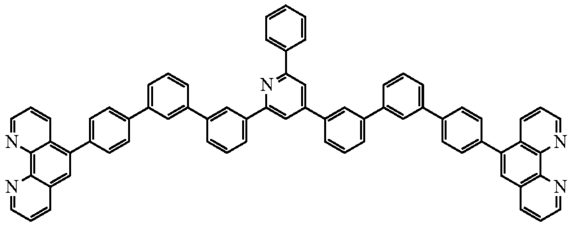

-continued
[B-22]
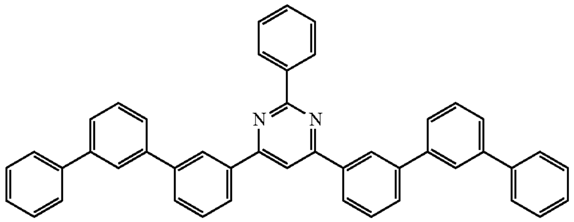
[B-23]
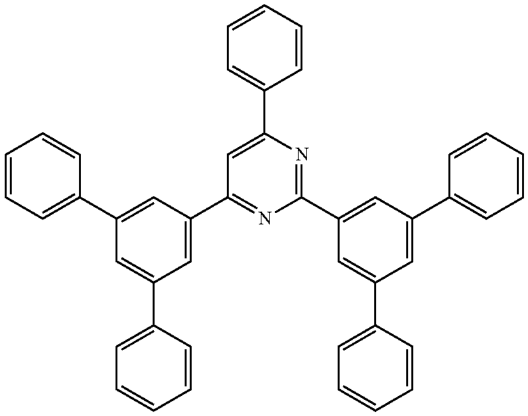
[B-24]
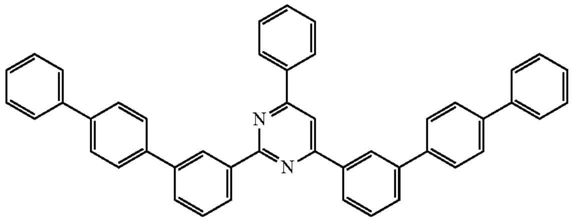
[B-25]
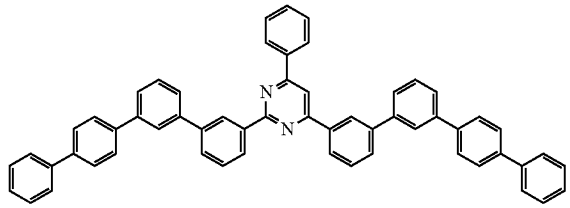
[B-26]
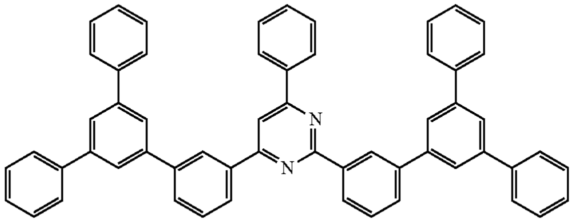
-continued
[B-27]
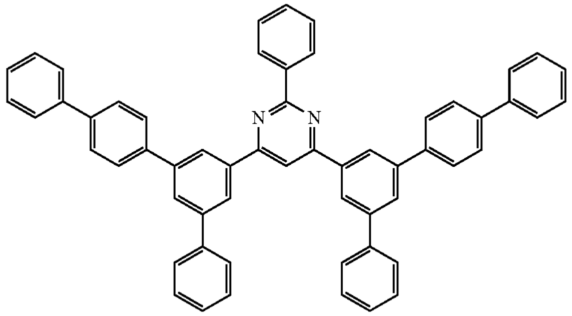
[B-28]
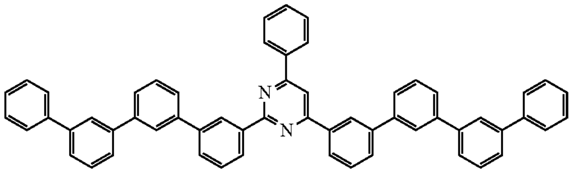
[B-29]
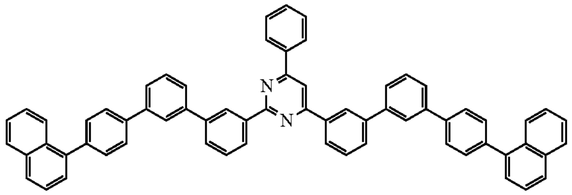
[B-30]
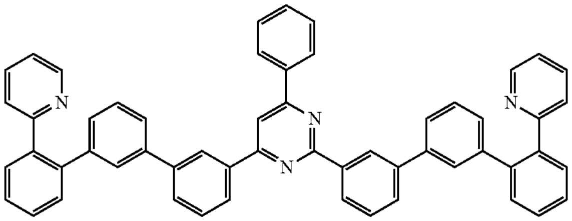
[B-31]
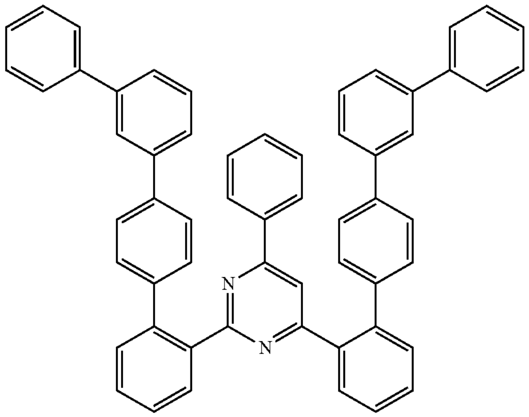

-continued
[B-32]
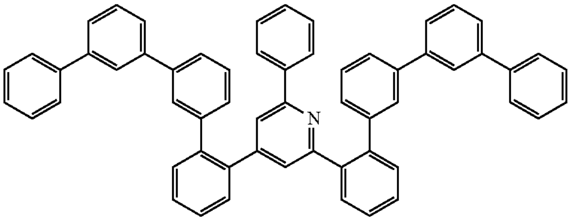
[B-33]
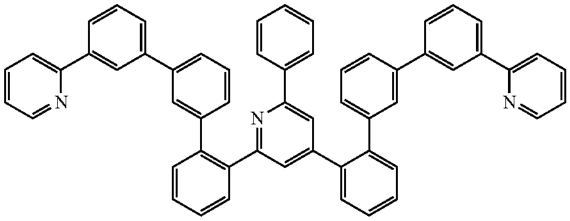
[B-34]
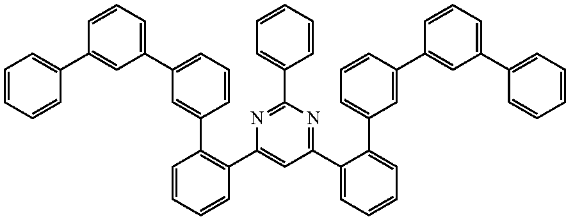
[B-35]
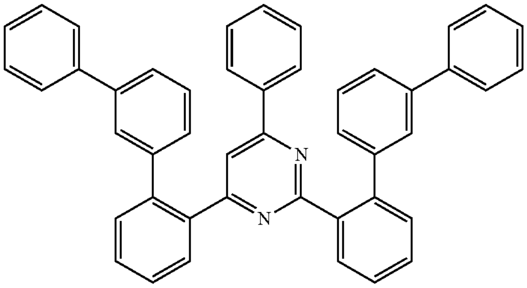
[B-36]
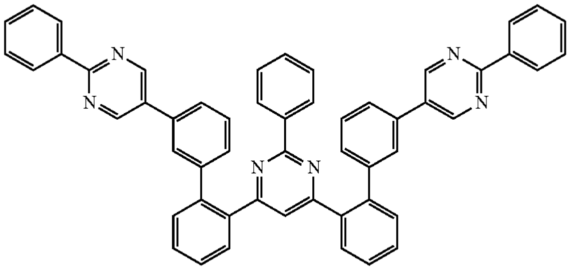
[B-37]
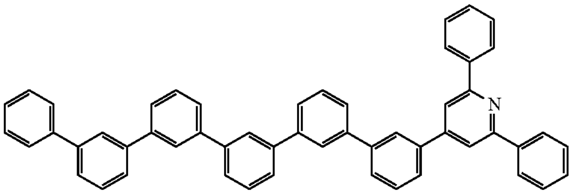
-continued
[B-38]
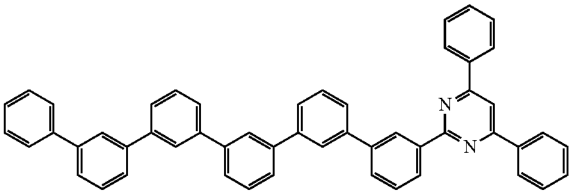
[B-39]
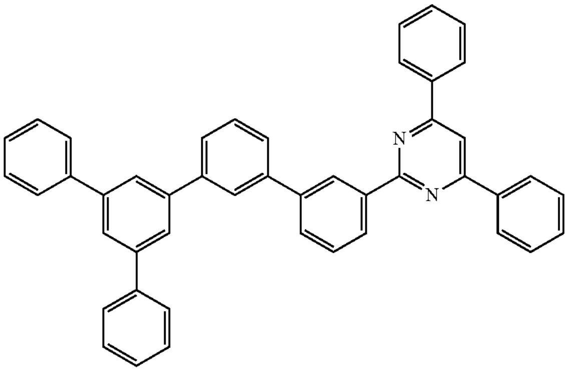
[B-40]
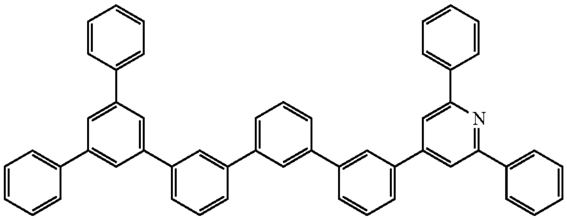
[B-41]
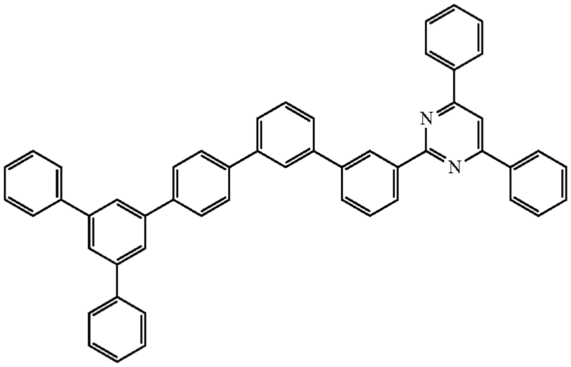
[B-42]
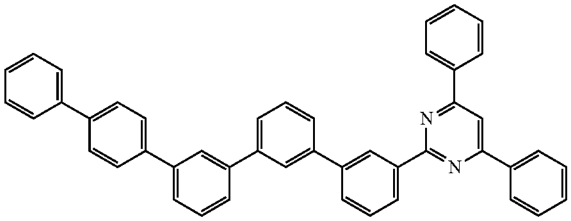

-continued
[B-43]
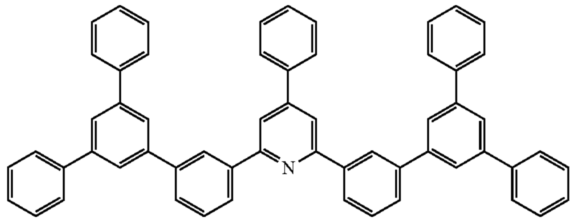
[B-44]
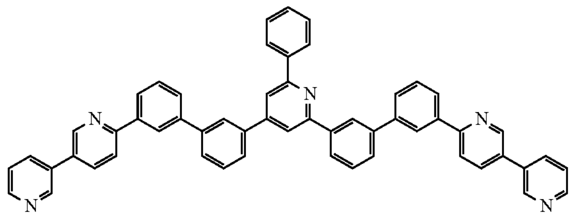
[B-45]
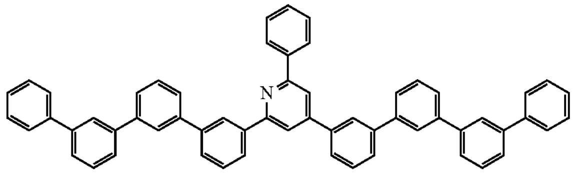
[B-46]
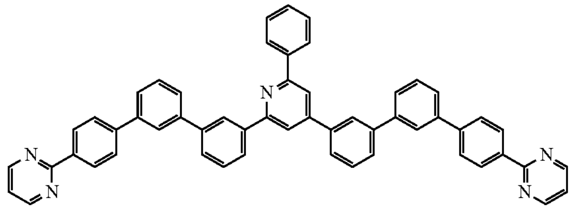
[B-47]
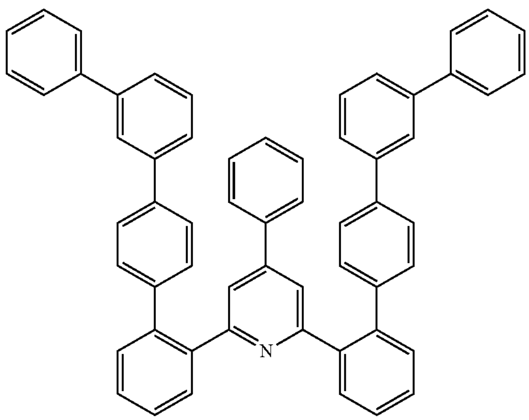
-continued
[B-48]
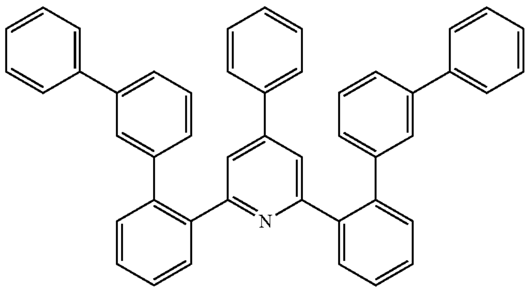
[B-49]
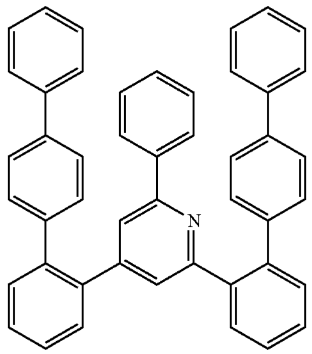
[B-50]
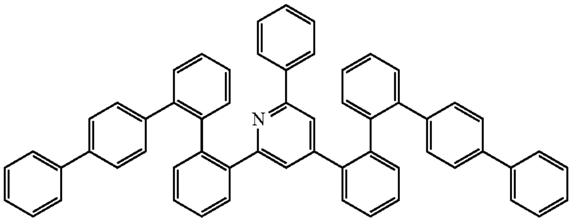
[B-51]
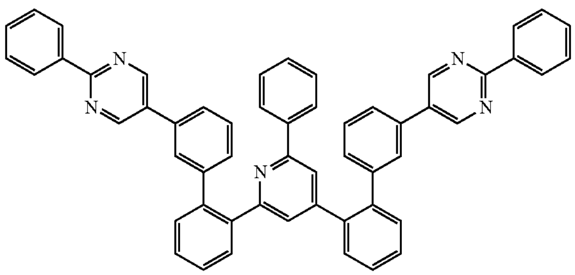

-continued
[B-52]
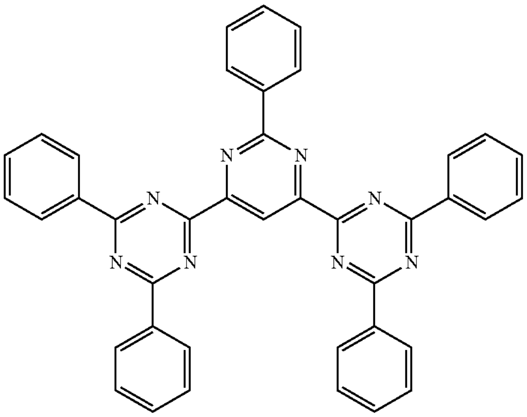
[B-53]
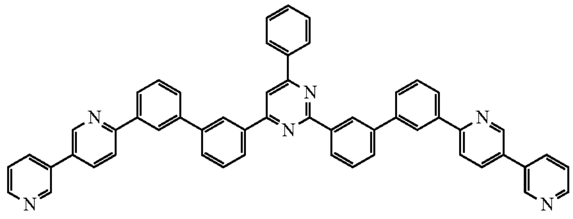
[B-54]
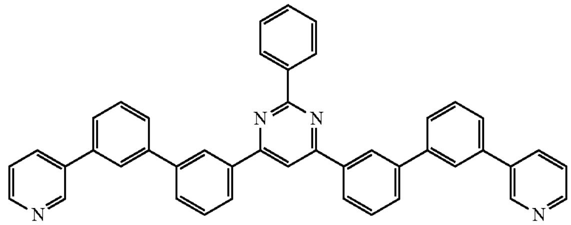
[B-55]
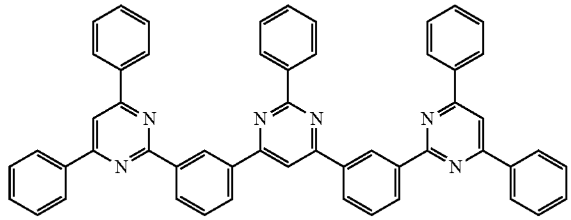
[B-56]
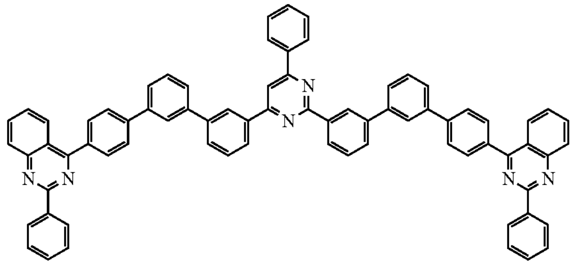
-continued
[B-57]
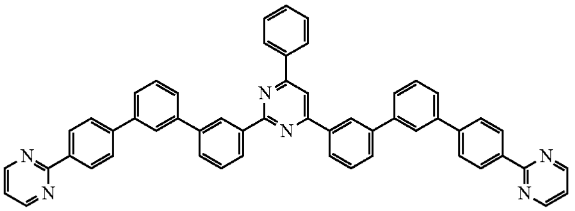
[B-58]
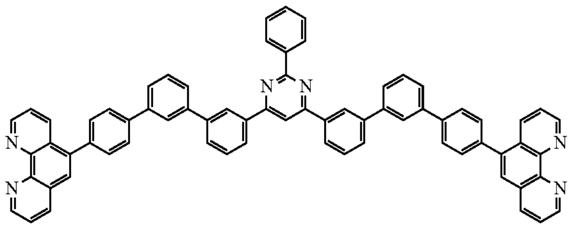
[B-59]
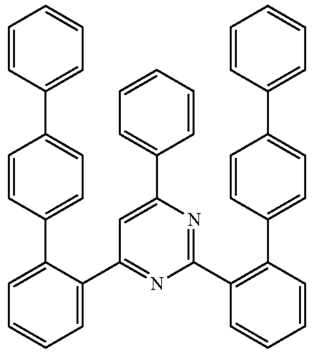
[B-60]
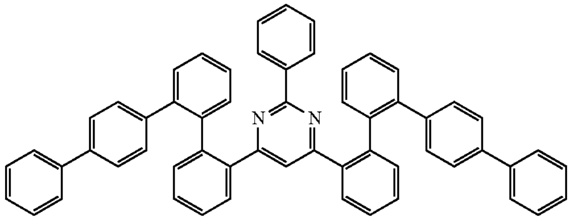
[B-61]
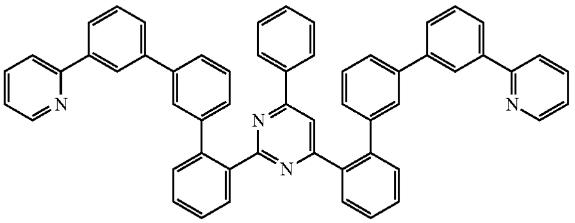
[C-1]
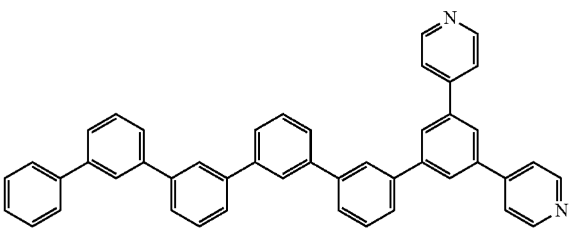

-continued

[C-2]

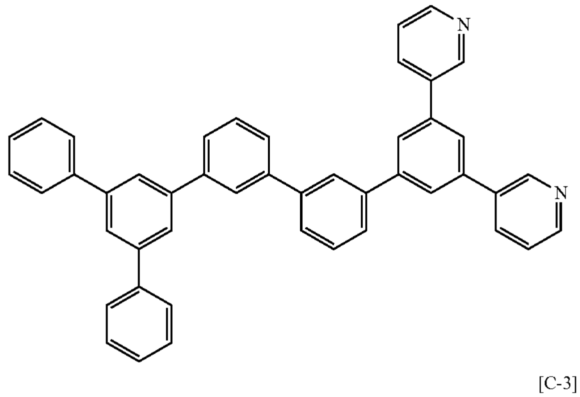

[C-3]

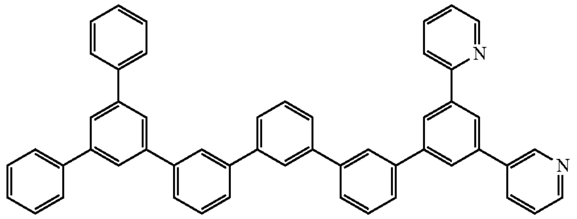

The first compound may be one or more kinds of the compounds of Group 2.

The auxiliary hole transport layer 33 includes the second compound having excellent hole transport characteristics and thus, may reduce a HOMO energy level difference between the hole transport layer 31 and the light-emitting layer 32, and adjust hole injection characteristics and resultantly, decrease accumulation of holes on the interface of the auxiliary hole transport layer 33 and the light-emitting layer 32 and thus, a quenching phenomenon that excitons become extinct on the interface due to polaron. Accordingly, the device may be less deteriorated and stabilized and thus, have improved efficiency and life-span.

The second compound may be a compound represented by a combination of a moiety represented by Chemical Formula 2, a moiety represented by Chemical Formula 3, and a moiety represented by Chemical Formula 4.

[Chemical Formula 2]

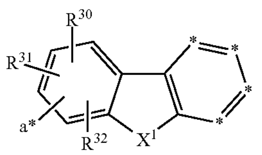

[Chemical Formula 3]

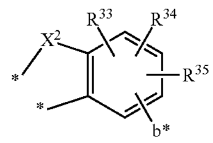

-continued

[Chemical Formula 4]

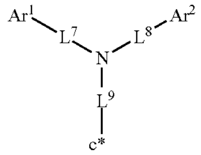

In Chemical Formulae 2 to 4, $X^1$ and $X^2$ are independently O, S, or $CR^cR^d$, $R^{30}$ to $R^{35}$, $R^c$, and $R^d$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, or a linking point with c* of Chemical Formula 5, $Ar^1$ and $Ar^2$ are independently a substituted or unsubstituted C6 to C30 aryl group or a substituted or unsubstituted C2 to C30 heteroaryl group, $L^7$ to $L^9$ are independently a single bond, a substituted or unsubstituted C6 to C30 arylene group, a substituted or unsubstituted heteroarylene group, or a combination thereof, adjacent two *'s of Chemical Formula 3 are bound to two *'s of Chemical Formula 4 to form a fused ring, one of a*, b*, and $R^{30}$ to $R^{35}$ of above Chemical Formula 3 or 4 is linked with c* of Chemical Formula 5 by a sigma bond, and a*, b*, and $R^{30}$ to $R^{35}$ that are not linked with c* of Chemical Formula 5 are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof.

The second compound may be for example represented by one of Chemical Formula 2-1 to Chemical Formula 2-3.

[Chemical Formula 2-1]

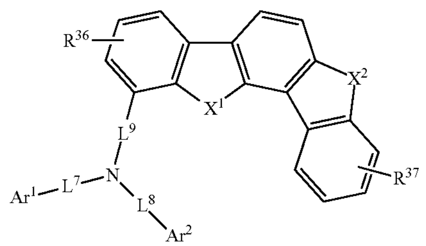

[Chemical Formula 2-2]

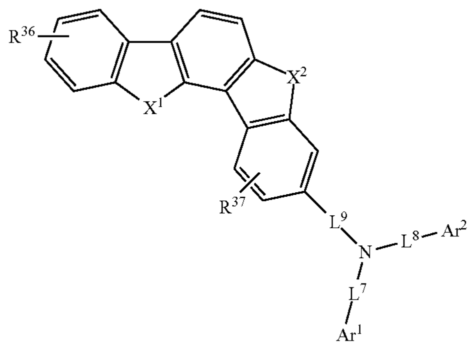

-continued

[Chemical Formula 2-3]

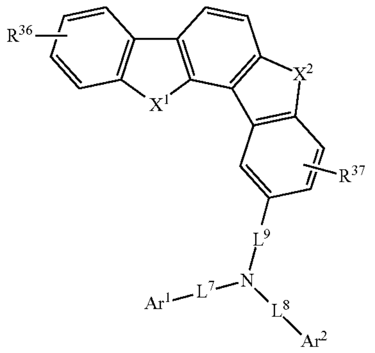

In Chemical Formulas 2-1 to 2-3, $X^1$, $X^2$, $Ar^1$, $Ar^2$, and $L^7$ to $L^9$ are the same as described above, $R^{36}$ and $R^{37}$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof.

For example, the second compound may be for example represented by one of Chemical Formula 2-4 to Chemical Formula 2-6.

[Chemical Formula 2-4]

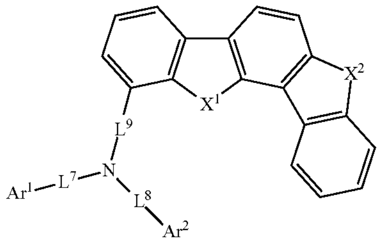

[Chemical Formula 2-5]

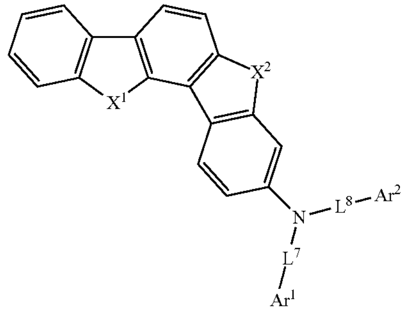

-continued

[Chemical Formula 2-6]

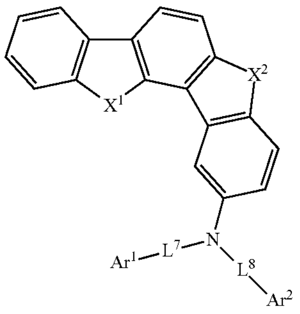

In Chemical Formulae 2-4 to 2-6, $X^1$, $X^2$, $Ar^1$, $Ar^2$, and $L^7$ to $L^9$ are the same as described above.

$Ar^1$ and $Ar^2$ may specifically be a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, a substituted or unsubstituted fluorenyl group, a substituted or unsubstituted pyridinyl group, a substituted or unsubstituted pyrimidinyl group, a substituted or unsubstituted triazinyl group, a substituted or unsubstituted carbazolyl group, a substituted or unsubstituted dibenzofuranyl group, a substituted or unsubstituted dibenzothiophenyl group, Chemical Formula w, Chemical Formula x, Chemical Formula y, Chemical Formula z, or a combination thereof.

[Chemical Formula w]

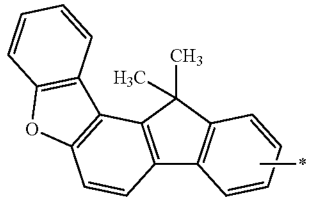

[Chemical Formula x]

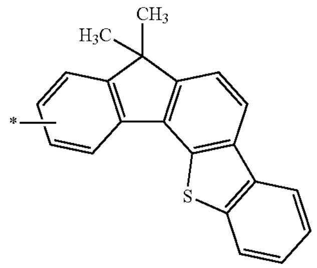

[Chemical Formula y]

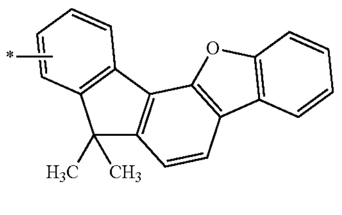

-continued

[Chemical Formula z]

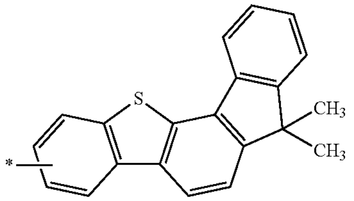

More specifically, they may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, a substituted or unsubstituted fluorenyl group, a substituted or unsubstituted dibenzofuranyl group, a substituted or unsubstituted dibenzothiophenyl group, or a combination thereof.

For example, the second compound may be represented by Chemical Formula 2-1 or Chemical Formula 2-2.

The second compound may be, for example selected from compounds of Group 3, but is not limited thereto.

[Group 3]

[E-1]

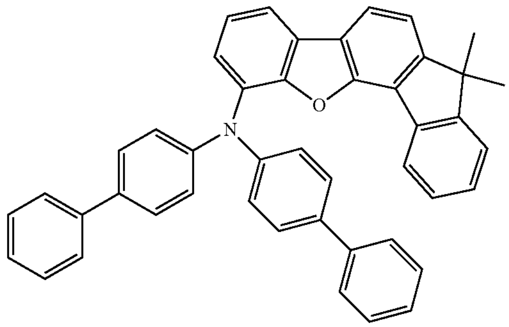

[E-2]

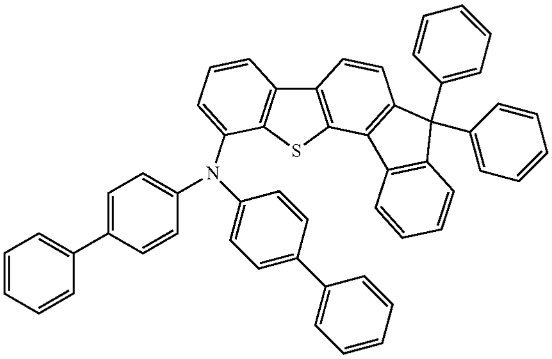

-continued

[E-3]

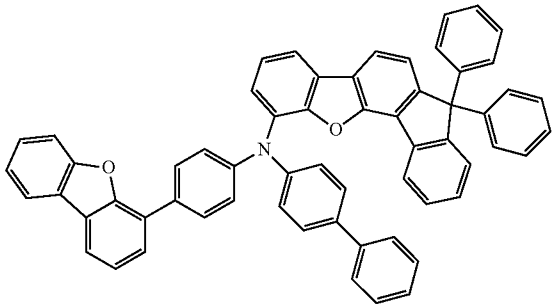

[E-4]

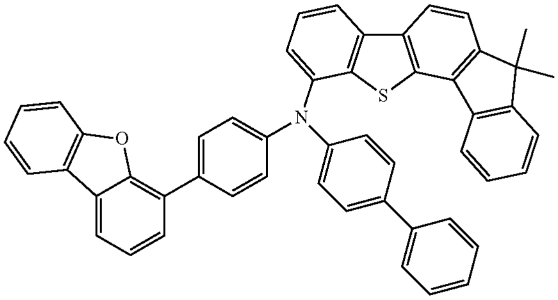

[E-5]

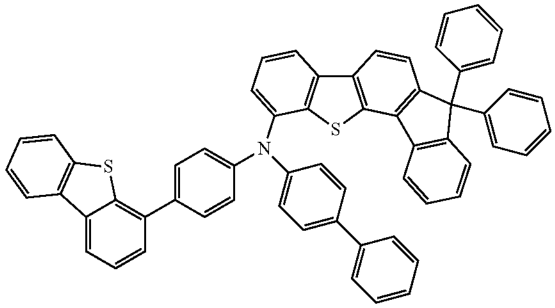

[E-6]

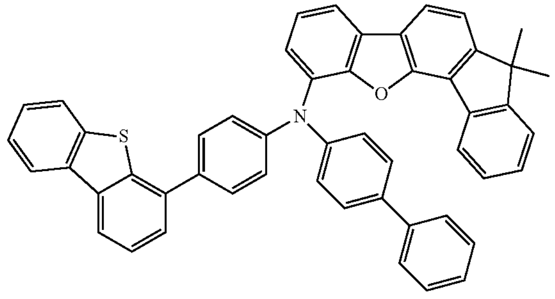

[E-7]

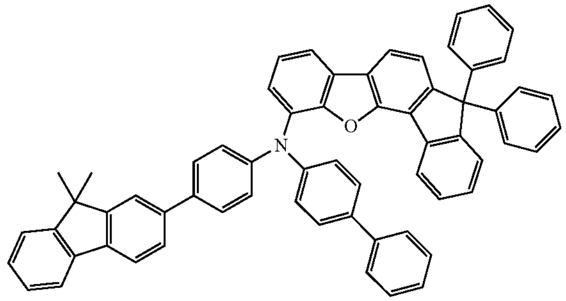

-continued
[E-8]
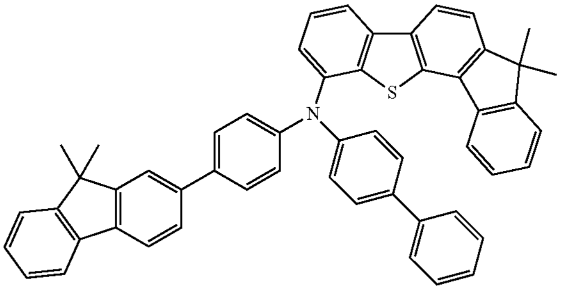
[E-9]
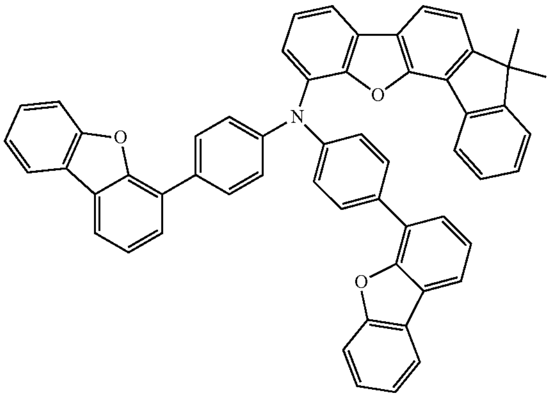
[E-10]
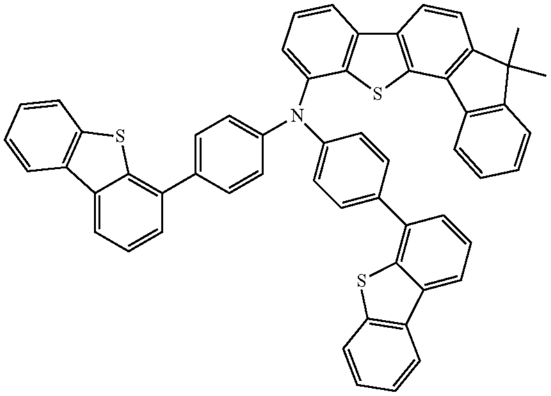
[E-11]
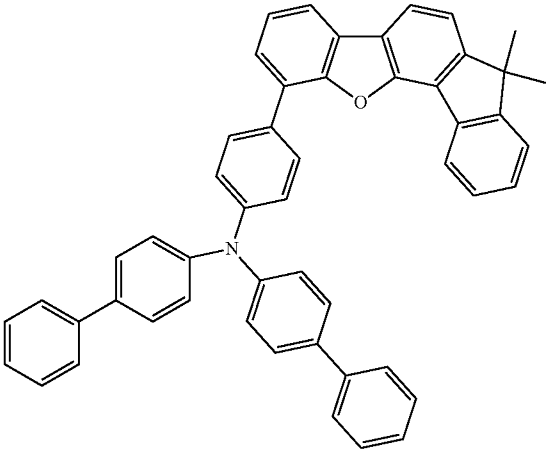
-continued
[E-12]
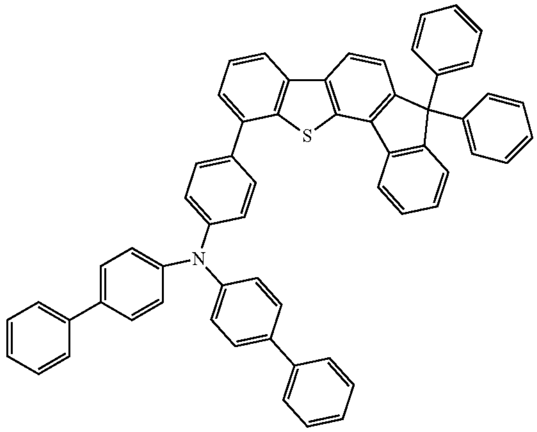
[E-13]
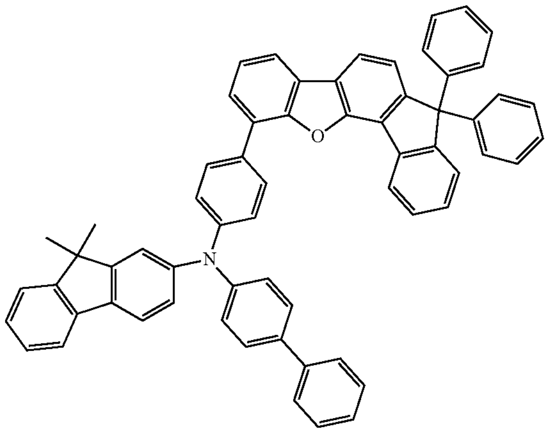
[E-14]
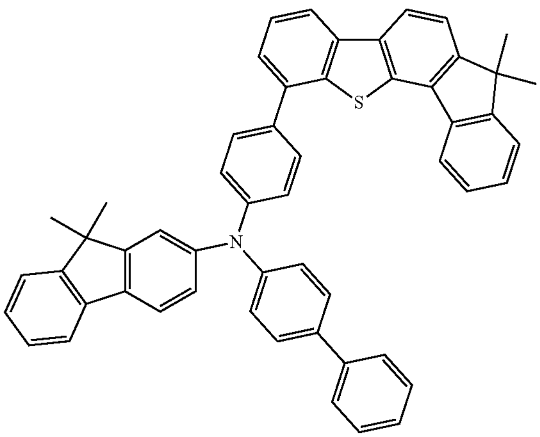

-continued
[E-15]
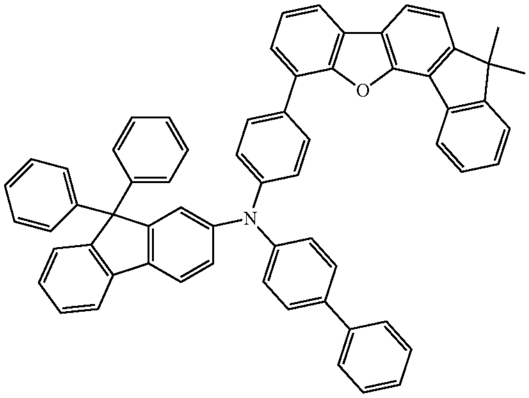
[E-16]
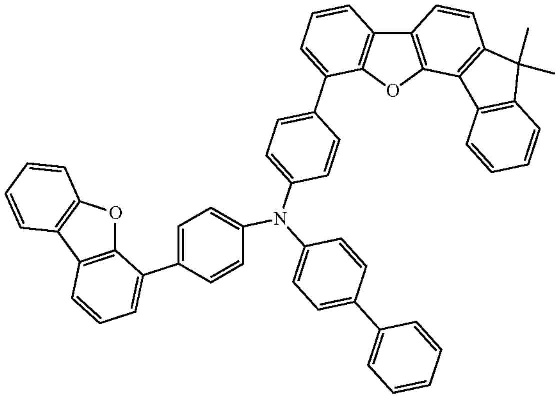
[E-17]
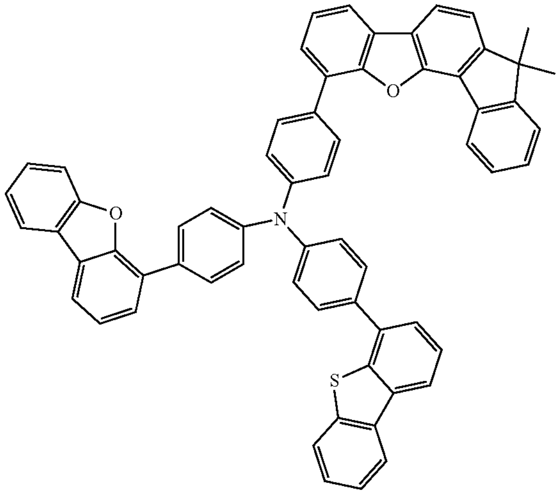
-continued
[E-18]
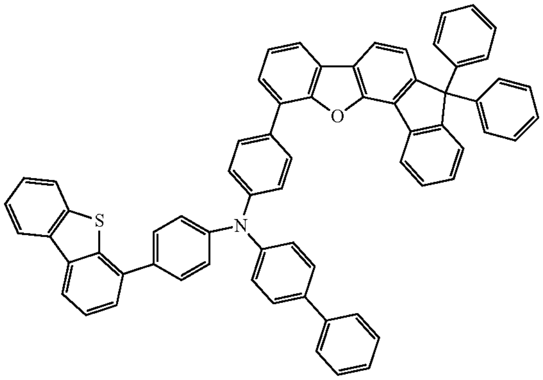
[E-19]
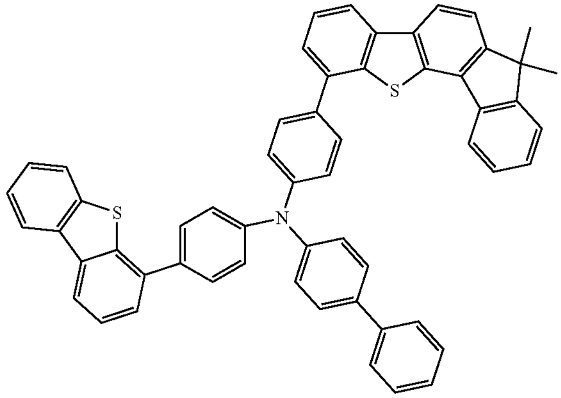
[E-20]
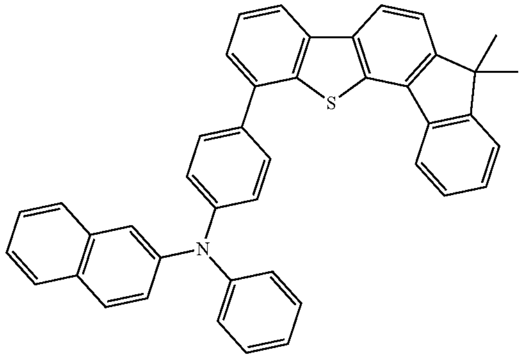

-continued
[E-21]
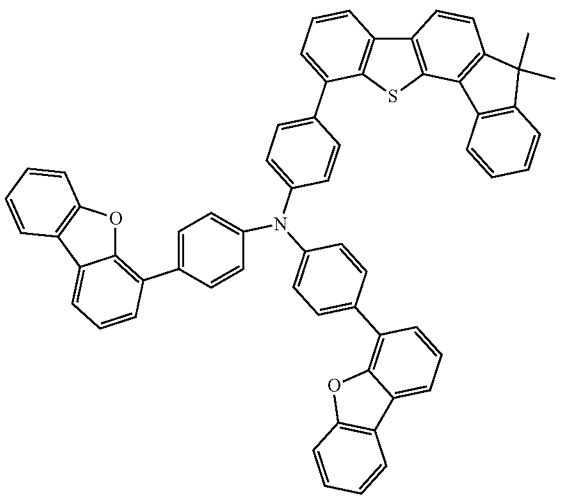
[E-22]
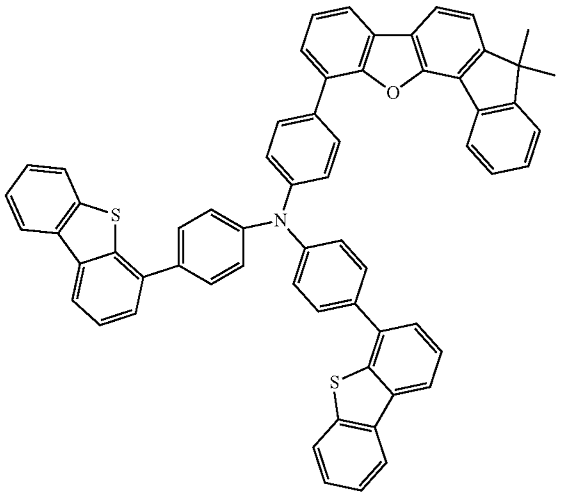
[E-23]
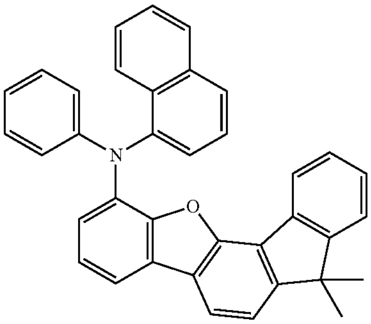
-continued
[E-24]
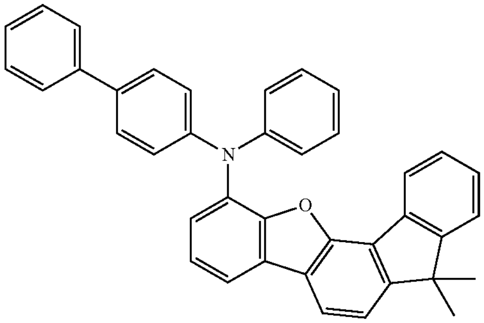
[E-25]
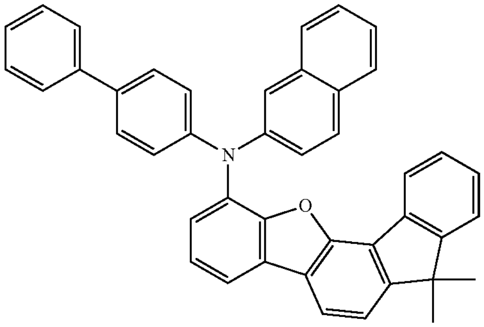
[E-26]
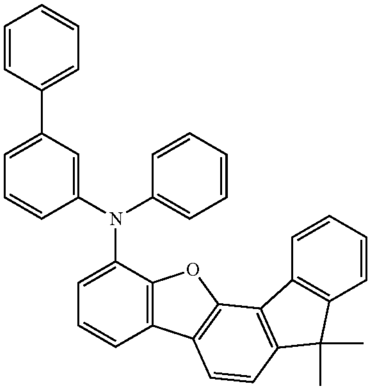
[E-27]
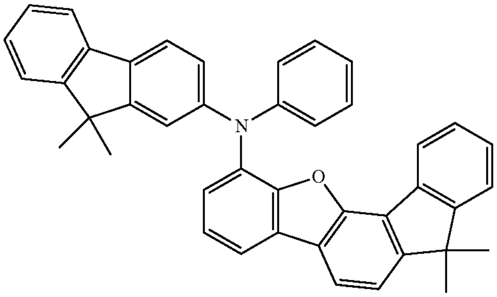

-continued
[E-28]
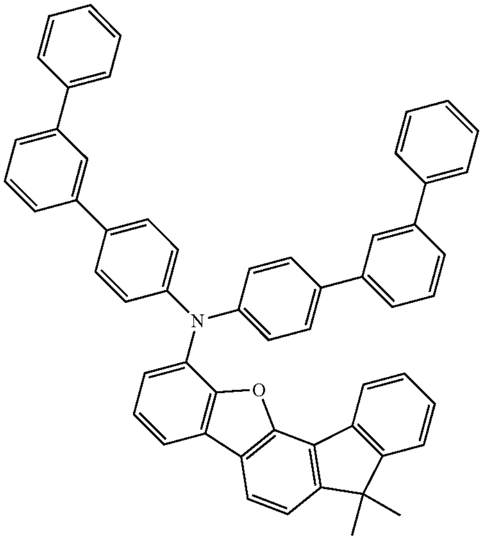
[E-29]
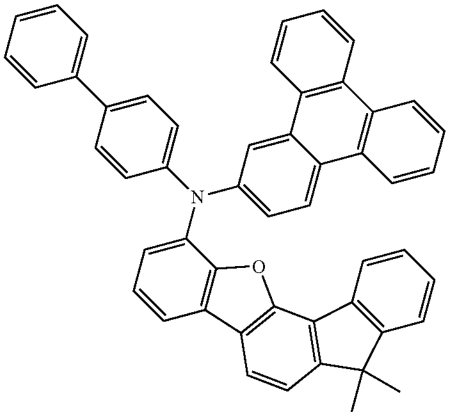
[E-30]
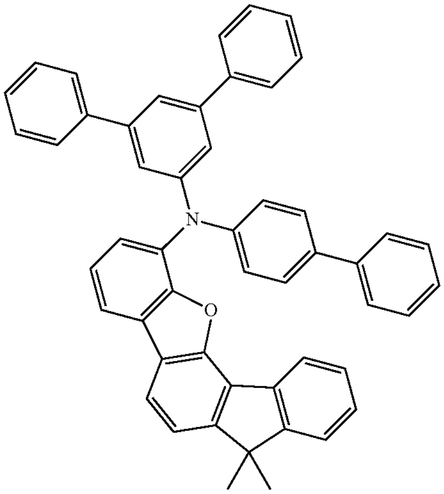
-continued
[E-31]
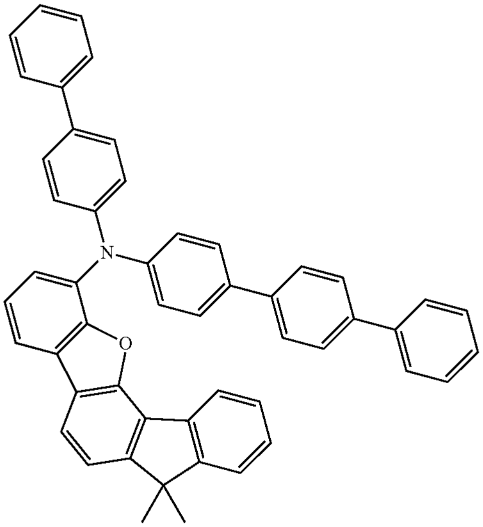
[E-32]
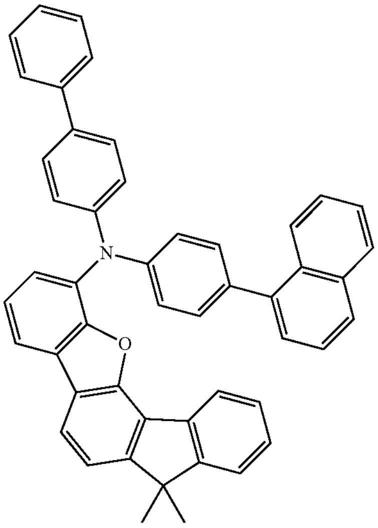
[E-33]
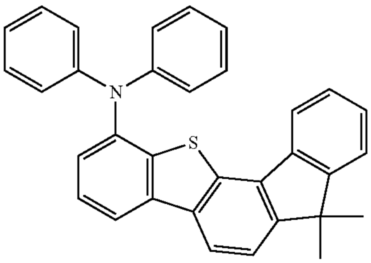
[E-34]
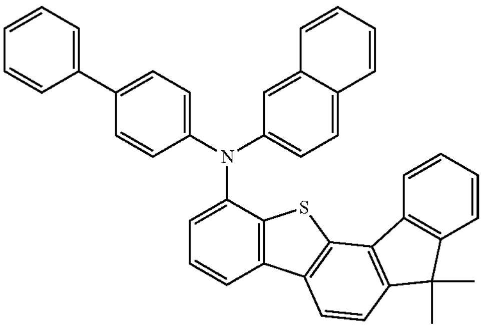

-continued
[E-35]
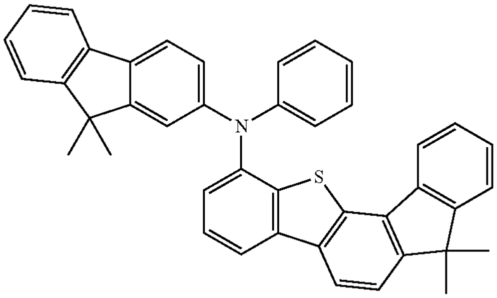
[E-36]
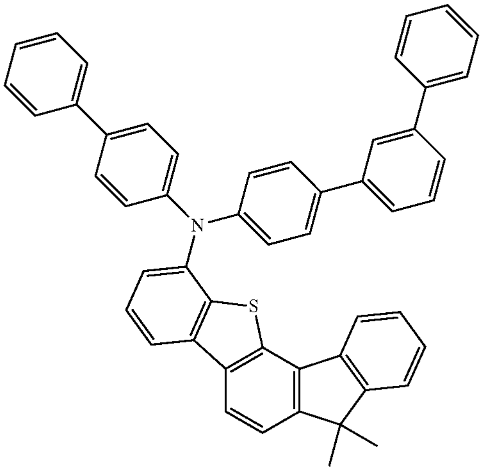
[E-37]
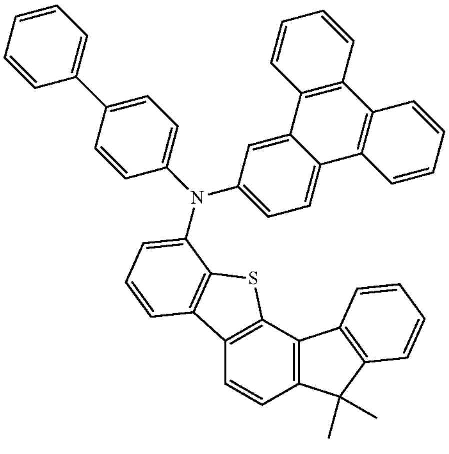
-continued
[E-38]
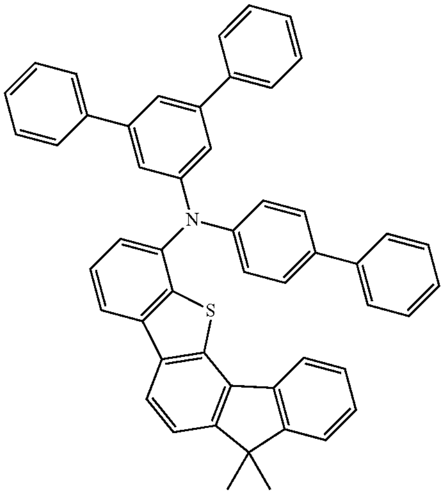
[E-39]
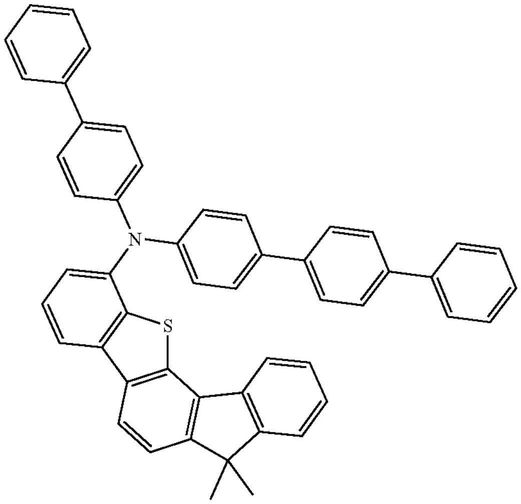
[E-40]
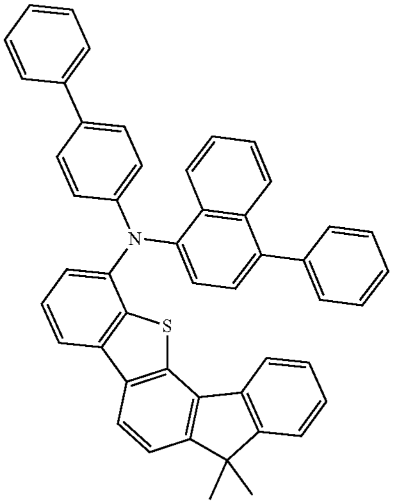

-continued
[E-41]
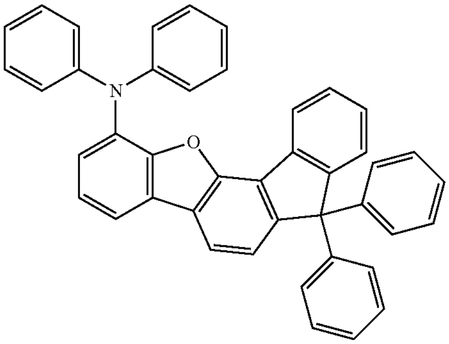
[E-42]
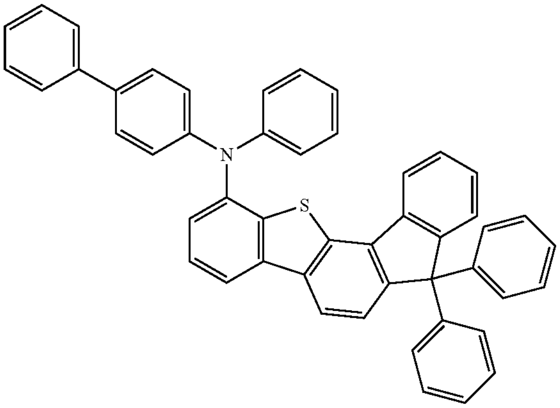
[E-43]
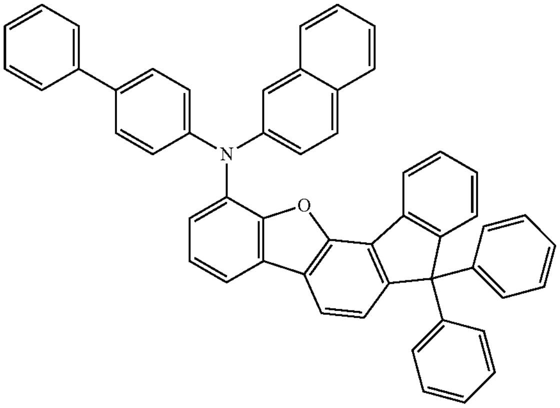
[E-44]
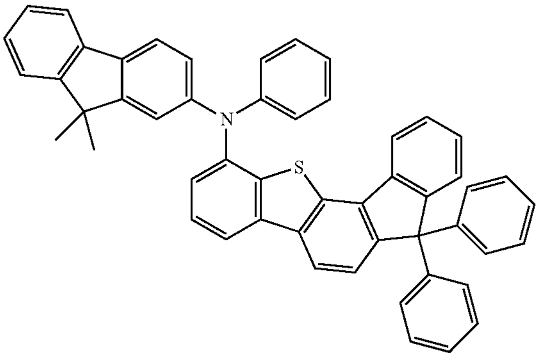
-continued
[E-45]
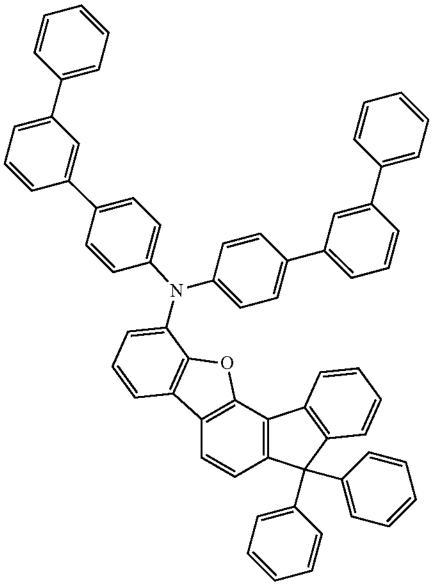
[E-46]
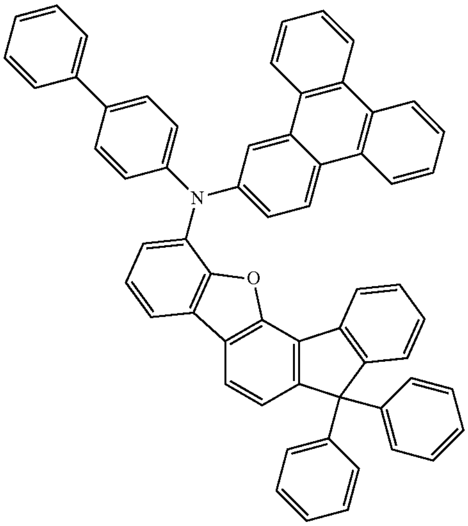

-continued
[E-47]
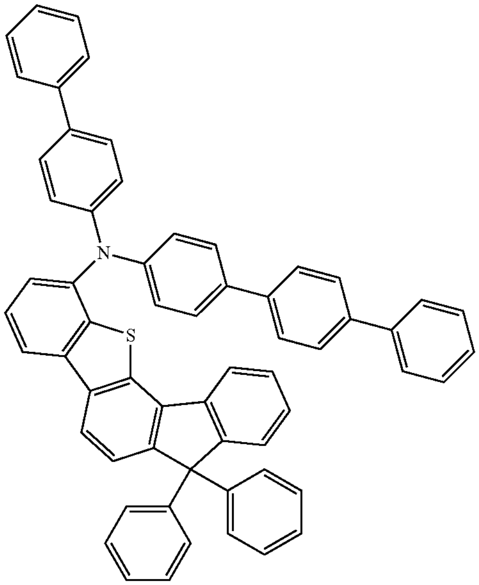
[E-48]
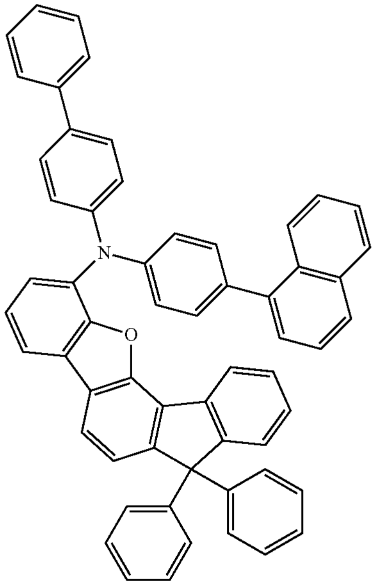
[E-49]
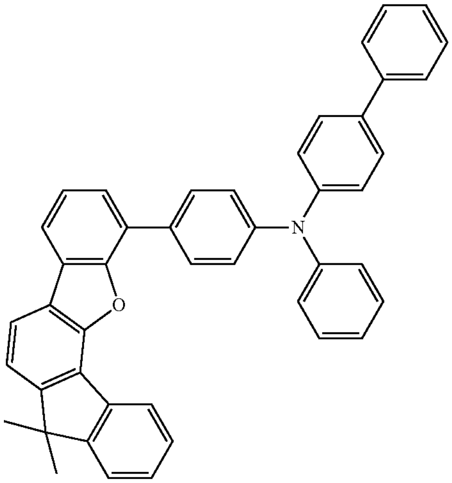
-continued
[E-50]
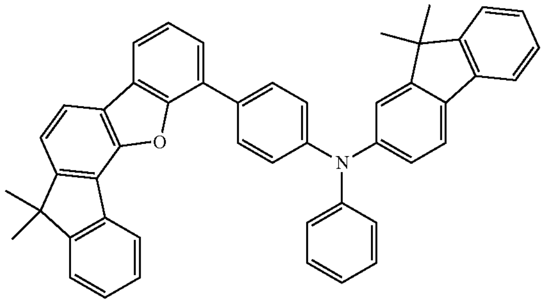
[E-51]
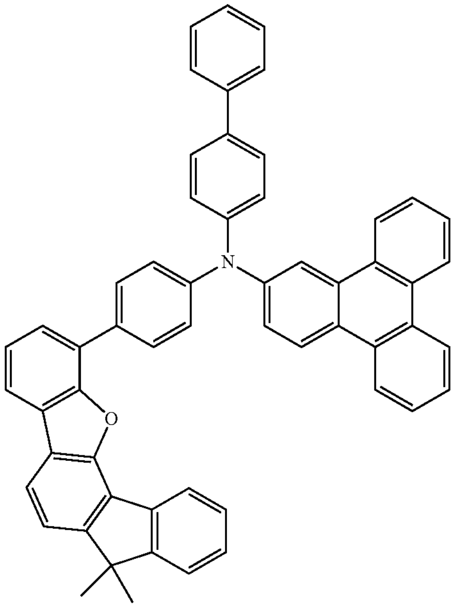
[E-52]
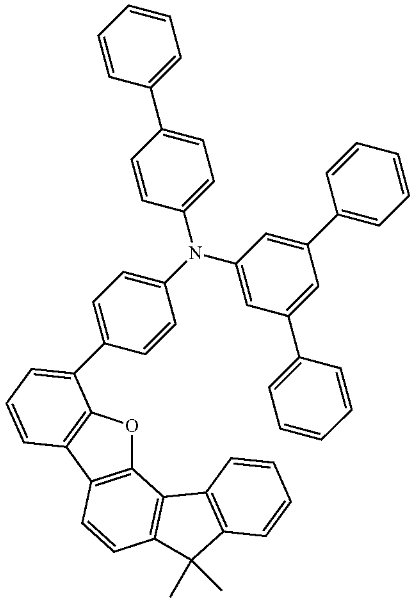

-continued
[E-53]
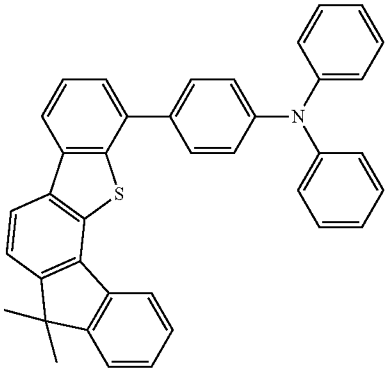
[E-54]
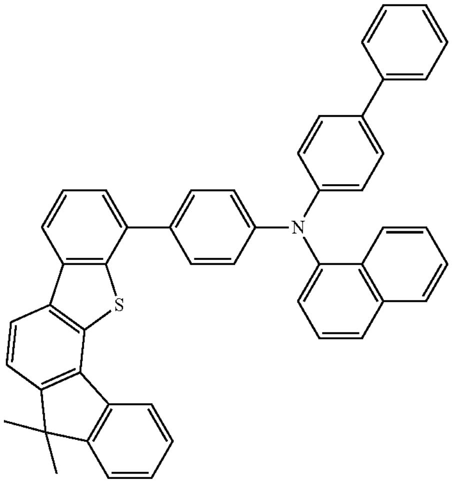
[E-55]
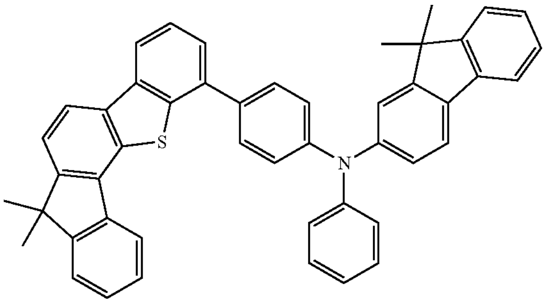
-continued
[E-56]
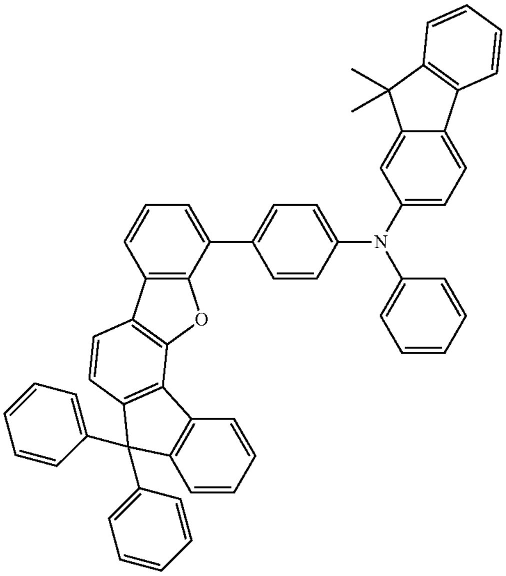
[E-57]
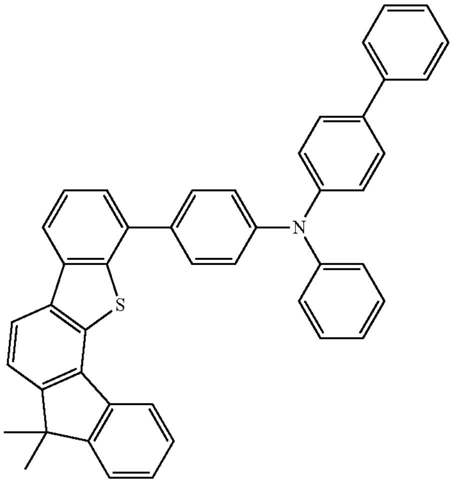
[F-1]
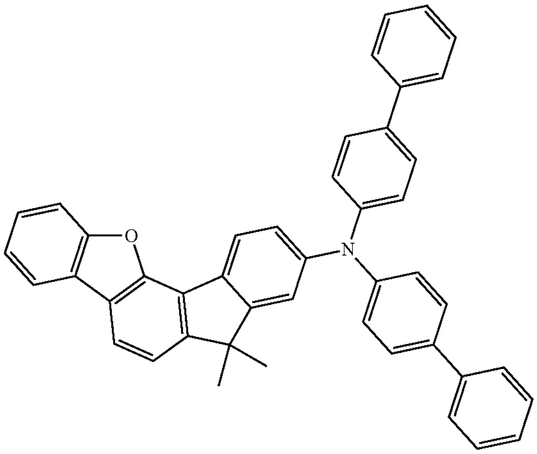

-continued
[F-2]
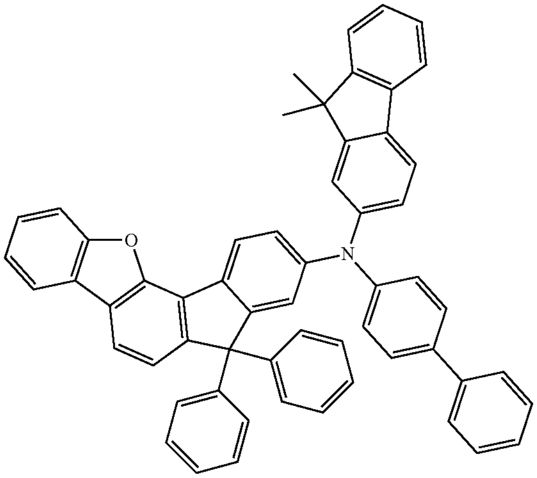
[F-3]
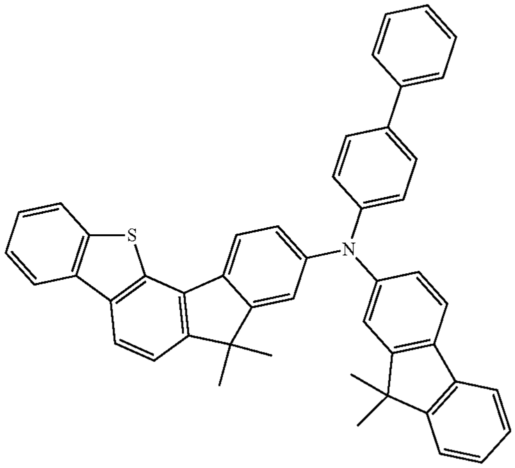
[F-4]
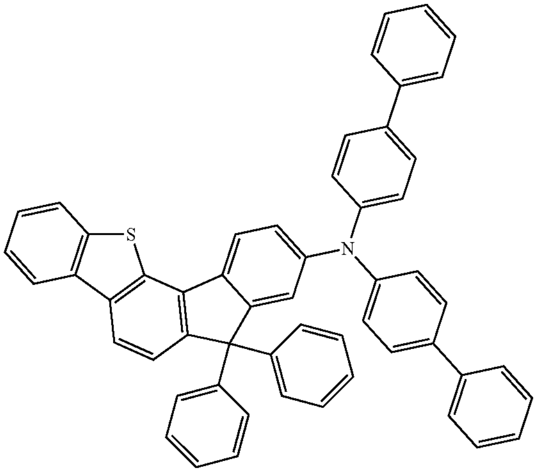
-continued
[F-5]
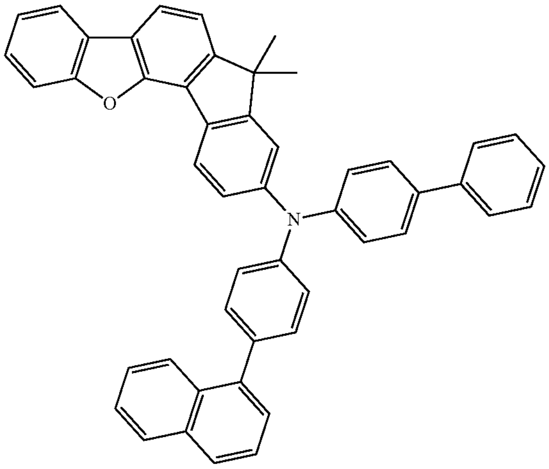
[F-6]
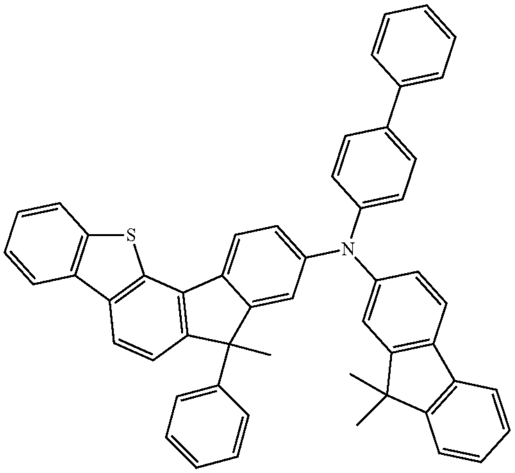
[F-7]
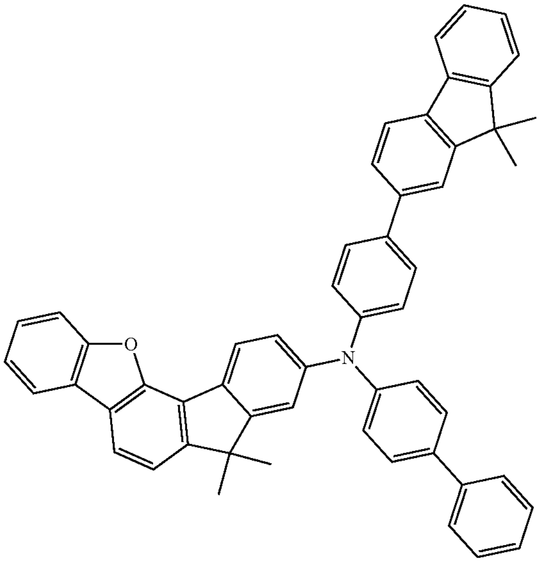

-continued
[F-8]
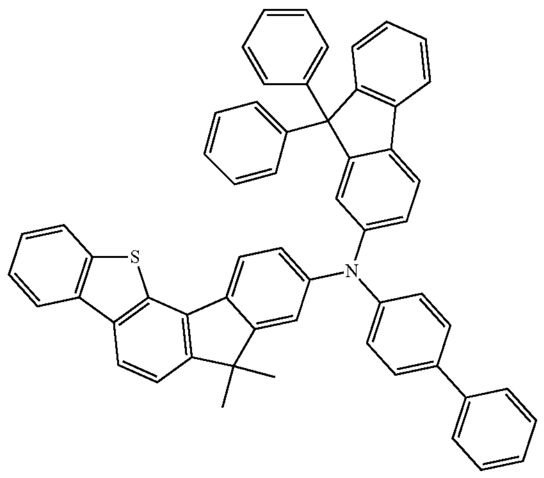
[F-9]
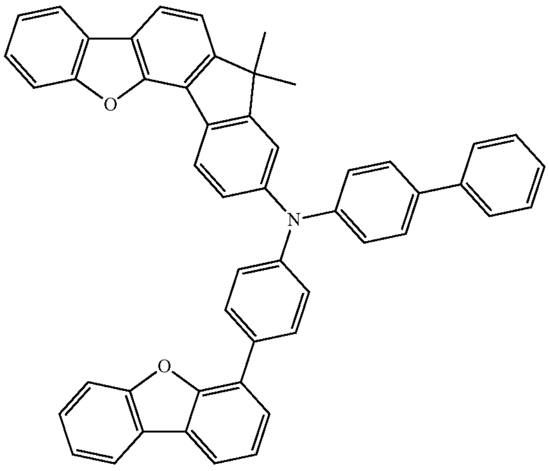
[F-10]
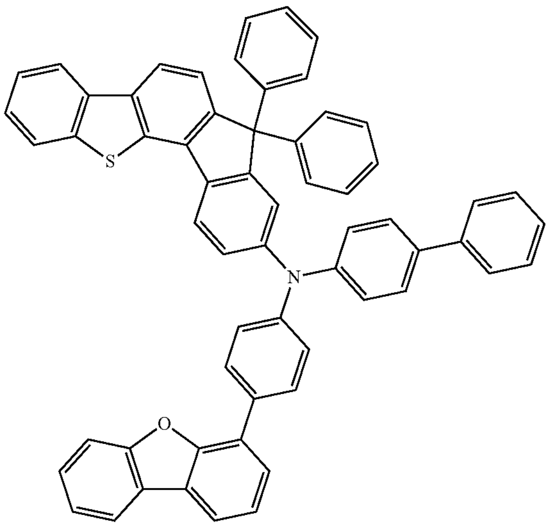
-continued
[F-11]
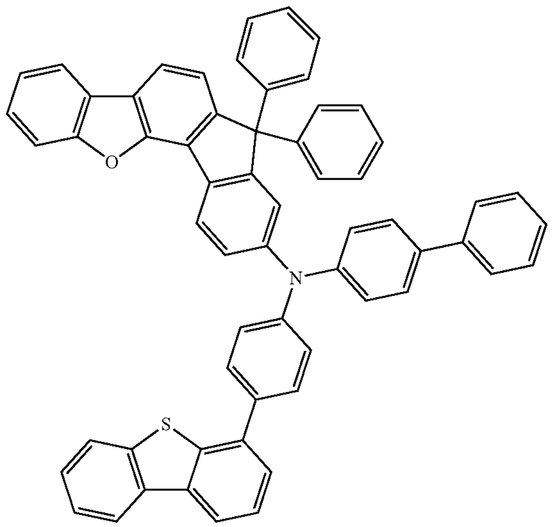
[F-12]
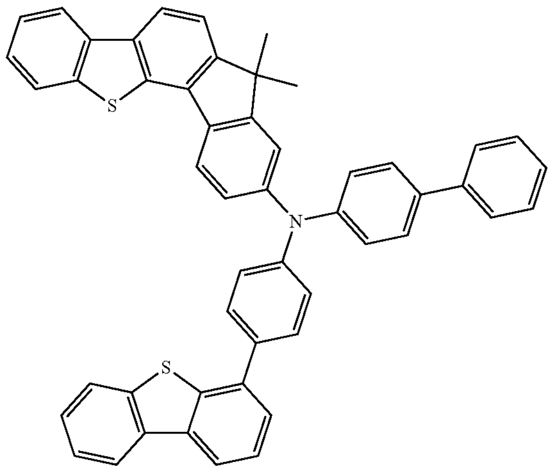
[F-13]
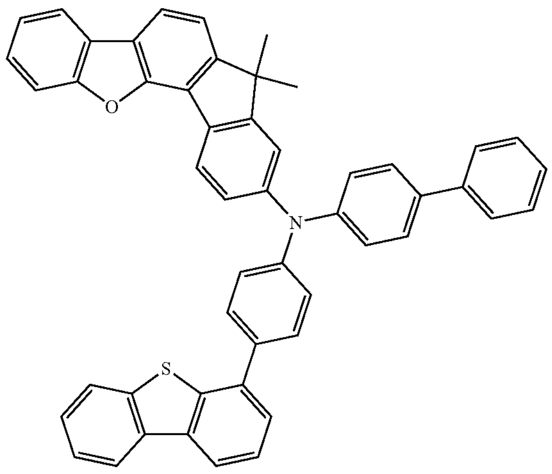

-continued
[F-14]
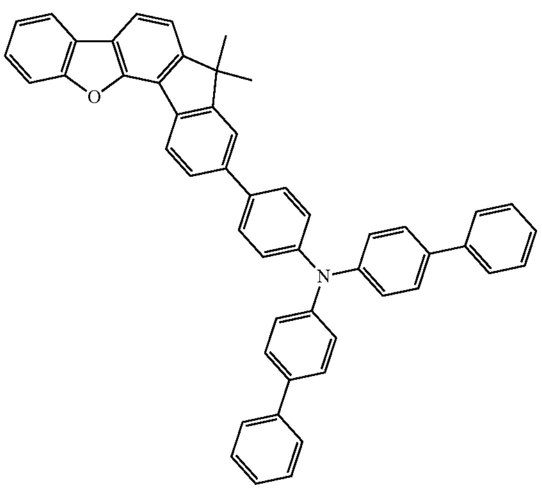
[F-15]
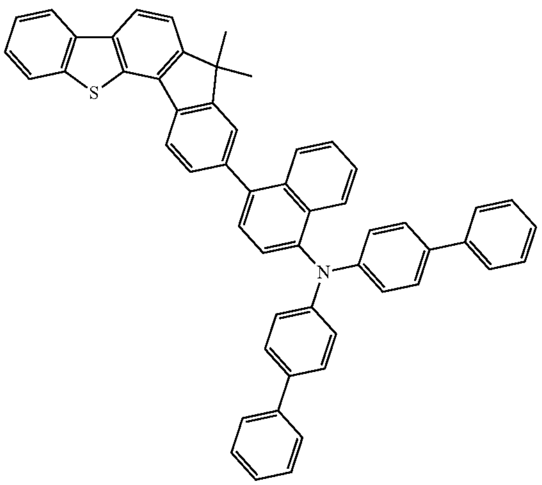
[F-16]
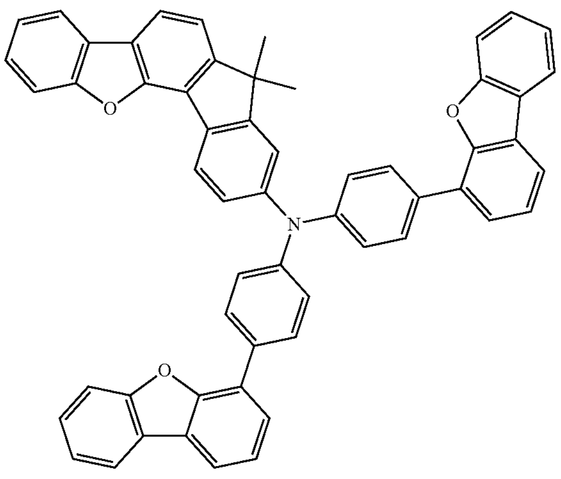
-continued
[F-17]
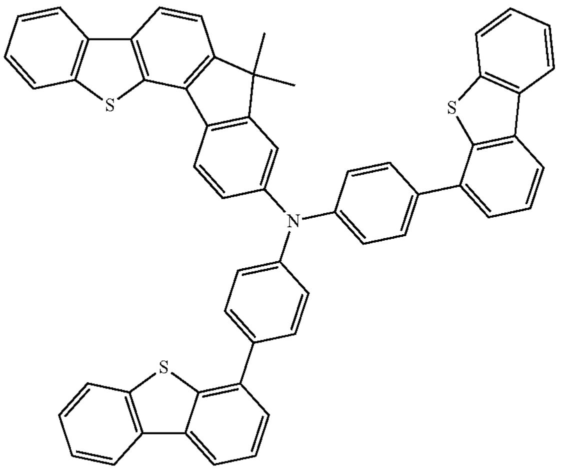
[F-18]
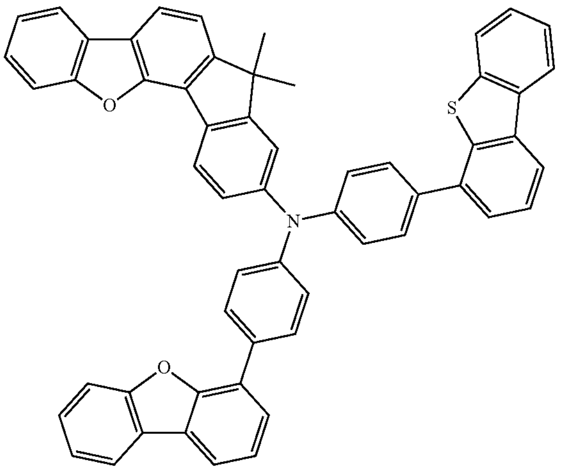
[F-19]
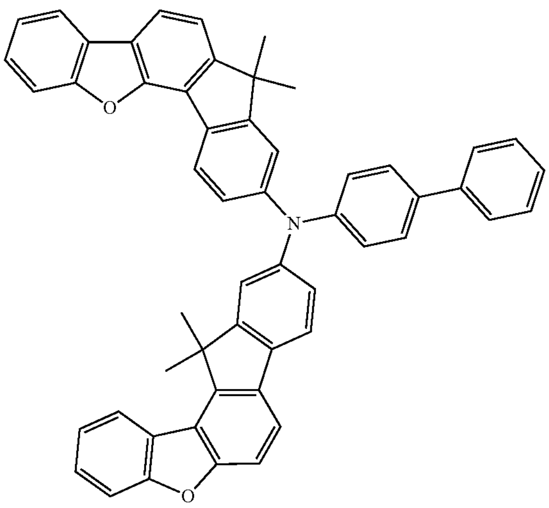

-continued
[F-20]
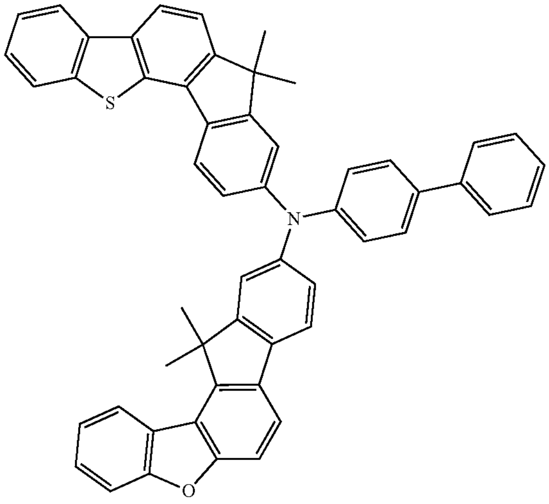
[F-21]
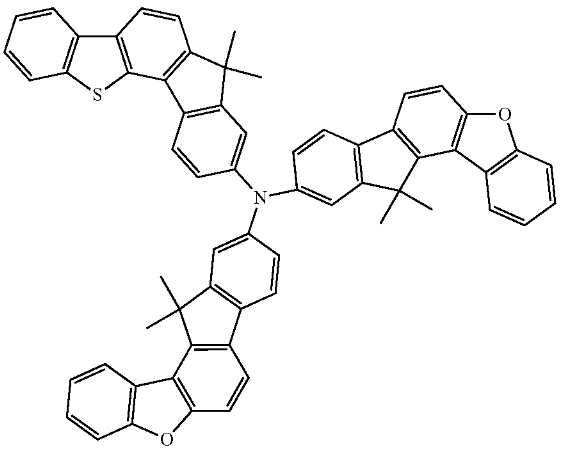
[F-22]
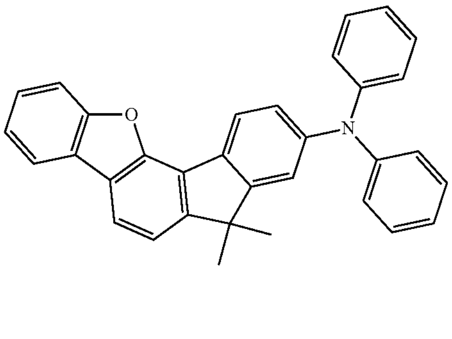
-continued
[F-23]
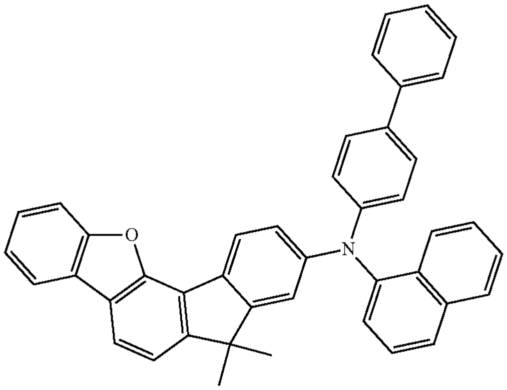
[F-24]
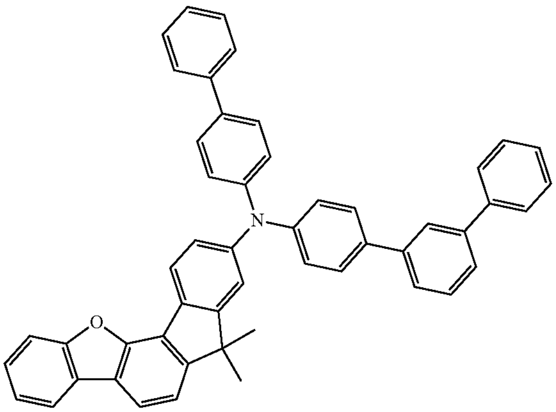
[F-25]
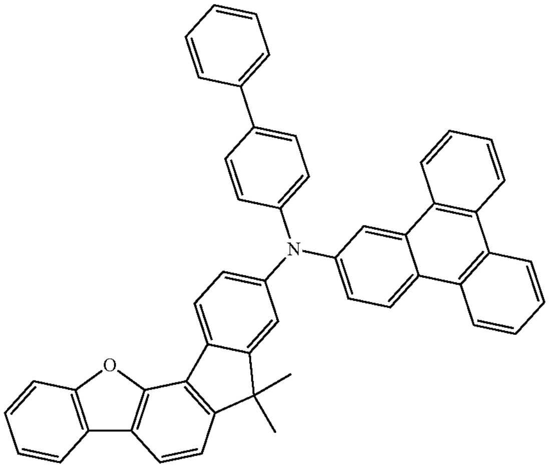
[F-26]
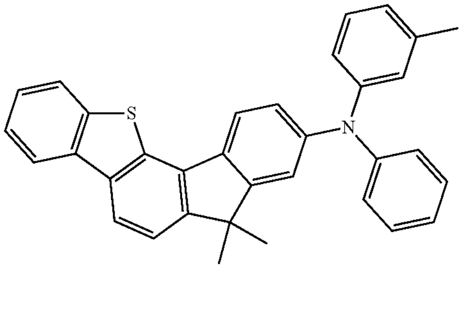

-continued
[F-27]
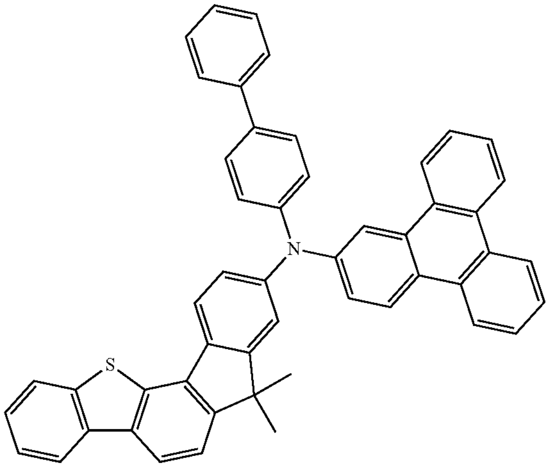
[F-28]
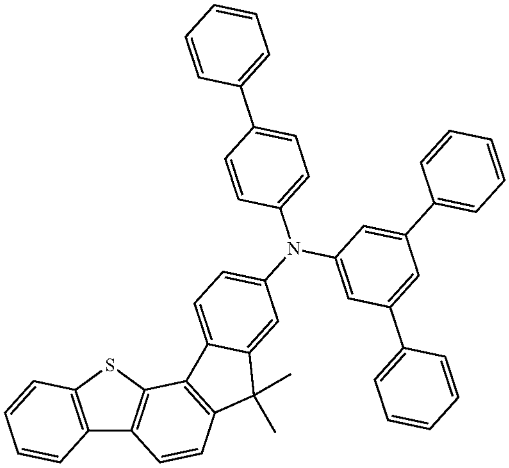
[F-29]
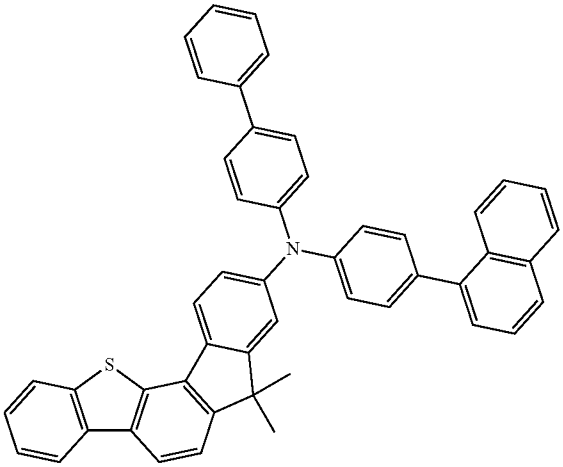
-continued
[F-30]
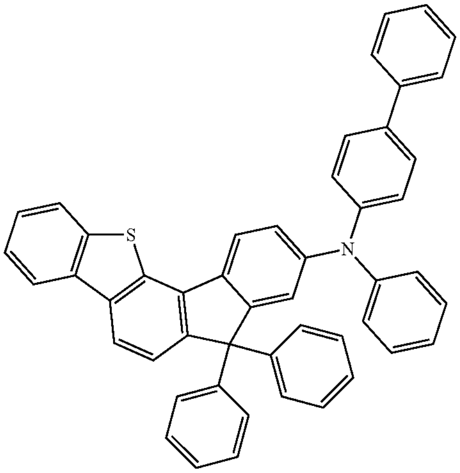
[F-31]
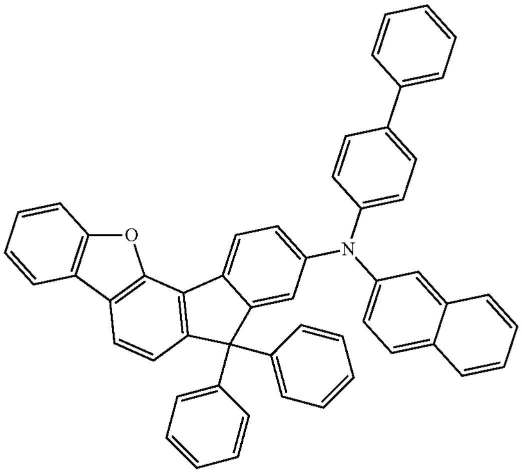
[F-32]
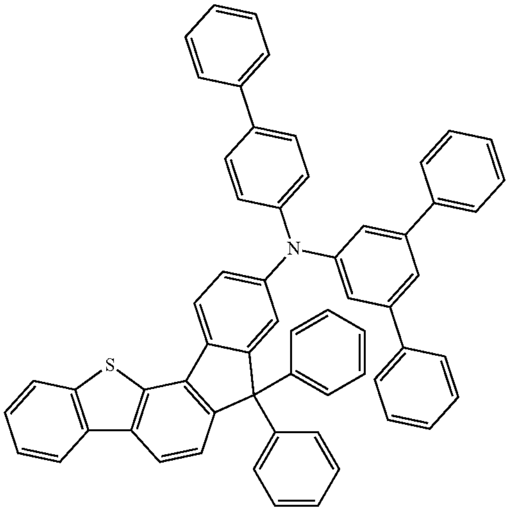

-continued
[F-33]
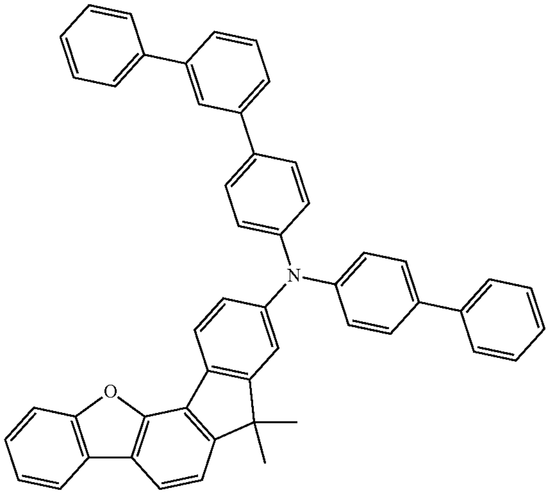
[F-34]
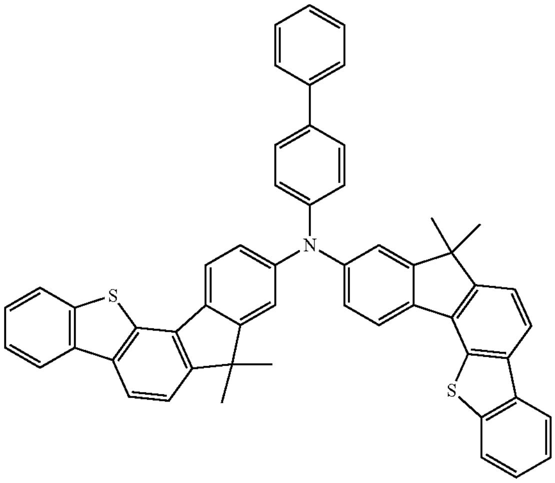
[F-35]
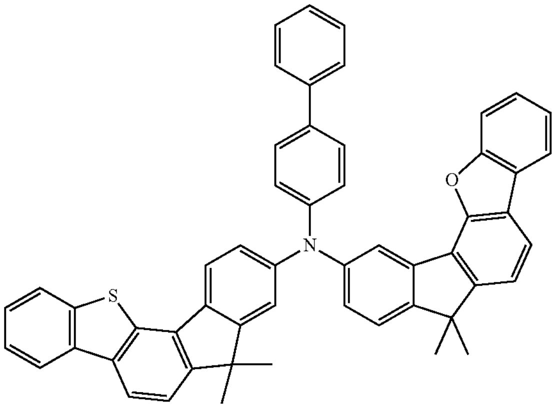
-continued
[F-36]
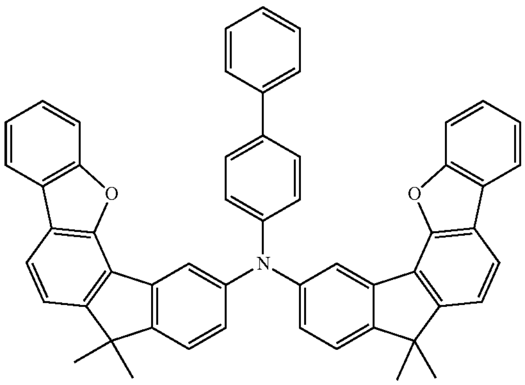
[F-37]
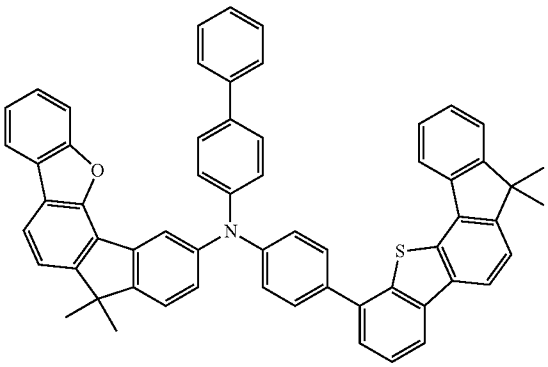
[G-1]
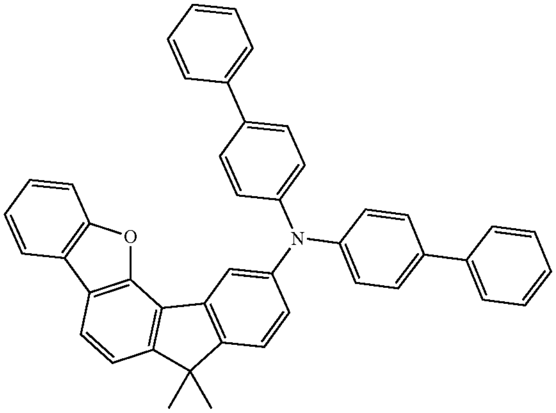
[G-2]
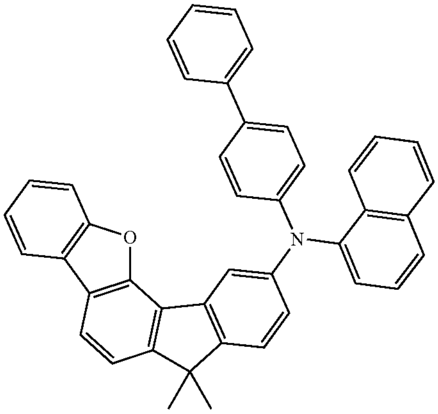

-continued
[G-3]
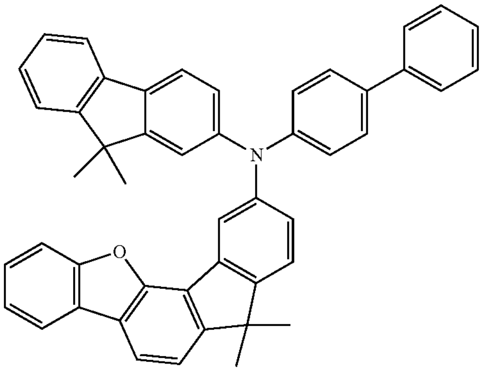
[G-4]
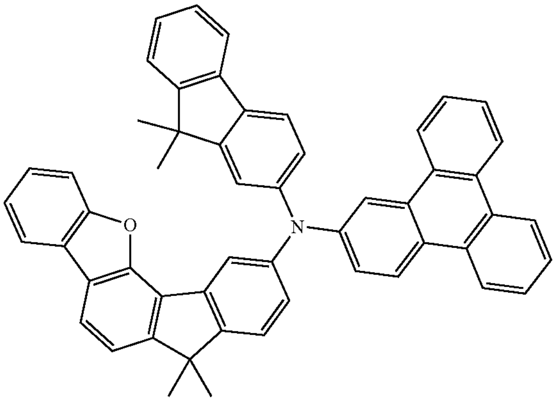
[G-5]
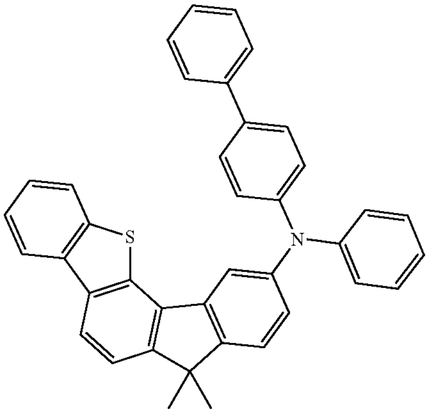
[G-6]
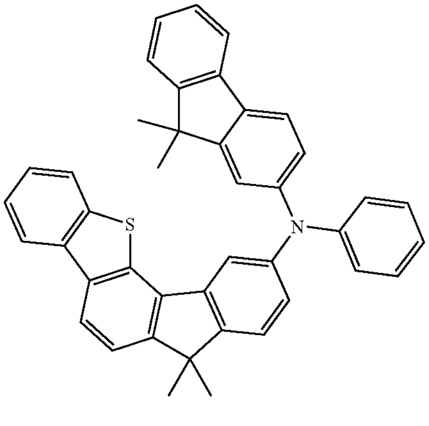
-continued
[G-7]
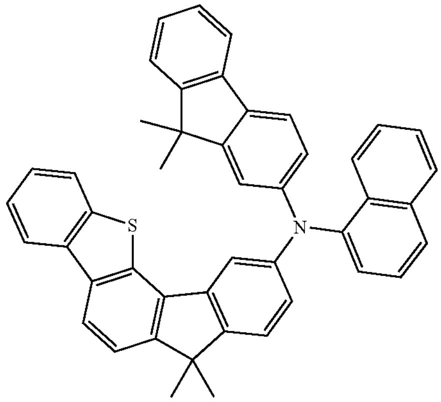
[G-8]
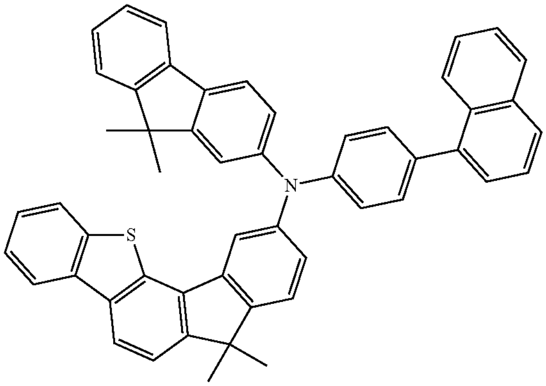
[G-9]
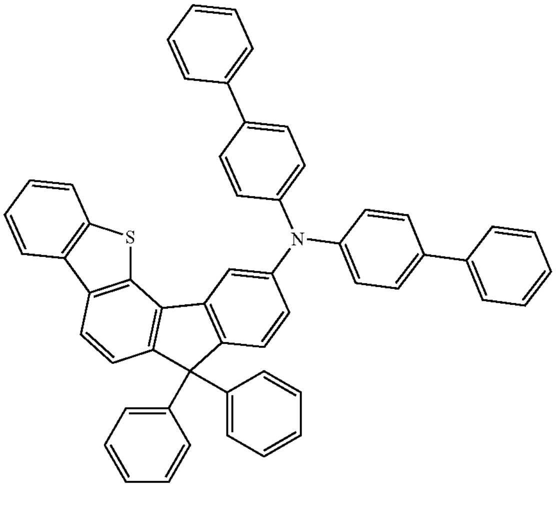

-continued
[G-10]
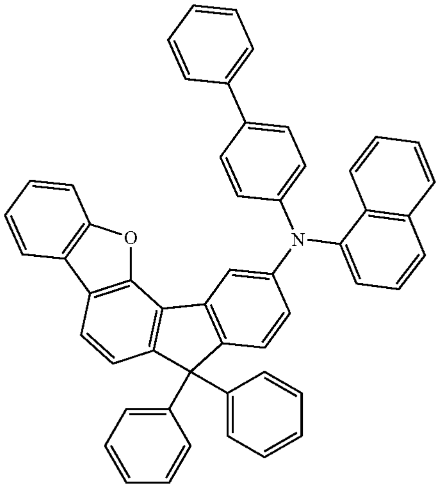
[G-11]
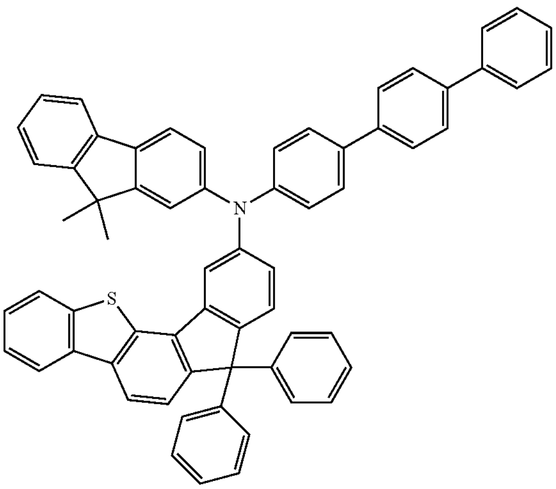
[G-12]
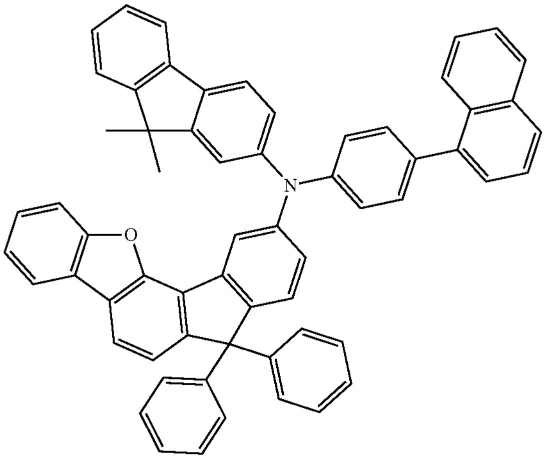
-continued
[G-13]
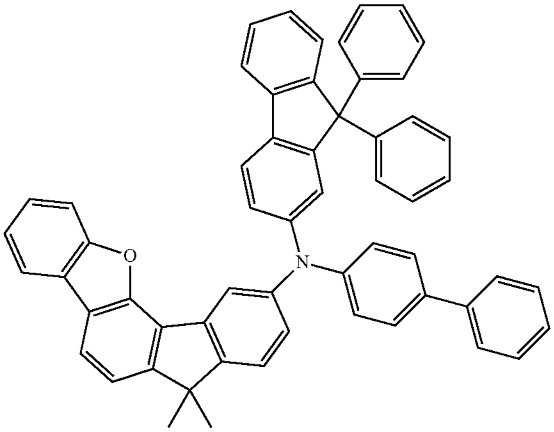
[G-14]
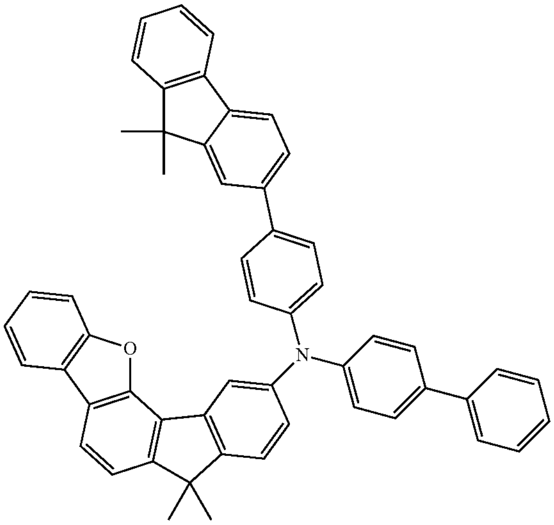
[G-15]
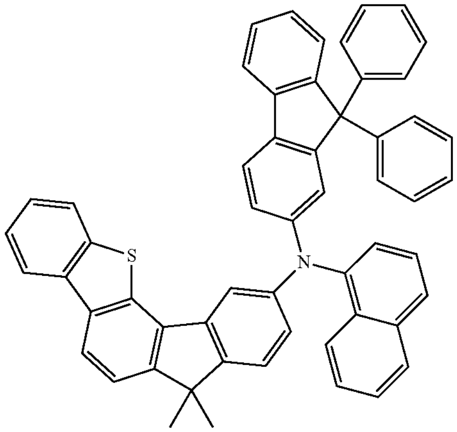

-continued
[G-16]
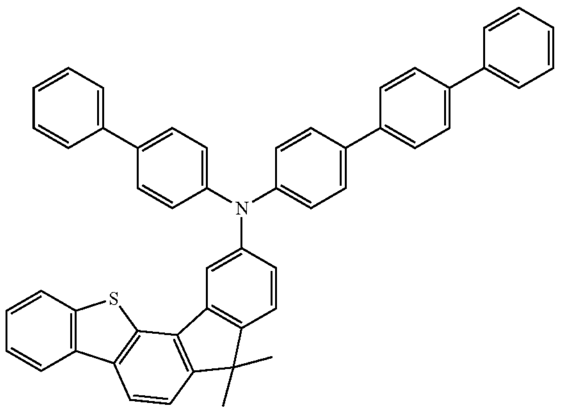
[G-17]
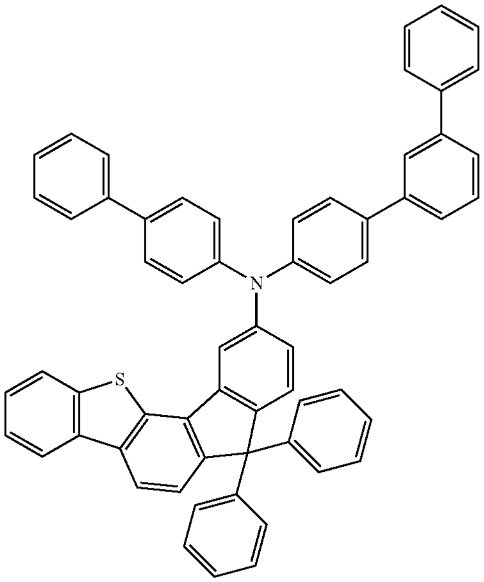
[G-18]
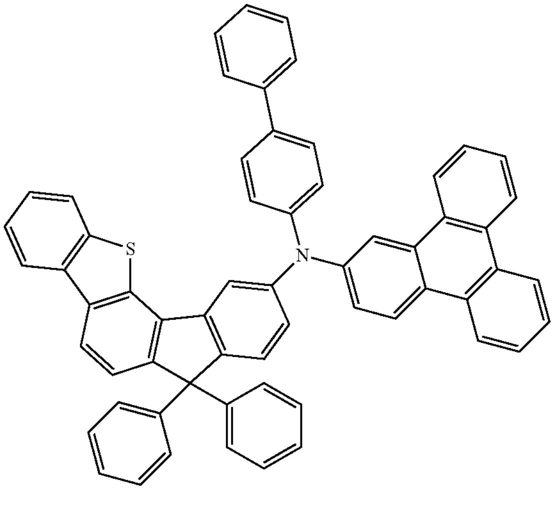
-continued
[G-19]
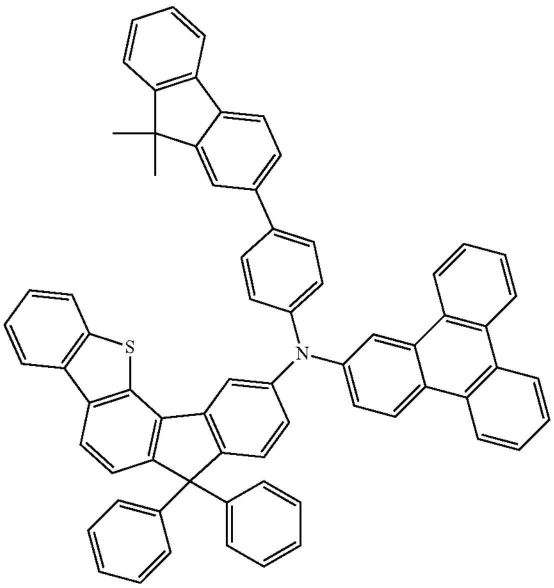
[G-20]
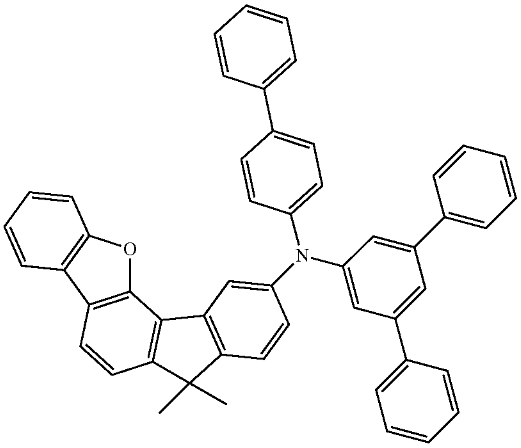
[G-21]
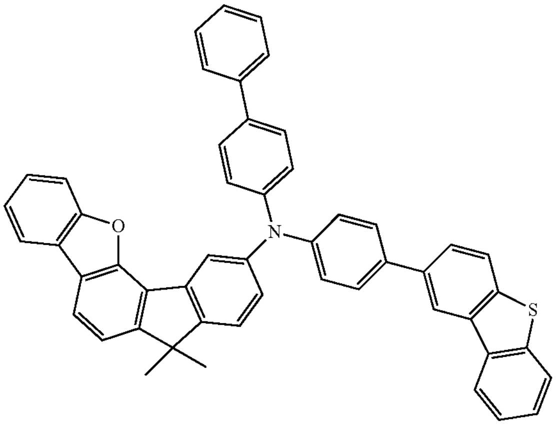

-continued
[G-22]
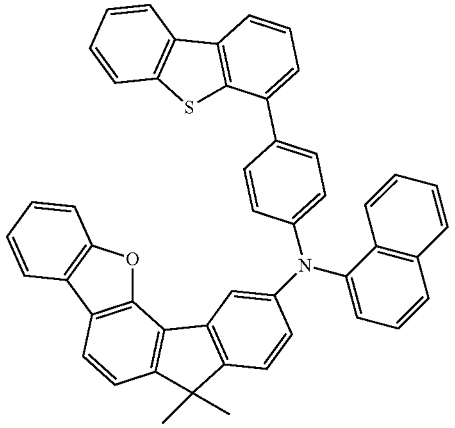
[G-23]
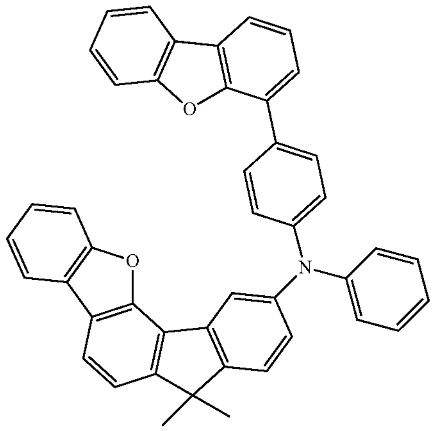
[G-24]
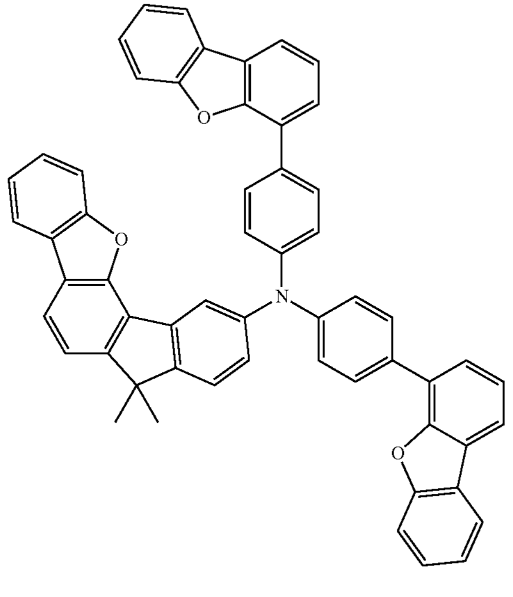
-continued
[G-25]
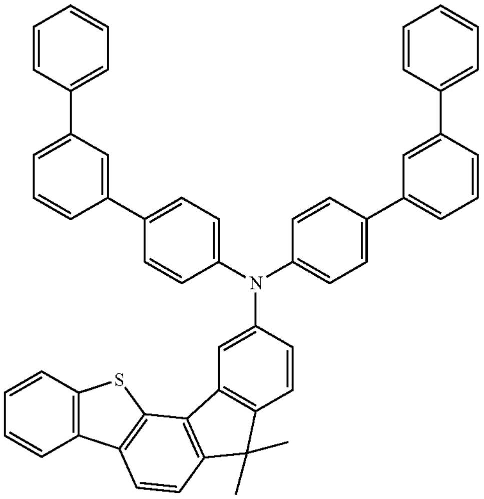
[G-26]
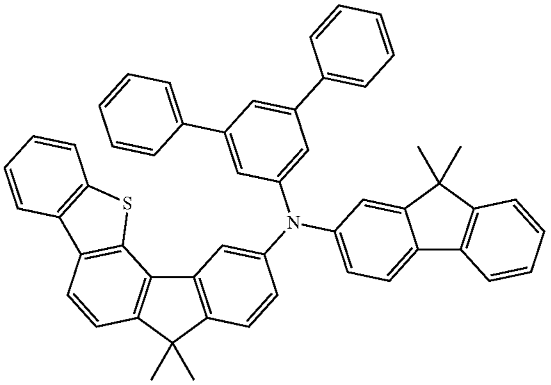
[G-27]
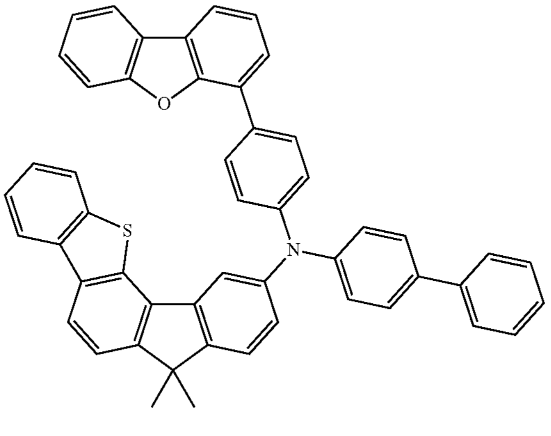

-continued

[G-28]

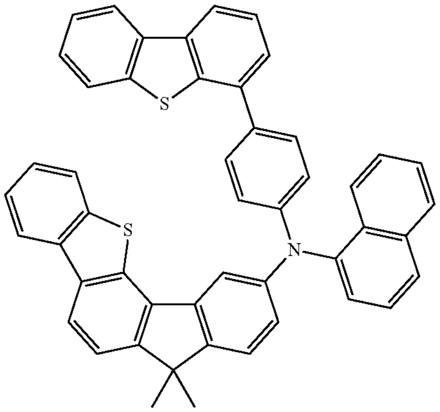

[G-29]

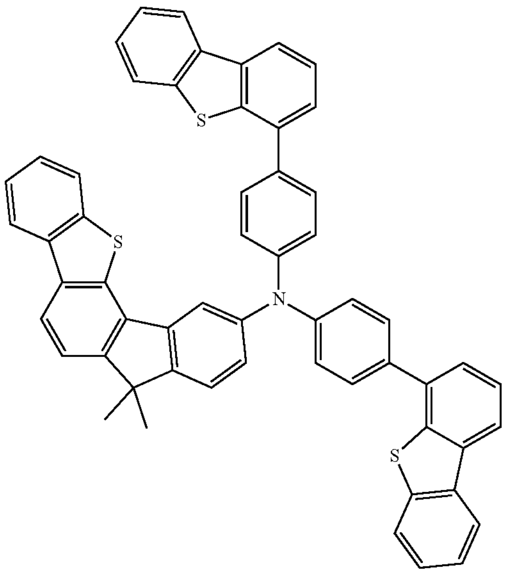

[G-30]

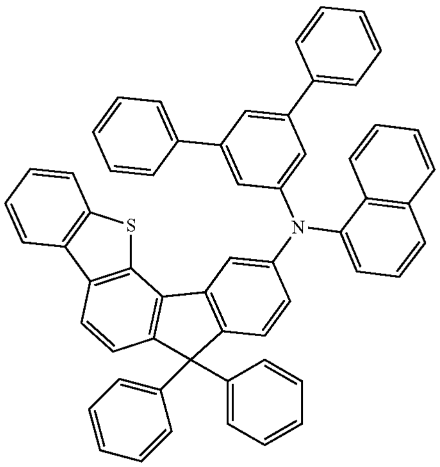

-continued

[G-31]

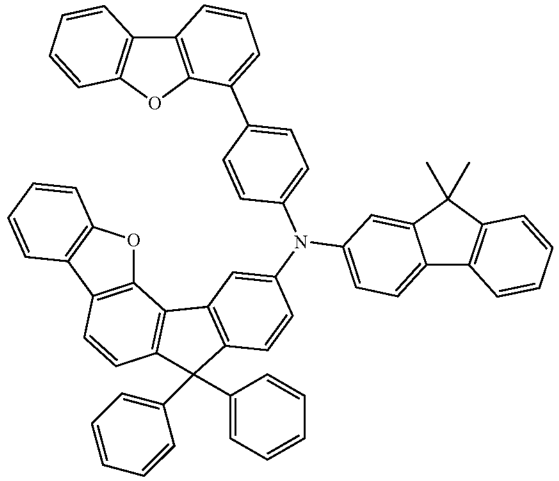

[G-32]

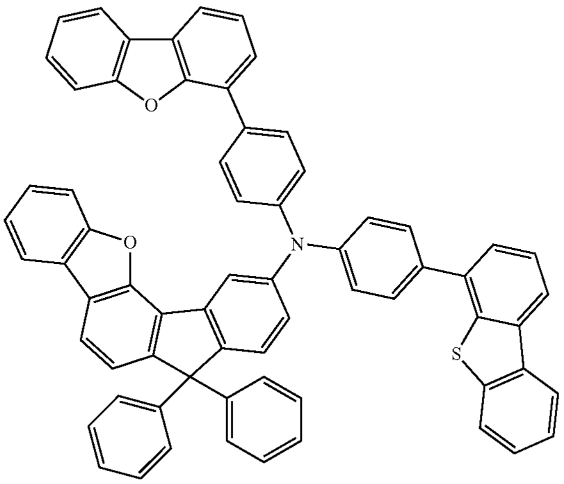

[G-33]

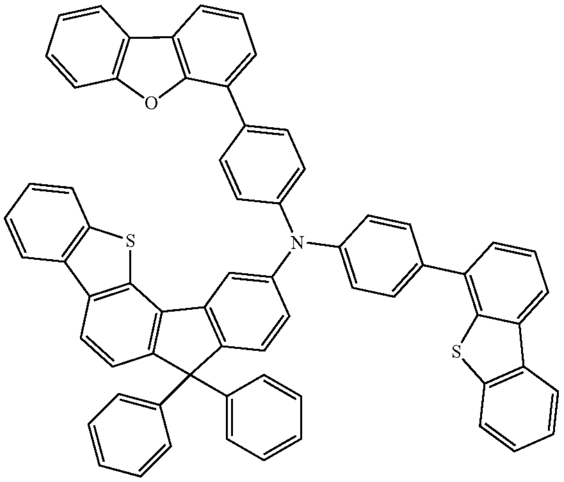

An organic optoelectronic device according to an embodiment of the present invention may include an auxiliary electron transport layer including the first compound having strong electron characteristics and an auxiliary hole transport layer including the second compound having hole transport characteristics which is capable of adjusting hole injection characteristics by reducing a HOMO energy level difference between the hole transport layer 31 and the light-emitting layer 32 simultaneously.

When these are used together, efficiency may be improved by adjusting a charge balance through hole injection-adjusting capability of the auxiliary hole transport layer and electron injection-adjusting capability of the auxiliary electron transport layer, and a life-span may be also improved by applying the hole and auxiliary electron transport layers and thus, preventing accumulation of charges on each interface of the organic layers and accordingly, reducing degradation of a device and stabilizing it.

Specifically, the auxiliary electron transport layer may include at least one of the first compound represented by Chemical Formula 1-IV or Chemical Formula 1-VII and the auxiliary hole transport layer may include at least one of the second compound represented by Chemical Formula 2-1 or Chemical Formula 2-2.

In one example of the present invention, the auxiliary electron transport layer may include at least one of the first compound represented by Chemical Formula 1-IV or Chemical Formula 1-VII and the auxiliary hole transport layer may include at least one of the second compound represented by Chemical Formula y or Chemical Formula z.

The auxiliary hole transport layer 33 and the auxiliary electron transport layer 35 may be coated on the hole transport layer by a deposition or inkjet process with a thickness of 0.1 nm to 20.0 nm, for example 0.2 nm to 10.0 nm, 0.3 nm to 5 nm, 0.3 nm to 2 nm, or 0.4 nm to 1.0 nm.

The organic layer 30 may further include a hole injection layer 37 between the anode 10 and the hole transport layer 31 and/or an electron injection layer 36 between the cathode 20 and the electron transport layer 34 as needed.

In an organic optoelectronic device according to one example of the present invention, the auxiliary hole transport layer may contact the hole transport layer and the light-emitting layer respectively and the auxiliary electron transport layer may contact the electron transport layer and the light-emitting layer.

In an example of the present invention, the light-emitting layer may further include a dopant, for example, a phosphorescent dopant, a fluorescent dopant, and the like.

In an embodiment, the organic optoelectronic device may be selected from an organic light emitting diode, an organic photoelectric device, an organic solar cell, an organic transistor, an organic photo conductor drum, and an organic memory device.

The organic light emitting diode may be applied to an organic light emitting display device.

Hereinafter, the embodiments are illustrated in more detail with reference to examples. These examples, however, are not in any sense to be interpreted as limiting the scope of the invention.

Hereinafter, starting materials and reactants used in Synthesis Examples and Examples were purchased from Sigma-Aldrich Corporation or TCI Inc. unless there was particularly mentioned.

Synthesis of First Compound

Synthesis Example 1: Synthesis of Intermediate I-1

[Reaction Scheme 1]

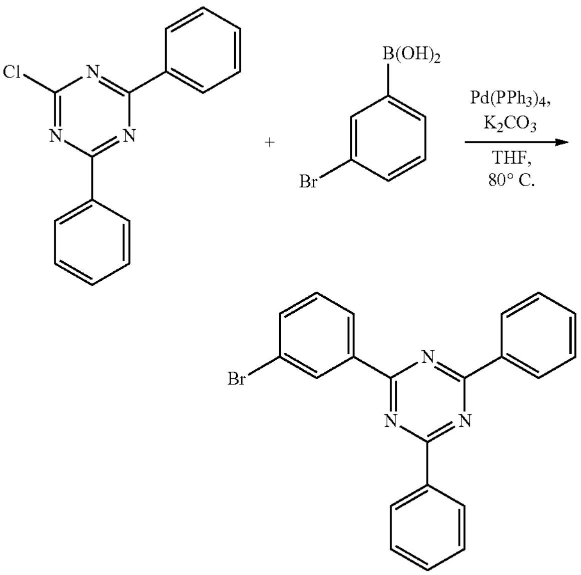

I-1

The compound, 2-chloro-4,6-diphenyl-1,3,5-triazine (50 g, 187 mmol, TCI Inc.) was dissolved in THF (1 L) under a nitrogen environment, (3-bromophenyl)boronic acid (45 g, 224.12 mmol, TCI Inc.) and tetrakis(triphenylphosphine) palladium (2.1 g, 1.87 mmol) were added thereto, and the mixture was stirred. Potassium carbonate saturated in water (64 g, 467 mmol) was added thereto, and the obtained mixture was heated and refluxed at 80° C. for 12 hours. When the reaction was complete, water was added to the reaction solution, and the mixture was extracted with dichloromethane (DCM), filtered after removing moisture with anhydrous $MgSO_4$, and concentrated under a reduced pressure. The obtained residue was separated and purified through column chromatography to obtain Intermediate I-1 (69 g and 95%).

HRMS (70 eV, EI+): m/z calcd for $C_{21}H_{14}BrN_3$: 387.0371, found: 387.

Elemental Analysis: C, 65%; H, 4%

Synthesis Example 2: Synthesis of Intermediate I-2

[Reaction Scheme 2]

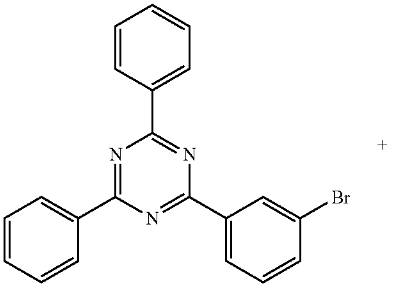

I-1

-continued

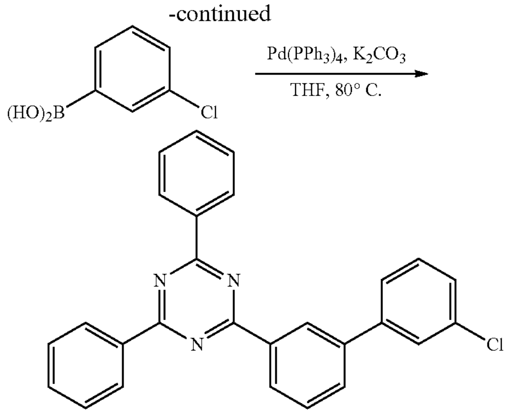

I-2

Intermediate I-2 (51 g, 95%) was obtained according to the same synthesis method as the method of synthesizing and purifying Intermediate I-1 by using Intermediate I-1 and 3-chlorophenyl boronic acid (TCI Inc.).

HRMS (70 eV, EI+): m/z calcd for $C_{27}H_{18}ClN_3$: 419.1189, found: 419.

Elemental Analysis: C, 77%; H, 4%

Synthesis Example 3: Synthesis of Intermediate I-3

[Reaction Scheme 3]

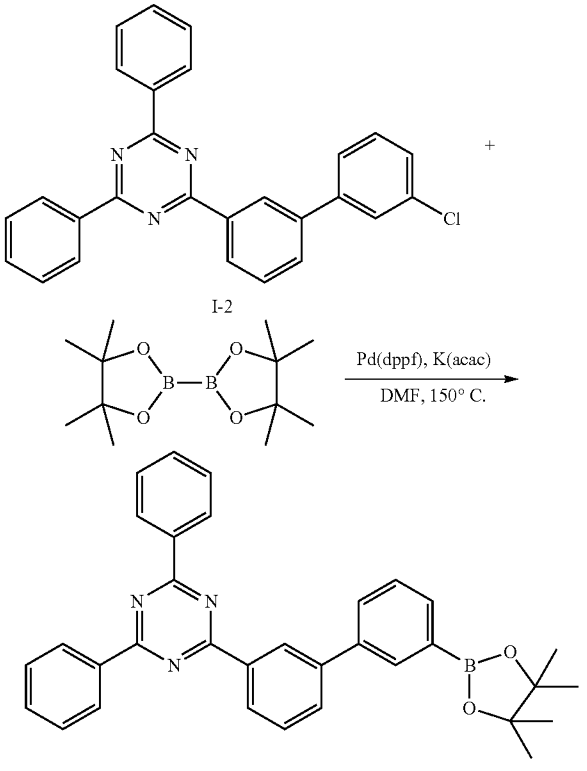

I-2

I-3

Intermediate I-2 (100 g, 238 mmol) was dissolved in dimethylformamide (DMF, 1 L) under a nitrogen environment, bis(pinacolato)diboron (72.5 g, 285 mmol, Sigma Aldrich Co., Ltd.), (1,1'-bis(diphenylphosphine)ferrocene)

dichloropalladium (II) (2 g, 2.38 mmol), and potassium acetate (58 g, 595 mmol) were added thereto, and the mixture was heated and refluxed at 150° C. for 48 hours. When the reaction was complete, water was added to the reaction solution, and the mixture was filtered and dried in a vacuum oven. The obtained residue was separated and purified through column chromatography to obtain Intermediate I-3 (107 g, 88%).

HRMS (70 eV, EI+): m/z calcd for $C_{33}H_{30}BN_3O_2$: 511.2431, found: 511.

Elemental Analysis: C, 77%; H, 6%

Synthesis Example 4: Synthesis of Intermediate I-4

[Reaction Scheme 4]

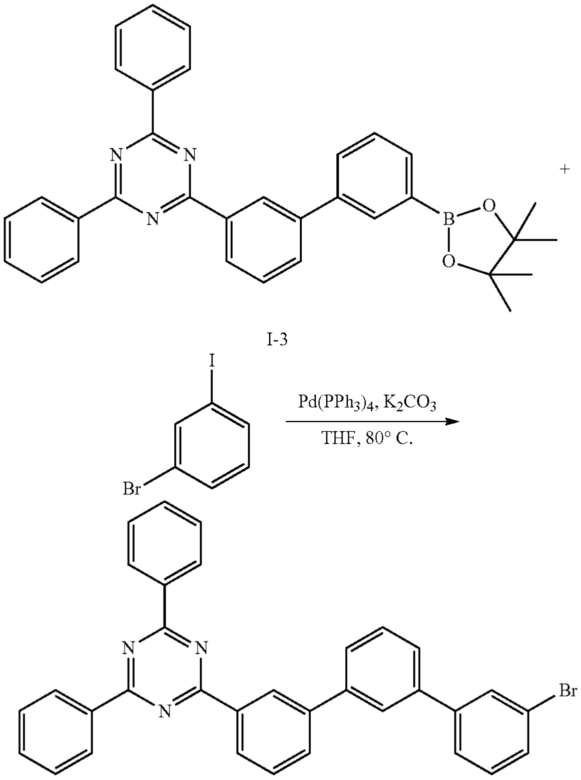

I-3

I-4

Intermediate I-3 (50 g, 98 mmol) was dissolved in THF (1 L) under a nitrogen environment, 1-bromo-3-iodobenzene (33 g, 117 mmol, Sigma Aldrich Co., Ltd.) and tetrakis (triphenylphosphine)palladium (1 g, 0.98 mmol) were added thereto, and the mixture was stirred. Potassium carbonate saturated in water (34 g, 245 mmol) was added thereto, and the obtained mixture was heated and refluxed at 80° C. for 12 hours. When the reaction was complete, water was added to the reaction solution, and the mixture was extracted with dichloromethane (DCM), filtered after removing moisture with anhydrous $MgSO_4$, and concentrated under a reduced pressure. This obtained residue was separated and purified through column chromatography to obtain Intermediate I-4 (50 g and 95%).

HRMS (70 eV, EI+): m/z calcd for $C_{30}H_{27}BO_2$: 539.0997, found: 539.

Elemental Analysis: C, 73.34; H, 4.10

Synthesis Example 5: Synthesis of Intermediate I-5

[Reaction Scheme 5]

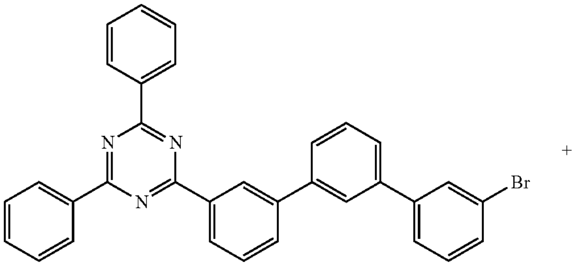

I-4

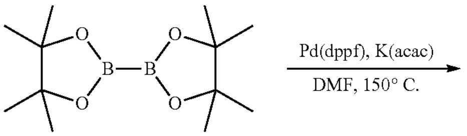

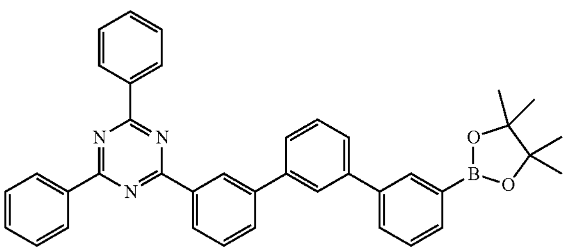

I-5

95 g (88%) of Intermediate I-5 was obtained by synthesis and purification in the same method as Intermediate I-3.

HRMS (70 eV, EI+): m/z calcd for $C_{39}H_{34}BN_3O_2$: 587.2744, found: 587.

Elemental Analysis: C, 80%; H, 6%

Synthesis Example 6: Synthesis of Intermediate I-10

[Reaction Scheme 6]

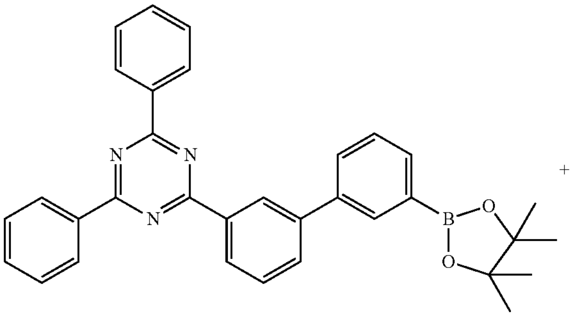

I-3

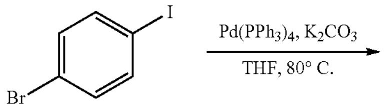

-continued

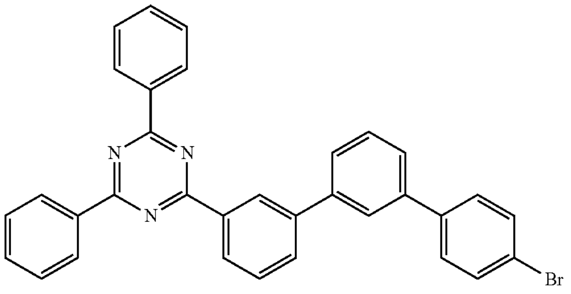

I-10

50 g (95%) of Intermediate I-10 was obtained by synthesis and purification in the same method as Intermediate I-4.

HRMS (70 eV, EI+): m/z calcd for $C_{30}H_{27}BO_2$: 539.0997, found: 539.

Elemental Analysis: C, 73.34; H, 4.10

Synthesis Example 7: Synthesis of Intermediate I-11

[Reaction Scheme 7]

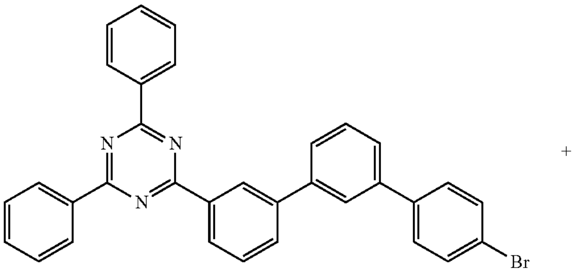

I-10

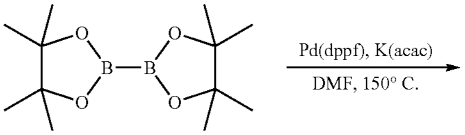

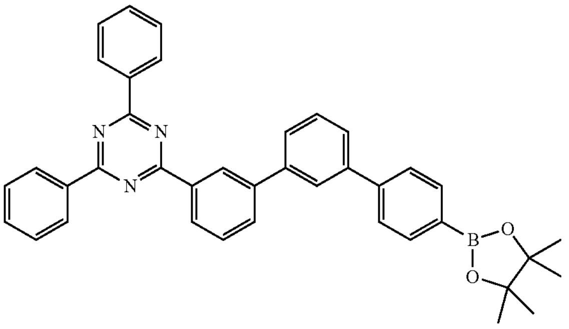

I-11

95 g (88%) of Intermediate I-11 was obtained by synthesis and purification in the same method as Intermediate I-3.

HRMS (70 eV, EI+): m/z calcd for $C_{39}H_{34}BN_3O_2$: 587.2744, found: 587.

Elemental Analysis: C, 80%; H, 6%

Synthesis Example 8: Synthesis of Intermediate I-27

[Reaction Scheme 8]

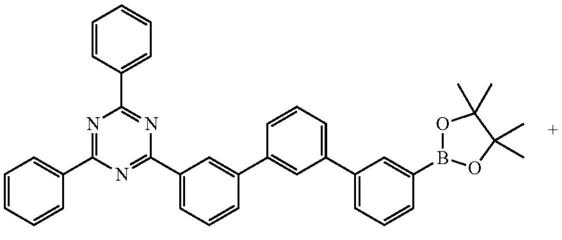

I-5

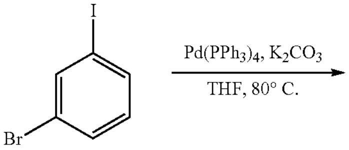

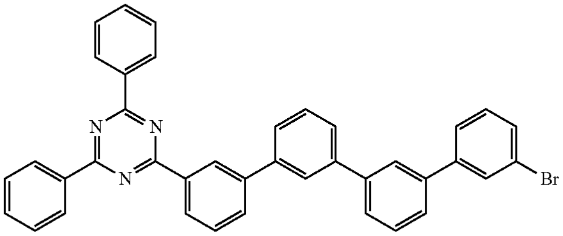

I-27

50 g (95%) of Intermediate I-27 was obtained by synthesis and purification in the same method as Intermediate I-4.

HRMS (70 eV, EI+): m/z calcd for $C_{39}H_{26}BrN_3$: 615.1310, found 616.

Elemental Analysis: C, 76%; H, 4%

Synthesis Example 9: Synthesis of Intermediate I-28

[Reaction Scheme 9]

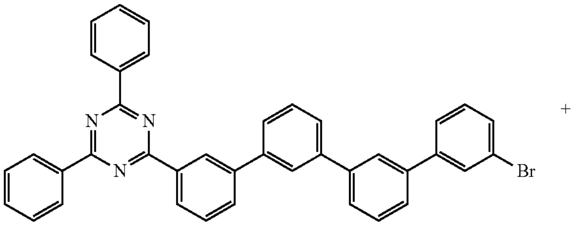

I-27

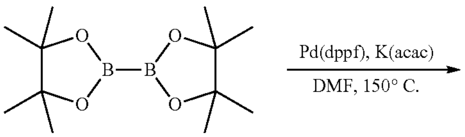

-continued

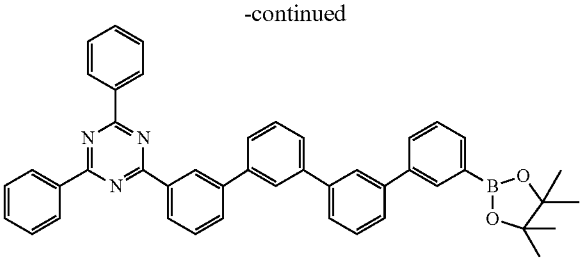

I-28

86 g (80%) of Intermediate I-28 was obtained by synthesis and purification in the same method as Intermediate I-3.

HRMS (70 eV, EI+): m/z calcd for $C_{45}H_{38}BN_3O_2$: 663.3057, found: 663.

Elemental Analysis: C, 81%; H, 6%

Synthesis Example 10: Synthesis of Intermediate I-37

[Reaction Scheme 10]

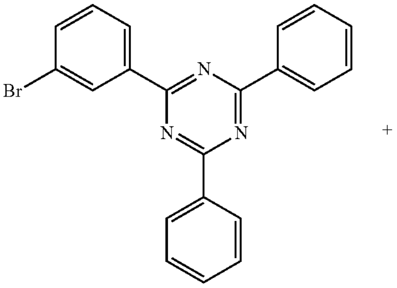

I-1

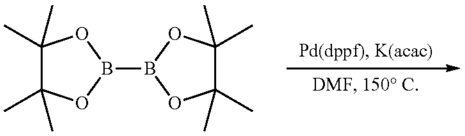

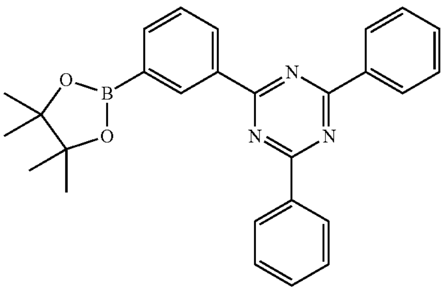

I-37

100 g (89%) of Intermediate I-37 was obtained by synthesis and purification in the same method as Intermediate I-3.

Synthesis Example 11: Synthesis of Intermediate I-38
[Reaction Scheme 11]
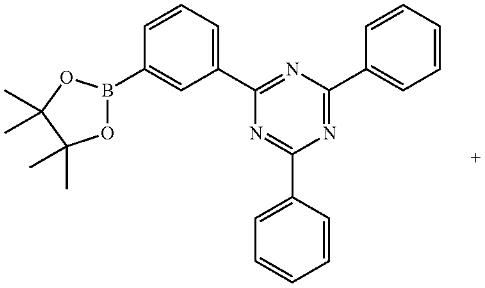
I-37
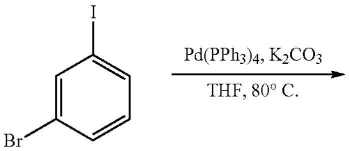
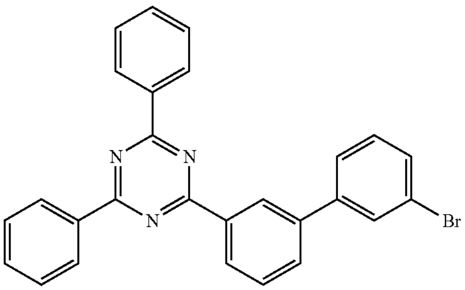
I-38
54 g (73%) of Intermediate I-38 was obtained by synthesis and purification in the same method as Intermediate I-4.
Synthesis Examples 12 to 16: Synthesis of Intermediate Having Pyridine Core
[Reaction Scheme 12]
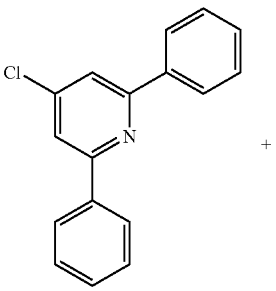
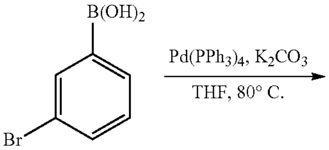
-continued
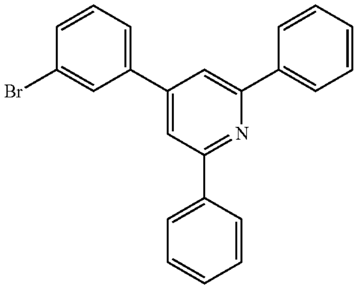
I-12
[Reaction Scheme 13]
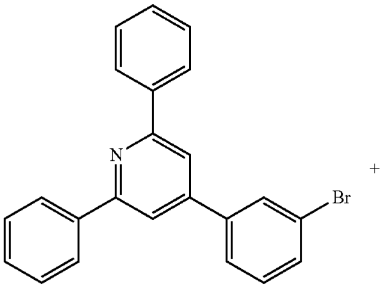
1-12
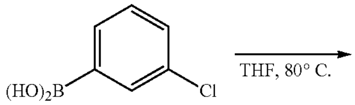
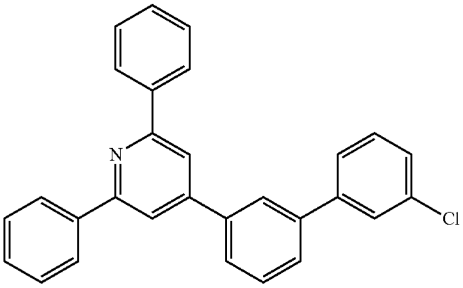
1-13
[Reaction Scheme 14]
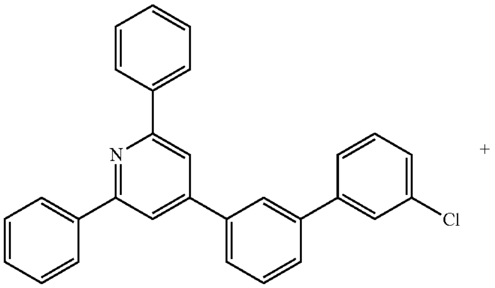
1-13

-continued

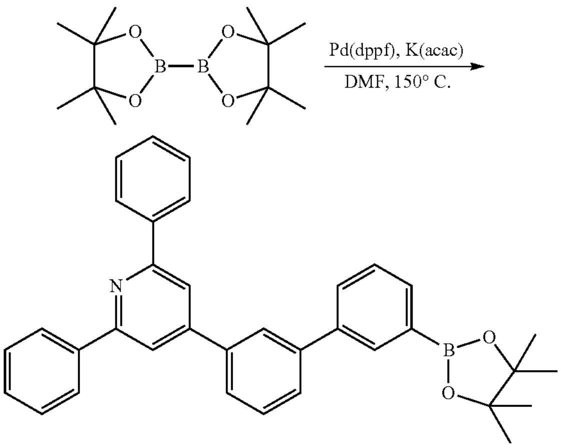

I-14

[Reaction Scheme 15]

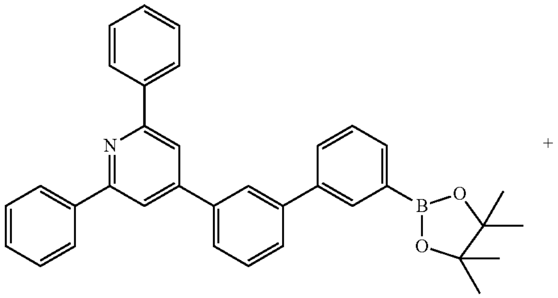

I-14

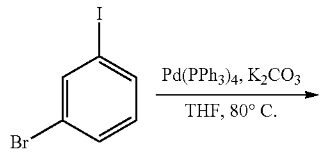

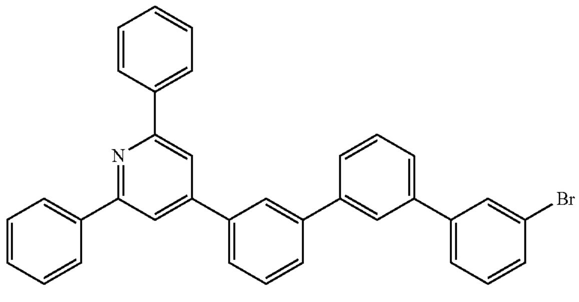

I-15

[Reaction Scheme 16]

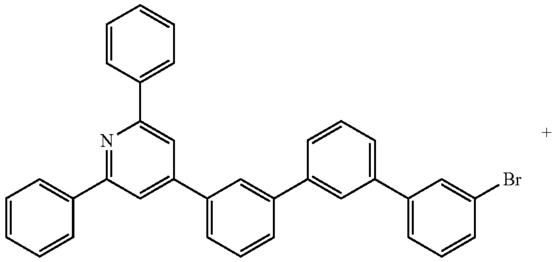

I-15

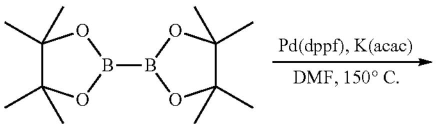

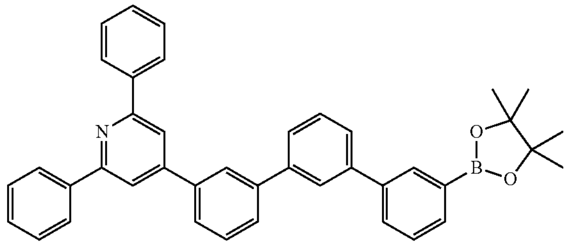

I-16

Intermediate I-12 to Intermediate I-16 were obtained by synthesis and purification in the same method as Intermediate I-1 to Intermediate I-5, Intermediate I-10, and Intermediate I-11 except for using 4-chloro-2,6-diphenylpyridine (TCI) instead of the 2-chloro-4,6-diphenyl-1,3,5-triazine.

Synthesis Examples 17 to 21: Synthesis of Intermediate Having Pyrimidine Core

[Reaction Scheme 17]

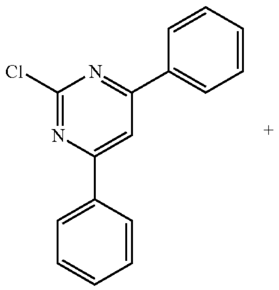

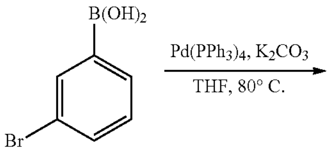

-continued
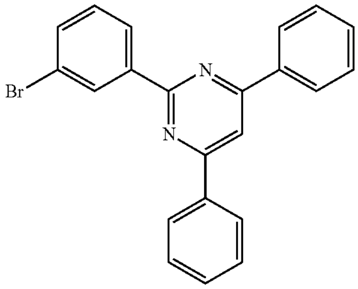
I-17
[Reaction Scheme 18]
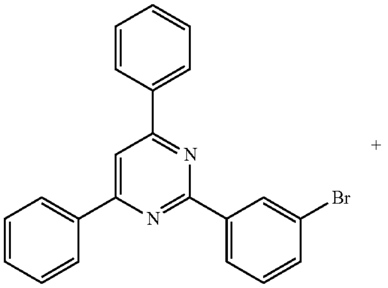
1-17
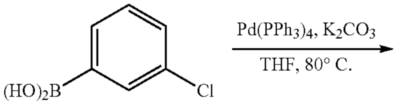
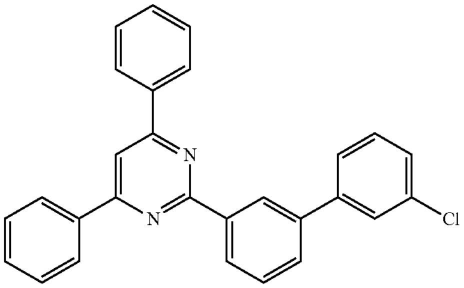
1-18
[Reaction Scheme 19]
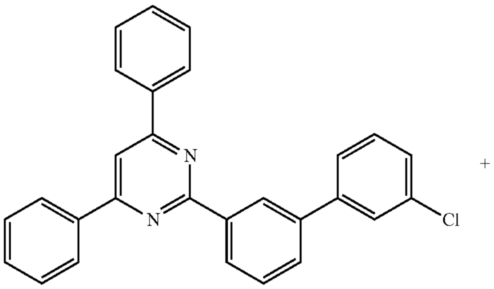
I-18
-continued
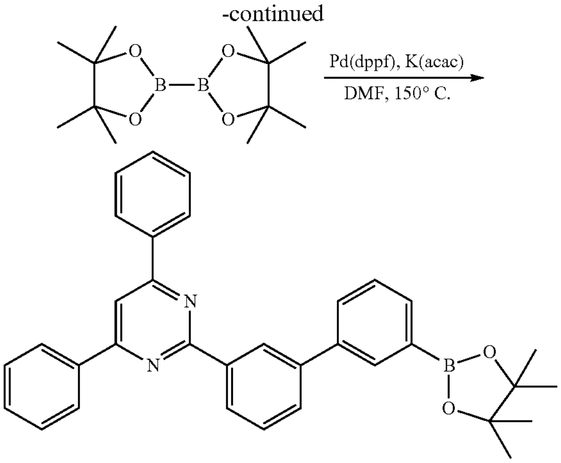
I-19
[Reaction Scheme 20]
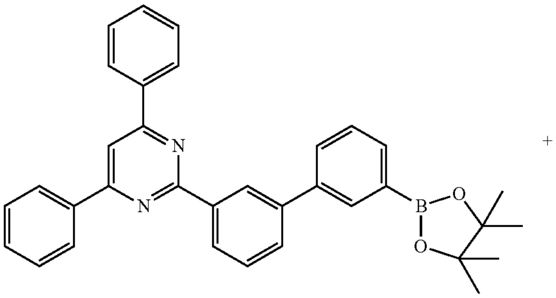
I-19
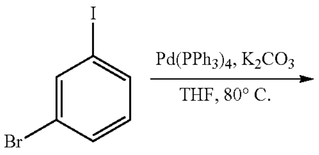
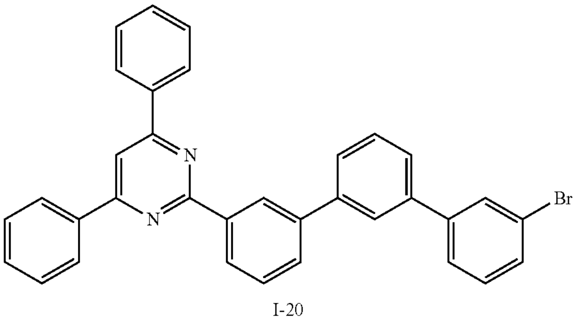
I-20

[Reaction Scheme 21]

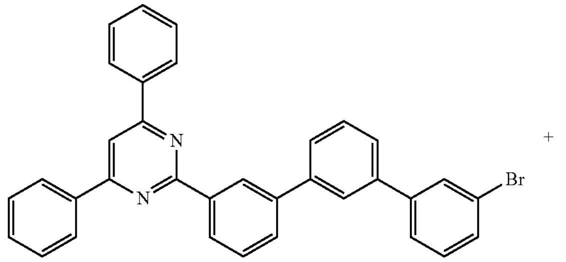

I-20

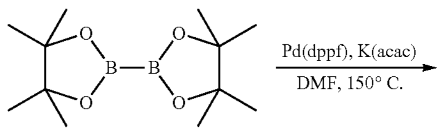

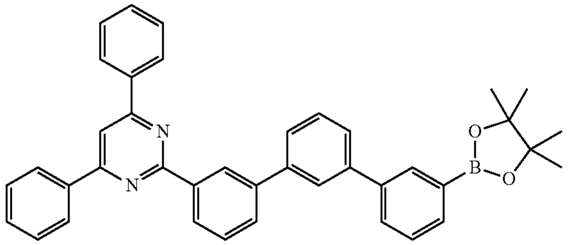

I-21

Intermediate I-17 to Intermediate I-21 were obtained by synthesis and purification in the same method as Intermediate I-1 to Intermediate I-5, Intermediate I-10, and Intermediate I-11 except for using 2-chloro-4,6-diphenyl-1,3-pyrimidine (TCI) instead of the 2-chloro-4,6-diphenyl-1,3,5-triazine.

Synthesis Examples 22 to 26: Synthesis of Intermediate having Phenylene Core

[Reaction Scheme 22]

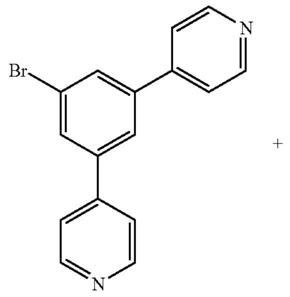

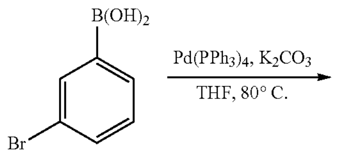

-continued

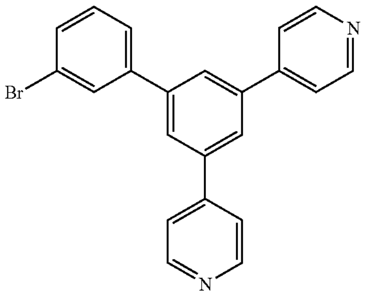

I-22

[Reaction Scheme 23]

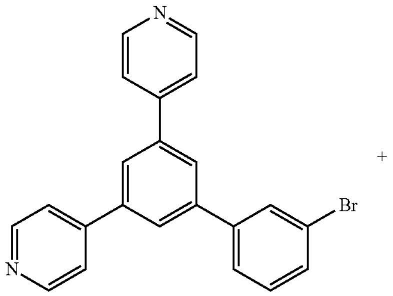

I-22

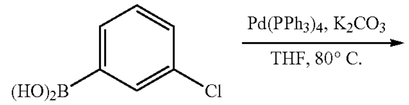

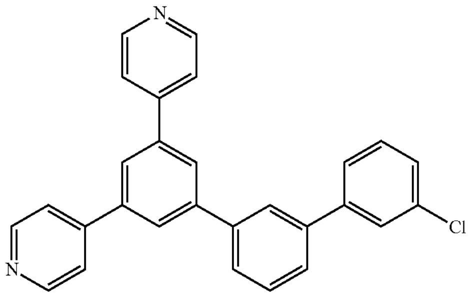

I-23

[Reaction Scheme 24]

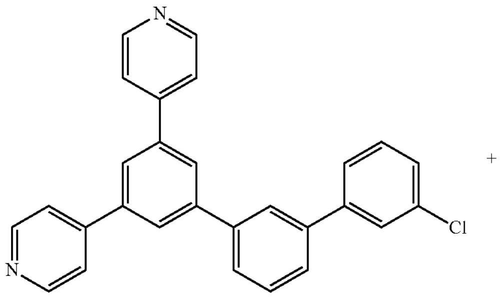

I-23

-continued

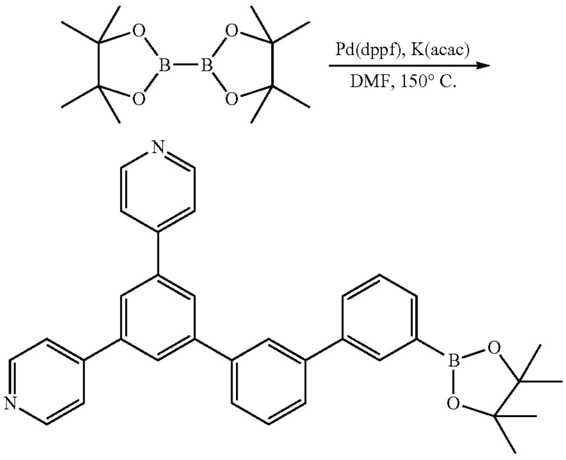

I-24

[Reaction Scheme 25]

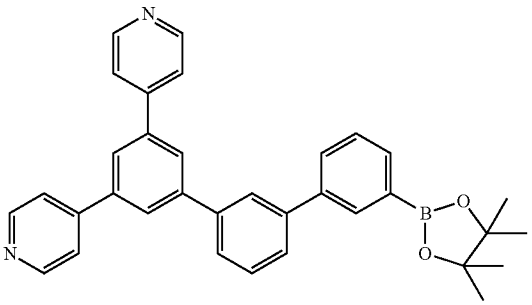

I-24

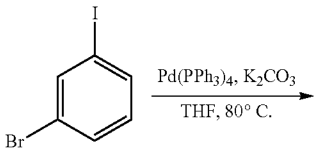

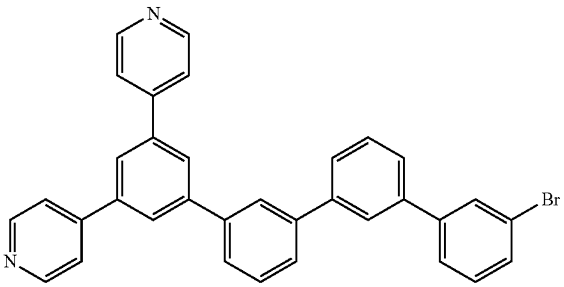

I-25

[Reaction Scheme 26]

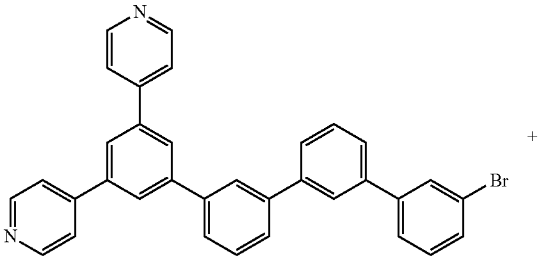

I-25

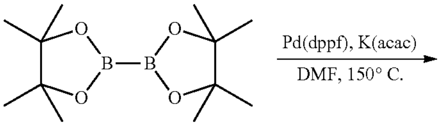

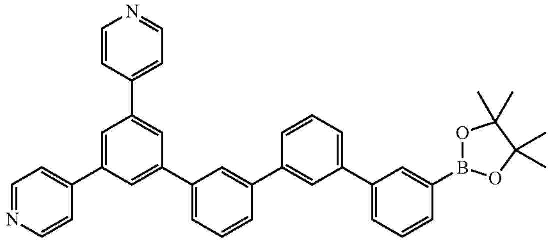

I-26

Intermediate I-22 to Intermediate I-26 were obtained by synthesis and purification in the same method as Intermediate I-1 to Intermediate I-5, Intermediate I-10, and Intermediate I-11 except for using 4,4'-(5-bromo-1,3-phenylene) dipyridine (refer to Example 1 of JP 2008-127326A, CHEMIPROKASEI KAISHA) instead of the 2-chloro-4,6-diphenyl-1,3,5-triazine.

Synthesis Example 27: Synthesis of Intermediate I-39

[Reaction Scheme 27]

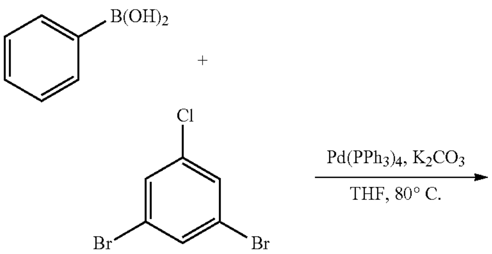

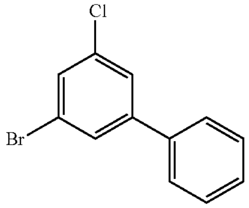

I-39

35 g (57%) of Intermediate I-39 was obtained by synthesis and purification in the same method as Intermediate I-4.

Synthesis Example 28: Synthesis of Intermediate I-40

[Reaction Scheme 28]

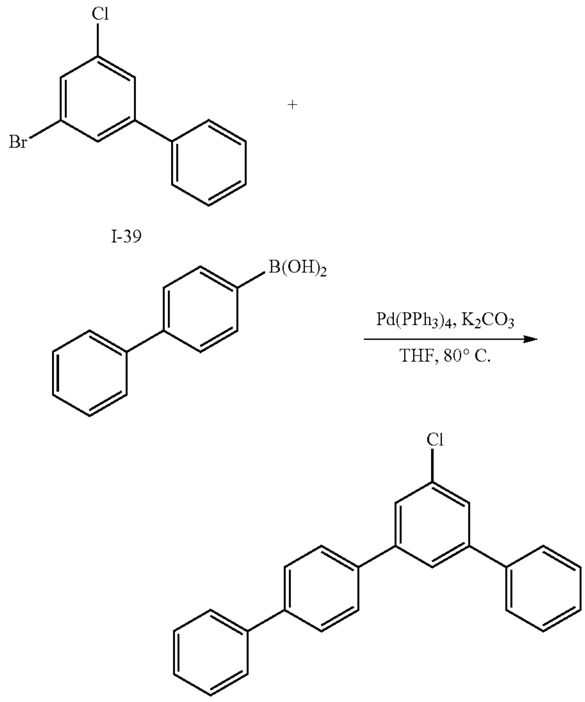

I-39

I-40

44 g (99%) of Intermediate I-40 was obtained by synthesis and purification in the same method as Intermediate I-4.

Synthesis Example 29: Synthesis of Intermediate I-41

[Reaction Scheme 29]

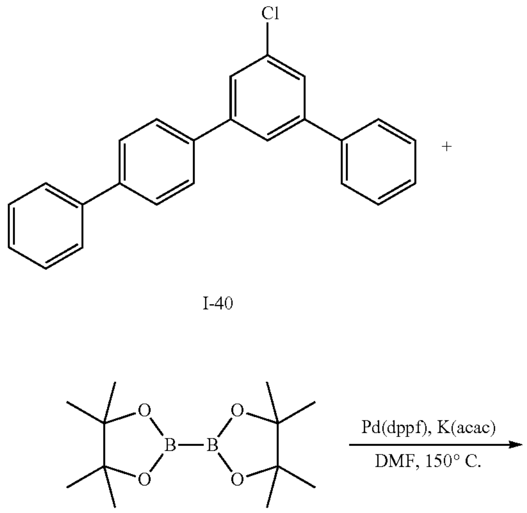

I-40

-continued

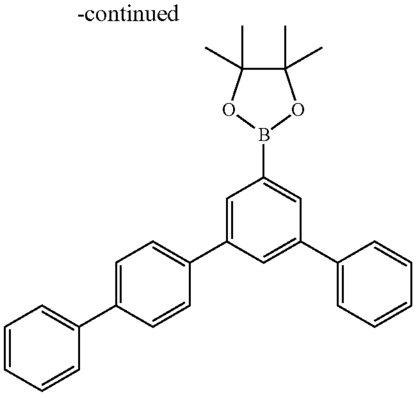

I-41

42 g (72%) of Intermediate I-41 was obtained by synthesis and purification in the same method as Intermediate I-3.

Synthesis Example 30: Synthesis of Intermediate L-1

[Reaction Scheme 30]

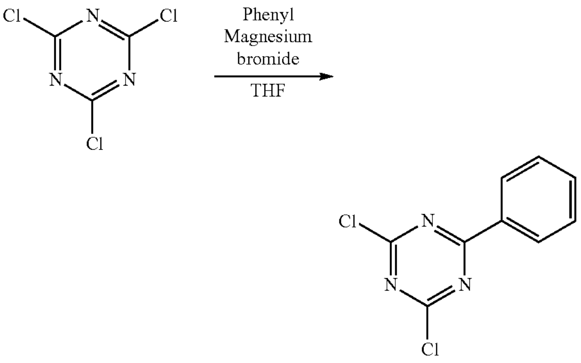

L-1

2,4,6-trichloro-1,3,5-triazine (30 g, 162.68 mmol, Sigma Aldrich Co., Ltd.) was dissolved in a solvent of tetrahydrofuran (325 ml) in a 500 mL flask. Then, phenylmagnesiumbromide (54.23 ml, 162.68 mmol) in a concentration of 3 M was dripped under a nitrogen stream through a dropping funnel, after cooling down the solvent of tetrahydrofuran by using ice water. When the phenyl magnesium bromide was completely added, a reaction was completed by stirring the obtained mixture for 30 minutes. The tetrahydrofuran was separated from water to remove the water and then, removed through a distiller to obtain a solid. The solid was stirred in 100 ml of methanol and then, filtered. The solid was stirred again in hexane and filtered to obtain Intermediate L-1 (27 g, 73%).

calcd. $C_9H_5Cl_2N_3$: C, 47.82; H, 2.23; Cl, 31.37; N, 18.59; found: C, 47.56; H, 2.12; Cl, 31.42; N, 18.43

Synthesis Examples 31 to 32: Synthesis of Intermediate L-7 and Intermediate L-8

Intermediates L-7 and L-8 were obtained according to the same synthesis method as the method of synthesizing Intermediates I-39, I-40, and I-41 according to Synthesis Examples 27 to 29 as specific examples of the compound of the present invention. (Use of three basic reactions: a Suzuki reaction, a Br boration reaction, a Cl boration reaction)

[Reaction Scheme 31]

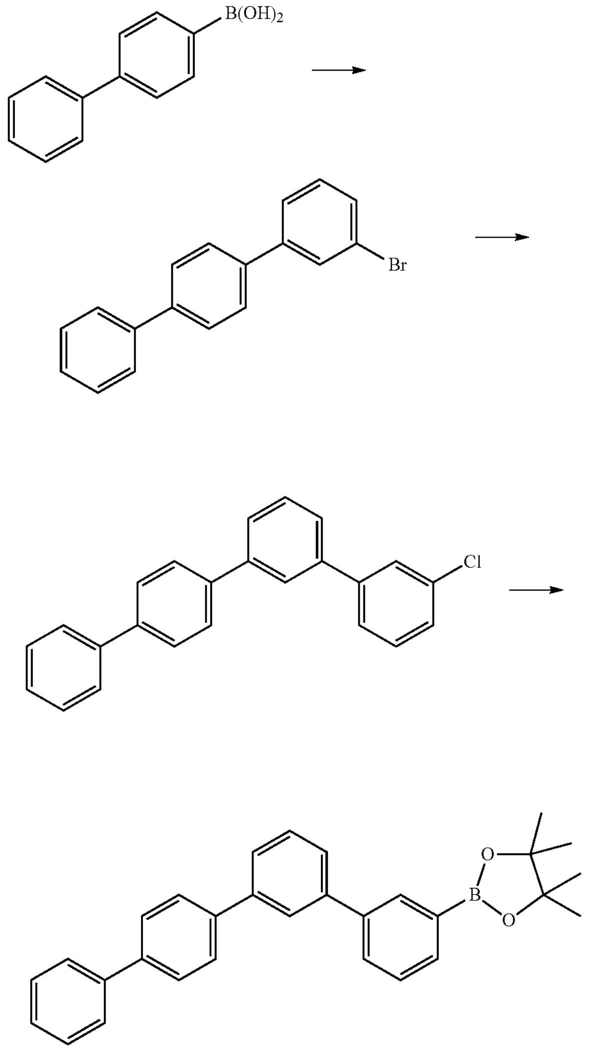

L-7

[Reaction Scheme 32]

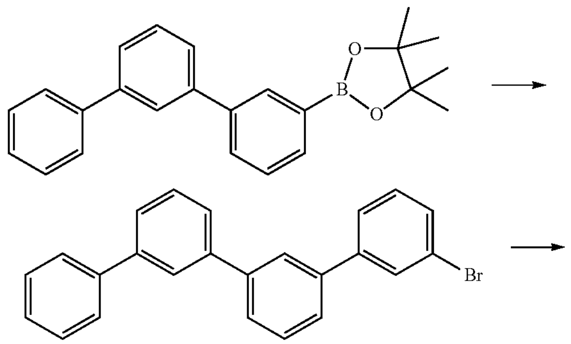

-continued

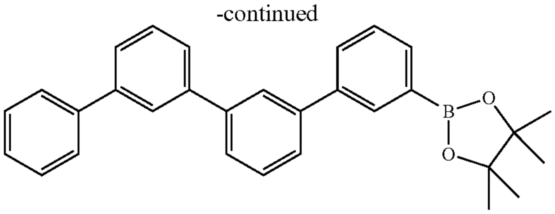

L-8

Synthesis Example 33: Synthesis of Compound A-1

[Reaction Scheme 33]

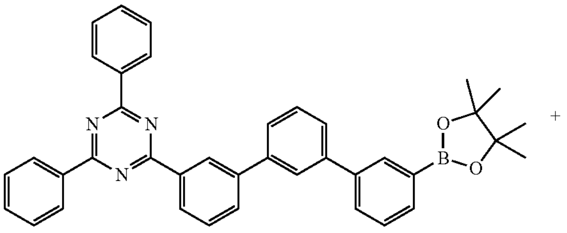

I-5

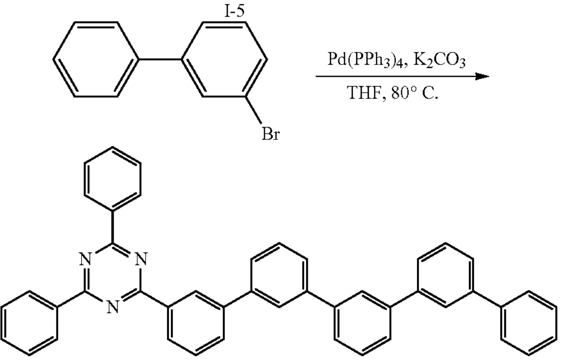

Intermediate I-5 (20 g, 34 mmol) was dissolved in tetrahydrofuran (THF, 0.2 L) under a nitrogen environment, 3-bromo-1,1'-biphenyl (9.5 g, 40 mmol) and tetrakis(triphenylphosphine)palladium (0.39 g, 0.34 mmol) were added thereto, and the mixture was stirred. Potassium carbonate saturated in water (12 g, 85 mmol) was added thereto, and the obtained mixture was heated and refluxed at 80° C. for 20 hours. When the reaction was complete, water was added to the reaction solution, and the mixture was extracted with dichloromethane (DCM), filtered after removing moisture with anhydrous $MgSO_4$, and concentrated under a reduced pressure. This obtained residue was separated and purified through column chromatography to obtain Compound A-1 (24 g and 70%).

HRMS (70 eV, EI+): m/z calcd for $C_{45}H_{31}N_3$: 613.2518, found: 613.

Elemental Analysis: C, 88%; H, 5%

Synthesis Example 34 to 39: Synthesis of Compound

Products in [Table 1] were manufactured by respectively synthesizing starting materials 1 and starting materials 2 in [Table 1] according to the synthesis method of Synthesis Example 33, and their yields and LC-Mass's were shown in [Table 1].

TABLE 1
| Synthesis Examples | Starting material 1 | Starting material 2 |
|---|---|---|
| 34 | 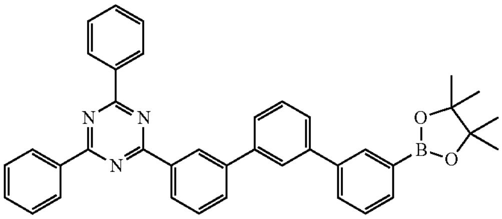 [SMILES: CC1(C)OB(c2cccc(-c3cccc(-c4cccc(-c5nc(-c6ccccc6)nc(-c6ccccc6)n5)c4)c3)c2)OC1(C)C] I-5 | 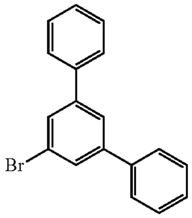 [SMILES: Brc1cc(-c2ccccc2)cc(-c2ccccc2)c1] (KR 2009-0126978A CATHOLIC UNIVERSITY INDUSTRY-ACADEMIC COOPERATION FOUNDATION, Reaction Scheme 1) |
| 35 | 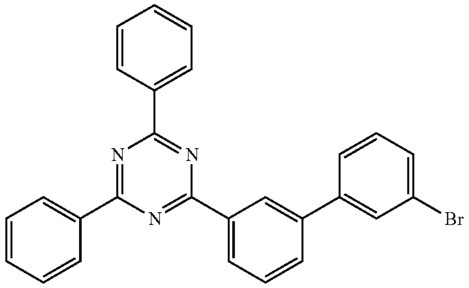 [SMILES: Brc1cccc(-c2cccc(-c3nc(-c4ccccc4)nc(-c4ccccc4)n3)c2)c1] I-38 | 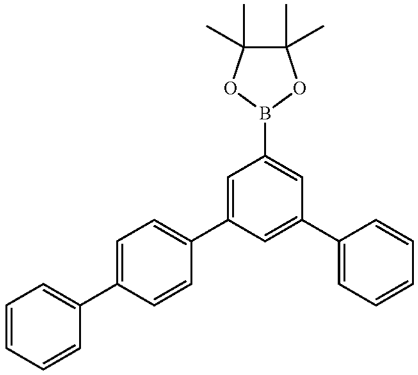 [SMILES: CC1(C)OB(c2cc(-c3ccccc3)cc(-c3ccc(-c4ccccc4)cc3)c2)OC1(C)C] I-41 |
| 36 | 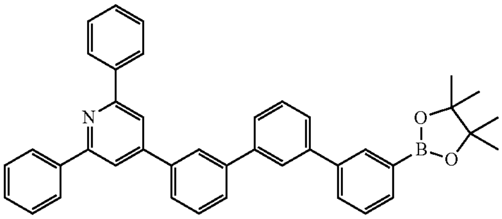 [SMILES: CC1(C)OB(c2cccc(-c3cccc(-c4cccc(-c5cc(-c6ccccc6)nc(-c6ccccc6)c5)c4)c3)c2)OC1(C)C] I-16 | 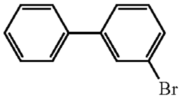 [SMILES: Brc1cccc(-c2ccccc2)c1] (TCI Inc.) |
| 37 | 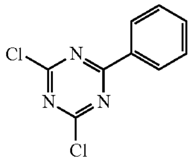 [SMILES: Clc1nc(Cl)nc(-c2ccccc2)n1] L-1 | 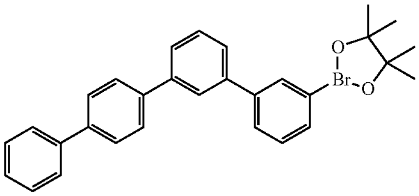 L-7 |
| 38 | 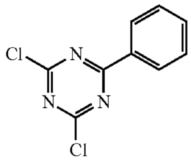 [SMILES: Clc1nc(Cl)nc(-c2ccccc2)n1] L-1 | 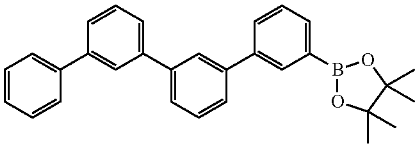 [SMILES: CC1(C)OB(c2cccc(-c3cccc(-c4cccc(-c5ccccc5)c4)c3)c2)OC1(C)C] L-8 |

TABLE 1-continued
| | | |
|---|---|---|
| 39 | 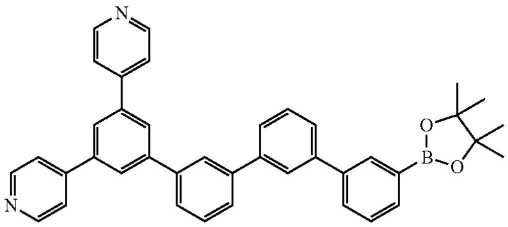 [SMILES: CC1(C)OB(c2cccc(-c3cccc(-c4cccc(-c5cc(-c6ccncc6)cc(-c6ccncc6)c5)c4)c3)c2)OC1(C)C] I-26 | 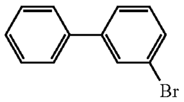 (TCI Inc.) |
| Synthesis Examples | Products | HRMS (70 eV, EI+) Found |
|---|---|---|
| 34 | 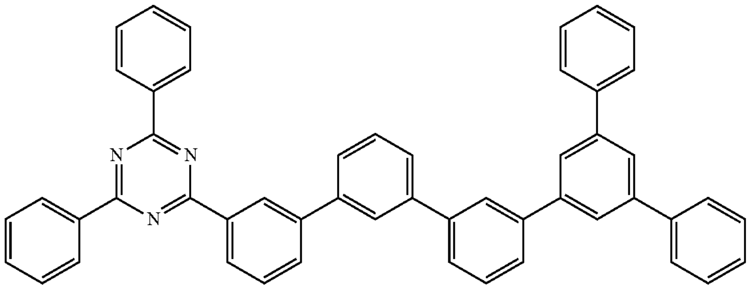 [SMILES: c1ccc(-c2cc(-c3ccccc3)cc(-c3cccc(-c4cccc(-c5cccc(-c6nc(-c7ccccc7)nc(-c7ccccc7)n6)c5)c4)c3)c2)cc1] A-7 | 689 |
| 35 | 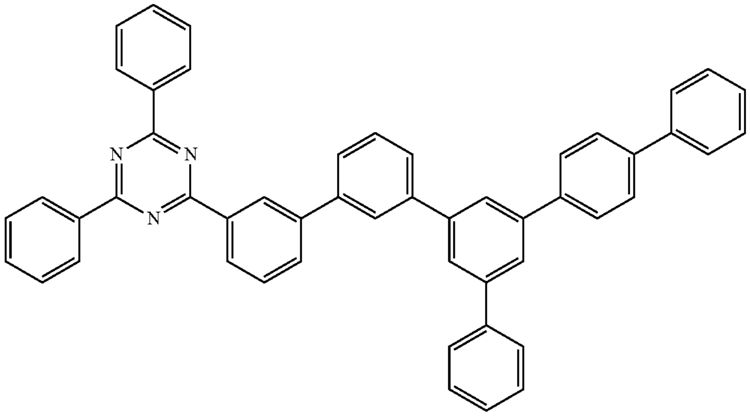 [SMILES: c1ccc(-c2ccc(-c3cc(-c4ccccc4)cc(-c4cccc(-c5cccc(-c6nc(-c7ccccc7)nc(-c7ccccc7)n6)c5)c4)c3)cc2)cc1] A-24 | 689 |
| 36 | 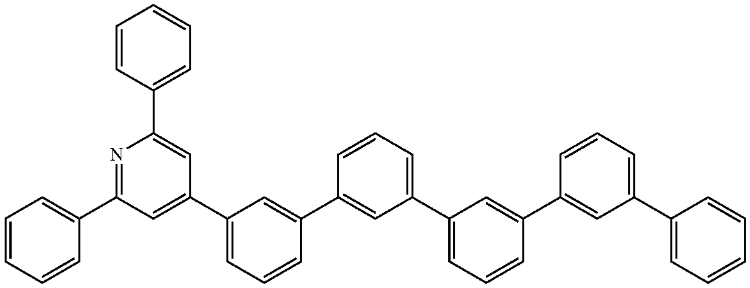 [SMILES: c1ccc(-c2cccc(-c3cccc(-c4cccc(-c5cccc(-c6cc(-c7ccccc7)nc(-c7ccccc7)c6)c5)c4)c3)c2)cc1] B-1 | 611 |

TABLE 1-continued

| | | |
|---|---|---|
| 37 | 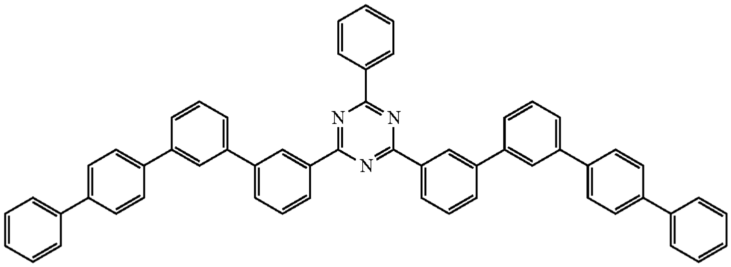 [SMILES: c1ccc(-c2ccc(-c3cccc(-c4cccc(-c5nc(-c6ccccc6)nc(-c6cccc(-c7cccc(-c8ccc(-c9ccccc9)cc8)c7)c6)n5)c4)c3)cc2)cc1]<br>A-37 | 765 |
| 38 | 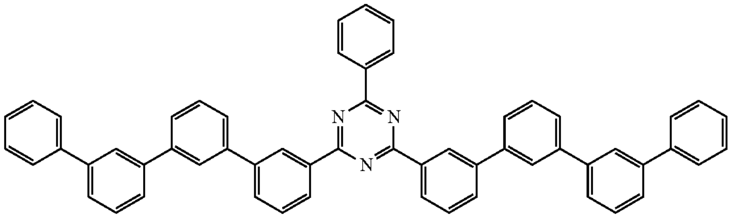 [SMILES: c1ccc(-c2cccc(-c3cccc(-c4cccc(-c5nc(-c6ccccc6)nc(-c6cccc(-c7cccc(-c8cccc(-c9ccccc9)c8)c7)c6)n5)c4)c3)c2)cc1]<br>A-46 | 765 |
| 39 | 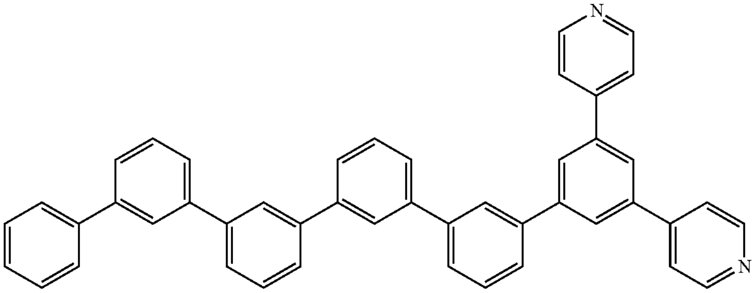 [SMILES: c1ccc(-c2cccc(-c3cccc(-c4cccc(-c5cccc(-c6cc(-c7ccncc7)cc(-c7ccncc7)c6)c5)c4)c3)c2)cc1]<br>C-1 | 612 |

Synthesis of Second Compound

Synthesis Example 40: Synthesis of Intermediate M-9

[Reaction Scheme 34]

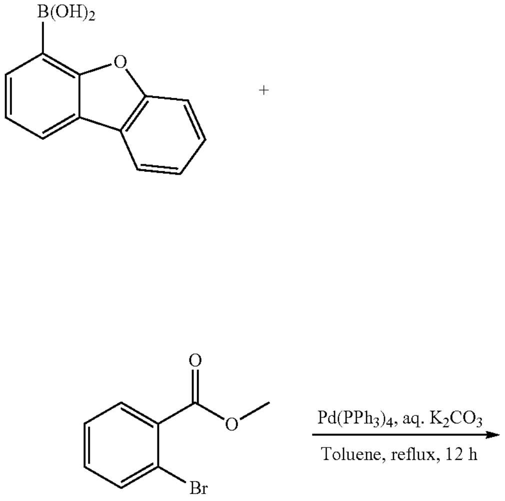

-continued

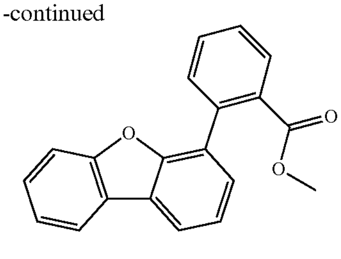

M-9

4-dibenzofuranboronic acid (20 g, 94.3 mmol, ACROS Organics) and methyl-2-bromobenzoate (20.3 g, 94.3 mmol, TCI Inc.) were put in a round-bottomed flask, toluene (313 ml) was added thereto to dissolve them, a solution obtained by dissolving potassium carbonate (19.5 g, 141.5 mmol) in an aqueous solution (117 ml) was added thereto, and the mixture was stirred. Then, tetrakistriphenylphosphine palladium (1.09 g, 0.94 mmol) was added thereto, and the obtained mixture was refluxed and stirred under a nitrogen atmosphere for 12 hours. When the reaction was complete, the resultant was extracted with ethylacetate, the extracted solution was dried with magnesium sulfate and filtered, and the filtered solution was concentrated under a reduced pressure. A product therefrom was purified through silica gel column chromatography with n-hexane/ethylacetate (9:1 of a volume ratio) to obtain a target compound, Intermediate M-9, (26.5 g, 93%).

LC-Mass (Theoretical value: 302.09 g/mol, Measured value: M+=302.18 g/mol)

Synthesis Example 41: Synthesis of Intermediate M-10

[Reaction Scheme 35]

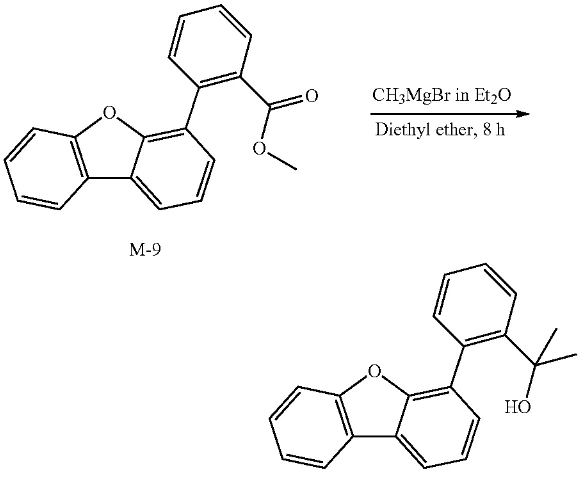

M-9

M-10

Intermediate M-9 (26 g, 86 mmol) was put in a round-bottomed flask heated and dried under a reduced pressure, anhydrous diethylether (430 ml) was added thereto to dissolve it, and the solution was cooled down to 0° C. and stirred under a nitrogen atmosphere. Subsequently, a 3.0 M methylmagnesium bromide diethylether solution (72 ml, 215 mmol) was slowly added thereto, and the mixture was stirred at room temperature under a nitrogen atmosphere for 12 hours. The reaction solution was cooled down to 0° C., a small amount of distilled water was added thereto to complete a reaction, a 2.0 M ammonium chloride aqueous solution (108 ml) was added thereto, the mixture was extracted with diethylether, the extracted solution was dried with magnesium sulfate and filtered, and the filtered solution was concentrated under a reduced pressure. A product therefrom was not additionally purified to obtain a target compound, Intermediate M-10 (25.7 g, 99%).

Synthesis Example 42: Synthesis of Intermediate M-11

[Reaction Scheme 36]

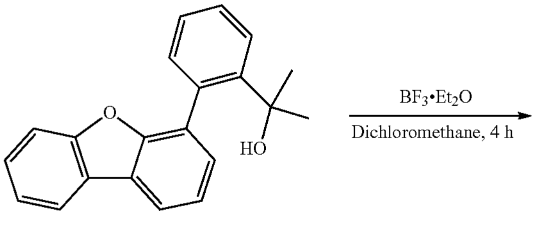

M-10

-continued

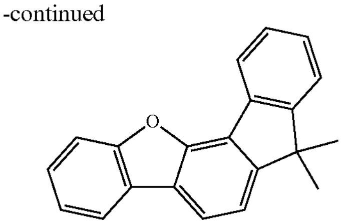

M-11

Intermediate M-10 (25.7 g, 85.1 mmol) was put in a round-bottomed flask heated and dried under a reduced pressure, anhydrous dichloromethane (255 ml) was added thereto to dissolve it, and the solution was cooled down to 0° C. and then, stirred under a nitrogen atmosphere. Then, boron trifluoride diethyl etherate (12.1 g, 85.1 mmol) was slowly added thereto, and the mixture was stirred at room temperature under a nitrogen atmosphere for 4 hours. The reaction solution was cooled down to 0° C., a small amount of distilled water was added thereto to complete a reaction, a 1.0 M sodium bicarbonate aqueous solution (85 ml) was added thereto, the mixture was extracted with dichloromethane, dried with magnesium sulfate, and filtered, and the filtered solution was concentrated under a reduced pressure. A product therefrom was purified through silica gel column chromatography with n-hexane/dichloromethane (9:1 of a volume ratio) to obtain a target compound, Intermediate M-11 (18.1 g, 75%).

LC-Mass (Theoretical value: 284.12 g/mol, Measured value: M+=284.18 g/mol)

Synthesis Example 43: Synthesis of Intermediate M-12

[Reaction Scheme 37]

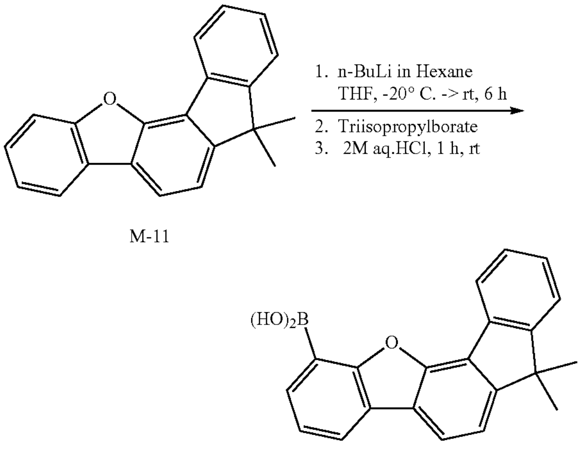

M-11

M-12

Intermediate M-11 (18 g, 63.3 mmol) was put in a round-bottomed flask heated and dried under a reduced pressure, anhydrous tetrahydrofuran (190 ml) was added thereto to dissolve it, and the solution was cooled down to −20° C. and then, stirred under a nitrogen atmosphere. Subsequently, a 2.5 M n-butyllithium normal hexane solution (31 ml, 76 mmol) was slowly added thereto, and the mixture was stirred at room temperature under a nitrogen atmosphere for 6 hours. The reaction solution was cooled down to −20° C., triisopropylborate (14.3 g, 76 mmol) was slowly added thereto, and the mixture was stirred at room temperature under a nitrogen atmosphere for 6 hours. The reaction solution was cooled down to 0° C., a small amount of distilled water was added thereto to complete a reaction, a 2.0 M hydrochloric acid aqueous solution (114 ml) was added thereto, the mixture was extracted with diethylether, the extracted solution was dried with magnesium sulfate and filtered, and the filtered solution was concentrated under a reduced pressure. The obtained residue was dissolved in acetone and recrystallized by adding n-hexane thereto. A solid produced therein was filtered under a reduced pressure to obtain a target compound, Intermediate M-12 (15.6 g, 75%).

LC-Mass (Theoretical value: 328.13 g/mol, Measured value: M+=328.21 g/mol)

Synthesis Example 44: Synthesis of Intermediate M-13

[Reaction Scheme 38]

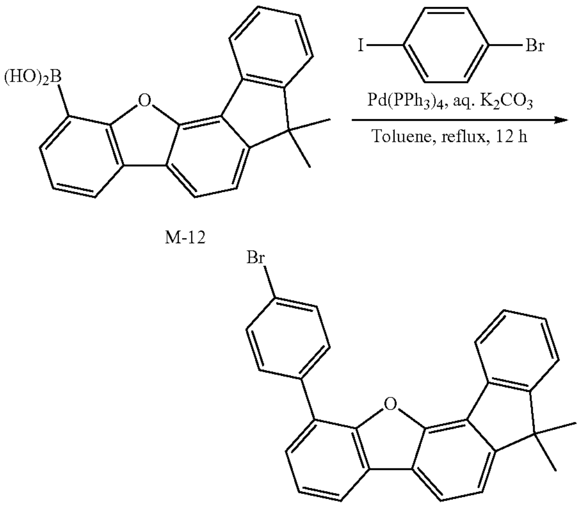

M-12

M-13

Intermediate M-12 (30.9 g, 94.3 mmol), 1-bromo-4-iodobenzene (26.7 g, 94.3 mmol) were put in a round-bottomed flask, toluene (313 ml) was added thereto to dissolve them, an aqueous solution (117 ml) obtained by dissolving potassium carbonate (19.5 g, 141.5 mmol) was added thereto, and the mixture was stirred. Subsequently, tetrakistriphenylphosphine palladium (1.09 g, 0.94 mmol) was added thereto, and the mixture was refluxed and stirred under a nitrogen atmosphere for 12 hours. When the reaction was complete, the resultant was extracted with ethylacetate, the extracted solution was dried with magnesium sulfate and filtered, and the filtered solution was concentrated under a reduced pressure. A product therefrom was purified through silica gel column chromatography with n-hexane/dichloromethane (9:1 of a volume ratio) to obtain a target compound, Intermediate M-13 (37 g, 90%).

LC-Mass (Theoretical value: 438.06 g/mol, Measured value: M+=438.17 g/mol, M+2=440.21 g/mol)

Synthesis Examples 45 to 49: Synthesis of Intermediate M-14 to Intermediate M-18

[Reaction Scheme 39]

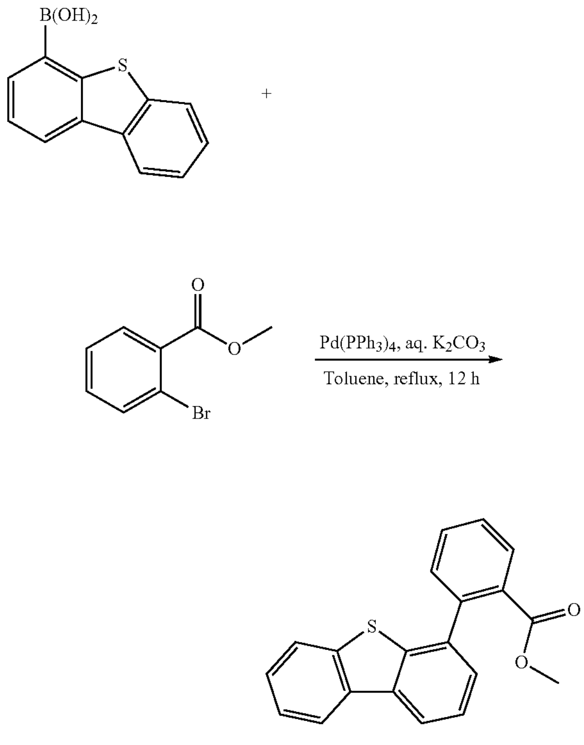

M-14

[Reaction Scheme 40]

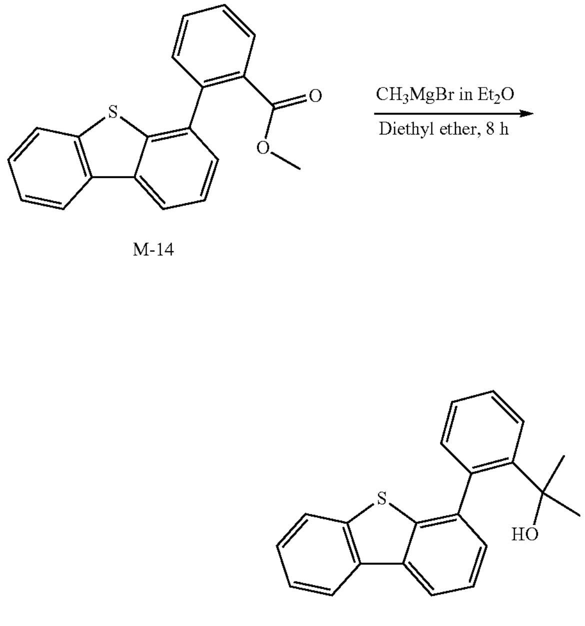

M-14

M-15

[Reaction Scheme 41]

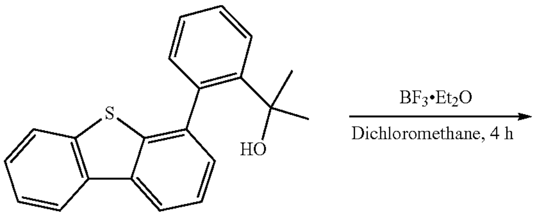

M-15

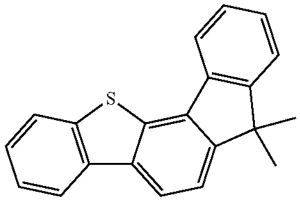

M-16

[Reaction Scheme 42]

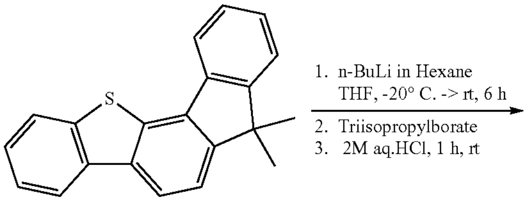

M-16

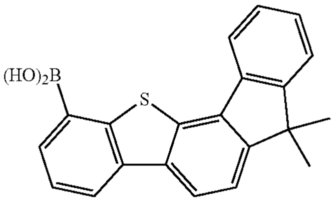

M-17

[Reaction Scheme 43]

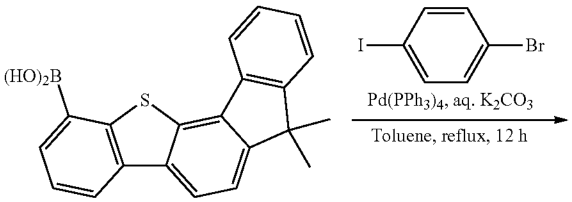

M-17

-continued

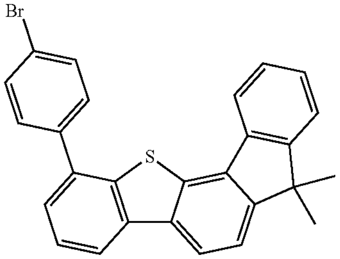

M-18

Intermediate M-14 to Intermediate M-18 were obtained by synthesis and purification in the same method as Intermediate M-9 to Intermediate M-13.

Synthesis Example 50: Synthesis of Intermediate M-19

[Reaction Scheme 44]

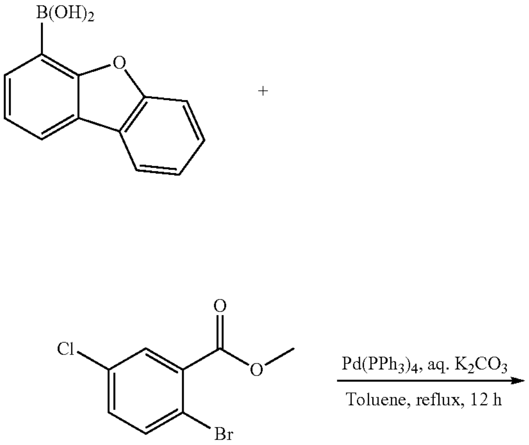

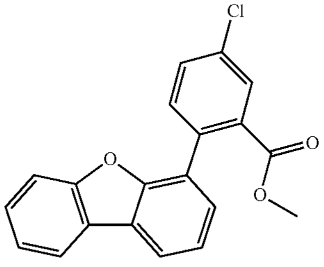

M-19

30 g (94%) of Intermediate M-19 was obtained by synthesis and purification in the same method as Intermediate M-9.

LC-Mass (Theoretical value: 336.06 g/mol, Measured value: M+=336.18 g/mol)

Synthesis Example 51: Synthesis of Intermediate M-20

[Reaction Scheme 45]

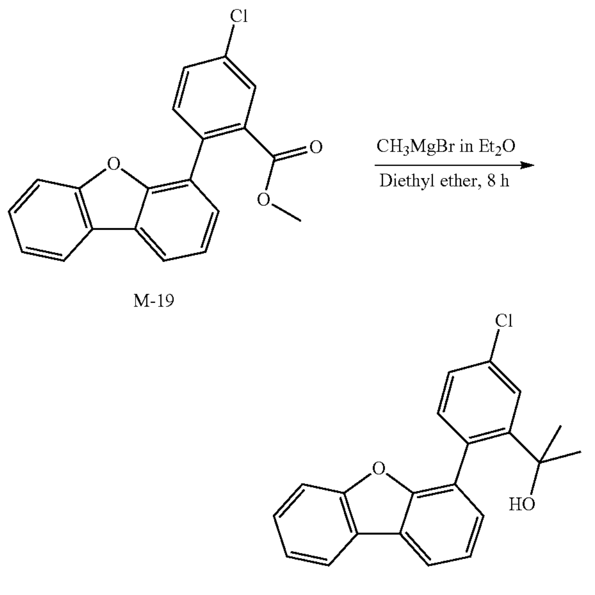

M-19

M-20

28.7 g (99%) of Intermediate M-20 was obtained by synthesis and purification in the same method as Intermediate M-10.

LC-Mass (Theoretical value: 336.09 g/mol, Measured value: M+=336.15 g/mol)

Synthesis Example 52: Synthesis of Intermediate M-21

[Reaction Scheme 46]

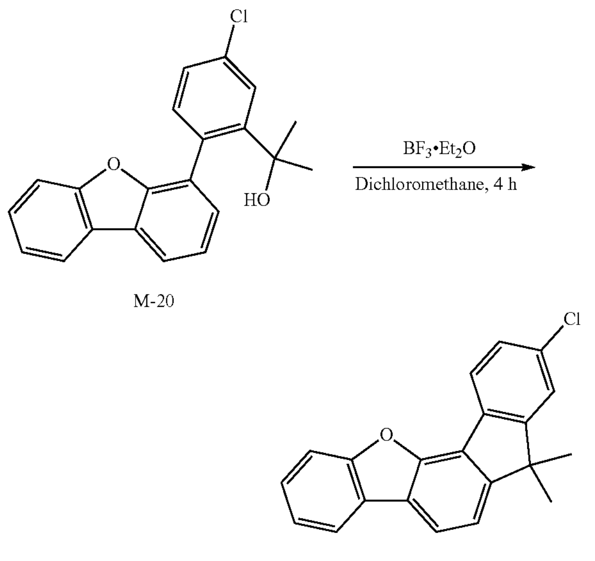

M-20

M-21

20.1 g (74%) of Intermediate M-21 was obtained by synthesis and purification in the same method as Intermediate M-11.

LC-Mass (Theoretical value: 318.08 g/mol, Measured value: M+=318.15 g/mol)

Synthesis Examples 53 to 55: Synthesis of Intermediate M-22 to Intermediate M-24

[Reaction Scheme 47]

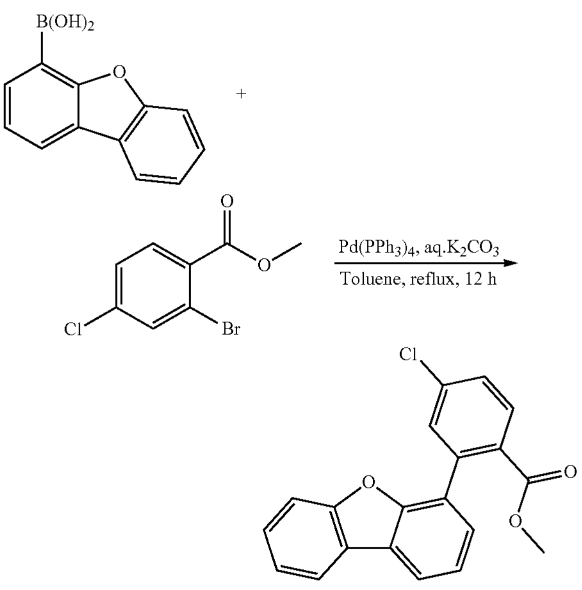

M-22

[Reaction Scheme 48]

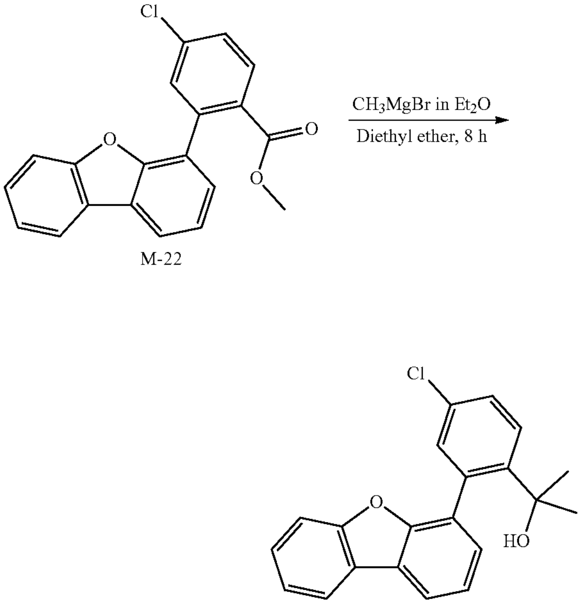

M-22

M-23

[Reaction Scheme 49]

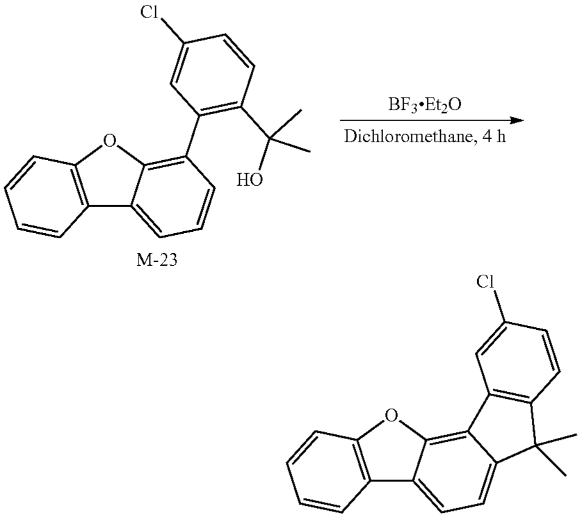

M-23

M-24

Intermediate M-22 to Intermediate M-24 were obtained by synthesis and purification in the same method as Intermediate M-19 to Intermediate M-21.

Synthesis Examples 56 to 58: Synthesis of Intermediate M-25 to Intermediate M-27

[Reaction Scheme 50]

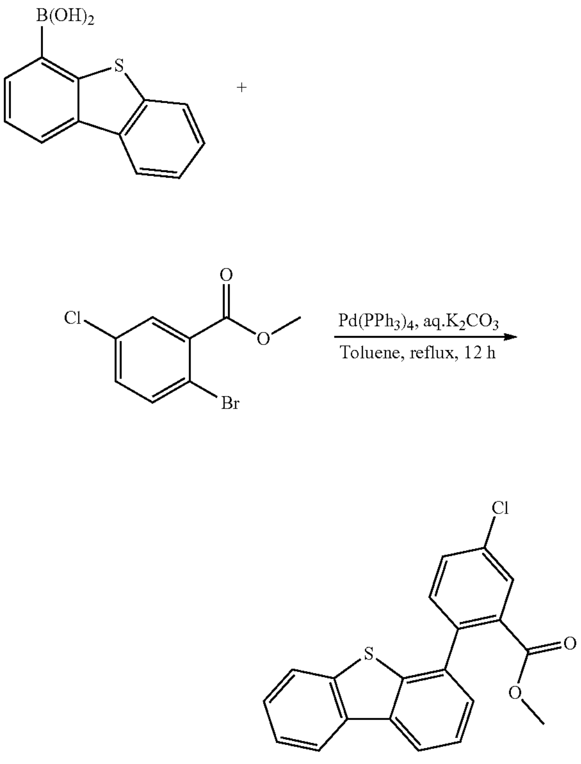

M-25

[Reaction Scheme 51]

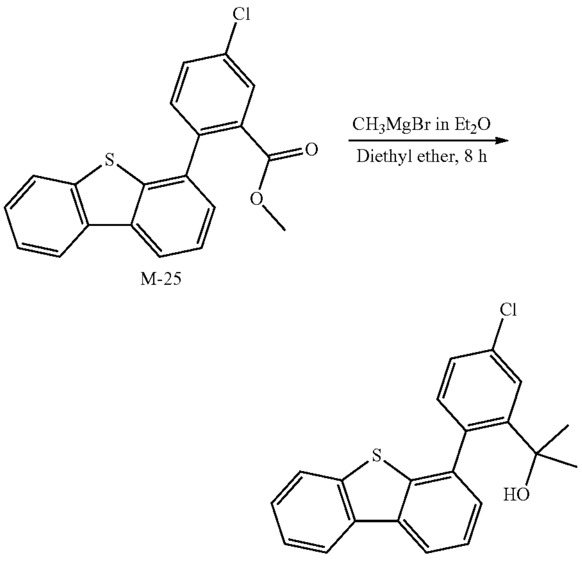

M-25

M-26

[Reaction Scheme 52]

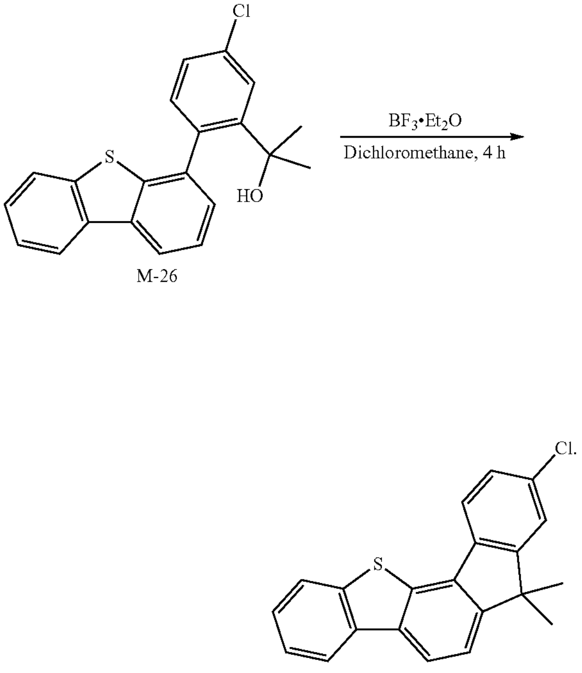

M-26

M-27

Intermediate M-25 to Intermediate M-27 were obtained by synthesis and purification in the same method as Intermediate M-19 to Intermediate M-21.

Synthesis Examples 59 to 61: Synthesis of Intermediate M-28 to Intermediate M-30
[Reaction Scheme 53]
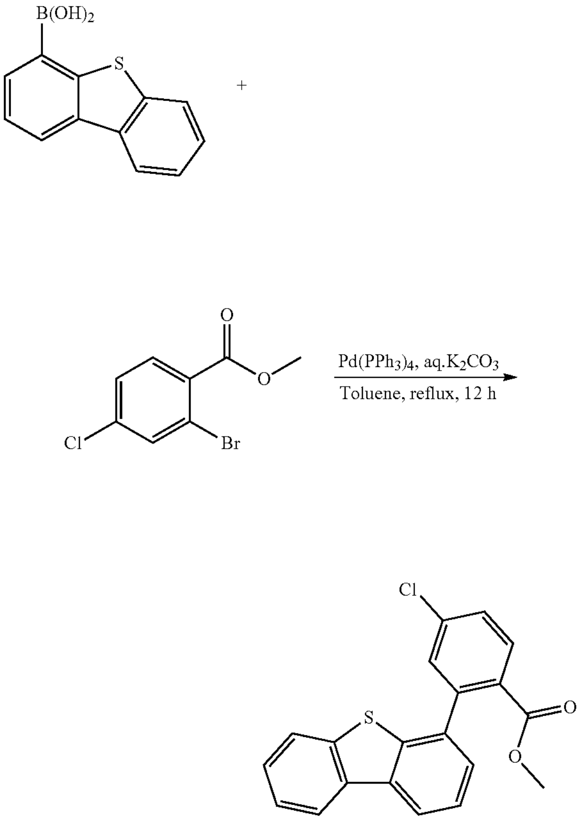
M-28
[Reaction Scheme 54]
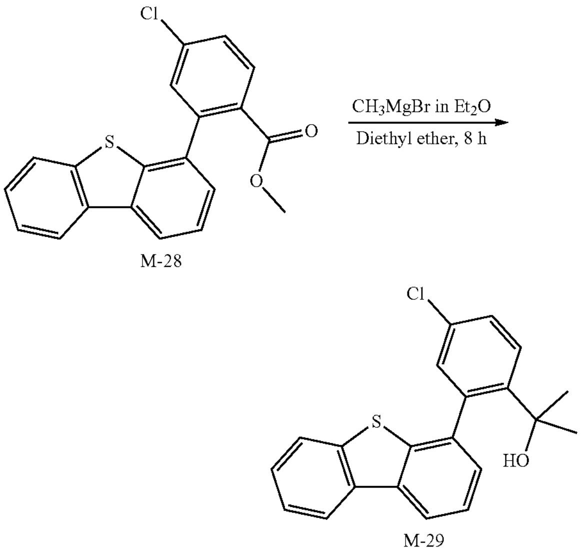
M-28
M-29
[Reaction Scheme 55]
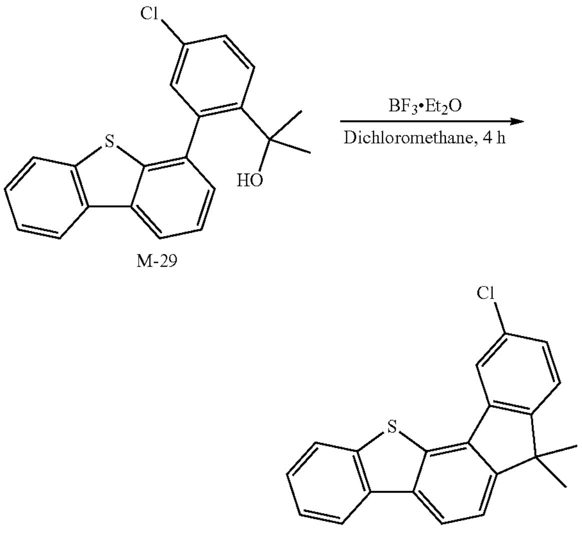
M-29
M-30
Intermediate M-28 to Intermediate M-30 were obtained by synthesis and purification in the same method as Intermediate M-19 to Intermediate M-21.
Synthesis Examples 62 and 63: Synthesis of Intermediate M-33 and Intermediate M-34
[Reaction Scheme 56]
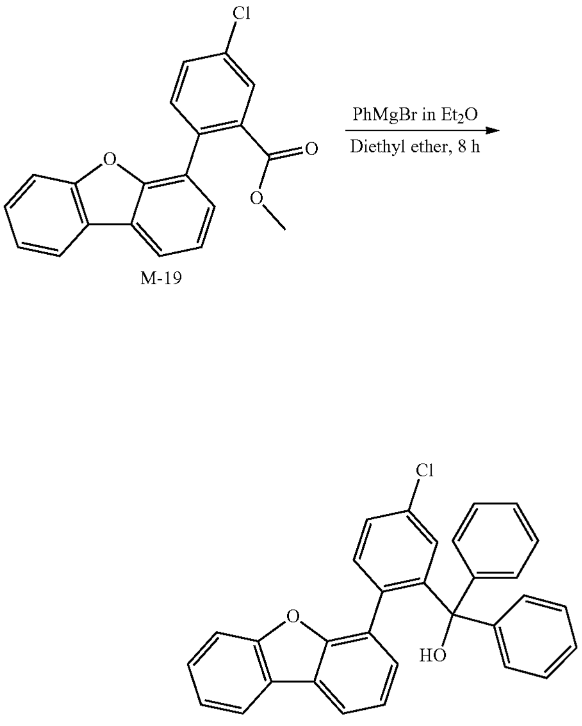
M-19
M-33

[Reaction Scheme 57]

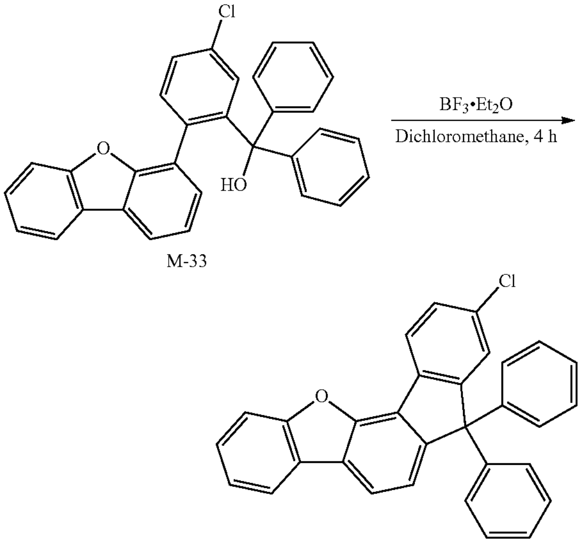

M-33

M-34

Intermediate M-33 and Intermediate M-34 were obtained by synthesis and purification in the same method as Intermediate M-10 and Intermediate M-11.

Synthesis Example 64: Synthesis of Intermediates K-1 to K-3

Synthesis of Intermediate K-1

[Reaction Scheme 58]

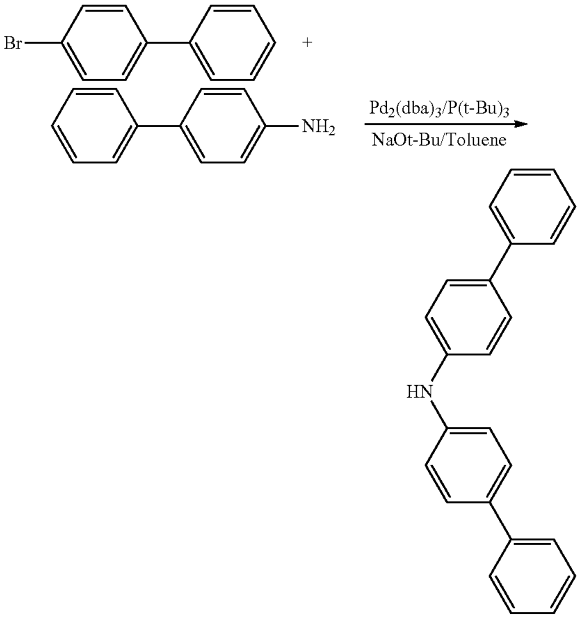

K-1

4-bromo-1-1'-biphenyl (50.00 g, 214.49 mmol) as a starting material was dissolved in toluene in a round flask, [1,1'-biphenyl]-4-amine (72.60 g, 428.98 mmol), $Pd_2(dba)_3$ (4.59 g, 5.0 mmol), 50% $P(t\text{-}Bu)_3$ (4.92 ml, 10.0 mmol), and NaOt-Bu (61.84 g, 643.47 mmol) were added thereto, and the mixture was stirred at 40° C. When a reaction was complete through a check with TLC, an organic layer extracted with $CH_2Cl_2$ and water was dried with $MgSO_4$ and concentrated, and a compound produced therein was silica-gel columned and recrystallized to obtain Compound K-1 (51.71 g, 160.87 mmol, 75%).

HRMS (70 eV, EI+): m/z calcd for $C_{24}H_{19}N$: 321.15, found: 321.

Elemental Analysis: C, 90%; H, 6%

Synthesis of Intermediate K-2

K-2

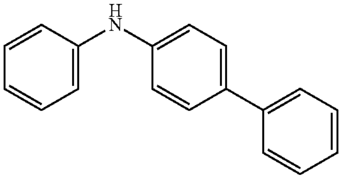

Compound K-2 was synthesized in the synthesis method of a) Intermediate K-1 of Synthesis Example 64 except for using bromophenyl instead of the 4-bromo-1-1'-biphenyl as a starting material.

HRMS (70 eV, EI+): m/z calcd for $C_{18}H_{15}N$: 245.32, found: 245.

Synthesis of Intermediate K-3

K-3

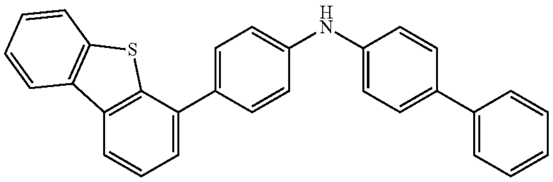

Step 1: Synthesis of Intermediate M-1

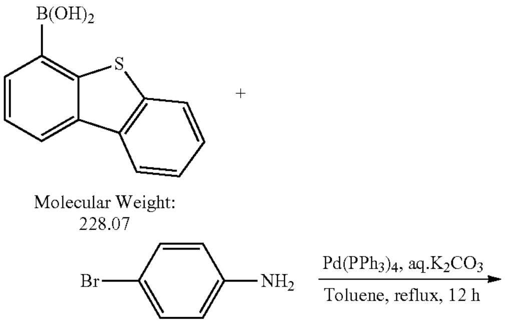

-continued

Exact Mass: 275.08

Molecular Weight: 275.37

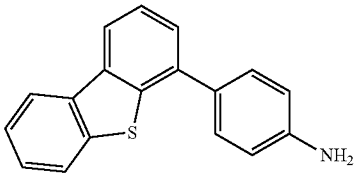

M-1

4-dibenzothiopheneboronic acid (21.5 g, 94.3 mmol) and 4-bromoaniline (16.2 g, 94.3 mmol) were put in a round-bottomed flask, toluene (300 ml) was added thereto to dissolve them, an aqueous solution (117 ml) obtained by dissolving potassium carbonate (19.5 g, 141.5 mmol) was added thereto, and the mixture was stirred. Subsequently, tetrakistriphenylphosphine palladium (1.09 g, 0.94 mmol) was added thereto, and the mixture was refluxed and stirred under a nitrogen atmosphere for 12 hours. When the reaction was complete, the resultant was extracted with ethylacetate, the extracted solution was dried with magnesium sulfate and filtered, and the filtered solution was concentrated under a reduced pressure. A product therefrom was purified through silica gel column chromatography with n-hexane/dichloromethane (7:3 of a volume ratio) to obtain a target compound, white solid Intermediate M-1 (18.7 g, 72%).

HRMS (70 eV, EI+): m/z calcd for $C_{18}H_{13}NS$: 275.37, found: 275.

Step 2: Synthesis of Intermediate K-3

Molecular Weight: 275.37

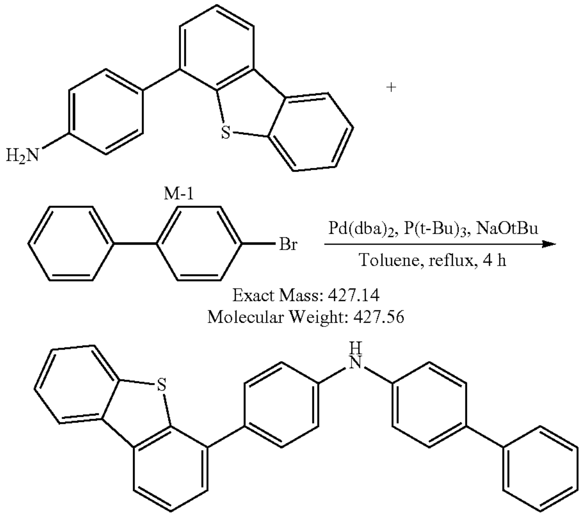

K-3

4-bromobiphenyl (30.9 mmol), Intermediate M-1 (10.2 g, 37.08 mmol), and sodium t-butoxide (5.35 g, 55.6 mmol) were dissolved by adding toluene (155 ml) thereto in a round-bottomed flask. Subsequently, $Pd(dba)_2$ (0.178 g, 0.31 mmol) and tri-tertiary-butylphosphine (0.125 g, 0.62 mmol) were sequentially added thereto, and the mixture was refluxed and stirred under a nitrogen atmosphere for 4 hours. When the reaction was complete, the resultant was extracted with toluene and distilled water, an organic layer was dried with magnesium sulfate and filtered, and the filtered solution was concentrated under a reduced pressure. A product therefrom was purified through silica gel column chromatography with n-hexane/dichloromethane (7:3 of a volume ratio) to obtain a target compound, white solid intermediate K-3 (10 g, 76%).

HRMS (70 eV, EI+): m/z calcd for $C_{30}H_{21}NS$: 427.56, found: 427.

Synthesis Example 65: Synthesis of Compound F-1

[Reaction Scheme 59]

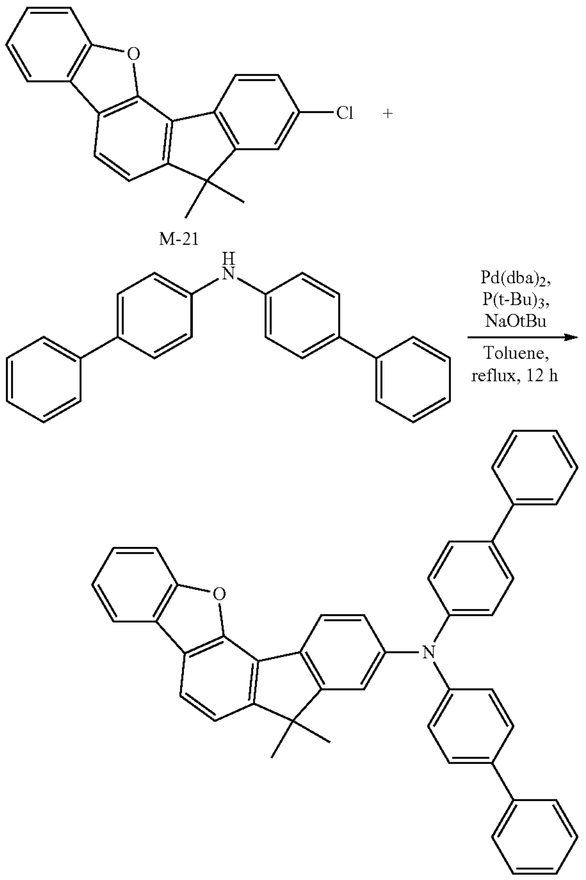

F-1

Intermediate M-21 (9.9 g, 30.9 mmol), bis(4-biphenyl) amine (9.9 g, 30.9 mmol), and sodium t-butoxide (4.5 g, 46.35 mmol) were dissolved in toluene (155 ml) in a round-bottomed flask. Then, $Pd(dba)_2$ (0.178 g, 0.31 mmol) and tri-tertiary-butylphosphine (0.125 g, 0.62 mmol) were sequentially added thereto, and the mixture was refluxed and stirred under a nitrogen atmosphere for 12 hours. When the reaction was complete, the resultant was extracted with toluene and distilled water, an organic layer was dried with magnesium sulfate and filtered, and the filtered solution was concentrated under a reduced pressure. A product therein was purified through silica gel column chromatography with n-hexane/dichloromethane (8:2 of a volume ratio) to obtain a target compound F-1 (17.0 g, 91%).

LC-Mass (Theoretical value: 603.26 g/mol, Measured value: M+=603.30 g/mol)

Synthesis Example 66 to 75: Synthesis of Compounds

Product in [Table 2] were obtained by synthesizing a starting material 1 and a starting material 2 in the method of Synthesis Example 65, and their yields and LC-Mass's were shown in [Table 2].

TABLE 2

| Synthesis Example | Starting material 1 | Starting material 2 |
| --- | --- | --- |
| 66 | 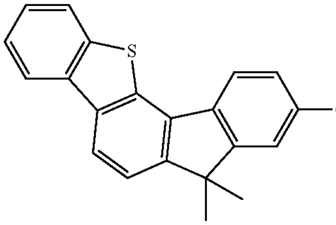 M-27 | 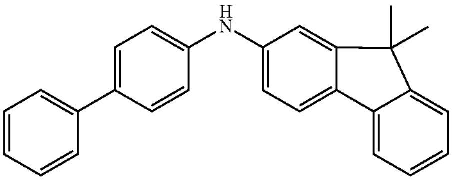 [SMILES: CC1(C)c2ccccc2-c2ccc(Nc3ccc(-c4ccccc4)cc3)cc21] (synthesis method: WO 2010-136109A (Merck) page. 57) |
| 67 | 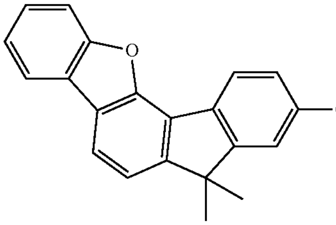 M-21 | 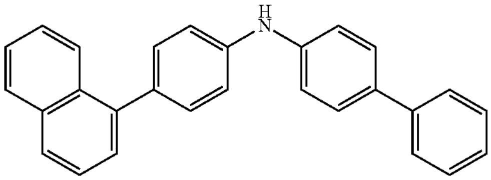 [SMILES: c1ccc(-c2ccc(Nc3ccc(-c4cccc5ccccc45)cc3)cc2)cc1] (synthesis method: WO 2006-073059 (IDEMITSU) Synthesis Example 19, (Intermediate 20)) |
| 68 | 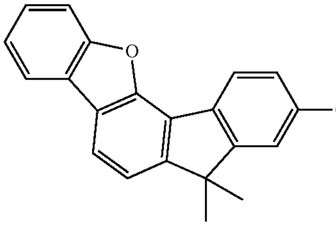 M-21 | 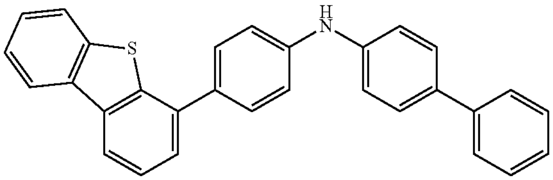 [SMILES: c1ccc(-c2ccc(Nc3ccc(-c4cccc5c4sc4ccccc45)cc3)cc2)cc1] K-3 |
| 69 | 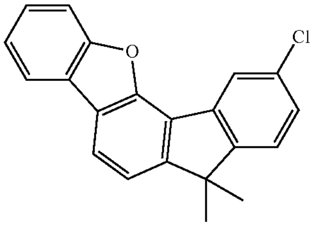 M-24 | 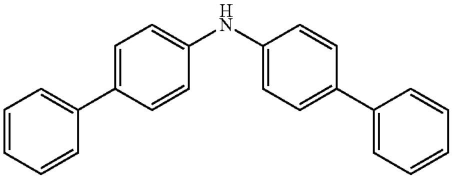 [SMILES: c1ccc(-c2ccc(Nc3ccc(-c4ccccc4)cc3)cc2)cc1] K-1 |
| 70 | 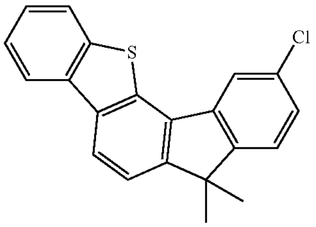 [SMILES: CC1(C)c2ccc(Cl)cc2-c2c1ccc1c2sc2ccccc21] M-30 | 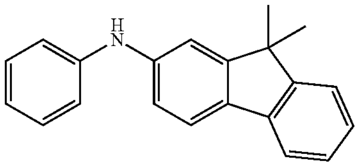 [SMILES: CC1(C)c2ccccc2-c2ccc(Nc3ccccc3)cc21] (synthesis method: synthesized by the same method as WO 2010-136109 (Merck) P.57, and aniline was used instead of [1,1'-biphenyl]-4-amine) |

TABLE 2-continued
| | | |
|---|---|---|
| 71 | 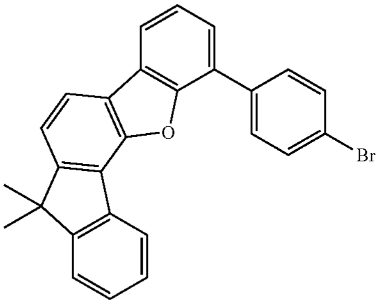 [SMILES: CC1(C)c2ccccc2-c2c1ccc1c2oc2c(-c3ccc(Br)cc3)cccc21]<br>M-13 | 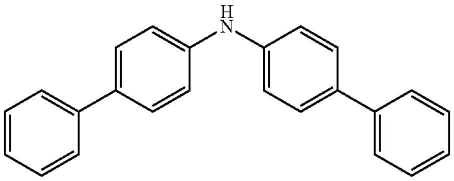 [SMILES: c1ccc(-c2ccc(Nc3ccc(-c4ccccc4)cc3)cc2)cc1]<br>K-1 |
| 72 | 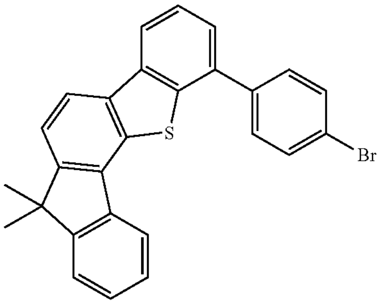<br>M-18 | 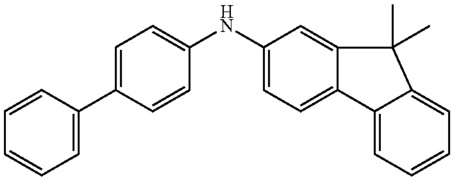 [SMILES: CC1(C)c2ccccc2-c2ccc(Nc3ccc(-c4ccccc4)cc3)cc21]<br>(synthesis method: WO 2010-136109A (Merck) P.57) |
| 73 | 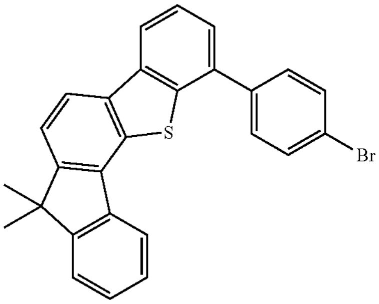<br>M-18 | 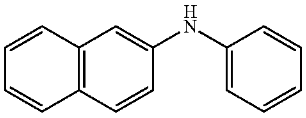 [SMILES: c1ccc(Nc2ccc3ccccc3c2)cc1]<br>(manufacturer: Aldrich Corporation) |
| 74 | 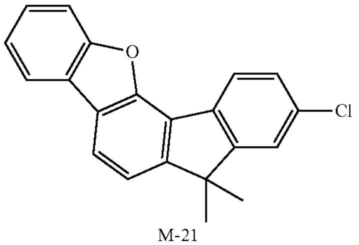<br>M-21 | 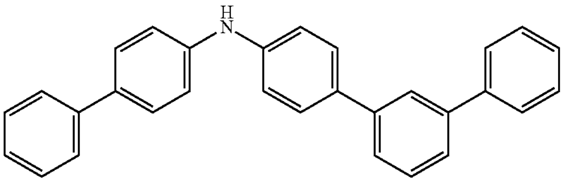 [SMILES: c1ccc(-c2ccc(Nc3ccc(-c4cccc(-c5ccccc5)c4)cc3)cc2)cc1]<br>(synthesis method: WO 2006-073059 (IDEMITSU) Synthesis Example 10 (Intermediate 11)) |
| 75 | 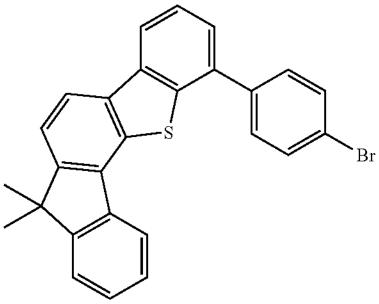<br>M-18 | 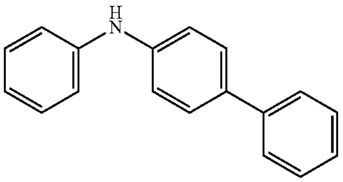 [SMILES: c1ccc(Nc2ccc(-c3ccccc3)cc2)cc1]<br>K-2 |

TABLE 2-continued
| Synthesis Exam-ple | Products | Yield (%) LC-Mass (M + H⁺) |
|---|---|---|
| 66 | 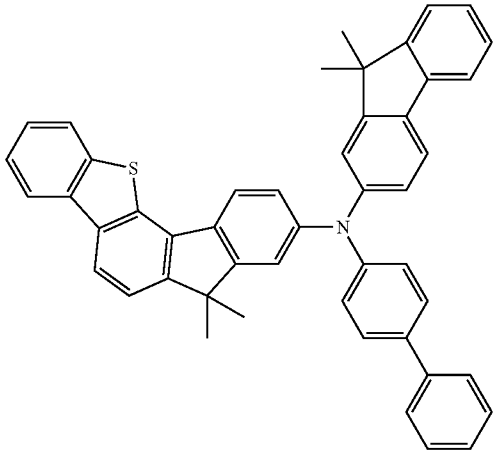 [SMILES: CC1(C)c2ccccc2-c2ccc(N(c3ccc(-c4ccccc4)cc3)c3ccc4c(c3)C(C)(C)c3ccc5c(sc6ccccc65)c3-4)cc21] F-3 | 89% 659.31 |
| 67 | 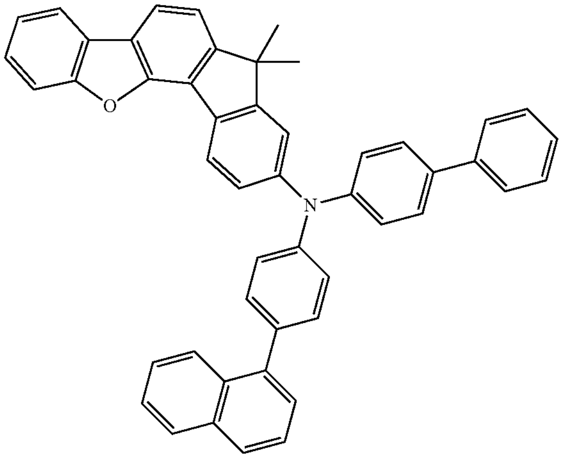 [SMILES: CC1(C)c2cc(N(c3ccc(-c4ccccc4)cc3)c3ccc(-c4cccc5ccccc45)cc3)ccc2-c2c1ccc1c2oc2ccccc21] F-5 | 88% 653.30 |
| 68 | 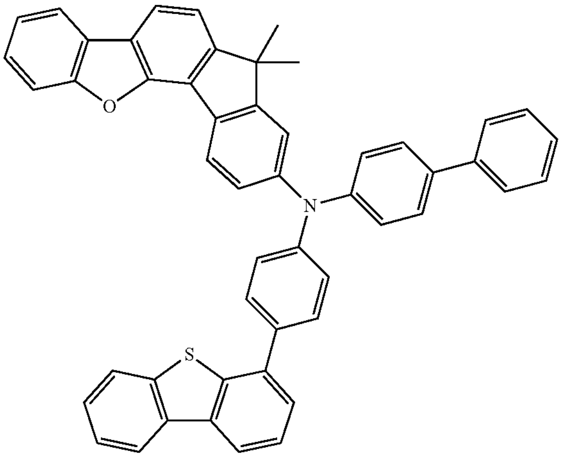 [SMILES: CC1(C)c2cc(N(c3ccc(-c4ccccc4)cc3)c3ccc(-c4cccc5c4sc4ccccc45)cc3)ccc2-c2c1ccc1c2oc2ccccc21] F-13 | 88% 709.31 |

TABLE 2-continued
69 89% 603.29
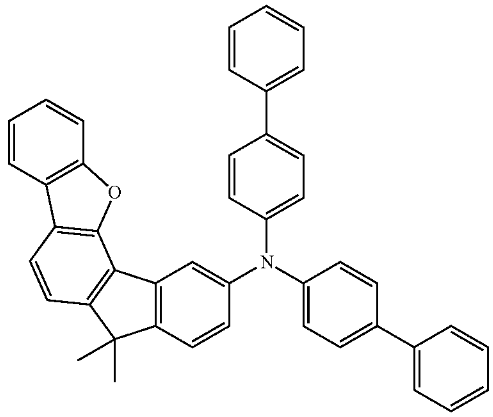 [SMILES: CC1(C)c2ccc(N(c3ccc(-c4ccccc4)cc3)c3ccc(-c4ccccc4)cc3)cc2-c2c1ccc1c2oc2ccccc21]
G-1
70 90% 598.33
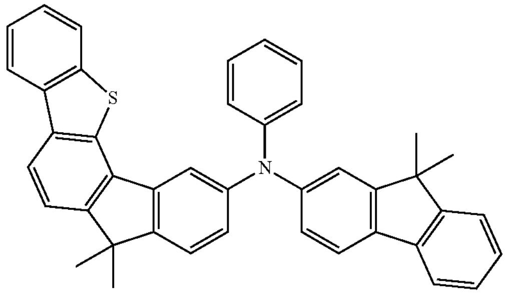 [SMILES: CC1(C)c2ccccc2-c2ccc(N(c3ccccc3)c3ccc4c(c3)-c3c(ccc5c3sc3ccccc35)C4(C)C)cc21]
G-6
71 93% 679.32
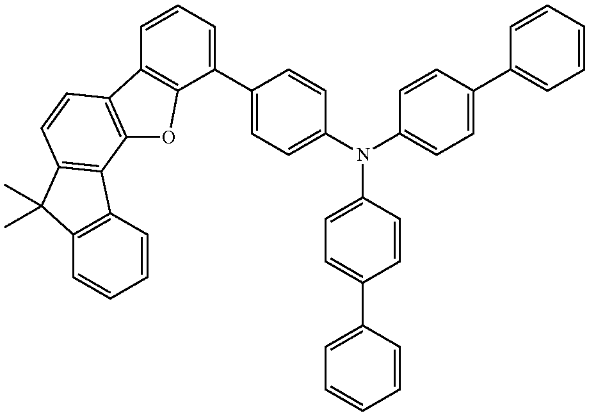 [SMILES: CC1(C)c2ccccc2-c2c1ccc1c2oc2c(-c3ccc(N(c4ccc(-c5ccccc5)cc4)c4ccc(-c5ccccc5)cc4)cc3)cccc21]
E-11
72 92% 735.32
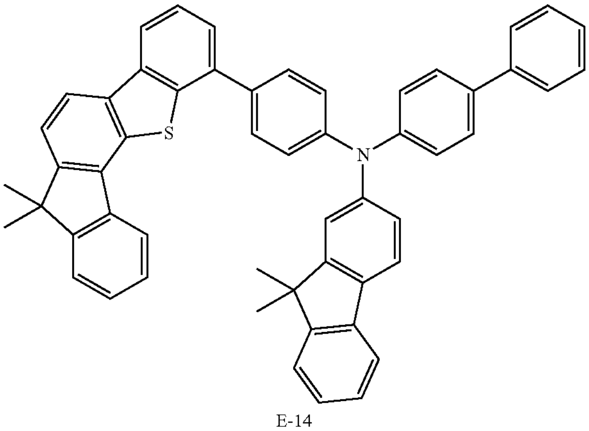
E-14

TABLE 2-continued

| | | |
|---|---|---|
| 73 | 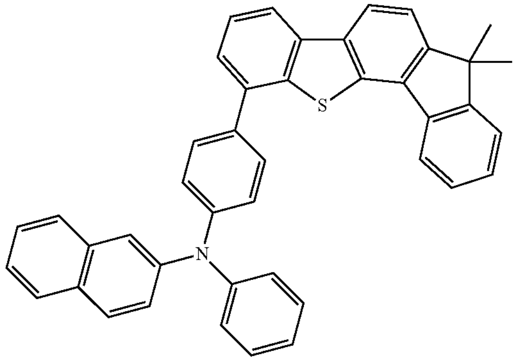 [SMILES: CC1(C)c2ccccc2-c2c1ccc1c2sc2c(-c3ccc(N(c4ccccc4)c4ccc5ccccc5c4)cc3)cccc21] E-20 | 85% 593.26 |
| 74 | 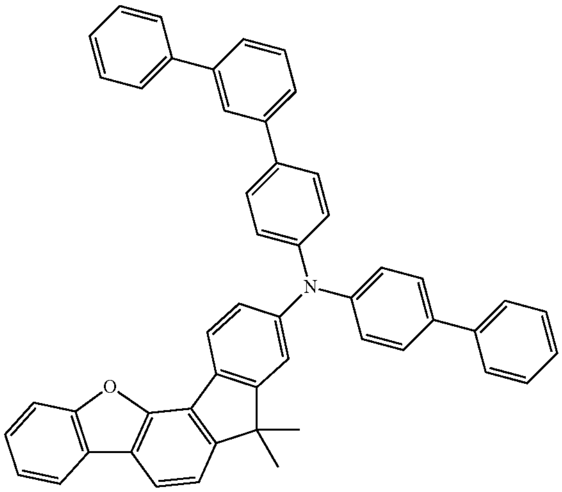 [SMILES: CC1(C)c2cc(N(c3ccc(-c4ccccc4)cc3)c3ccc(-c4cccc(-c5ccccc5)c4)cc3)ccc2-c2c1ccc1c2oc2ccccc21] F-33 | 83% 679.34 |
| 75 | 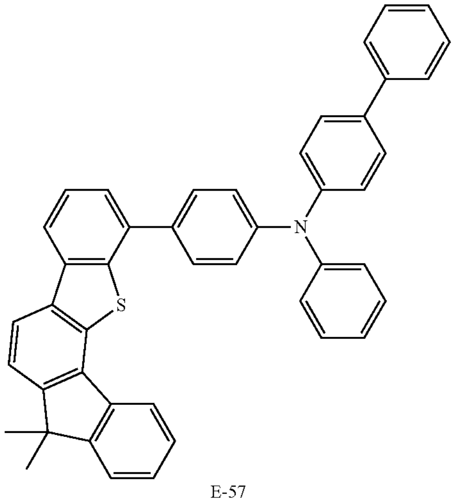 E-57 | 90% 619.26 |

Manufacture of Organic Light Emitting Diode

Example 1

A glass substrate coated with ITO (indium tin oxide) to be 1500 Å thick was ultrasonic wave-washed with a distilled water. Subsequently, the glass substrate was ultrasonic wave-washed with a solvent such as isopropyl alcohol, acetone, methanol, and the like, moved to a plasma cleaner, cleaned by using oxygen plasma for 10 minutes, and then, moved to a vacuum depositor. This ITO transparent electrode was used as an anode, a 700 Å-thick hole injection layer (HIL) was formed thereon by vacuum-depositing N4,N4'-diphenyl-N4,N4'-bis(9-phenyl-9H-carbazol-3-yl)biphenyl-4,4'-diamine) (Compound A), and a hole transport layer was formed on the hole injection layer (HIL) by depositing 1,4,5,8,9,11-hexaazatriphenylene-hexacarbonitrile (HAT-CN) (Compound B) to be 50 Å thick and then, N-(biphenyl-4-yl)-9,9-dimethyl-N-(4-(9-phenyl-9H-carbazol-3-yl)phenyl)-9H-fluoren-2-amine) (Compound C) to be 700 Å thick. On the hole transport layer, a 50 Å-thick auxiliary hole transport layer was formed by vacuum-depositing Compound E-57 according to Synthesis Example 74. Subsequently, on the auxiliary hole transport layer, a 200 Å-thick light-emitting layer was formed by depositing BH113 and BD370 available from SFC as a blue fluorescent light emitting host and a dopant wherein 5 wt % of BD370 was used. Then, Compound A-37 was vacuum-deposited on the light-emitting layer upper to form a 50 Å-thick auxiliary electron transport layer.

Then, 8-(4-(4-(naphthalen-2-yl)-6-(naphthalen-3-yl)-1,3,5-triazin-2-yl)phenyl)quinoline) (Compound E) and Liq were simultaneously vacuum-deposited in a 1:1 ratio on the auxiliary electron transport layer to form a 310 Å-thick electron transport layer and Liq (15 Å) and Al (1200 Å) were sequentially vacuum-deposited on the electron transport layer to form a cathode, manufacturing an organic light emitting diode.

The organic light emitting diode had a six-layered organic thin film structure and specifically, ITO/A (700 Å)/B (50 Å)/C (700 Å)/auxiliary hole transport layer [E-57 50 Å]/EML [BH113:BD370 (95:5 wt %)]200 Å/auxiliary electron transport layer [A-37 50 Å/E: Liq=1:1 (300 Å)/Liq (15 Å)/Al (1200 Å).

Example 2

An organic light emitting diode was manufactured according to the same method as Example 1 except for using Compound F-5 according to Synthesis Example 67 instead of Compound E-57 to form the auxiliary hole transport layer.

Example 3

An organic light emitting diode was manufactured according to the same method as Example 1 except for using Compound F-33 according to Synthesis Example 74 instead of Compound E-57 to form the auxiliary hole transport layer.

Example 4

An organic light emitting diode was manufactured according to the same method as Example 1 except for using Compound F-13 according to Synthesis Example 68 instead of Compound E-57 to form the auxiliary hole transport layer.

Example 5

An organic light emitting diode was manufactured according to the same method as Example 1 except for using Compound F-13 according to Synthesis Example 68 instead of Compound E-57 to form the auxiliary hole transport layer and Compound A-7 according to Synthesis Example 34 instead of Compound A-37 to form the auxiliary electron transport layer.

Example 6

An organic light emitting diode was manufactured according to the same method as Example 1 except for using Compound F-13 according to Synthesis Example 68 instead of Compound E-57 to form the auxiliary hole transport layer and Compound A-24 according to Synthesis Example 35 instead of Compound A-37 to form the auxiliary electron transport layer.

Reference Example 1

An organic light emitting diode was manufactured according to the same method as Example 1 except for using Compound C instead of Compound E-57 to form the auxiliary hole transport layer.

Reference Example 2

An organic light emitting diode was manufactured according to the same method as Example 1 except for using Compound A-24 according to Synthesis Example 35 instead of Compound A-37 to form the auxiliary electron transport layer.

Comparative Example 1

An organic light emitting diode was manufactured according to the same method as Example 1 except for forming no auxiliary electron transport layer.

Evaluation

Luminous efficiency and roll-off of each organic light emitting diode according to Examples 1 to 6, Reference Examples 1 and 2 and Comparative Example 1 were evaluated.

Specific measurement methods are as follows, and the results are shown in Table 3.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Roll-Off Measurement

Efficiency roll-off was calculated as a percentage through (Max measurement−Measurement at 6000 cd/m$^2$/Max measurement) among the measurements of (3).

TABLE 3

| | Auxiliary hole transport layer | Auxiliary electron transport layer | Driving voltage (V) | Luminous efficiency (cd/A) | Roll-off (%) |
|---|---|---|---|---|---|
| Example 1 | E-57 | A-37 | 4.22 | 7.0 | 4.1 |
| Example 2 | F-5 | A-37 | 4.11 | 7.4 | 1.4 |
| Example 3 | F-33 | A-37 | 4.15 | 7.2 | 3.0 |
| Example 4 | F-13 | A-37 | 4.07 | 7.8 | 2.4 |
| Example 5 | F-13 | A-7 | 3.74 | 7.9 | 0.6 |
| Example 6 | F-13 | A-24 | 3.85 | 8.1 | 0.3 |
| Reference Example 1 | Compound C | A-37 | 4.23 | 6.2 | 11.5 |
| Reference Example 2 | Compound C | A-24 | 4.06 | 6.9 | 10.4 |
| Comparative Example 1 | Compound C | — | 4.25 | 6.0 | 8.4 |

Referring to Table 3, the organic light emitting diodes according to Examples 1 to 6 showed remarkably improved luminous efficiency and roll-off characteristics simultaneously compared with the organic light emitting diodes according to Reference Example 1, Reference Example 2, and Comparative Example 1.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

<Description of Symbols>

| | |
|---|---|
| 10: anode | 20: cathode |
| 30: organic layer | 31: hole transport layer |
| 32: light-emitting layer | 33: auxiliary hole transport layer |
| 34: electron transport layer | 35: auxiliary electron transport layer |
| 36: electron injection layer | 37: hole injection layer |

What is claimed is:

1. An organic optoelectronic device, comprising an anode and a cathode facing each other, a light-emitting layer positioned between the anode and the cathode, a hole transport layer positioned between the anode and the light-emitting layer, an auxiliary hole transport layer positioned between the hole transport layer and the light-emitting layer, an electron transport layer positioned between the cathode and the light-emitting layer, and an auxiliary electron transport layer positioned between the electron transport layer and the light-emitting layer, wherein the auxiliary electron transport layer includes at least one kind of a first compound represented by at least one of Chemical Formulae 1-III to 1-IX, and the auxiliary hole transport layer includes at least one kind of a second compound represented by at least one of Chemical Formula 2-1 to Chemical Formula 2-3:

[Chemical Formula 1-III]

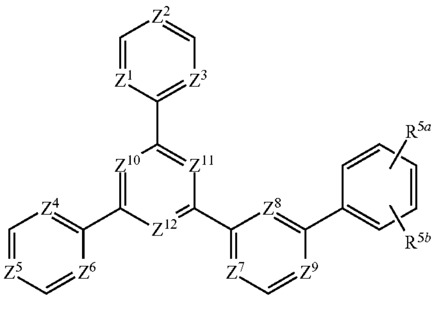

-continued

[Chemical Formula 1-IV]

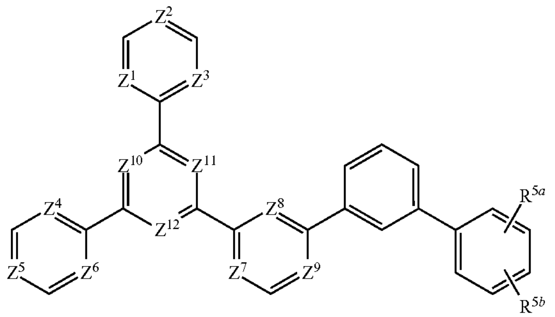

[Chemical Formula 1-V]

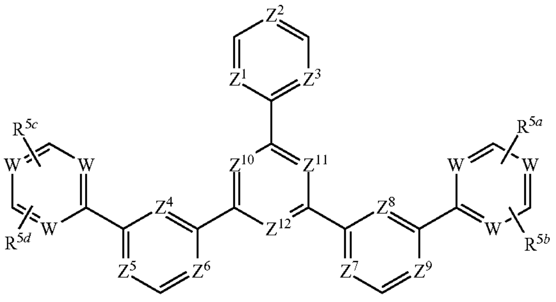

[Chemical Formula 1-VI]

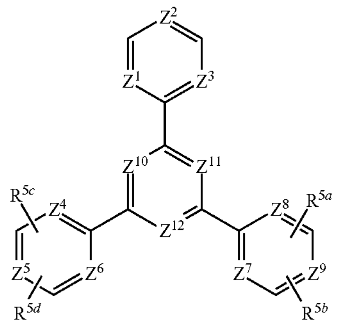

[Chemical Formula 1-VII]

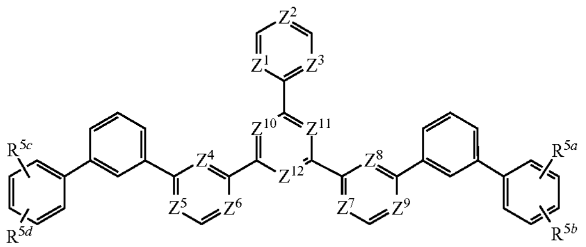

[Chemical Formula 1-VIII]

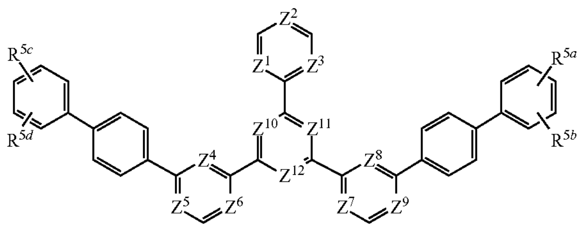

-continued

[Chemical Formula 1-IX]

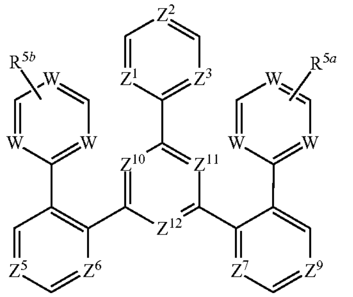

wherein, in Chemical Formulae 1-III to 1-IX, $Z^1$ to $Z^3$ are $CR^a$, wherein $R^a$ for $Z^1$ to $Z^3$ is independently hydrogen, deuterium, or a substituted or unsubstituted C1 to C10 alkyl group, $Z^4$ to $Z^{12}$ are independently N or $CR^a$, provided that at least one of $Z^4$ to $Z^{12}$ is N, each W is independently $CR^b$, $R^{5a}$ to $R^{5d}$ and $R^b$ are independently hydrogen, deuterium, a substituted or unsubstituted C1 to C10 alkyl group, a substituted or unsubstituted C6 to C30 aryl group, or a combination thereof, $R^a$ for $Z^4$, $Z^6$, $Z^7$, $Z^8$ and $Z^{10}$ to $Z^{12}$ are independently hydrogen, deuterium, a substituted or unsubstituted C1 to C10 alkyl group, a substituted or unsubstituted C6 to C30 aryl group, or a combination thereof, and $R^a$ for $Z^5$ and $Z^9$ are independently hydrogen, deuterium, a substituted or unsubstituted C1 to C10 alkyl group, or a combination thereof, wherein, "substituted" in Chemical Formulae 1-III to 1-IX refers to replacement of at least one hydrogen by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C1 to C20 alkoxy group, a fluoro group, a C1 to C10 trifluoroalkyl group, or a cyano group,

[Chemical Formula 2-1]

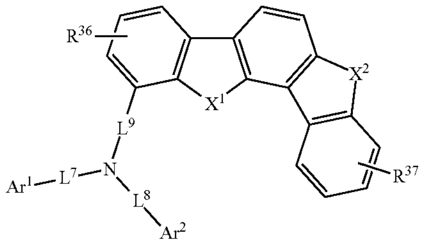

-continued

[Chemical Formula 2-2]

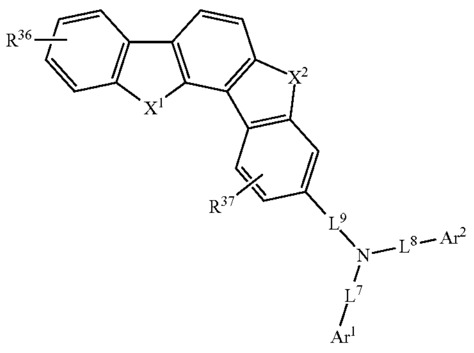

[Chemical Formula 2-3]

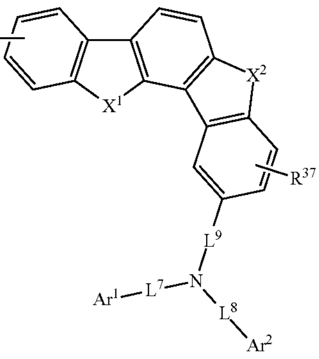

wherein, in Chemical Formulae 2-1 to 2-3, $X^1$ and $X^2$ are independently O, S, or $CR^cR^d$, $R^{36}$ and $R^{37}$, $R^c$, and $R^d$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, $Ar^1$ and $Ar^2$ are independently a substituted or unsubstituted C6 to C30 aryl group or a substituted or unsubstituted C2 to C30 heteroaryl group, and $L^7$ to $L^9$ are independently a single bond, a substituted or unsubstituted C6 to C30 arylene group, a substituted or unsubstituted heteroarylene group, or a combination thereof, wherein, "substituted" in Chemical Formulae 2-1 to 2-3 refers to replacement of at least one hydrogen by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C1 to C20 alkoxy group, a fluoro group, a C1 to C10 trifluoroalkyl group, or a cyano group.

2. The organic optoelectronic device as claimed in claim 1, wherein the first compound is represented by Chemical Formula 1-IV or Chemical Formula 1- VII.

3. The organic optoelectronic device as claimed in claim 1, wherein the first compound is at least one of compounds of Group 1,

[Group 1]
[A-1]
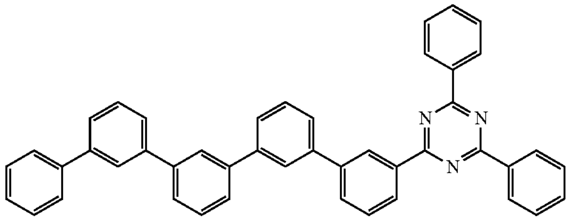
[A-3]
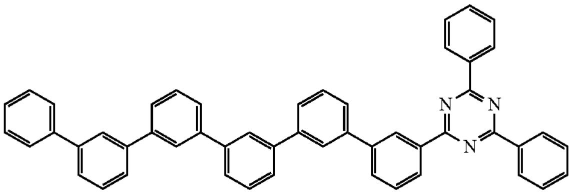
[A-5]
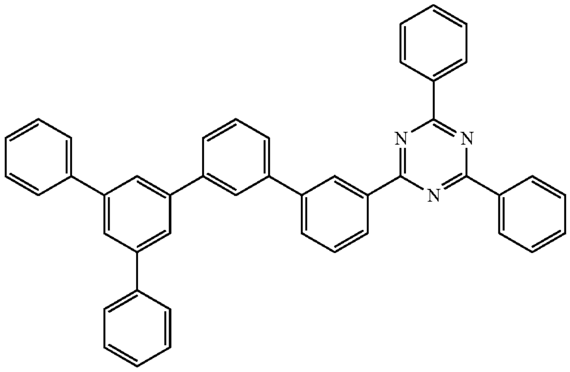
[A-7]
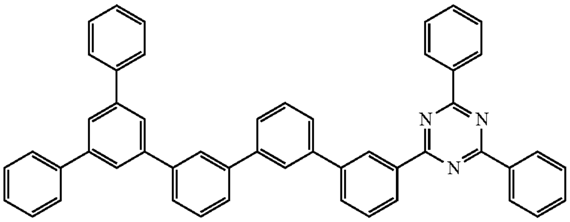
[A-9]
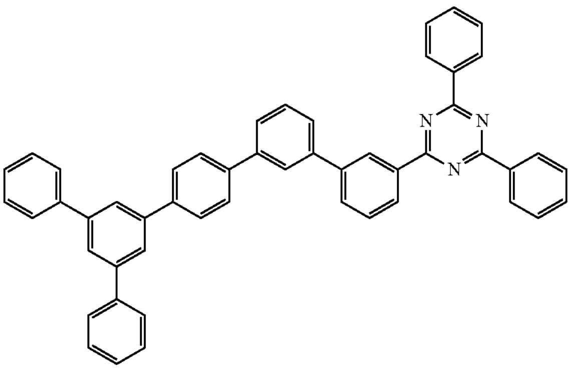
-continued
[A-11]
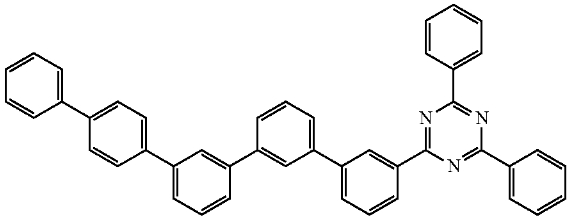
[A-13]
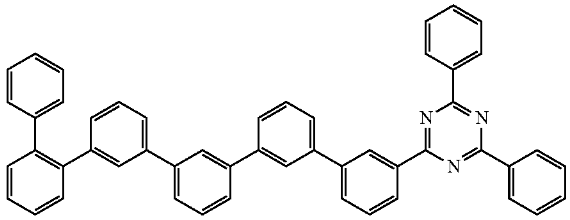
[A-14]
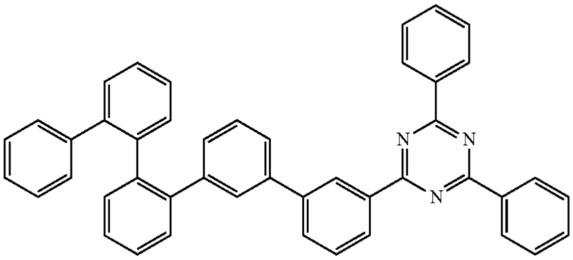
[A-15]
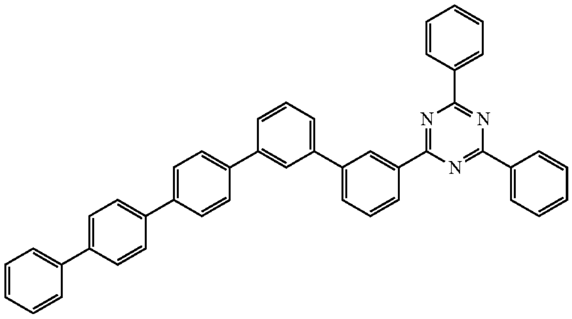
[A-16]
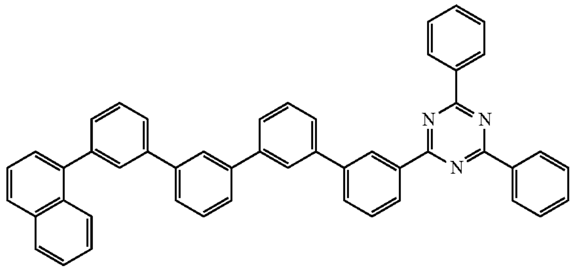

-continued
[A-17]
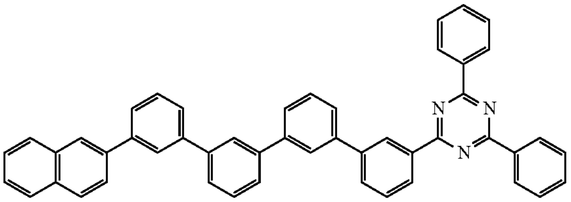
[A-18]
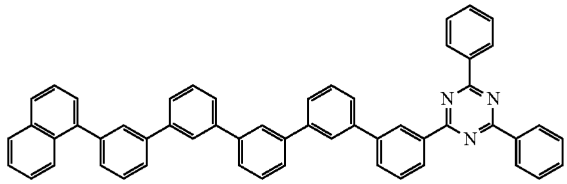
[A-19]
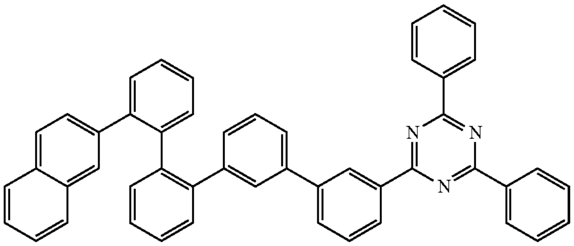
[A-20]
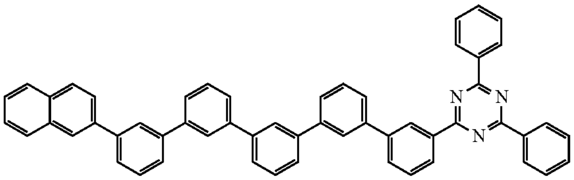
[A-21]
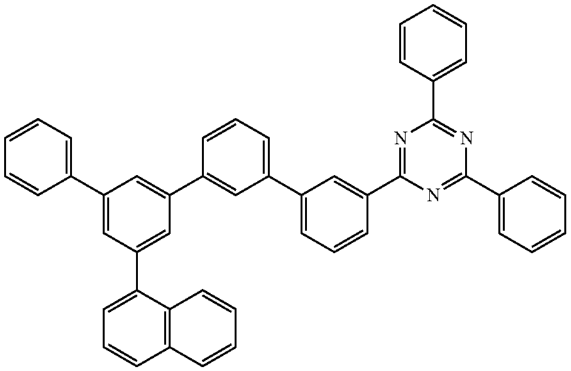
-continued
[A-22]
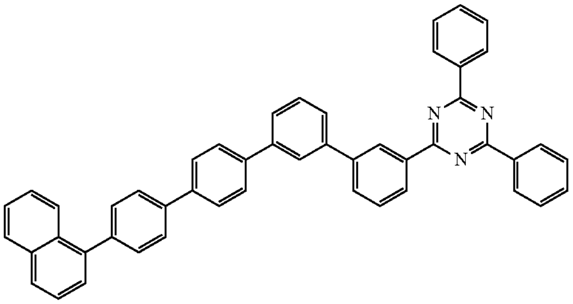
[A-23]
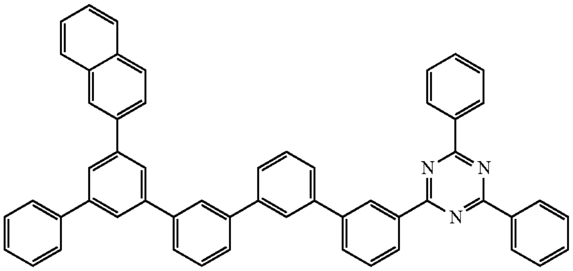
[A-24]
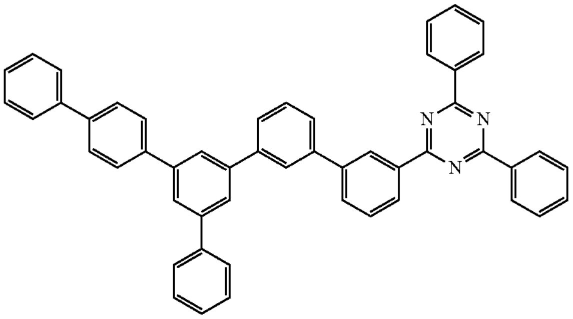
[A-25]
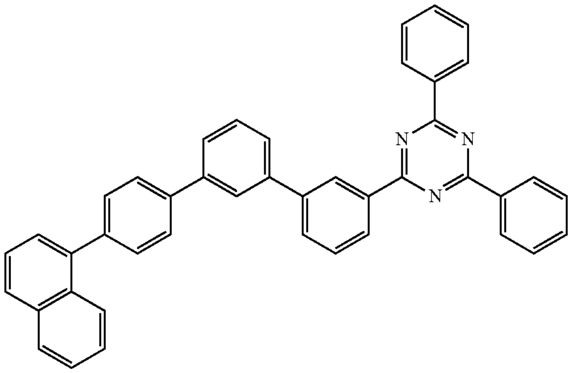

-continued
[A-26]
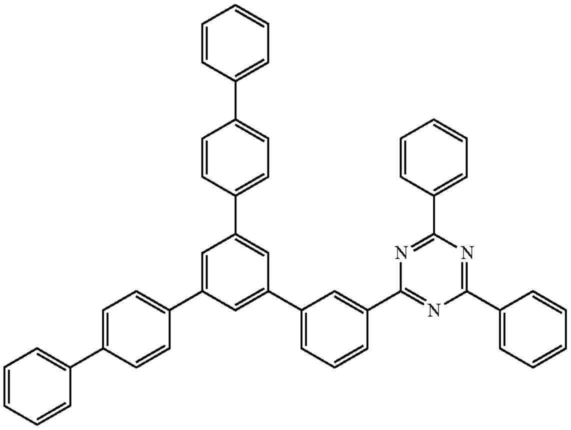
[A-27]
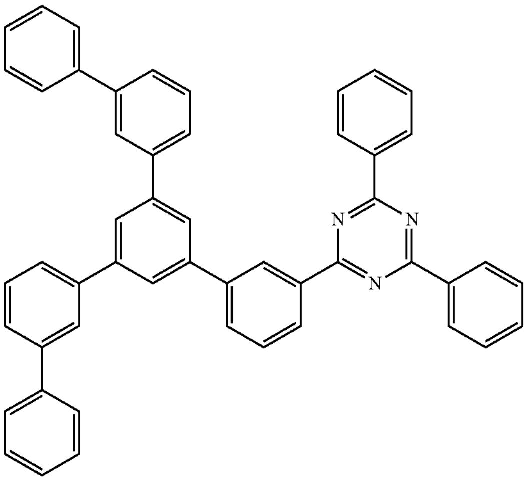
[A-28]
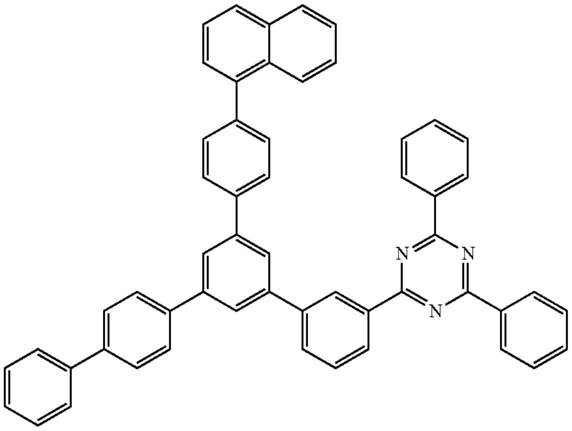
-continued
[A-29]
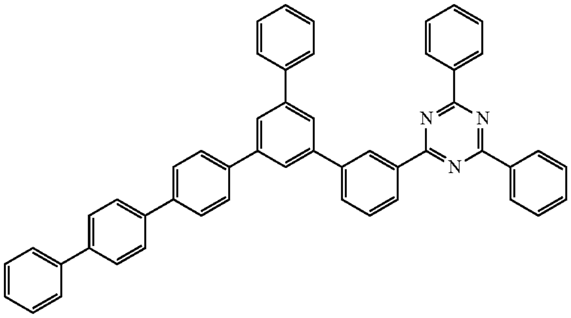
[A-30]
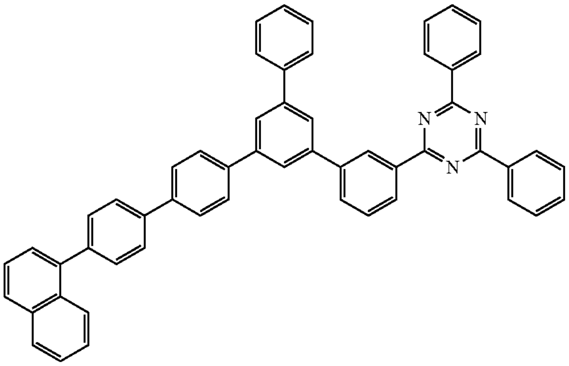
[A-31]
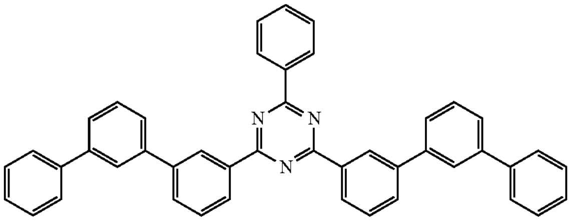
[A-32]
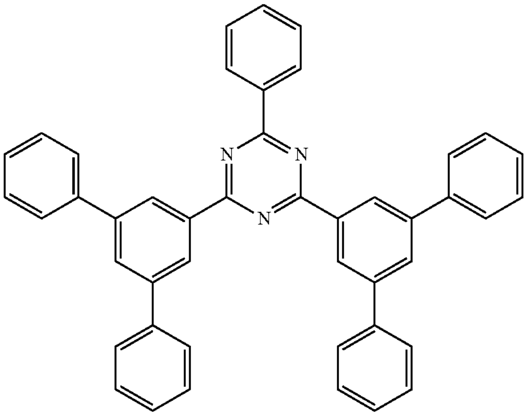

-continued
[A-33]
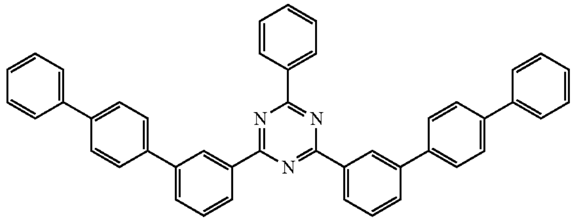
[A-34]
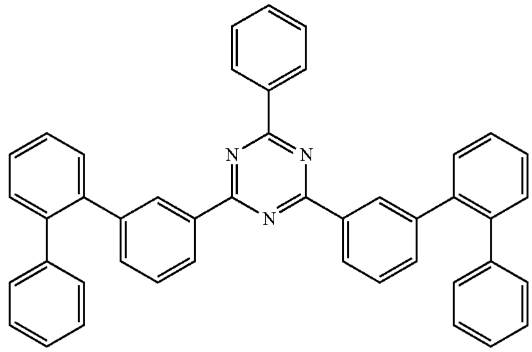
[A-35]
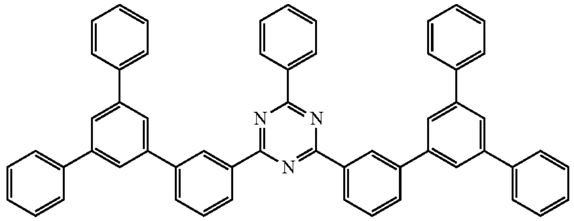
[A-36]
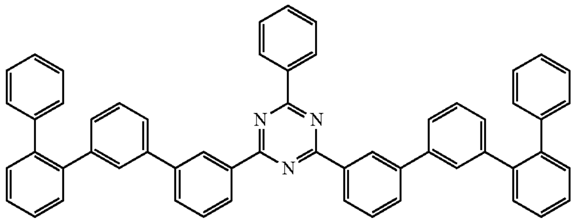
[A-37]
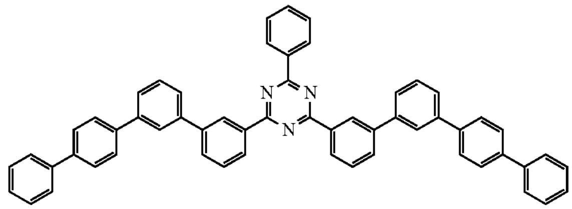
-continued
[A-38]
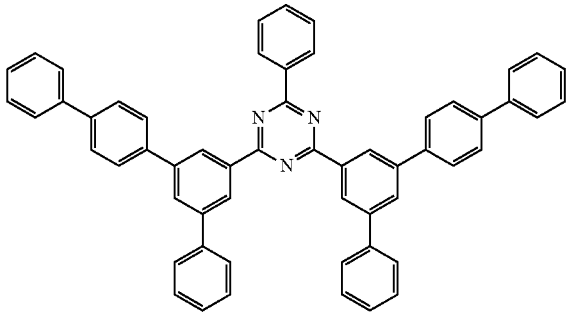
[A-39]
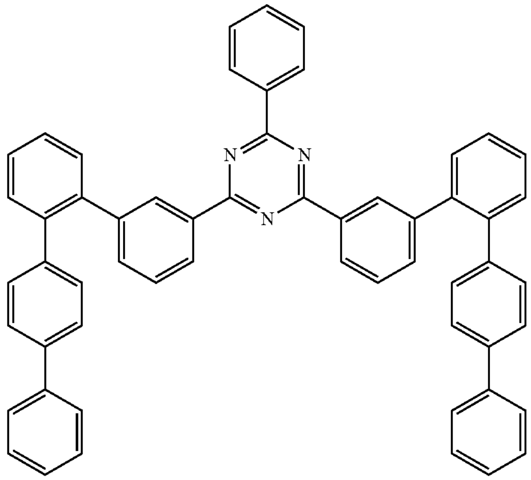
[A-40]
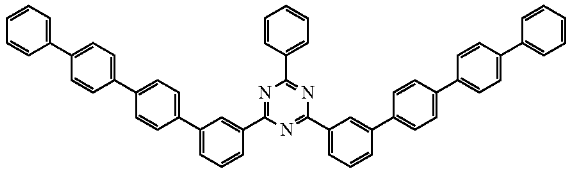
[A-41]
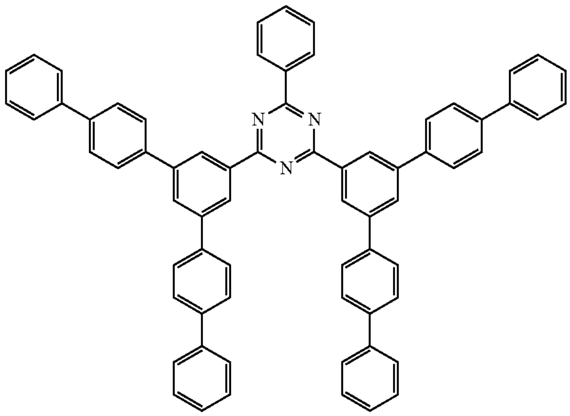

-continued
[A-45]
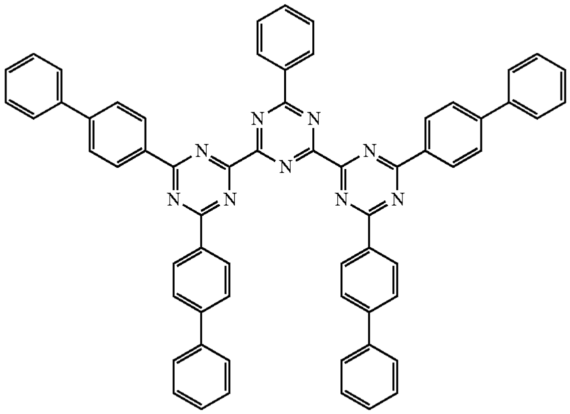
[A-46]
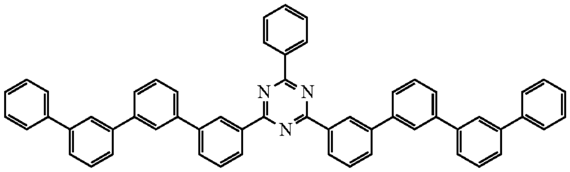
[A-48]
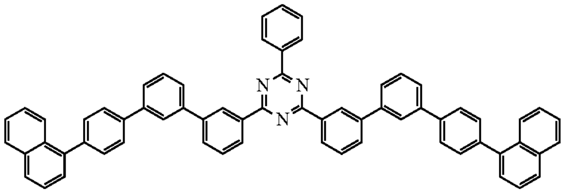
[A-49]
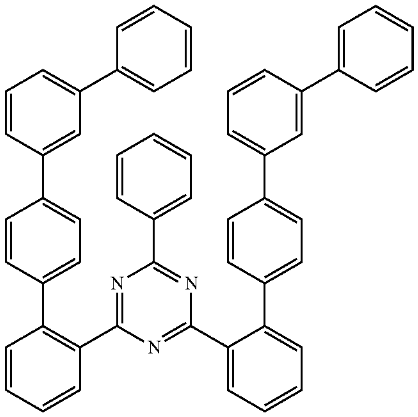
[A-50]
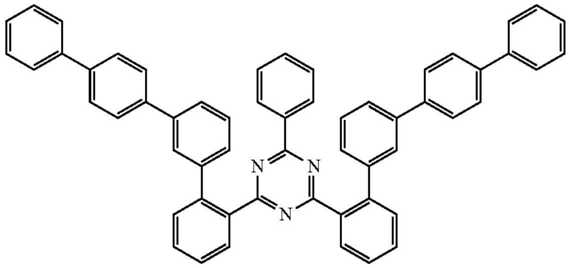
-continued
[A-51]
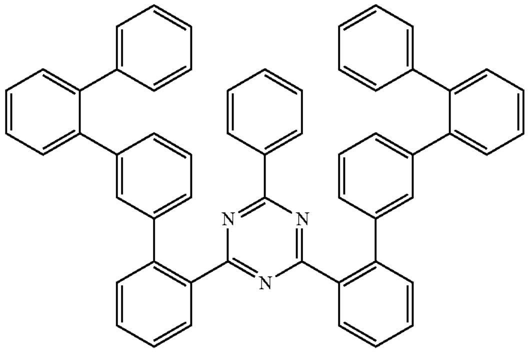
[A-52]
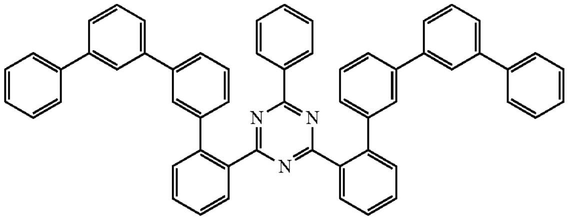
[A-53]
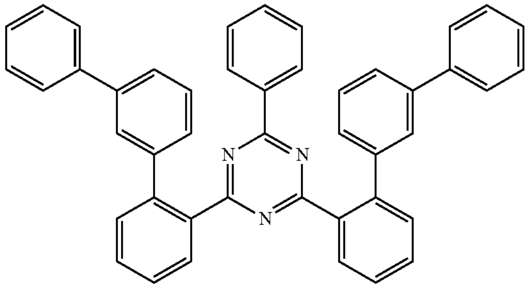
[A-54]
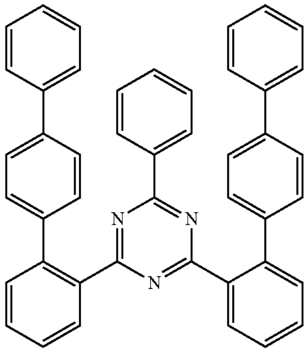
[A-55]
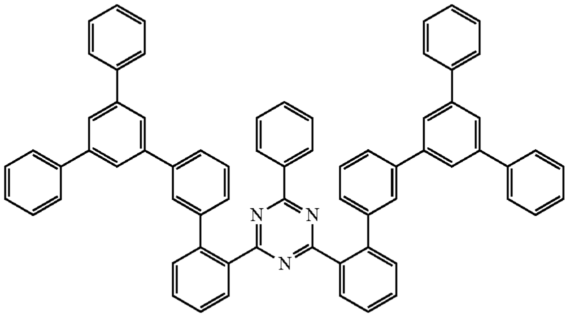

-continued
[A-56]
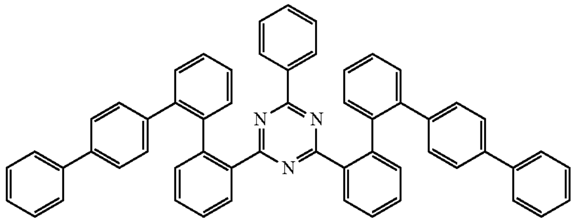
[A-57]
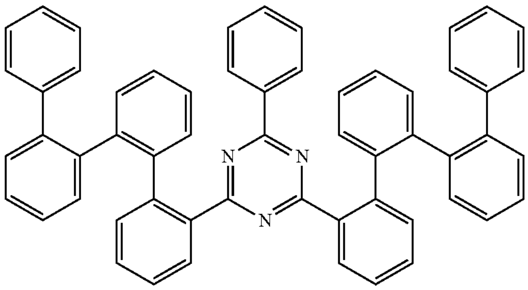
[A-61]
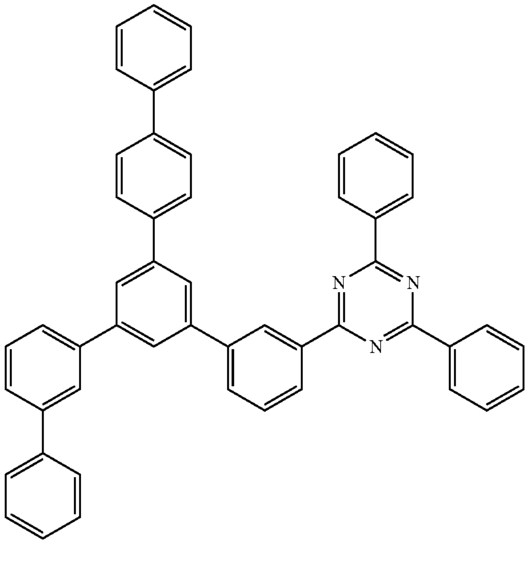
-continued
[A-62]
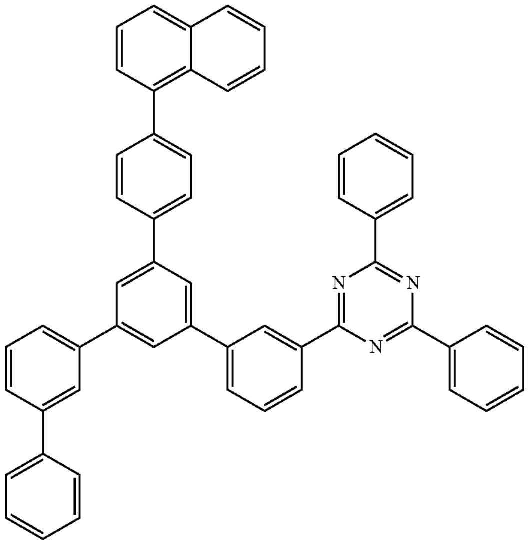
[A-63]
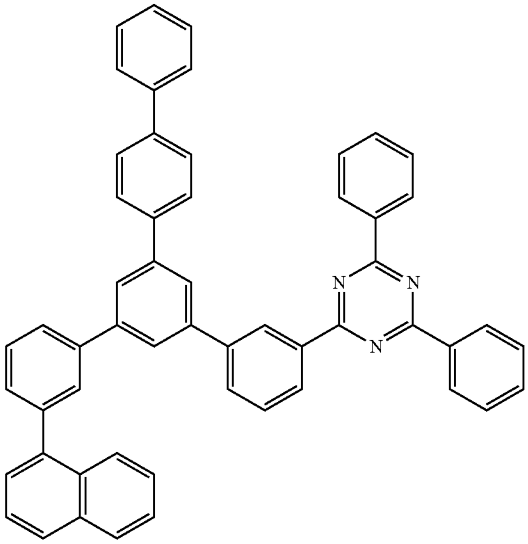

-continued
[A-64]
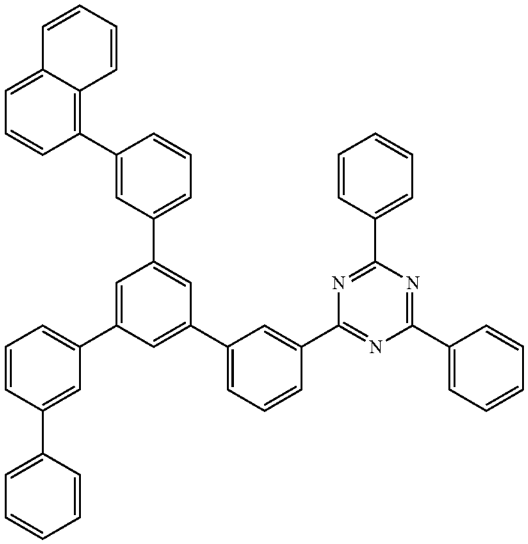
[A-65]
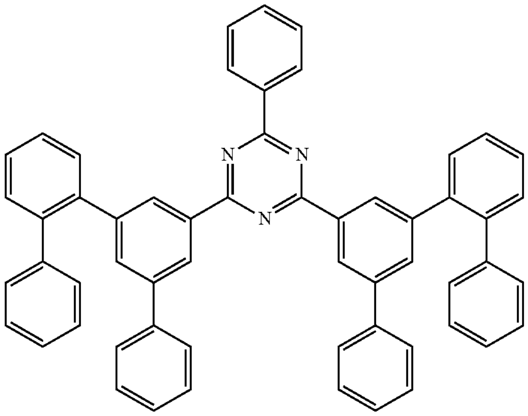
[A-66]
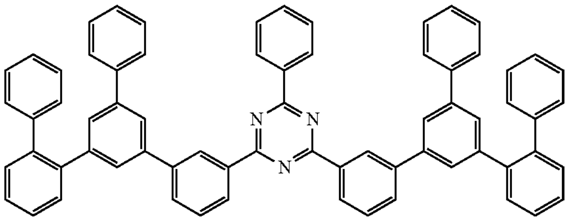
[A-67]
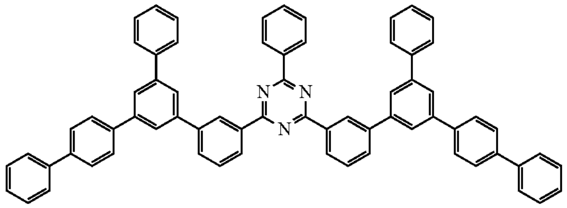
-continued
[A-68]
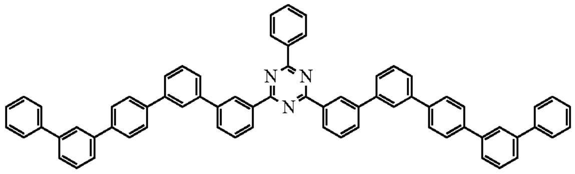
[A-70]
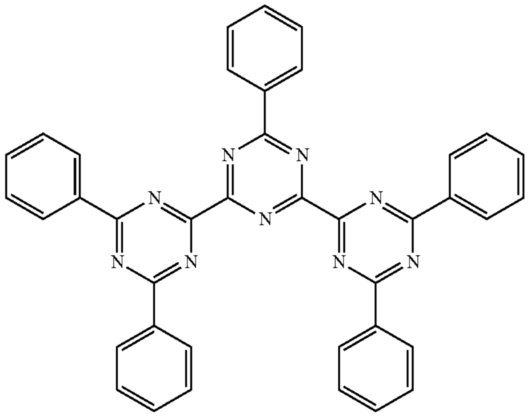
[A-76]
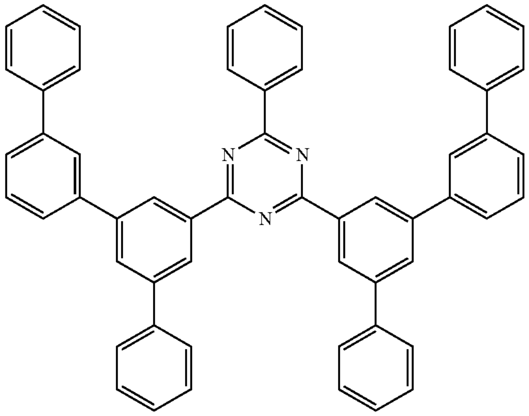
[A-80]
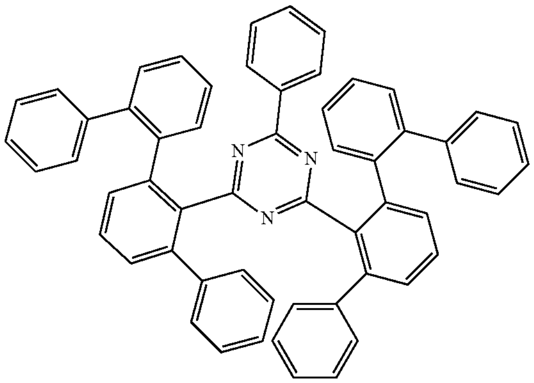

-continued
[A-81]
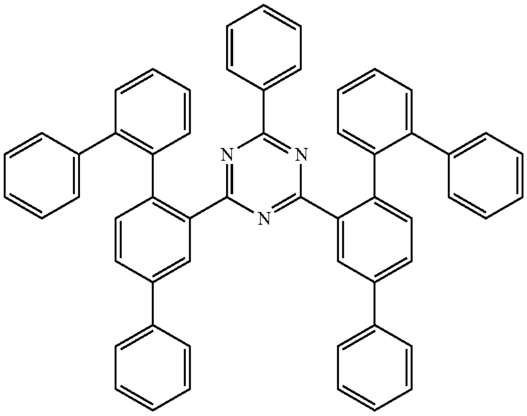
[A-82]
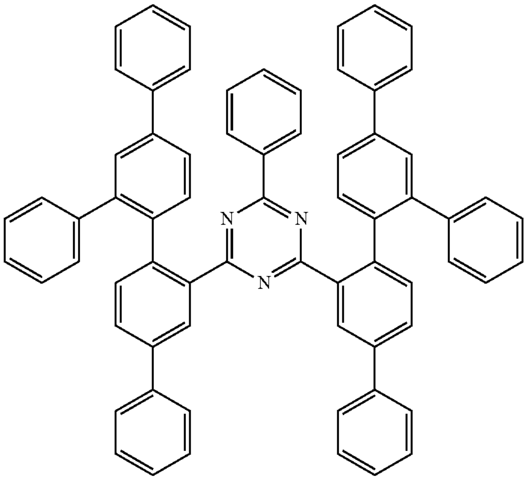
[A-86]
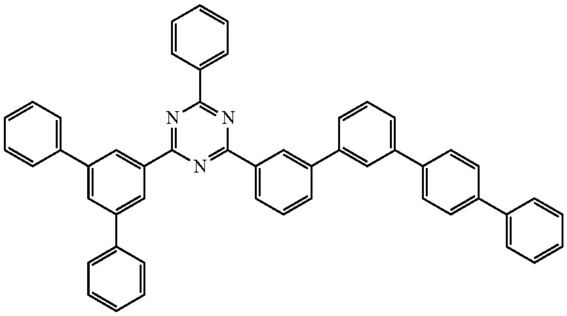
[A-87]
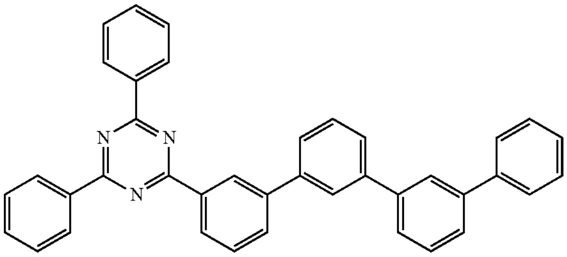
-continued
[A-88]
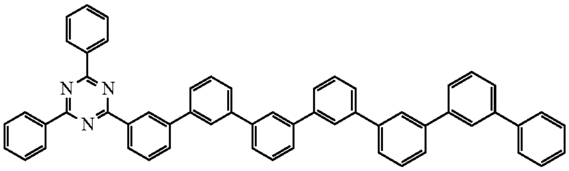
[B-1]
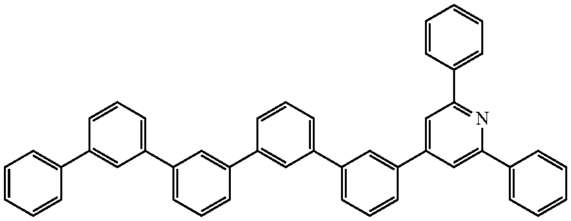
[B-2]
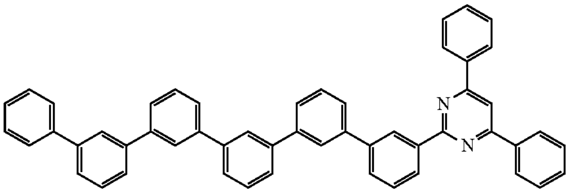
[B-3]
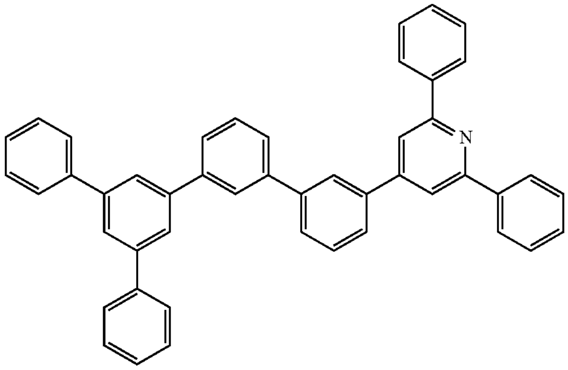
[B-4]
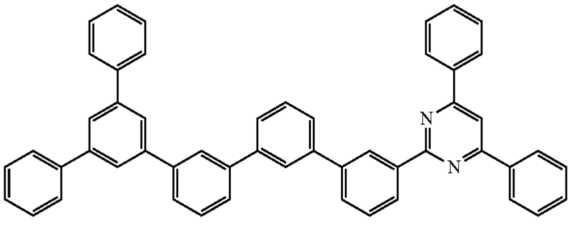

-continued
[B-5]
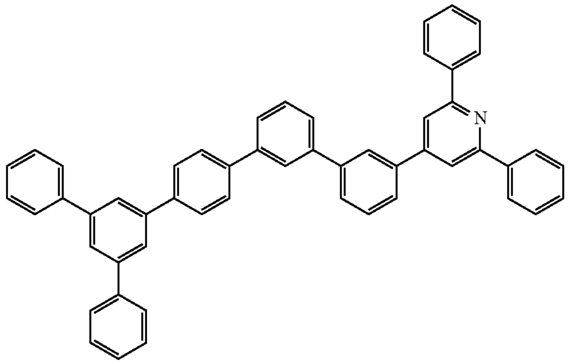
[B-6]
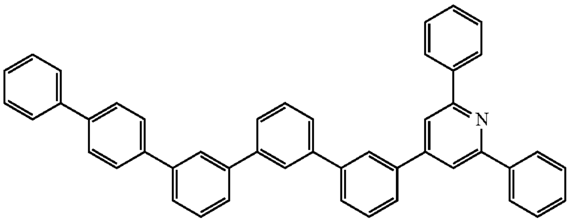
[B-7]
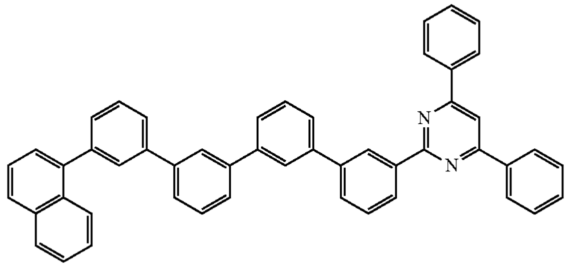
[B-8]
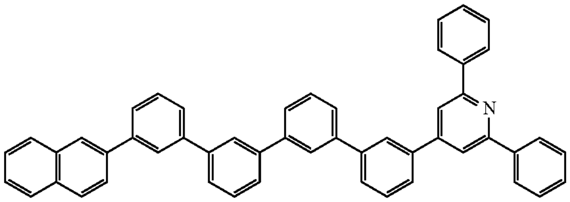
[B-9]
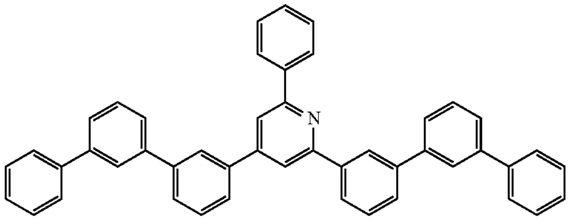
-continued
[B-10]
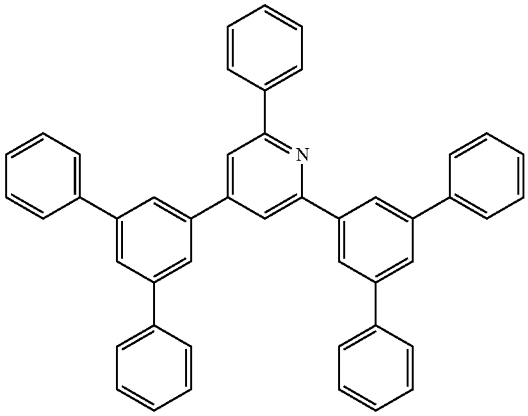
[B-11]
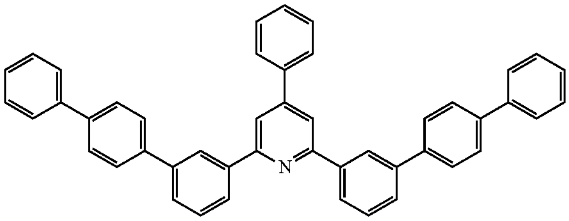
[B-12]
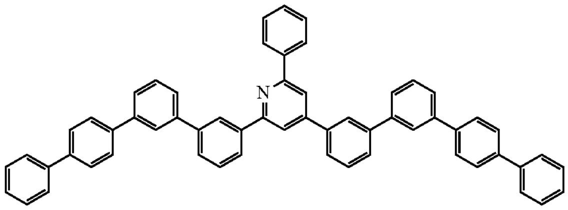
[B-13]
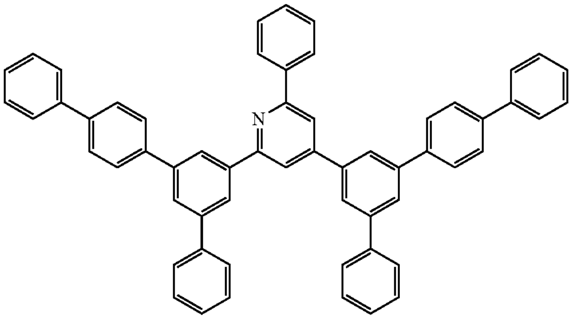
[B-14]
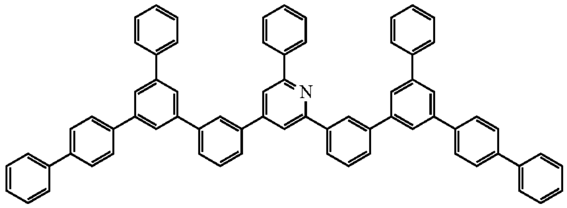

-continued
[B-15]
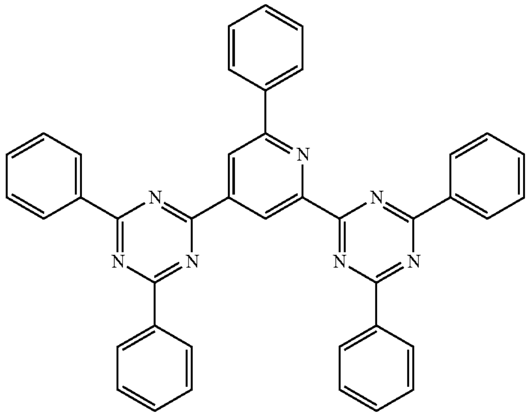
[B-17]
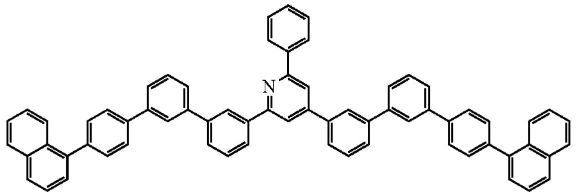
[B-18]
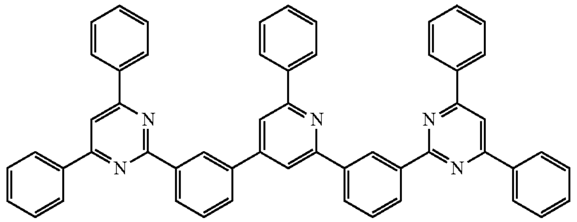
[B-22]
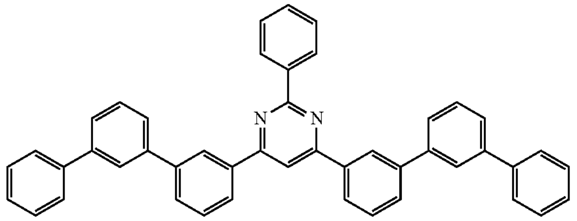
[B-23]
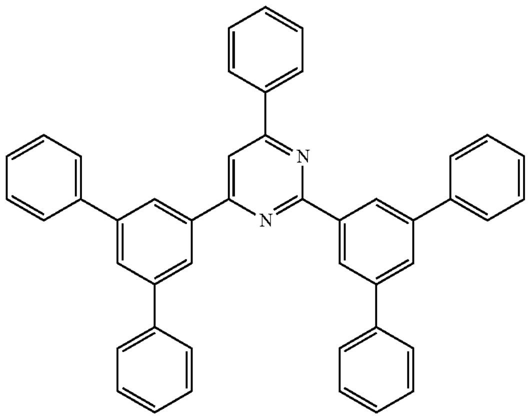
-continued
[B-24]
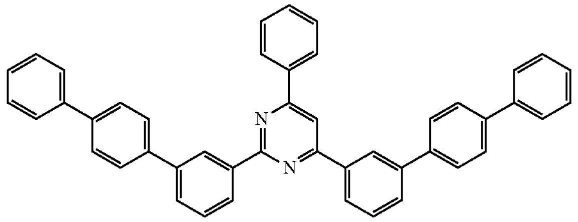
[B-25]
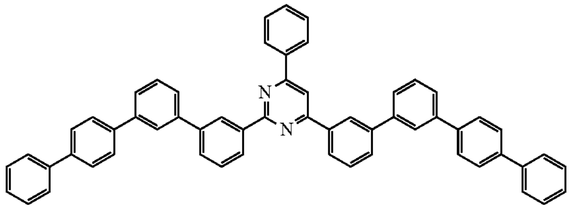
[B-26]
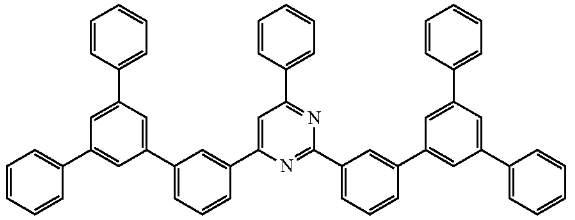
[B-27]
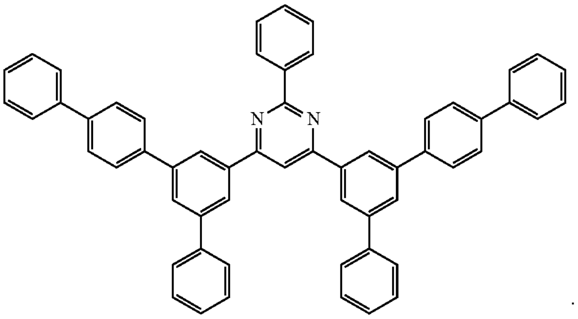
[B-28]
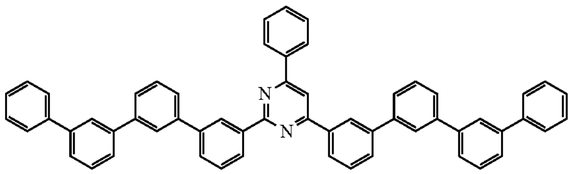
[B-29]
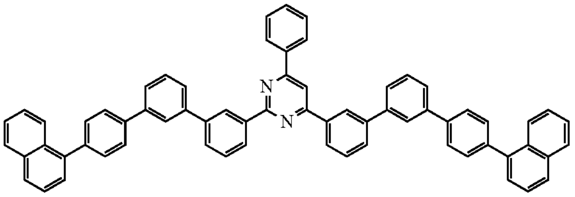

-continued
[B-31]
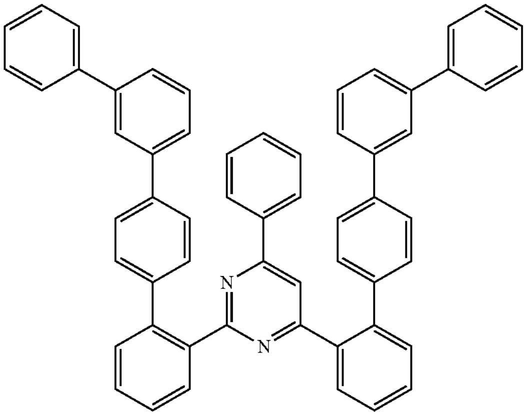
[B-32]
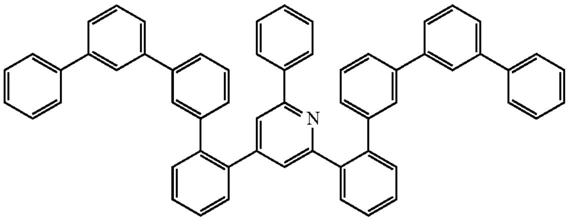
[B-34]
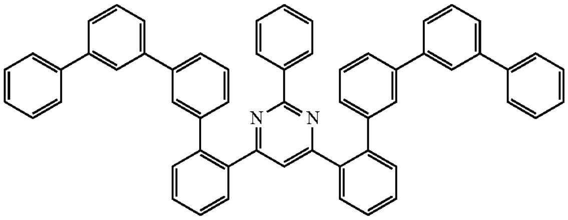
[B-35]
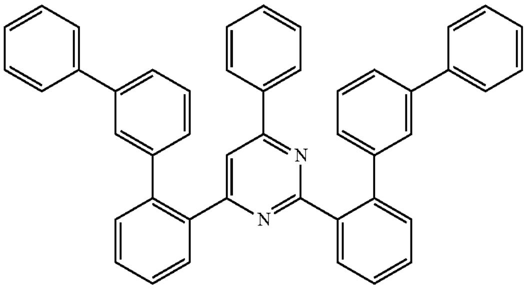
[B-37]
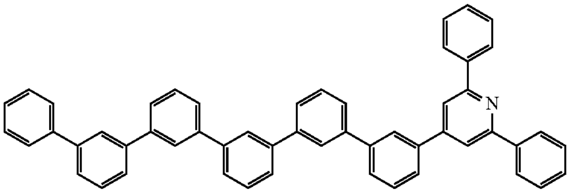
-continued
[B-38]
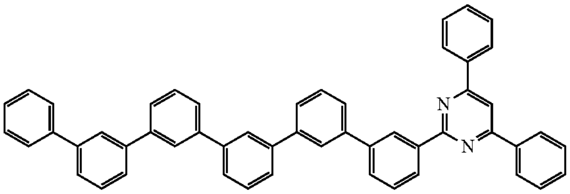
[B-39]
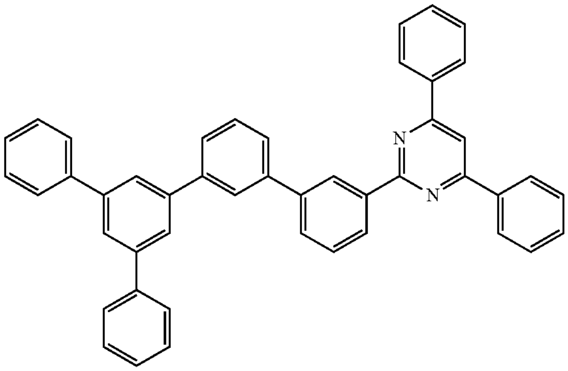
[B-40]
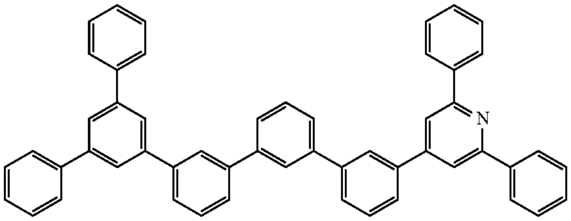
[B-41]
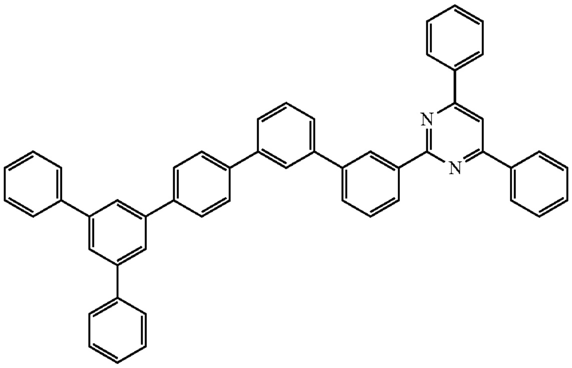
[B-42]
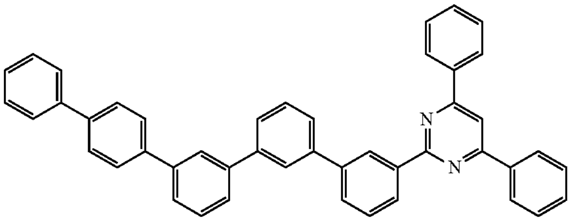

-continued

[B-43]

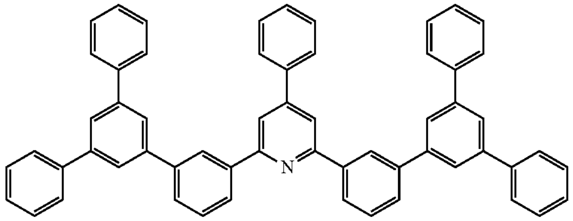

[B-45]

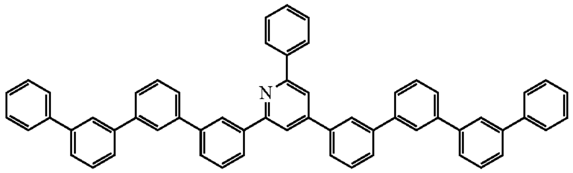

[B-47]

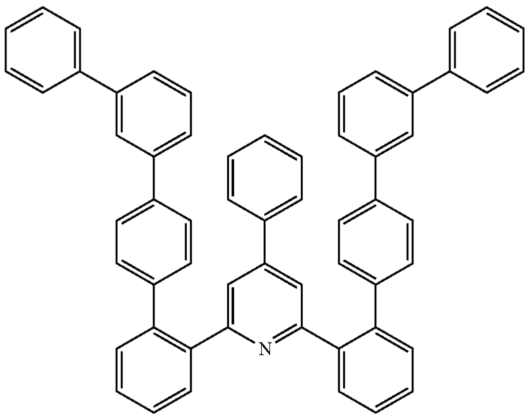

[B-48]

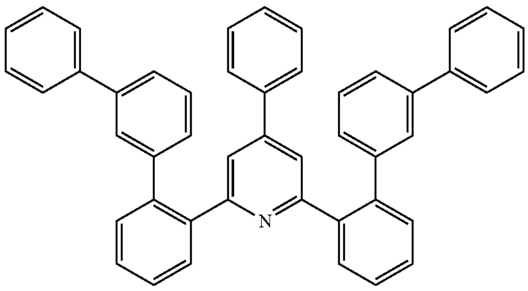

[B-49]

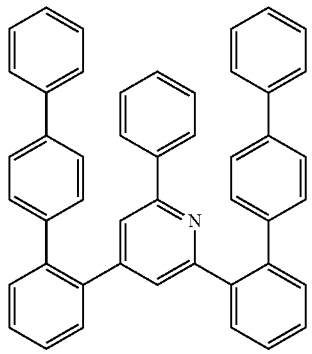

-continued

[B-50]

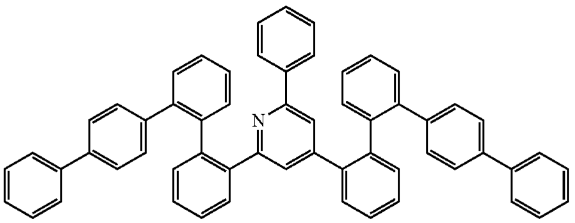

[B-52]

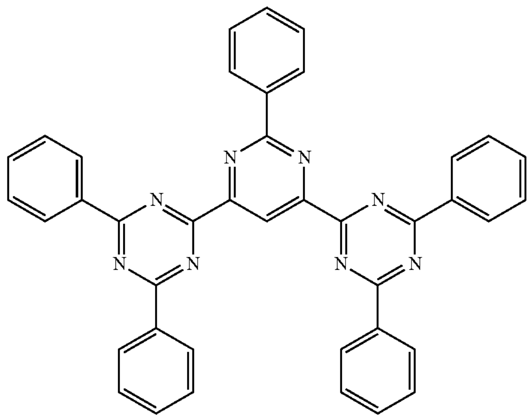

[B-59]

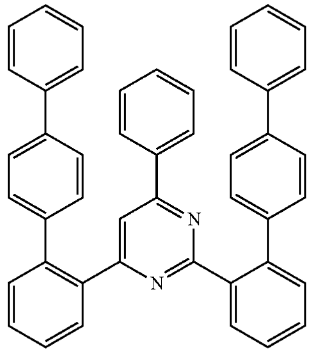

[B-60]

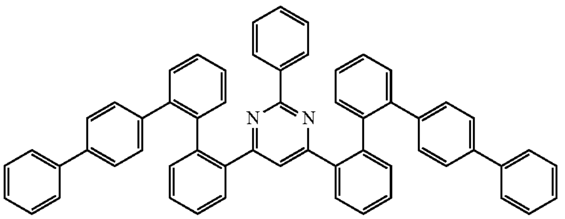

4. The organic optoelectronic device as claimed in claim 1, wherein, in Chemical Formulae 2-1 to 2-3, $Ar^1$ and $Ar^2$ are independently a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted triphenylene group, a substituted or unsubstituted fluorenyl group, a substituted or unsubstituted pyridinyl group, a substituted or unsubstituted pyrimidinyl group, a substituted or unsubstituted triazinyl group, a substituted or unsubstituted carbazolyl group, a substituted or unsubstituted dibenzofuranyl group, a substituted or unsubstituted dibenzothiophenyl group, Chemical Formula w, Chemical Formula x, Chemical Formula y, Chemical Formula z, or a combination thereof,

[Chemical Formula w]

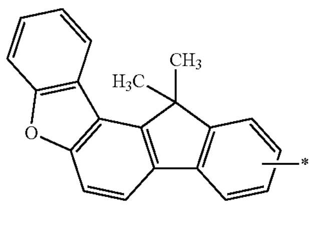

[Chemical Formula x]

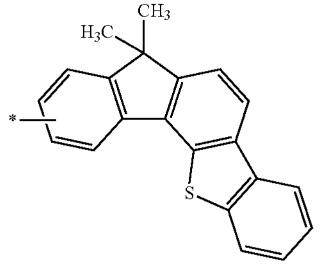

[Chemical Formula y]

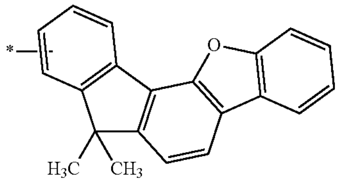

[Chemical Formula z]

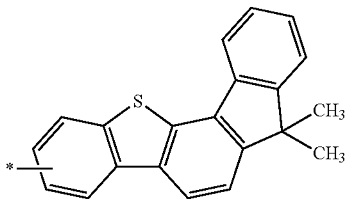

wherein "substituted" refers to replacement of at least one hydrogen by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C1 to C20 alkoxy group, a fluoro group, a C1 to C10 trifluoroalkyl group, or a cyano group.

5. The organic optoelectronic device as claimed in claim 1, wherein the second compound is represented by Chemical Formula 2-1 or Chemical Formula 2- 2.

6. The organic optoelectronic device as claimed in claim 1, wherein:

the auxiliary electron transport layer includes at least one of the first compound represented by Chemical Formula 1-IV or Chemical Formula 1-VII, and the auxiliary hole transport layer includes at least one of the second compound represented by Chemical Formula 2-1 or Chemical Formula 2-2:

[Chemical Formula 2-1]

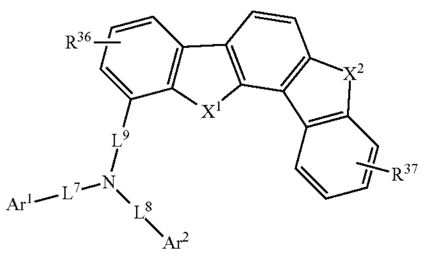

[Chemical Formula 2-2]

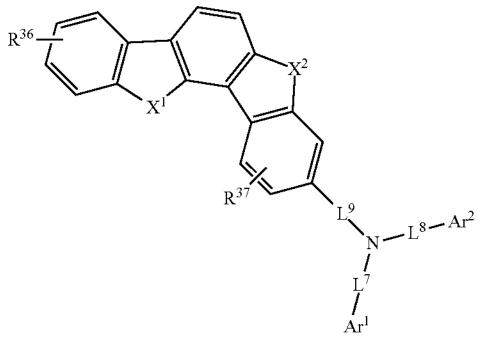

wherein, in Chemical Formulae 2-1 and 2-2, $X^1$ is O or S, $X^2$ is $CR^cR^d$, $R^{36}$ and $R^{37}$, $R^c$, and $R^d$ are independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof, $Ar^1$ and $Ar^2$ are independently a substituted or unsubstituted C6 to C30 aryl group or a substituted or unsubstituted C2 to C30 heteroaryl group, and $L^7$ to $L^9$ are independently a single bond, a substituted or unsubstituted C6 to C30 arylene group, a substituted or unsubstituted heteroarylene group, or a combination thereof, wherein, "substituted" in Chemical Formulae 2-1 and 2-2 refers to replacement of at least one hydrogen by deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C3 to C30 cycloalkyl group, a C2 to C30 heterocycloalkyl group, a C6 to C30 aryl group, a C1 to C20 alkoxy group, a fluoro group, a C1 to C10 trifluoroalkyl group, or a cyano group.

7. The organic optoelectronic device as claimed in claim 1, wherein the auxiliary hole transport layer contacts the hole transport layer and the light-emitting layer respectively, and the auxiliary electron transport layer contacts the electron transport layer and the light-emitting layer respectively.

8. The organic optoelectronic device as claimed in claim 1, wherein the light-emitting layer further includes a fluorescent dopant.

9. The organic optoelectronic device as claimed in claim 1, wherein the organic optoelectronic device is selected from an organic light emitting diode, an organic photoelectric device, an organic solar cell, an organic transistor, an organic photo conductor drum, and an organic memory device.

10. A display device comprising the organic optoelectronic device as claimed in claim 1.

* * * * *